US009155795B2

(12) United States Patent
Looby et al.

(10) Patent No.: US 9,155,795 B2
(45) Date of Patent: Oct. 13, 2015

(54) CXCR4 RECEPTOR COMPOUNDS

(75) Inventors: Richard J. Looby, Reading, MA (US); Boris Tchernychev, Chestnut Hill, MA (US)

(73) Assignee: Anchor Therapeutics, Inc., Cambridge, MA (US)

( * ) Notice: Subject to any disclaimer, the term of this patent is extended or adjusted under 35 U.S.C. 154(b) by 0 days.

(21) Appl. No.: 13/580,775

(22) PCT Filed: Feb. 25, 2011

(86) PCT No.: PCT/US2011/026322
§ 371 (c)(1),
(2), (4) Date: Aug. 23, 2012

(87) PCT Pub. No.: WO2011/106703
PCT Pub. Date: Sep. 1, 2011

(65) Prior Publication Data
US 2013/0005944 A1  Jan. 3, 2013

Related U.S. Application Data

(60) Provisional application No. 61/308,831, filed on Feb. 26, 2010.

(51) Int. Cl.
C07K 7/08    (2006.01)
C07K 14/00   (2006.01)
A61K 47/48   (2006.01)
C07K 14/715  (2006.01)
A61K 38/00   (2006.01)

(52) U.S. Cl.
CPC ..... *A61K 47/48046* (2013.01); *A61K 47/48123* (2013.01); *C07K 14/7158* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,864,229 B2 | 3/2005 | Kuliopulos et al. | |
| 7,166,702 B1 | 1/2007 | McDonald et al. | |
| 7,214,384 B2 | 5/2007 | Zuckermann et al. | |
| 7,304,127 B2 | 12/2007 | Saxinger | |
| 7,423,007 B2 | 9/2008 | Fujii et al. | |
| 7,696,168 B2 | 4/2010 | Kuliopulos et al. | |
| 2005/0202019 A1 | 9/2005 | Murphy et al. | |
| 2006/0166274 A1 | 7/2006 | Kuliopulos et al. | |
| 2006/0257869 A1 | 11/2006 | Ben-Sasson et al. | |
| 2007/0003558 A1 | 1/2007 | von Andrian et al. | |
| 2007/0179090 A1 | 8/2007 | Kuliopulos et al. | |
| 2007/0258893 A1 | 11/2007 | Shim et al. | |
| 2008/0214451 A1* | 9/2008 | Kuliopulos et al. | 514/12 |
| 2008/0214648 A1 | 9/2008 | De Kock et al. | |
| 2008/0312178 A1 | 12/2008 | Soppet et al. | |
| 2009/0175877 A1 | 7/2009 | Mueller et al. | |
| 2009/0270322 A1 | 10/2009 | Kuliopulos et al. | |
| 2010/0062003 A1 | 3/2010 | Murphy et al. | |
| 2010/0137207 A1 | 6/2010 | Kuliopulos et al. | |
| 2011/0070244 A1 | 3/2011 | von Andrian et al. | |
| 2013/0210709 A1 | 8/2013 | McMurry et al. | |

FOREIGN PATENT DOCUMENTS

| | | |
|---|---|---|
| CN | 101094866 A | 12/2007 |
| WO | WO 01/16182 A2 | 3/2001 |
| WO | WO 2004/087068 A2 | 10/2004 |
| WO | WO 2004/110341 A2 | 12/2004 |
| WO | WO 2006/052723 A2 | 5/2006 |
| WO | WO 2009/148947 A1 | 12/2009 |
| WO | WO 2010/053550 A2 | 5/2010 |
| WO | WO 2011/106703 A2 | 9/2011 |

OTHER PUBLICATIONS

Struyf et al., J Immunology. 2009;182:666-674.*
Tchernychev, B., et al., "Discovery of a CXCR4 agonist pepducin that mobilizes bone marrow hematopoietic cells", *PNAS*, 107(51): 22255-22259 (2010).
Notification of Transmittal of the International Search Report and the Written Opinion of the International Searching Authority or the Declaration for International Application No. PCT/US09/05979, Titled: "CXCR4 Receptor Compounds," Date of Mailing: May 20, 2010.
Notification Concerning Transmittal of International Preliminary Report on Patentability (Chapter I of the Patent Cooperation Treaty) for International Application No. PCT/US2009/005979, Titled: "CXCR4 Receptor Compounds," Date of Mailing: May 19, 2011.
Notification of Transmittal of the International Search Report and the Written Opinion of the International Searching Authority, or the Declaration for International Application No. PCT/US11/26322, Titled: "CXCR4 Receptor Compounds," Date of Mailing: Aug. 29, 2011.
Notification Concerning Transmittal of International Preliminary Report on Patentability (Chapter I of the Patent Cooperation Treaty) for International Application No. PCT/US2011/026322, Titled: "CXCR4 Receptor Compounds," Date of Mailing: Sep. 7, 2012.

(Continued)

*Primary Examiner* — Amber D Steele
*Assistant Examiner* — Schuyler Milton
(74) *Attorney, Agent, or Firm* — Foley Hoag LLP

(57) ABSTRACT

The invention relates generally to compounds which are allosteric modulators {e.g., positive and negative allosteric modulators, and allosteric agonists) of the G protein coupled receptor for stromal derived factor 1 (SDF-I), also known as the CXCR4 receptor. The CXCR4 receptor compounds are derived from the intracellular loops and domains of the CXCR4 receptor. The invention also relates to the use of these CXCR4 receptor compounds and pharmaceutical compositions comprising the CXCR4 receptor compounds in the treatment of diseases and conditions associated with CXCR4 modulation such as bone marrow transplantation, chemosensitization, cancer, metastatic disease (e.g., cancer), auto-immune disease (e.g., rheumatoid arthritis), fibrosis disease (e.g., pulmonary), AIDS infection, cardiovascular disease, uveitis, inflammatory diseases, celiac disease HIV infection and stem cell-based regenerative medicine.

12 Claims, 3 Drawing Sheets

(56) References Cited

OTHER PUBLICATIONS

Brinckerhoff, L.H., et al., "Terminal Modifications Inhibit Proteolytic Degradation of an Immunogenic Mart-1$_{27-35}$Peptide: Implications for Peptide Vaccines," *Int. J. Cancer*, 83:326-334 (1999).

Covic, L., et al., "Activation and Inhibition of G Protein-Coupled Receptors by Cell-Penetrating Membrane-Tethered Peptides," *PNAS*, 99(2):643-648 (2002).

Roland, J., et al., "Role of the Intracellular Domains of CXCR4 in SDF-1-mediated Signaling," Blood, 101(2):399-406 (2003).

Office Action, U.S. Appl. No. 13/127,443, Dated: Mar. 31, 2014.

Kaneider, N.C., et al., "Reversing Systemic Inflammatory Response Syndrome with Chemokine Receptor Pepducins," Nature Medicine, 11(6):661-665 (2005).

\* cited by examiner

CXCR4 RECEPTOR COMPOUNDS

RELATED APPLICATION

This application is the U.S. National Stage of International Application No. PCT/US2011/026322, filed Feb. 25, 2011, which designates the U.S., published in English, and claims the benefit of U.S. Provisional Application No. 61/308,831, filed Feb. 26, 2010. The entire teachings of the above applications are incorporated herein by reference.

BACKGROUND OF THE INVENTION

G protein coupled receptors (GPCRs) constitute one of the largest families of genes in the human genome. GPCRs are integral membrane signaling proteins. Hydrophobicity mapping of the amino acid sequences of G-protein coupled receptors has led to a model of the typical G-protein-coupled receptor as containing seven hydrophobic membrane-spanning regions with the amino terminal on the extracellular side of the membrane and the carboxyl terminal on the intracellular side of the membrane.

GPCRs mediate the transmission of intracellular signals ("signal transduction") by activating guanine nucleotide-binding proteins (G proteins) to which the receptor is coupled. GPCRs are activated by a wide range of endogenous stimuli, including peptides, amino acids. hormones, light, and metal ions. The following reviews are incorporated by reference: Hill, *British J. Pharm* 147: s27 (2006); Palczeski, *Ann Rev Biochemistry* 75: 743-767 (2006); Dorsham & Gutkind, *Nature Reviews* 7: 79-94 (2007); Kobilka & Schertler, *Trends Pharmacol Sci.* 2: 79-83 (2008).

GPCRs are important targets for drug discovery as they are involved in a wide range of cellular signaling pathways and are implicated in many pathological conditions (e.g., cardiovascular and mental disorders, cancer, AIDS). In fact, GPCRs are targeted by 40-50% of approved drugs, illustrating the critical importance of this class of pharmaceutical targets. Interestingly, this number represents only about 30 GPCRs, a small fraction of the total number of GPCRs thought to be relevant to human disease. Over 1000 GPCRs are known in the human genome, and GPCRs remain challenging targets from a research and development perspective in part because these are membrane bound receptors with complex pharmacology.

There remains a need for the development of new pharmaceuticals that are allosteric modulators of GPCRs (e.g., negative and positive allosteric modulators, allosteric agonists, and ago-allosteric modulators).

SUMMARY OF THE INVENTION

The invention relates generally to compounds which are allosteric modulators (e.g., negative and positive allosteric modulators, allosteric agonists, and ago-allosteric modulators) of the G protein coupled receptor for stromal cell-derived factor 1 (SDF-1, CXCL12), also known as the CXCR4 receptor. The CXCR4 receptor compounds are derived from the intracellular loops and domains of the CXCR4 receptor. The invention also relates to the use of these CXCR4 receptor compounds and pharmaceutical compositions comprising the CXCR4 receptor compounds in the treatment of diseases and conditions associated with CXCR4 receptor modulation such as bone marrow transplantation, chemosensitization, cancer, metastatic disease (e.g., cancer), auto-immune disease (e.g., rheumatoid arthritis), fibrosis disease (e.g., pulmonary), AIDS infection, cardiovascular disease, uveitis, inflammatory diseases, celiac disease HIV infection and stem cell-based regenerative medicine. Other treatment methods associated with stem cell-based regeneration for which these CXCR4 receptor compounds may be used include treatment of bone injury, treatment of cardiac tissue damage, treatment of ischemia, promotion of wound healing, reduction of scarring at a wound and increasing homing or trafficking of stem cells to an area of injury.

The compounds of the invention or pharmaceutically acceptable salts thereof, are represented by Formula I, Formula A, Formula A-1 and Formula II, as described herein.

Specifically, the invention relates to compounds represented by Formula I:

$$T-L-P,$$

or pharmaceutically acceptable salts thereof, wherein:
P is a peptide comprising at least three contiguous amino-acid residues of an intracellular i1, i2, i3 loop or an intracellular i4 domain of the CXCR4 receptor;
L is a linking moiety bonded to P
And T is a lipophilic tether moiety bonded to L.

More specifically, the invention relates to compounds represented by Formula I:

$$TLP,$$

or a pharmaceutically acceptable salt thereof, wherein:
P is a peptide comprising at least three contiguous amino-acid residues of an intracellular i1, i2, i3 loop or an intracellular i4 domain of the CXCR4 receptor;
L is a linking moiety bonded to P at an N-terminal nitrogen of an N-terminal amino acid residue selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), or N(R$^3$)C*(=NH) wherein L is bonded to P at the atom marked with an asterisk (*) and R$^3$ is H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, or heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl optionally and independently substituted;
and T is a lipophilic tether moiety bonded to L, wherein the C-terminal amino acid residue of P is optionally functionalized.

In a particular embodiment of Formula I, L is a linking moiety represented by C(O).

The invention also relates to pharmaceutical compositions comprising one or more compounds of the invention and a carrier, and the use of the disclosed compounds and compositions in methods of treating diseases and conditions responsive to modulation (inhibition or activation) of the CXCR4 receptor.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1A:
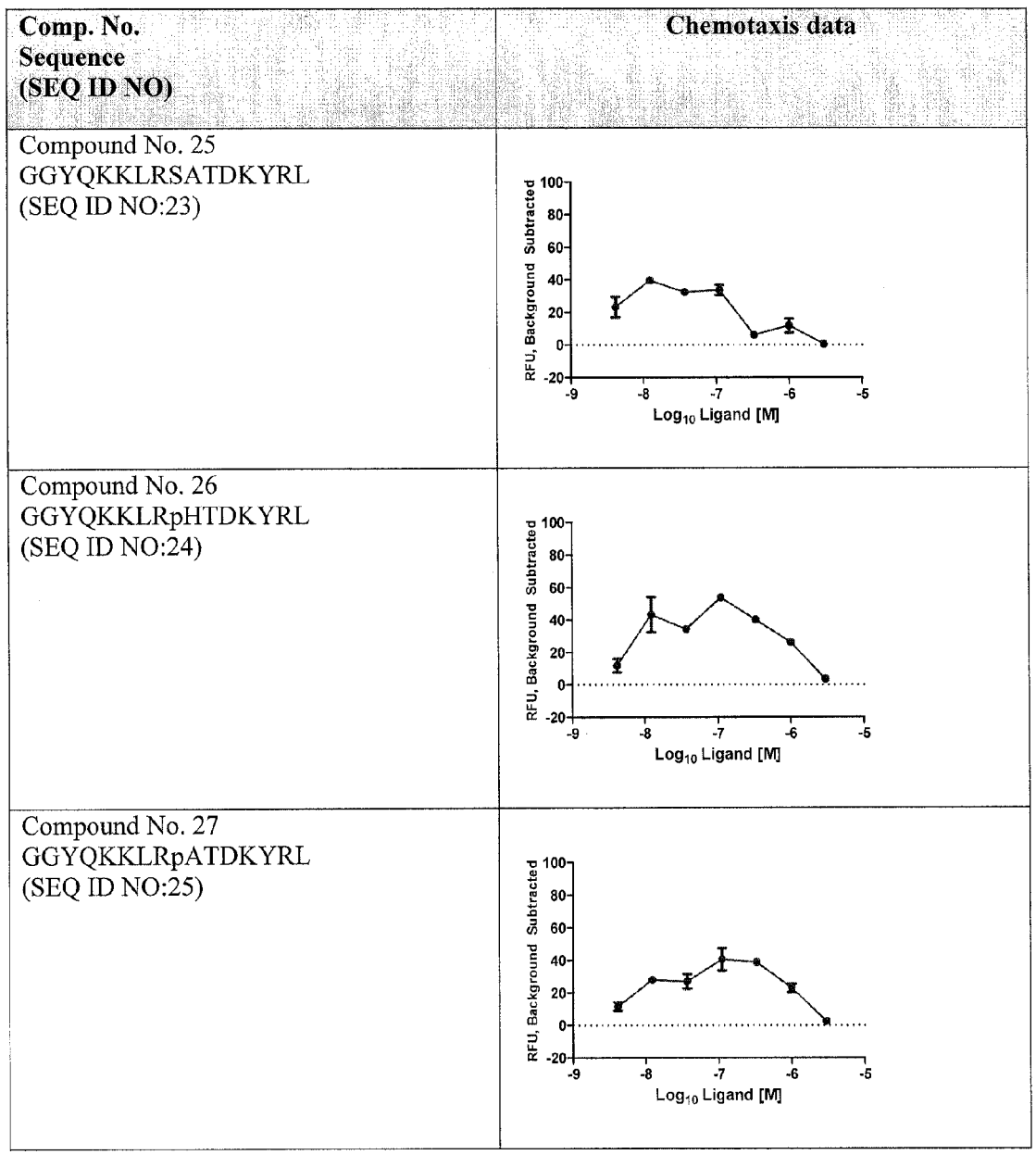
FIGS. 1A-1C are a series of graphical representations of compounds of the invention derived from the i1 loop in a chemotaxis assay.

A description of example embodiments of the invention follows.

G protein coupled receptors (GPCRs)

G protein coupled receptors (GPCRs) constitute one of the largest superfamilies of genes in the human genome; these transmembrane proteins enable the cell to respond to its environment by sensing extracellular stimuli and initiating intracellular signal transduction cascades. GPCRs mediate signal transduction through the binding and activation of guanine nucleotide-binding proteins (G proteins) to which the receptor is coupled. Wide arrays of ligands bind to these receptors, which in turn orchestrate signaling networks integral to many cellular functions. Diverse GPCR ligands include small proteins, peptides, amino acids, biogenic amines, lipids, ions, odorants and even photons of light. The following reviews are incorporated by reference: Hill, *British J Pharm* 147: s27 (2006); Dorsham & Gutkind, *Nature Reviews* 7: 79-94 (2007).

In addition to modulating a diverse array of homeostatic processes, GPCR signaling pathways are integral components of many pathological conditions (e.g., cardiovascular and mental disorders, cancer, AIDS). In fact, GPCRs are targeted by 40-50% of approved drugs illustrating the critical importance of this class of pharmaceutical targets. Interestingly, this number represents only about 30 GPCRs, a small fraction of the total number of GPCRs thought to be relevant to human disease. GPCRs are membrane bound receptors that exhibit complex pharmacological properties and remain challenging targets from a research and development perspective. Given their importance in human health combined with their prevalence (over 1000 known GPCRs in the human genome), GPCRs represent an important target receptor class for drug discovery and design.

GPCRs are integral membrane proteins that mediate diverse signaling cascades through an evolutionarily conserved structural motif. All GPCRs are thought to consist of seven hydrophobic transmembrane spanning α-helices with the amino terminus on the extracellular side of the membrane and the carboxyl terminus on the intracellular side of the membrane. The transmembrane helices are linked together sequentially by extracellular (e1, e2, e3) and intracellular (cytoplasmic) loops (i1, i2, i3). The intracellular loops or domains are intimately involved in the coupling and turnover of G proteins and include: i1, which connects TM1-TM2; i2, connecting TM3-TM4; i3, connecting TM5-TM6; and a portion of the C-terminal cytoplasmic tail (domain 4). Due in part to the topological homology of the 7™ domains and the recent high resolution crystal structures of several GPCRs (Palczewski et al., *Science*, 289, 739-45 (2000), Rasmussen, S. G. et al., *Nature*, 450, 383-7 (2007)) skilled modelers are now able to predict the general boundaries of GPCR loop domains through the alignment of several related receptors. These predictions are aided in part by a number of programs used by computational biologists, including EMBOSS, ClustalW2, Kalign, and MAFFT (Multiple Alignment using Fast Fourier Transform). Importantly, many of these programs are publically available (see, for example, The European Bioinformatics Institute (EMBL-EBI) web site http://www.ebi.ac.uk/Tools/) and most have web-based interfaces.

GPCR mediated signal transduction is initiated by the binding of a ligand to its cognate receptor. In many instances GPCR ligand binding is believed to take place in a hydrophilic pocket generated by a cluster of helices near the extracellular domain. However, other ligands, such as large peptides, are thought to bind to the extracellular region of protein and hydrophobic ligands are postulated to intercalate into a receptor binding pocket through the membrane between gaps in the helices. The process of ligand binding induces conformational changes within the receptor. These changes involve the outward movement of helix 6, which in turn alters the conformations of the intracellular loops and ultimately results in a receptor form that is able to bind and activate a heterotrimeric G protein (Farrens, D., et al. *Science*, 274, 768-770 (1996), Gether, U. and Kobilka, B., *J. Biol. Chem.*, 273, 17979-17982 (1998)). Upon binding the receptor catalyzes the exchange of GTP for GDP in the alpha subunit of the heterotrimeric G protein, which results in a separation of the G protein from the receptor as well a dissociation of the alpha and beta/gamma subunits of the G protein itself. Notably, this process is catalytic and results in signal amplification in that activation of one receptor may elicit the activation and turnover of numerous G proteins, which in turn may regulate multiple second messenger systems. Signaling diversity is further achieved through the existence of numerous G protein types as well as differing isoforms of alpha, beta and gamma subunits. Typically, GPCRs interact with G proteins to regulate the synthesis or inhibition of intracellular second messengers such as cyclic AMP, inositol phosphates, diacylglycerol and calcium ions, thereby triggering a cascade of intracellular events that eventually leads to a biological response.

GPCR signaling may be modulated and attenuated through cellular machinery as well as pharmacological intervention. Signal transduction may be 'switched off' with relatively fast kinetics (seconds to minutes) by a process called rapid desensitization. For GPCRs, this is caused by a functional uncoupling of receptors from heterotrimeric G proteins, without a detectable change in the total number of receptors present in cells or tissues. This process involves the phosphorylation of the receptor C terminus, which enables the protein arrestin to bind to the receptor and occlude further G protein coupling. Once bound by arrestin the receptor may be internalized into the cell and either recycled back to the cell surface or degraded. The alpha subunit of the G protein possesses intrinsic GTPase activity, which attenuates signaling and promotes re-association with the beta/gamma subunits and a return to the basal state. GPCR signaling may also be modulated pharmacologically. Agonist drugs act directly to activate the receptors, whereas antagonist drugs act indirectly to block receptor signaling by preventing agonist activity through their associating with the receptor. GPCR binding and signaling can also be modified through allosteric modulation, that is by ligands that bind not at the orthosteric binding site but through binding at an allosteric site elsewhere in the receptors. Allosteric modulators can include both positive and negative modulators of orthosteric ligand mediated activity, allosteric agonists (that act in the absence of the orthosteric ligand), and ago-allosteric modulators (ligands that have agonist activity on their own but that can also modulate the activity of the orthosteric ligand).

The large superfamily of GPCRs may be divided into subclasses based on structural and functional similarities. GPCR families include Class A Rhodopsin like, Class B Secretin like, Class C Metabotropic glutamate/pheromone, Class D Fungal pheromone, Class E cAMP receptors (Dictyostelium), the Frizzled/Smoothened family, and various orphan GPCRs. In addition, putative families include Ocular albinism proteins, Insect odorant receptors, Plant Mlo receptors, Nematode chemoreceptors, Vomeronasal receptors (VIR & V3R) and taste receptors.

Class A GPCRs, also called family A or rhodopsin-like, are the largest class of receptors and characteristically have relatively small extracellular loops that form the basis for selectivity vs. endogenous agonists and small-molecule drugs. In addition, Class A receptors also have relatively small intracellular loops. Class A receptors include amine family members such as dopamine and serotonin, peptide members such as chemokine and opioid, the visual opsins, odorant receptors and an array of hormone receptors.

The CXCR4 receptor (SDF-1 receptor) is a Class A receptor that has been implicated in conditions such as cancer, metastatic disease, leukocyte homeostasis, hematopoietic stem cell homing to the bone marrow, hematopoietic cell engraftment, inflammatory diseases, response to ischemia and HIV tropism.

Tissue repair and regeneration following injury is believed to be mediated by stem and progenitor cells that are either recruited from circulating blood, or already resident in tissues (Kollet et al., "HGF,SDF-1, and MMP-9 are Involved in Stress-induced Human $CD34^+$ Stem Cell Recruitment to the Liver," *J. Clin. Invest.* 112:160-169 (2003)). The natural agonist ligand for CXCR4, CXCL12 (SDF-1α), is found in areas of tissue damage. The CXCR4 receptor is found on the cell surface of several types of progenitor cells, including CD34+ and CD133+ cells. Cells expressing CXCR4 are attracted to areas with higher concentrations of agonists for this receptor, such as areas of tissue damage and hypoxia. Progenitor cells resident in niches of various organs such as bone marrow and myocardium may potentially be activated by CXCR4 receptor activation.

Under conditions of ischemia, low oxygen levels or other insults, heart muscle can be damaged or killed, resulting in compromised function (cardiomyopathy). Primary treatment of myopathy is the restoration of circulation and with it, oxygen delivery, and the treatment of other contributing factors such as inflammation. However, if tissue damage has already occurred further treatments can be used to improve or restore function of the damaged heart muscle.

One tactic used to treat tissue damage and hence cardiomyopathy is to employ progenitor cells that can differentiate into new heart muscle cells or cardiomyocytes. These progenitor cells can be harvested and directly administered, pharmacologic methods can be used to release them from the bone marrow and other storage sites, or pharmacological methods can be used to attract circulating progenitor cells to the damaged heart muscle. Additionally, the resident and circulating progenitor cells may potentially be activated.

There is evidence that damaged tissue releases natural cytokines like CXCL12/SDF-1α that can attract and activate progenitor cells, and this may be a part of the body's physiological repair systems. Clinical studies have examined the use of both harvested progenitor cells and pharmaceutical agents (plexifor and G-CSF) that promote the release of stem cells from the bone marrow, with some evidence of positive results such as increased time to or decreased progression to congestive heart failure measured by such endpoints as left ventricular ejection fraction in both ischemic and non-ischemic settings.

The instant disclosure concerns the administration of a CXCR4 compound that attracts progenitor cells to the area of damaged heart muscle. Supplementing natural CXCR4 agonist levels in a subject with cardiac tissue damage and hence cardiomyopathy will attract and potentially activate more progenitor cells, resulting in more healthy cardiomyocytes and better restoration of heart muscle function. The CXCR4 compounds may be administered systemically to increase the number of circulating progenitor cells which would be exposed to the natural CXCR4 agonist levels. CXCR4 compounds may be administered locally to a site in the proximity of the area of damage to provide a local gradient to attract progenitor cells and/or supplement the natural agonist levels.

Additional diseases that may benefit from systemic administration of the CXCR4 compounds of the instant invention include diabetic nephropathy and diabetic retinopathy.

Fractures due to trauma, with or without underlying bone pathology are one of the most common injuries in humans. Fracture healing is a complex physiological process that involves recruitment and differentiation of progenitor cells, many types of cytokine, chemokines and growth factors, an appropriate scaffold and mechanical stability. The lack of one of these factors due to underlying disease or inability to stabilize, for example, can lead to delayed healing or non-union, which in turn greatly increases the disability and suffering related to the fracture.

Each of these factors have been the subject of many studies as a point of intervention. Stabilization of the fracture site has long been the standard of care. Recently, more attention has turned to the other factors, especially as cell surface marker analysis, proteomic and genomic studies have elucidated the complex milieu invoked in a healing fracture site. Several studies point to a key role in CXCR4-expressing cells in fracture healing, due to presumed effects as progenitor cells that differentiate into bony tissue and also because of apparent effects on angiogenesis and other supportive physiological processes. Studies have reported a beneficial effect of administering SDF1 to a fracture site, including faster healing time.

Avascular necrosis (AVN), also known as osteonecrosis, aseptic necrosis, ischemic bone necrosis, or osteochondritis dissecans, is an impairment of blood flow to bone tissues resulting in the subsequent death of the bone tissue and eventual fracture. Although it can occur in any bone, AVN most commonly affects the ends of long bones or the epiphysis, such as the femur. Other common sites are the humerus, knees, shoulders, and ankles. The disease can affect one or more bones at the same time or at different times. AVN can also be involved in other bones diseases, such as osteoarthritis.

The loss of blood supply to the bone can be caused by traumatic or non-traumatic injuries, or increased pressure within the bone that causes the blood vessels to narrow and thus decreasing blood flow to bone tissues. During traumatic injuries, such as fractures or dislocations, the blood vessels can be damaged leading to comprised blood flow. The most common sites of post-traumatic AVN are the femoral and humeral heads, the body of the talus, and the carpal scaphoid. Post-traumatic AVN arises because of impaired blood flow and is therefore dependent on the relative contributions of arterial blood flow to the femoral or humeral head and the extent of anastomoses for collateral blood flows. A method of improving the treatment of AVN would be through stimulating angiogenesis or increasing the blood supply to the AVN area through the stimulation of blood vessel generation. The use of the compounds of the instant disclosure is intended to supplement local factors at the target site thereby generating new blood vessel growth.

The CXCR4 compounds of the instant disclosure could be systemically administered to release bone marrow-derived progenitor cells, and/or locally applied via direct injection or sustained release device to provide a local gradient to attract CXCR4-expressing cells, This administration could lead to accelerated fracture healing, higher healing rates, prevention of non-union and other complications, and shorter rehabilitation periods.

Wounds result in tissue disruption and coagulation of the microvasculature at the wound face. Repair of such tissue represents an orderly, controlled cellular response to injury.

All soft tissue wounds, regardless of size heal in a similar manner Tissue growth and repair are biologic systems wherein cellular proliferation and angiogenesis occur in the presence of an oxygen gradient. The sequential morphological and structural changes which occur during tissue repair have been characterized in great detail and have in some instances been quantified (Hunt, T. K., et al., "Coagulation and macrophage stimulation of angiogenesis and wound healing," in The surgical wound, pp. 1-18, ed. F. Dineen & G. Hildrick-Smith (Lea & Febiger, Philadelphia: 1981)).

The cellular morphology of a wound consists of three distinct zones. The central avascular space of the wound, which isoxygen deficient, acidotic and hypercarbic, and has high lactate levels. Adjacent to this space is a gradient zone of local ischemia which is populated by dividing fibroblasts. Behind the leading zone is an area of active collagen synthesis characterized by mature fibroblasts and numerous newly-formed capillaries (i.e., neovascularization). New blood vessel growth (angiogenesis) is necessary for the proper healing of wounded tissue.

Administering SDF-1α in close proximity to the wound has been shown to accelerate wound healing. (Rabbany, S. Y, et al., "*Continuous Delivery of Stromal Cell-Derived Factor-*1 *From Alginate Scaffolds Accelerates Wound Healing*", Cell Transplantation, Vol. 19, pp. 399-408, 2010. In one aspect, the CXCR4 compounds of the instant disclosure are systemically administered to release bone marrow-derived progenitor cells, and/or locally applied via direct injection or sustained release device to provide a local gradient to attract CXCR4-expressing cells. This administration could lead to accelerated wound healing, higher healing rates, prevention of complications, and shorter rehabilitation periods. Patients with diabetes mellitus are known to be at increased risk of developing chronic dermal ulcers such as an ulcer on the leg or foot in the presence of established long-term complications of the disease. Local tissue ischemia is a major contributing factor to diabetic ulcer formation. Patients with diabetes not only have large vessel disease, but suffer additional threat to their skin perfusion by involvement of the non-conduit arteries in the process of atherosclerosis and, perhaps more importantly, impairment of the microcirculatory control mechanisms, so-called small vessel disease. Under normal circumstances, blood flow increases in response to injury to facilitate healing. In the presence of small vessel disease (and ischemia) this response is significantly blunted and this, together with the tendency to thrombosis in the microcirculation during low flow, is probably important in ulcer formation.

The CXCR4 compounds of the instant disclosure could be systemically administered to release bone marrow-derived progenitor cells, and/or locally applied via direct injection or sustained release device to provide a local gradient to attract CXCR4-expressing cells. This administration could lead to accelerated diabetic ulcer healing, higher healing rates, and prevention of other complications, including amputation.

Peptides

As defined herein, P is a peptide comprising at least three contiguous amino-acid residues (e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) of an intracellular i1, i2 or i3 loop or intracellular i4 domain of the CXCR4 receptor. It is understood that, the N-terminal nitrogen of the N-terminal amino acid residue of P to which the linking moiety (e.g., C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), or N(R$^3$)C*(=NH)) is bonded can be one of the at least three contiguous amino acid residues or it can be an amino acid residue distinct from the at least three contiguous amino acid residues.

Intracellular i1 loop as used herein refers to the loop which connects TM1 to TM2 and the corresponding transmembrane junctional residues.

Intracellular i2 loop as used herein refers to the loop which connects TM3 to TM4 and the corresponding transmembrane junctional residues.

Intracellular i3 loop as used herein refers to the loop which connects TM5 to TM6 and the corresponding transmembrane junctional residues.

Intracellular i4 domain as used herein refers to the C-terminal cytoplasmic tail and the transmembrane junctional residue.

In a specific embodiment, P comprises at least three, at least four, at least five, at least six, at least seven, at least eight, at least nine, at least ten, at least eleven, at least twelve, at least thirteen, at least fourteen, at least fifteen, at least sixteen contiguous amino acid residues of the intracellular i1, i2 or i3 loop or intracellular i4 domain of the CXCR4 receptor.

In certain embodiment, P is cyclized. The amino acids can be cyclized via their side chains or end to end.

In a more specific embodiment, the at least three contiguous amino acids of P (e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) are derived from the intracellular i1, i2 or i3 loop or intracellular i4 domain of the CXCR4 receptor, wherein the amino acid sequence of each loop and the i4 domain is as described in Table 1A.

TABLE 1A

| Intracellular Loop Or Domain | CXCR4 Receptor |
|---|---|
| i1 | MGYQKKLRSMTDKYRLH (SEQ ID NO: 41) |
| i2 | DRYLAIVHATNSQRPRKLLAEK (SEQ ID NO: 42) |
| i3 | IIISKLSHSKGHQKRKALKTTVI (SEQ ID NO: 43) |

TABLE 1A-continued

| Intracellular Loop or Domain | CXCR4 Receptor |
|---|---|
| i4 | GAKFKTSAQHALTSVSRGSSLKILSKGKRGGHSSVSTESESSSFHSS (SEQ ID NO: 44) |

It is understood that in addition to the amino acids listed in the sequences in Table 1A, the intracellular loop for the i1 loop, i2 loop, i3 loop and i4 domain can also include the transmembrane junctional residues. For example, the i1 loop can include SEQ ID NO:41 where one or more residues from the transmembrane junctional residues are included on either the C-terminus, the N-terminus or both. For example, SEQ ID NO:41 can include either a leucine residue, leucine-serine residue, or a leucine-serine-valine residue at the C-terminus, SEQ ID NOS: 45, 46 and 47, respectively. Similarly, the N-terminus of the i1 loop sequence described in Table 1 can also be extended to include a valine residue (SEQ ID NO:48) or -leucine-valine residues (SEQ ID NO:49), or by -isoleucine-leucine-valine residues (SEQ ID NO:50) or by -valine-isoleucine-leucine-valine residues (SEQ ID NO:51).

In certain embodiments, at least three contiguous amino acids of P (e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) are derived from the intracellular i1, i2 or i3 loop or intracellular i4 domain of the CXCR4 receptor and transmembrane junctional residues, wherein the amino acid sequence of each loop and portions of the transmembrane junction is as described in Table 1B. The amino acid sequence of each loop is underlined.

TABLE 1B

| Intracellular Loop or Domain | CXCR4 Receptor |
|---|---|
| i1 | GNGLVILV<u>MGYQKKLRSMTDKYRL</u>HLSVADLLF (SEQ ID NO: 53) |
| i2 | LILAFIS<u>LDRYLAIVHATNSQRPRKLLAEK</u>VVYVGVWI (SEQ ID NO: 54) |
| i3 | IVILSCYC<u>IIISKLSHSKGHQKRKALKTTV</u>ILILAFFAC (SEQ ID NO: 55) |
| i4 | NPILYAFL<u>GAKFKTSAQHALTSVSRGSSLKILSKGKRGGHSSVSTESESSSFHSS</u> (SEQ ID NO: 56) | acid; Cha is Cyclohexyl alanine; Pra is Propargyl glycine; Dpr is 2,3, Diamino proionic acid; Hyp is Hydroxyproline; and photoLeu is photoleucine.

TABLE 2

| CXCR4 i-Loop | Sequence | SEQ ID NO: |
|---|---|---|
| i1 | KKLRSMTDkYRLH | 1 |
| i1 | KKLRSMTDKyRLH | 2 |
| i1 | MGQKKLRSMTDKYrL | 3 |
| i1 | MGYQKPLRSMTDKYRL | 4 |
| i1 | MGYQKKLPRSMTDKYRL | 5 |
| i1 | MGYQKKLRPSMTDKYRL | 6 |
| i1 | MGYQKKLRSpMTDKYRL | 7 |
| i1 | MGYQKKLRSMpTDKYRL | 8 |
| i1 | MGYQKKLRSMTDKYRV | 9 |

In another embodiment, P comprises at least three, at least four, at least five, at least six, at least seven, at least eight, at least nine, at least ten, at least eleven, at least twelve, at least thirteen, at least fourteen, at least fifteen, or at least sixteen contiguous amino acid residues of the i1 intracellular loop of the CXCR4 receptor.

In an even more specific embodiment, P is selected from the group consisting of SEQ ID NOS:1-39 as listed in Table 2 below. Amino acids designated as lower case letters indicate D-amino acids. Amino acids designated with are "J" or "Nle" is Norleucine. In the sequences, the following designation are included: Cit is Citrulline, x is Homoserine; z is Methylserine, NaI is 2-naphthylalanine; Aib is 2-amino Isobutyric TABLE 2-continued

| CXCR4 i-Loop | Sequence | SEQ ID NO: |
|---|---|---|
| i1 | MGYQKKLRSMTDKYRJ | 10 |
| i1 | MGYQKKLRSMTDKYKL | 11 |
| i1 | MGYQKKLRSMTDKY(Cit)L | 12 |
| i1 | MGYQKKLRSMTDKFRL | 13 |

TABLE 2-continued

| CXCR4 i-Loop | Sequence | SEQ ID NO: |
|---|---|---|
| i1 | MGYQKKLRSMTDK(Nal)RL | 14 |
| i1 | MGYQKKLRSJTDKYRL | 15 |
| i1 | MGYQKKLRSHTDKYRL | 16 |
| i1 | MGYQKKLRSGTDKYRL | 17 |
| i1 | GYQKKLRSJTDKYRI | 18 |
| i1 | MGYQ(Aib)KL(Cha)SMTRKYRL | 19 |
| i1 | xGYQKKLRSxTDKYRL | 20 |
| i1 | zGYQKKLRSzTDKYRL | 21 |
| i1 | (Pra)GYQKKLRSMTDKYRL | 22 |
| i1 | GGYQKKLRSATDKYRL | 23 |
| i1 | GGYQKKLRpHTDKYRL | 24 |
| i1 | GGYQKKLRpATDKYRL | 25 |
| i1 | GGYQKKpRpATDKYRL | 26 |
| i1 | GGYQKKLRpATDKFRL | 27 |
| i1 | CGYQKKLRSATDKYRL | 28 |
| i1 | GGYQKKLRppHTDKYRL | 29 |
| i1 | GGYQKKLRpWTDKYRL | 30 |
| i1 | GGYQKKLRp(Dpr)TDKYRL | 31 |
| i1 | GGYQKKLR(Hyp)HTDKYRL | 32 |
| i1 | GGYQKKLRp(Hyp)TDKYRL | 33 |
| i1 | GGYQKK(photoLeu)RSATDKYRL | 34 |
| i1 | GGYQKKHRSATDKYRL | 35 |
| i1 | GGYQKK1RSATDKYRL | 36 |
| i1 | GGYQKKLRSATDKYRLH | 37 |
| i1 | GGYQKKLRTATDKYRL | 38 |

In another specific embodiment, the at least three contiguous amino acids of P (e.g., at least 3, 4, 5, 6, 7, 8, 9, 10, 11, 12, 13, 14, 15, 16, 17, 18, 19, 20, 21, or 22) are derived from the i3 intracellular loop of the CXCR4 receptor.

In a more specific embodiment, P is SEQ ID NO:39 as listed in Table 3 below.

TABLE 3

| CXCR4 i-Loop | Sequence | SEQ ID NO: |
|---|---|---|
| i3 | SKLSHSKGHQKRKALKTTVIL | 39 |

In further specific embodiment, P comprises at least three contiguous amino (e.g., at least 3, 4, 5, 6, 7, 8, 9, 10, 11, 12, 13, 14, 15 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or 47) of the i4 intracellular domain of the CXCR4 receptor.

In a more specific embodiment, P is SEQ ID NO:40 as listed in Table 4 below.

TABLE 4

| CXCR4 i-Loop | Sequence | SEQ ID NO: |
|---|---|---|
| i4 | GAKFKTASAQHALTSVR | 40 |

It is understood that the sequences presented in Tables 2-4 can be optionally functionalized at the C-terminus. Functionalized at the C-terminus means that the acid moiety present at the C-terminus is replaced by some other functional group. Suitable functional groups include —C(O)N(R$_2$)$_2$, —C(O)OR$_3$, or C(O)NHC(O)OR$_2$, where R$_2$ is hydrogen or an alkyl group, for example a (C$_1$-C$_{10}$) alkyl group and R$_3$ is an alkyl group, for example, a (C$_1$-C$_{10}$) alkyl group.

In another embodiment, the C-terminus of P has a lipophilic tether moiety as described herein. In certain embodiments, the lipophilic tether moiety is attached to a NH capped C-terminus of P.

It is understood that as long as P comprises the indicated number of contiguous amino acids residues from the CXCR4 intracellular loop (i1, i2 or i3) or domain (i4) from which it is derived, the remainder of the peptide, if present, can be selected from:

(a) any natural amino acid residue, unnatural amino acid residue or a combination thereof;

(b) a peptide sequence comprising natural amino acid residues, non-natural amino acid residues and combinations thereof;

(c) a peptide sequence according to (b) comprising one or more peptide backbone modifications;

(d) a peptide sequence according to (c) comprising one or more retro-inverso peptide linkages;

(e) a peptide sequence according to (c) wherein one or more peptide bonds are replaced by

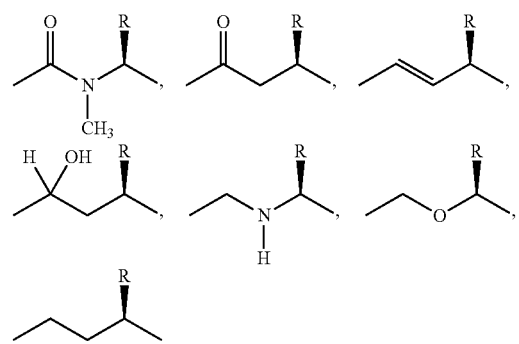

or a combination thereof;

(f) a peptide sequence according to (c) comprising one or more depsipeptide linkages, wherein the amide linkage is replaced with an ester linkage; and (g) a peptide sequence according to (c) comprising one or more conformational restrictions; and (h) a peptide sequence according to (c) comprising one or more of (d)-(g).

The length of the peptide sequence P can be from 3 amino acids in length to 90 amino acids in length. For example, the length of P is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 amino acids in length.

Furthermore, it is understood that even within the indicated number of contiguous amino acid residues derived from the GPCR intracellular loop (i1, i2 or i3) or domain (i4), there can be: peptide backbone modifications such as, but not limited to, those described in (e) above; retro-inverso peptide linkages; despsipeptide linkages; conformational restrictions; or a combination thereof.

It is noted that P of Formula A, Formula A-1, Formula I or Formula II can be optionally functionalized at the C-terminus. Functionalized at the C-terminus means that the acid moiety present at the C-terminus is replaced by some other functional group. Suitable functional groups include —C(O)N($R_2$)$_2$, —C(O)O$R_3$, or C(O)NHC(O)O$R_2$, where $R_2$ is hydrogen or an alkyl group, for example a ($C_1$-$C_{10}$) alkyl group and $R_3$ is an alkyl group, for example a ($C_1$-$C_{10}$) alkyl group. Functionalization of the C-terminus can result from the methods used to prepare.

Peptidomimetic as used herein refers to a compound comprising non-peptidic structural elements in place of a peptide sequence.

As used herein, the term "amino acid" includes both a naturally occurring amino acid and a non-natural amino acid.

As used herein, the term "naturally occurring amino acid" means a compound represented by the formula $NH_2$—CHR—COOH, wherein R is the side chain of a naturally occurring amino acids such as Lysine, Arginine, Serine, Tyrosine, etc. as shown in the Table below.

Table of Common Naturally Occurring Amino Acids

| | Amino acid | Three letter code | One letter code |
|---|---|---|---|
| Non-polar; neutral at pH 7.4 | Alanine | Ala | A |
| | Isoleucine | Ile | I |
| | Leucine | Leu | L |
| | Methionine | Met | M |
| | Phenylalanine | Phe | F |
| | Proline | Pro | P |
| | Tryptophan | Trp | W |
| | Valine | Val | V |
| Polar, uncharged at pH 7.0 | Asparagine | Asn | N |
| | Cysteine | Cys | C |
| | Glycine | Gly | G |
| | Glutamine | Gln | Q |
| | Serine | Ser | S |
| | Threonine | Thr | T |
| | Tyrosine | Tyr | Y |
| Polar; charged at pH 7 | Glutamic acid | Glu | E |
| | Arginine | Arg | R |
| | Aspartic acid | Asp | D |
| | Histidine | His | H |
| | Lysine | Lys | K |

"Non-natural amino acid" means an amino acid for which there is no nucleic acid codon. Examples of non-natural amino acids include, for example, the D-isomers of the natural α-amino acids such as D-proline (D-P, D-Pro) as indicated above; natural α-amino acids with non-natural side chains (e.g.,

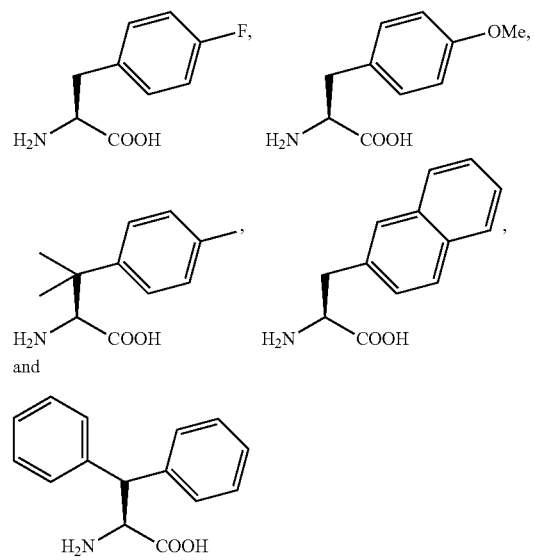

related to Phenylalanine); Aib (Aminobutyric acid), bAib (3-Aminoisobutyric acid), Nva (Norvaline), β-Ala, Aad (2-Aminoadipic acid), bAad (3-Aminoadipic acid), Abu (2-Aminobutyric acid), Gaba (γ-Aminobutyric acid), Acp (6-Aminocaproic acid), Dbu (2,4-Diaminobutryic acid), α-Aminopimelic acid, TMSA (Trimethylsilyl-Ala), aIle (Allo-isoleucine), Nle (Norleucine), tert-Leu, Cit (Citrulline), Orn (Arnithine, O), Dpm (2,2'-Diaminopimelic acid), Dpr (2,3-Diaminopropionic acid), α or β-Nal, Cha (Cyclohexyl-Ala), Hydroxyproline, Sar (Sarcosine), x (Homoserine), z (Methylserine), Nal (2-Naphthylalanine), Pra (Propargyl glycine), Hyp (Hydroxyproline), photoLeu (photoleucine), and the like.

Unnatural amino acids also include cyclic amino acids; and amino acid analogs, for example, $N^α$-alkylated amino acids such as MeGly ($N^α$-methylglycine), EtGly ($N^α$-ethylglycine) and EtAsn ($N^α$-ethylasparagine); and amino acids in which the α-carbon bears two side-chain substituents. As with the natural amino acids, the residues of the unnatural amino acids are what are left behind when the unnatural amino acid becomes part of a peptide sequence as described herein.

Amino acid residues are amino acid structures as described above that lack a hydrogen atom of the amino group or the hydroxyl moiety of the carboxyl group or both resulting in the units of a peptide chain being amino-acid residues.

The D-isomers of the natural amino acids are designated herein with a lower case letter of the corresponding naturally occurring amino acid. For example, d-Proline is designated "p" rather than "P" as is used for naturally occurring proline.

Linkers (L)

The linker "L" of the invention connects the lipophilic tether moiety, T, to the N-terminal nitrogen of the N-terminal amino acid residue of P. The linker can be linear or branched and optionally substituted. The linker can in some instance be used to vary the distance between T and P providing a more desirable interaction of P with its cognate GPCR. In other instances, the linker can confer improvements on the physicochemical and pharmacological properties of the T-L-P compound as compared with the T-P compound alone. For example, the introduction of the linker can alter one or more of lipophilicity, solubility, partition coefficient, stability, and biological half life.

In a first embodiment, L is a linking moiety bonded to P at an N-terminal nitrogen of an N-terminal amino acid residue selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), or N(R$^3$)C*(=NH) wherein L is bonded to P at the atom marked with an asterisk (*) and R$^3$ is H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, or heteroaralkyl; wherein said alkyl, alkenyl, alkynyl, alkoxy, cycloalkyl, heterocycloalkyl, aryl, aryloxy, heteroaryloxy, aralkyl, heteroaryl, and are heteroaralkyl optionally and independently substituted.

In another specific embodiment, R$^3$ is H or D.

In a further specific embodiment, L is selected from the group: C(O), S*(O)$_2$, NHC*(O), NHC*(S) and OC*(O). In an even further specific embodiment, L is selected from C(O), S*(O)$_2$ and OC*(O). In a most specific embodiment, L is C(O).

Linkers can be attached to the N-terminal nitrogen of the N-terminal amino acid residue of P using chemistries that are compatible with covalent linkage to nitrogen, including, but not limited to, alkylation, amide bond, urea, thiourea, carbamate, and sulfonamide formation.

Tethers (T)

T of Formula A, Formula A-1, Formula I or Formula II is a lipophilic tether moiety which imparts lipophilicity to the CXCR4 receptor compounds of the invention. The lipophilicity which T imparts, can promote penetration of the CXCR4 receptor compounds into the cell membrane and tethering of the CXCR4 receptor compounds to the cell membrane. As such, the lipophilicity imparted by T can facilitate interaction between the CXCR4 receptor compounds of the invention and the cognate receptor.

The relative lipophilicity of compounds suitable for use as the lipophilic tether moiety of Formula A, Formula A-1, Formula I or Formula II can be quantified by measuring the amount of the compound that partitions into an organic solvent layer (membrane-like) vs. an aqueous solvent layer (analogous to the extracellular or cytoplasmic environment). The partition coefficient in a mixed solvent composition, such as octanol/water or octanol/PBS, is the ratio of compound found at equilibrium in the octanol vs. the aqueous solvent (Partition coeff P=[compound]$_{octanol}$/[compound]$_{aqueous}$.). Frequently, the partition coefficient is expressed in logarithmic form, as the log P. Compounds with greater lipophilicity have a more positive log P than more hydrophilic compounds and tend to interact more strongly with membrane bilayers.

Computational programs are also available for calculating the partition coefficient for compounds suitable for use as the lipophilic tether moiety (T). In situations where the chemical structure is being varied in a systematic manner, for example by adding additional methylene units (—CH$_2$—) onto to an existing alkyl group, the trend in log P can be calculated using, for example, ChemDraw (CambridgeSoft, Inc).

In one embodiment, T is an optionally substituted (C$_6$-C$_{30}$)alkyl, (C$_6$-C$_{30}$)alkenyl, (C$_6$-C$_{30}$)alkynyl wherein 0-3 carbon atoms are replaced with oxygen, sulfur, nitrogen or a combination thereof.

In a specific embodiment, the (C$_6$-C$_{30}$)alkyl, (C$_6$-C$_{30}$)alkenyl, (C$_6$-C$_{30}$)alkynyl are substituted at one or more substitutable carbon atoms with halogen, —CN, —OH, —NH$_2$, NO$_2$, —NH(C$_1$-C$_6$)alkyl, —N((C$_1$-C$_6$)alkyl)$_2$, (C$_1$-C$_6$)alkyl, (C$_1$-C$_6$)haloalkyl, (C$_1$-C$_6$)alkoxy, (C$_1$-C$_6$)haloalkoxy, aryloxy, (C$_1$-C$_6$)alkoxycarbonyl, —CONH$_2$, —OCONH$_2$, —NHCONH$_2$, —N(C$_1$-C$_6$)alkylCONH$_2$, —N(C$_1$-C$_6$)alkylCONH(C$_1$-C$_6$)alkyl, —NHCONH(C$_1$-C$_6$)alkyl, —NHCON((C$_1$-C$_6$)alkyl)$_2$, —N(C$_1$-C$_6$)alkylCON((C$_1$-C$_6$)alkyl)$_2$, —NHC(S)NH$_2$, —N(C$_1$-C$_6$)alkylC(S)NH$_2$, —N(C$_1$-C$_6$)alkylC(S)NH(C$_1$-C$_6$)alkyl, —NHC(S)NH(C$_1$-C$_6$)alkyl, —NHC(S)N((C$_1$-C$_6$)alkyl)$_2$, —N(C$_1$-C$_6$)alkylC(S)N((C$_1$-C$_6$)alkyl)$_2$, —CONH(C$_1$-C$_6$)alkyl, —OCONH(C$_1$-C$_6$)alkyl, —CON((C$_1$-C$_6$)alkyl)$_2$, —C(S)(C$_1$-C$_6$)alkyl, —S(O)$_p$(C$_1$-C$_6$)alkyl, —S(O)$_p$NH$_2$, —S(O)$_p$NH(C$_1$-C$_6$)alkyl, —S(O)$_p$N((C$_1$-C$_6$)alkyl)$_2$, —CO(C$_1$-C$_6$)alkyl, —OCO(C$_1$-C$_6$)alkyl, —C(O)O(C$_1$-C$_6$)alkyl, —OC(O)O(C$_1$-C$_6$)alkyl, —C(O)H or —CO$_2$H; and p is 1 or 2.

In a specific embodiment, T is selected from the group consisting of: CH$_3$(CH$_2$)$_9$OPh-, CH$_3$(CH$_2$)$_6$C=C(CH$_2$)$_6$, CH$_3$(CH$_2$)$_{11}$O(CH$_2$)$_3$, CH$_3$(CH$_2$)$_9$—O—(CH$_2$)$_2$ and CH$_3$(CH$_2$)$_{13}$.

In a specific embodiment, T is selected from the group consisting of: CH$_3$(CH$_2$)$_{16}$, CH$_3$(CH$_2$)$_{15}$, CH$_3$(CH$_2$)$_{14}$, CH$_3$(CH$_2$)$_{13}$, CH$_3$(CH$_2$)$_{12}$, CH$_3$(CH$_2$)$_{11}$, CH$_3$(CH$_2$)$_{10}$, CH$_3$(CH$_2$)$_9$, CH$_3$(CH$_2$)$_8$, CH$_3$(CH$_2$)$_9$OPh-, CH$_3$(CH$_2$)$_6$C=C(CH$_2$)$_6$, CH$_3$(CH$_2$)$_{11}$O(CH$_2$)$_3$, and CH$_3$(CH$_2$)$_9$—O—(CH$_2$)$_2$ and CH$_3$(CH$_2$)$_{13}$.

It is understood that the lipophilic moiety (T) of Formula A, Formula A-1, Formula I or Formula II can be derived from precursor liphophilic compounds (e.g., fatty acids and bile acids). As used herein, "derived from" with regard to T, means that T is derived from a precursor lipophilic compound and that reaction of the precursor lipophilic compound in preparing the CXCR4 receptor compounds of Formula A, Formula A-1, Formula I or Formula II, results in a lipophilic tether moiety represented by T in Formula A, Formula A-1, Formula I or Formula II that is structurally modified in comparison to the precursor lipophilic compound.

For example, the lipophilic tether moiety, T of Formula A, Formula A-1, Formula I or Formula II, can be derived from a fatty acid or a bile acid. It is understood that in accordance with Formula A, Formula A-1, Formula I or Formula II, when T is derived from a fatty acid (i.e., a fatty acid derivative) it is attached to L-P at the carbon atom alpha to the carbonyl carbon of the acid functional group in the fatty acid from which it is derived. For example, when T is derived from palmitic acid

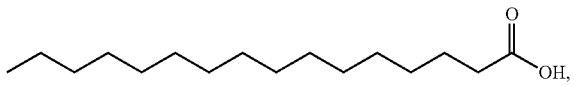

T of Formula A, Formula A-1, Formula I or Formula II has the following structure:

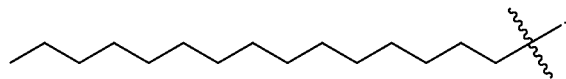

Similarly, when T is derived from stearic acid,

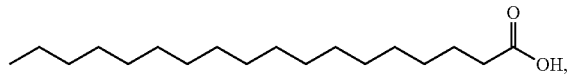 [SMILES: CCCCCCCCCCCCCCCCCC(=O)O]

T of Formula A, Formula A-1, Formula I or Formula II has the following structure:

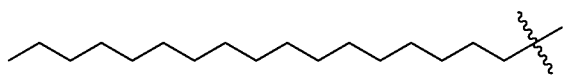

Similarly, when T is derived from 3-(dodecyloxy)propanoic acid,

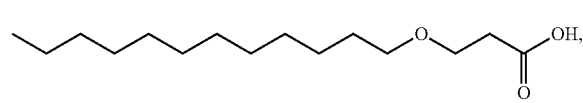 [SMILES: CCCCCCCCCCCCOCCC(=O)O]

T of Formula A, Formula A-1, Formula I or Formula II has the following structure:

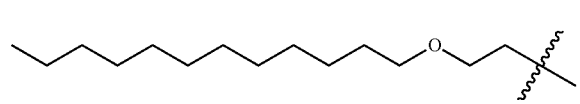

Similarly, when T is derived from 4-(undecyloxy)butanoic acid,

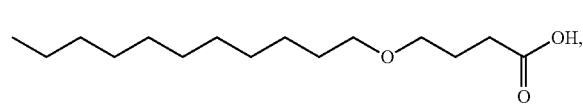 [SMILES: CCCCCCCCCCCOCCCC(=O)O]

T of Formula A, Formula A-1, Formula I or Formula II has the following structure

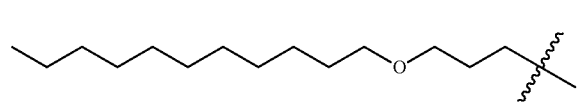

Similarly, when T is derived from elaidic acid,

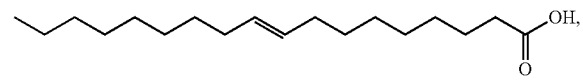 [SMILES: CCCCCCCC/C=C/CCCCCCCC(=O)O]

T of Formula A, Formula A-1, Formula I or Formula II has the following structure:

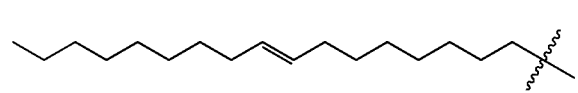

Similarly, when T is derived from oleic acid,

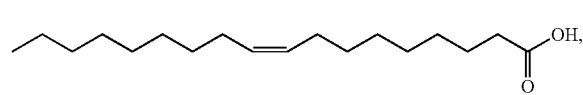 [SMILES: CCCCCCCC/C=C\CCCCCCCC(=O)O]

T of Formula A, Formula A-1, Formula I or Formula II has the following structure:

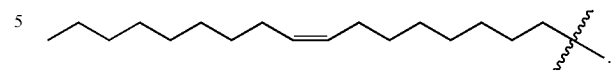

Similarly, when T is derived from 16-hydroxypalmitic acid,

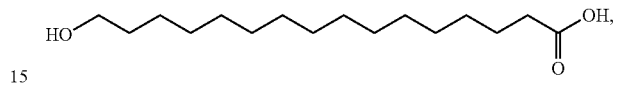

T of Formula A, Formula A-1, Formula I or Formula II has the following structure:

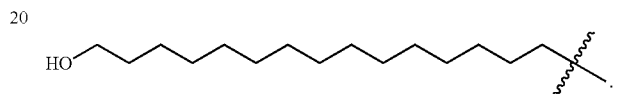

Similarly, when T is derived from 2-aminooctadecanoic acid

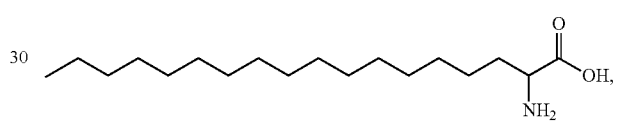

T of Formula A, Formula A-1, Formula I or Formula II has the following structure:

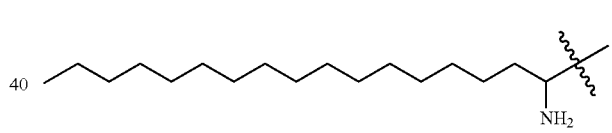

Similarly, when T is derived from 2-amino-4-(dodecyloxy) butanoic acid,

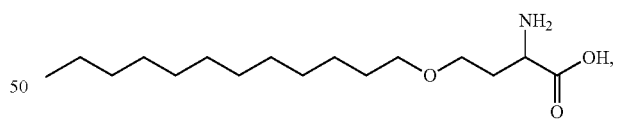

T of Formula A, Formula A-1, Formula I or Formula II has the following structure:

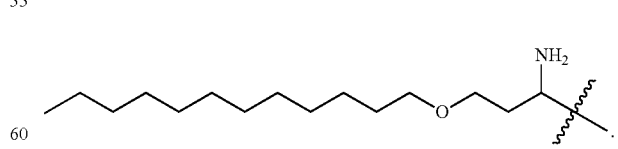

In a further embodiment, T is derived from a fatty acid. In a specific embodiment, T is derived from a fatty acid selected from the group consisting of: butyric acid, caproic acid, caprylic acid, capric acid, lauric acid, myristic acid, palmitic acid, stearic acid, arachidic acid, behenic acid, and lignoceric acid.

In another specific embodiment, T is derived from a fatty acid selected from the group consisting of: myristoleic acid, palmitoleic acid, oleic acid, linoleic acid, α-linolenic acid, arachidonic acid, eicosapentaenoic acid, erucic acid, docosahexaenoic acid.

In another embodiment, T of Formula A, Formula A-1, Formula I or Formula II can be derived from a bile acid. Similar to the embodiment where T is a fatty acid derivative, it is understood that in accordance with Formula A, Formula A-1, Formula I or Formula II, when T is derived from a bile acid (i.e., a bile acid derivative) it is attached to L-P at the carbon atom alpha to the carbonyl carbon of the acid functional group in the bile acid from which it is derived. For example, when T is derived from lithocholic acid,

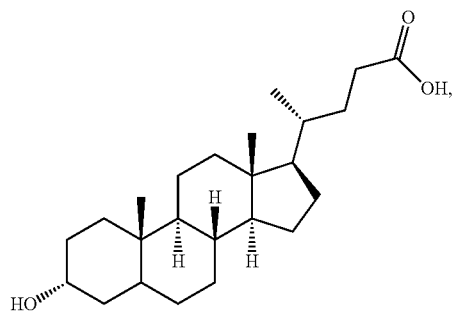

T of Formula A, Formula A-1, Formula I or Formula II has the following structure:

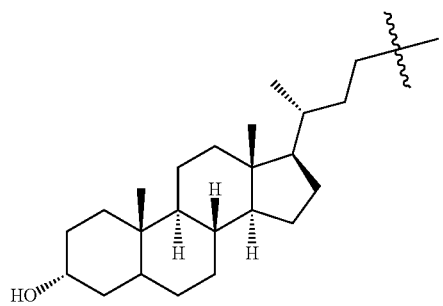

In a further embodiment, T is derived from a bile acid. In a specific embodiment, T is derived from a bile acid selected from the group consisting of: lithocholic acid, chenodeoxycholic acid, deoxycholic acid, cholanic acid, cholic acid, ursocholic acid, ursodeoxycholic acid, isoursodeoxycholic acid, lagodeoxycholic acid, dehydrocholic acid, hyocholic acid, hyodeoxycholic acid and the like.

For example, T is selected from:

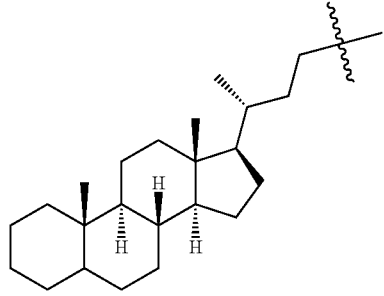

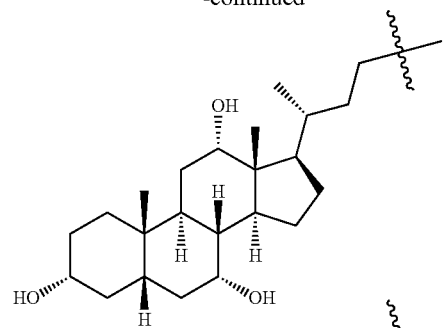

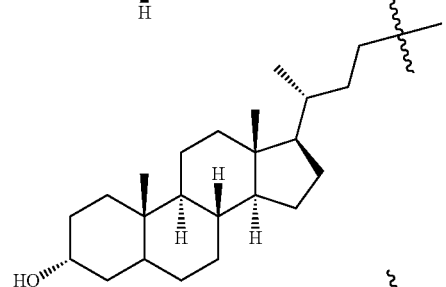

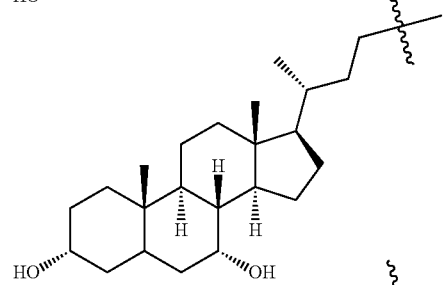

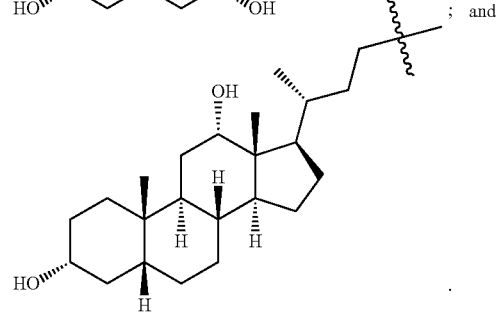

; and

In another further embodiment, T is derived from a bile acid described above that has been modified at other than the acid functional group. For example, T can be derived from any of the bile acids described above, where the hydroxy position has been modified to form an ester or a halo ester. For example, T can be:

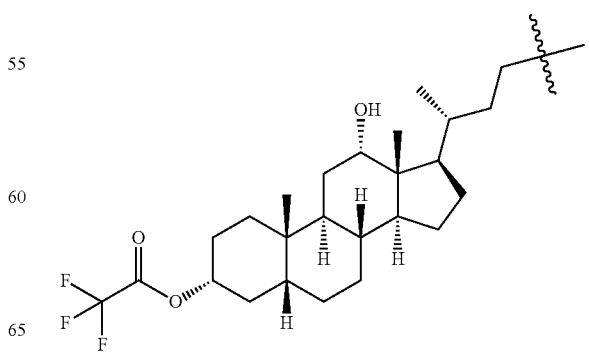

Other lipophilic moieties suitable for use as the lipophilic membrane tether, T, of Formula A, Formula A-1, Formula I or Formula II, include but are not limited to steroids. Suitable steroids include, but are not limited to, sterols; progestagens; glucocorticoids; mineralcorticoids; androgens; and estrogens. Generally any steroid capable of attachment or which can be modified for incorporation into Formula A, Formula A-1, Formula I or Formula II can be used. It is understood that the lipophilic membrane tether, T, may be slightly modified from the precursor lipophilic compound as a result of incorporation into Formula A, Formula A-1, Formula I or Formula II.

Suitable sterols for use in the invention at T, include but are not limited to: cholestanol, coprostanol, cholesterol, epicholesterol, ergosterol, ergocalciferol, and the like. Preferred sterols are those that provide a balance of lipophilicity with water solubility.

Suitable progestagens include, but are not limited to progesterone. Suitable glucocorticoids include, but are not limited to cortisol. Suitable mineralcorticoids include, but are not limited to aldosterone. Suitable androgens include, but are not limited to testosterone and androstenedione. Suitable estrogens include, but are not limited to estrone and estradiol.

In another specific embodiment, T can be derived from 2-tetradecanamideooctadecanoid acid. Similar to the embodiment where T is a fatty acid derivative, it is understood that in accordance with Formula A, Formula A-1, Formula I or Formula II, when T is derived from 2-tetradecanamideooctadecanoid acid it is attached to L-P at the carbon atom alpha to the carbonyl carbon of the acid functional group in the bile acid from which it is derived. For example, when T is derived from 2-tetradecanamideooctadecanoid acid, the tether is:

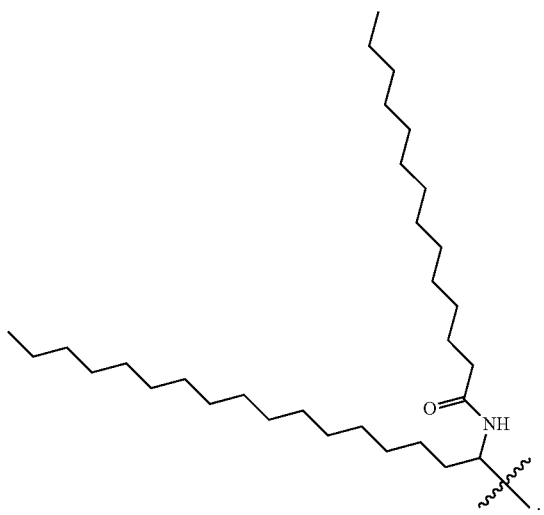 [SMILES: *C(CCCCCCCCCCCCCCCC)NC(=O)CCCCCCCCCCCCC]

In another embodiment, T of Formula A, Formula A-1, Formula I or Formula II can be derived from 2-(5-((3aS,4S, 6aR)-2-oxohexahydro-1H-thieno[3,4-d]imidazol-4-yl)pentanamido)octadecanoic acid. For example, when T is derived from 2-(5-((3aS,4S,6aR)-2-oxohexahydro-1H-thieno[3,4-d] imidazol-4-yl)pentanamido)octadecanoic acid, the tether is:

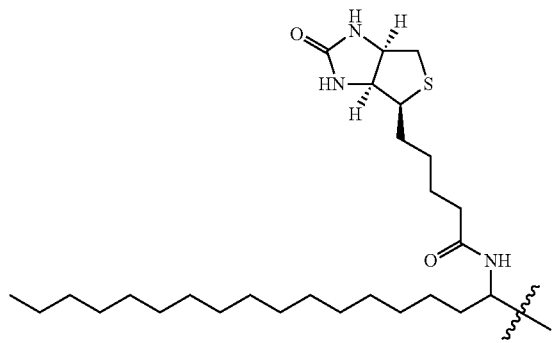

In yet another embodiment, T of Formula A, Formula A-1, Formula I or Formula II can be:

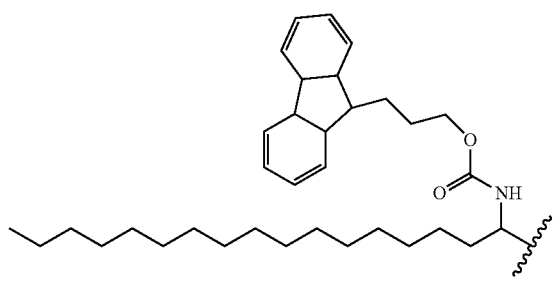

It is understood, that the compounds can contain one of more tether moieties. In certain aspects, the tether moieties are the same. In other embodiments, the tether moieties are different. In the compounds of the invention, tether moieties are attached through amide, thioamide, sulfonamide, urea, thiourea, carbamate, thiocarbamate, carbamodithioate, imine, imidamide, or guanidine bonds to the N-terminal amine.

Compounds (T-L-P)

The GPCR Compound of the invention is represented by Formula I:

T-L-P, or a pharmaceutically acceptable salt thereof, wherein:
P is a peptide comprising at least three contiguous amino-acid residues of an intracellular i1, i2, i3 loop or an intracellular i4 domain of the CXCR4 receptor;
L is a linking moiety bonded to P at an N-terminal nitrogen of an N-terminal amino-acid residue selected from: C(O), C(S), S(O)$_2$, N(R$^3$)S*(O), N(R$^3$)S*(O)$_2$, N(R$^3$)C*(O), N(R$^3$) C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$) alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted; and T is a lipophilic tether moiety bonded to L, wherein the C-terminal amino acid residue of P is optionally functionalized;

In a first aspect of Formula I, P comprises at least eight contiguous amino acid residues. In a first embodiment of the first aspect, L is C(O). In a second aspect of Formula I, P comprises at least six contiguous amino acid residues. In a first embodiment of the second aspect, L is C(O).

In a third aspect, P comprises at least 3 contiguous amino acids of the i1 loop. In a first embodiment of the third aspect, L is C(O).

The length of the peptide sequence P can be from 3 amino acids in length to 90 amino acids in length. For example, the length of P is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 amino acids in length.

In a specific embodiment of the third aspect and its first embodiment, the i1 loop of the CXCR4 receptor from which P is derived has the following sequence: MGYQKKLRSMTDKYRLH (SEQ ID NO:41).

TABLE 5

In another embodiment of the third aspect and its first embodiment, P is a sequence selected from:

| CXCR4 i-Loop | Sequence | SEQ ID NO: |
|---|---|---|
| i1 | KKLRSMTDkYRLH | 1 |
| i1 | KKLRSMTDKyRLH | 2 |
| i1 | MGQKKLRSMTDKYrL | 3 |
| i1 | MGYQKPLRSMTDKYRL | 4 |
| i1 | MGYQKKLPRSMTDKYRL | 5 |
| i1 | MGYQKKLRPSMTDKYRL | 6 |
| i1 | MGYQKKLRSpMTDKYRL | 7 |
| i1 | MGYQKKLRSMpTDKYRL | 8 |
| i1 | MGYQKKLRSMTDKYRV | 9 |
| i1 | MGYQKKLRSMTDKYRJ | 10 |
| i1 | MGYQKKLRSMTDKYKL | 11 |
| i1 | MGYQKKLRSMTDKY(Cit)L | 12 |
| i1 | MGYQKKLRSMTDKFRL | 13 |
| i1 | MGYQKKLRSMTDK(Nal)RL | 14 |
| i1 | MGYQKKLRSJTDKYRL | 15 |
| i1 | MGYQKKLRSHTDKYRL | 16 |
| i1 | MGYQKKLRSGTDKYRL | 17 |
| i1 | GYQKKLRSJTDKYRI | 18 |
| i1 | MGYQ(Aib)KL(Cha)SMTRKYRL | 19 |
| i1 | xGYQKKLRSxTDKYRL | 20 |
| i1 | zGYQKKLRSzTDKYRL | 21 |
| i1 | (Pra)GYQKKLRSMTDKYRL | 22 |
| i1 | GGYQKKLRSATDKYRL | 23 |
| i1 | GGYQKKLRpHTDKYRL | 24 |
| i1 | GGYQKKLRpATDKYRL | 25 |

TABLE 5-continued

In another embodiment of the third aspect and its first embodiment, P is a sequence selected from:

| CXCR4 i-Loop | Sequence | SEQ ID NO: |
|---|---|---|
| i1 | GGYQKKpRpATDKYRL | 26 |
| i1 | GGYQKKLRpATDKFRL | 27 |
| i1 | CGYQKKLRSATDKYRL | 28 |
| i1 | GGYQKKLRppHTDKYRL | 29 |
| i1 | GGYQKKLRpWTDKYRL | 30 |
| i1 | GGYQKKLRp(Dpr)TDKYRL | 31 |
| i1 | GGYQKKLR(Hyp)HTDKYRL | 32 |
| i1 | GGYQKKLRp(Hyp)TDKYRL | 33 |
| i1 | GGYQKK(photoLeu)RSATDKYRL | 34 |
| i1 | GGYQKKHRSATDKYRL | 35 |
| i1 | GGYQKKIRSATDKYRL | 36 |
| i1 | GGYQKKLRSATDKYRLH | 37 |
| i1 | GGYQKKLRTATDKYRL | 38 |

In a more specific embodiment of the third aspect, P is selected from SEQ ID NO: 21, 23-27, 29, 31, 32, 35 and 36.

It is understood that for the aspects and embodiments presented herein, that when the amino acid residues of P are represented by X, W, Y or Z that the C-terminal amino acid residue does not include the —OH of the amino acid and that the end group R1 that is bonded to the C-terminal residue includes —OH as well as other moieties defined herein.

In a more specific embodiment, the compounds are selected from any one of Compound Nos. 1-3, 6-42, and 45-47 or a pharmaceutically acceptable salt thereof.

In a more specific embodiment, the compound is selected from: Compound 23, 25, 31, 42, 26, 27, 28, 29, 32, 34, 45, 46, and 47 and or a pharmaceutically acceptable salt thereof.

In a fourth aspect, P comprises at least 3 contiguous amino acids of the i3 loop. In a first embodiment of the fourth aspect, L is C(O).

In a specific embodiment of the fourth aspect and its first embodiment, the i3 loop of the CXCR4 receptor from which P is derived has the following sequence:

IIISKLSHSKGHQKRKALKTTVI.    (SEQ ID NO: 43)

In another embodiment of the fourth aspect and its first embodiment, P has the following sequence:

| CXCR4 i-Loop | Sequence | SEQ ID NO: |
|---|---|---|
| i3 | SKLSHSKGHQKRKALKTTVIL | 39 |

In a more specific embodiment of the fourth aspect, the compound is Compound No. 43 or a pharmaceutically acceptable salt thereof.

In a fifth aspect, P comprises at least 3 continuous amino acids of the i4 loop.

In a first embodiment of the firth aspect, L is C(O). In a specific embodiment of the fifth aspect and its first embodiment, the i4 loop of the CXCR4 receptor from which P is derived has the following sequence:

(SEQ ID NO: 44)
GAKFKTSAQHALTSVSRGSSLKILSKGKRGGHSSVSTESESSSFHSS.

In another embodiment of the fifth aspect and its first embodiment, P has the following sequence:

| CXCR4 i-Loop | Sequence | SEQ ID NO: |
|---|---|---|
| i4 | GAKFK-TASAQHALTSVR | 40 |

In a more specific embodiment of the fifth aspect, the compound is Compound No. 44 or a pharmaceutically acceptable salt thereof.

In a sixth aspect of Formula I, T is an optionally substituted $(C_6-C_{30})$alkyl, $(C_6-C_{30})$alkenyl, $(C_6-C_{30})$alkynyl, wherein 0-3 carbon atoms are replaced with oxygen, sulfur, nitrogen or a combination thereof. This value of T is applicable to the first, second, third, fourth, and fifth aspects and the embodiments (i.e., specific, more specific, most specific and first, second, etc.) of same.

In a first embodiment of the sixth aspect, L is C(O).

In a specific embodiment of the sixth aspect or its first embodiment, T is selected from: $CH_3(CH_2)_{16}$, $CH_3(CH_2)_{15}$, $CH_3(CH_2)^{14}$, $CH_3(CH_2)_{13}$, $CH_3(CH_2)_{12}$, $CH_3(CH_2)_{11}$, $CH_3(CH_2)_{10}$, $CH_3(CH_2)_9$, $CH_3(CH_2)_8$, $CH_3(CH_2)_9$OPh-, $CH_3(CH_2)_6C{=}C(CH_2)_6$, $CH_3(CH_2)_{11}O(CH_2)_3$, and $CH_3(CH_2)_9$—O—$(CH_2)_2$. This value of T is applicable to the first, second, third, fourth, and fifth aspects and the embodiments (i.e., specific, more specific, most specific and first, second, etc.) of same.

In another specific embodiment of the sixth aspect or its first embodiment, T is a fatty acid derivative. This value of T is applicable to the first, second, third, fourth, and fifth aspects and the embodiments (i.e., specific, more specific, most specific and first, second, etc.) of same.

In a more specific embodiment of the sixth aspect or its first embodiment, the fatty acid is selected from the group consisting of: butyric acid, caproic acid, caprylic acid, capric acid, lauric acid, myristic acid, palmitic acid, stearic acid, arachidic acid, behenic acid, lignoceric acid, myristoleic acid, palmitoleic acid, oleic acid, linoleic acid, α-linolenic acid, arachidonic acid, eicosapentaenoic acid, erucic acid, docosahexaenoic acid. This value of T is applicable to the first, second, third, fourth, and fifth aspects and the embodiments (i.e., specific, more specific, most specific and first, second, etc.) of same.

In a seventh aspect of formula I, T is a bile acid derivative. This value of T is applicable to the first, second, third, fourth, and fifth aspects and the embodiments (i.e., specific, more specific, most specific and first, second, etc.) of same.

In a first embodiment of the seventh aspect, L is C(O).

In a specific embodiment of the seventh aspect and its first embodiment, the bile acid is selected from the group consisting of: lithocholic acid, chenodeoxycholic acid, deoxycholic acid, cholanic acid, cholic acid, ursocholic acid, ursodeoxycholic acid, isoursodeoxycholic acid, lagodeoxycholic acid, dehydrocholic acid, hyocholic acid, and hyodeoxycholic acid. This value of T is applicable to the first, second, third, fourth, and fifth aspects and the embodiments (i.e., specific, more specific, most specific and first, second, etc.) of same.

In an eighth aspect of Formula I, T is selected from sterols; progestagens; glucocorticoids; mineralcorticoids; androgens; and estrogens. This value of T is applicable to the first, second, third, fourth, and fifth aspects and the embodiments (i.e., specific, more specific, most specific and first, second, etc.) of same.

In a ninth aspect of Formula I, T-L of Formula I is represented by a moiety selected from the group consisting of:

$CH_3(CH_2)_{15}$—C(O);

$CH_3(CH_2)_{13}$—C(O);

$CH_3(CH_2)_9O(CH_2)_2C(O)$;

$CH_3(CH_2)_{10}O(CH_2)_2C(O)$;

$CH_3(CH_2)_6C{=}C(CH_2)_6$—C(O);

LCA-C(O); and $CH_3(CH_2)_9$OPh-C(O) wherein

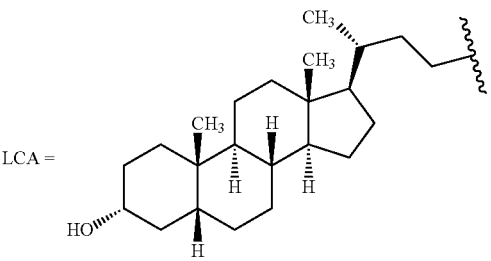

These value of T-L are applicable to the first, second, third, fourth, and fifth aspects and the embodiments (i.e., specific, more specific, most specific and first, second, etc.) of same.

In the tenth aspect, T of Formula I is represented by a moiety selected from the group consisting of:

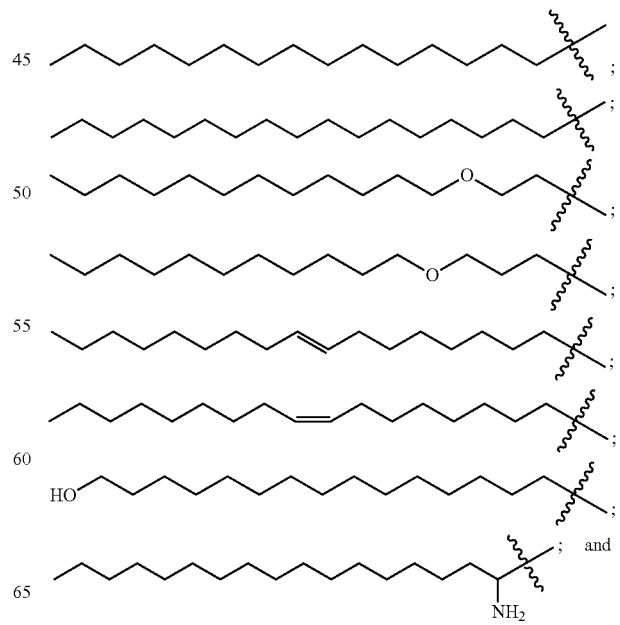

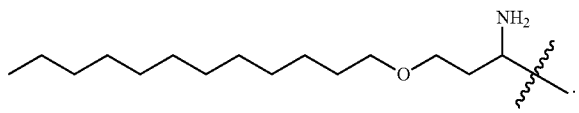

These values of T are applicable to the first, second, third, fourth, and fifth aspects and the embodiments (i.e., specific, more specific, most specific and first, second, etc.) of same.

In an eleventh aspect, the CXCR4 receptor compounds are selected from the compounds represented in Tables 6-11, excluding controls and those compounds not with the structure of Formula A, Formula A-1, Formula I or Formula II or a pharmaceutically acceptable salt thereof.

TABLE 6

CXCR4 i1 loop compounds

| Comp. No.: | Loop | Sequence | Lipid | MW | MS observed |
|---|---|---|---|---|---|
| 1 | i1 | KKLRSMTDkYRLH (SEQ ID NO: 1) | Pal | 1913.42 | 638.4 |
| 2 | i1 | KKLRSMTDKyRLH (SEQ ID NO: 2) | Pal | 1913.42 | 638.3 |
| 3 | i1 | MGQKKLRSMTDKYrL (SEQ ID NO: 3) | Pal | 2092.657 | 1046.3 |
| 6 | i1 | MGYQKPLRSMTDKYRL (SEQ ID NO: 4) | Pal | 2224.773 | 1112.7 |
| 7 | i1 | MGYQKKLPRSMTDKYRL (SEQ ID NO: 5) | Pal | 2352.946 | 1176.7 |
| 8 | i1 | MGYQKKLRPSMTDKYRL (SEQ ID NO: 6) | Pal | 2352.946 | 1176.3 |
| 9 | i1 | MGYQKKLRSpMTDKYRL (SEQ ID NO: 7) | Pal | 2352.946 | 1176.3 |
| 10 | i1 | MGYQKKLRSMpTDKYRL (SEQ ID NO: 8) | Pal | 2352.946 | 1176.7 |
| 11 | i1 | MGYQKKLRSMTDKYRV (SEQ ID NO: 9) | Pal | 2241.804 | 1121.2 |
| 12 | i1 | MGYQKKLRSMTDKYR(Nle) (SEQ ID NO: 10) | Pal | 2255.831 | 1128.2 |
| 13 | i1 | MGYQKKLRSMTDKYKL (SEQ ID NO: 11) | Pal | 2227.817 | 1114.2 |
| 14 | i1 | MGYQKKLRSMTDKY(Cit)L (SEQ ID NO: 12) | Pal | 2256.815 | 1128.3 |

TABLE 6-continued

CXCR4 i1 loop compounds

| Comp. No.: | Loop | Sequence | Lipid | MW | MS observed |
|---|---|---|---|---|---|
| 15 | i1 | MGYQKKLRSMTDKFRL (SEQ ID NO: 13) | Pal | 2239.831 | 1119.8 |
| 16 | i1 | MGYQKKLRSMTDK(Nal)RL (SEQ ID NO: 14) | Pal | 2289.89 | 1145.7 |
| 17 | i1 | MGYQKKLRS(Nle)TDKYRL (SEQ ID NO: 15) | Pal | 2237.792 | 1118.8 |
| 18 | i1 | MGYQKKLRSHTDKYRL (SEQ ID NO: 16) | Pal | 2261.774 | 1130.8 |
| 19 | i1 | MGYQKKLRSGTDKYRL (SEQ ID NO: 17) | Pal | 2181.686 | 1091.2 |
| 20 | i1 | GYQKKLRS(Nle)TDKYRI (SEQ ID NO: 18) | Pal | 2106.596 | 1053.3 |
| 21 | i1 | MGYQ(Aib)KL(Cha)SMTRKYRL (SEQ ID NO: 19) | Pal | 2250.897 | 1126.3 |
| 22 | i1 | xGYQKKLRSxTDKYRL (SEQ ID NO: 20) | Pal | 2223.7 | 1112.4 |
| 23 | i1 | zGYQKKLRSzTDKYRL (SEQ ID NO: 21) | Pal | 2195.646 | 1098.7 |
| 24 | i1 | (Pra)GYQKKLRSMTDKYRL (SEQ ID NO: 22) | Pal | 2219.734 | 1110.5 |
| 25 | i1 | GGYQKKLRSATDKYRL (SEQ ID NO: 23) | Pal | 2121.568 | 1061.5 |
| 26 | i1 | GGYQKKLRpHTDKYRL (SEQ ID NO: 24) | Pal | 2197.667 | 1098.9 |
| 27 | i1 | GGYQKKLRpATDKYRL (SEQ ID NO: 25) | Pal | 2131.606 | 1066.7 |
| 28 | i1 | GGYQKKpRpATDKYRL (SEQ ID NO: 26) | Pal | 2115.563 | 1058.7 |
| 29 | i1 | GGYQKKLRpATDKFRL (SEQ ID NO: 27) | Pal | 2115.606 | 1058.8 |
| 30 | i1 | CGYQKKLRSATDKYRL (SEQ ID NO: 28) | Pal | 2167.659 | 1084.7 |
| 31 | i1 | GGYQKKLRSATDKYRL (SEQ ID NO: 23) | 3-(dodecyloxy)propanoate | 2123.54 | 1062.7 |

TABLE 6-continued

CXCR4 i1 loop compounds

| Comp. No.: | | Loop Sequence | Lipid | MW | MS observed |
|---|---|---|---|---|---|
| 32 | i1 | GGYQKKLRpp HTDKYRL (SEQ ID NO: 29) | Pal | 2294.782 | 765.0 |
| 33 | i1 | GGYQKKLRpW TDKYRL (SEQ ID NO: 30) | Pal | 2246.738 | 1123.8 |
| 34 | i1 | GGYQKKLRp (Dpr)TDKYRL (SEQ ID NO: 31) | Pal | 2146.62 | 1074.2 |
| 35 | i1 | GGYQKKLR(Hyp)HTDKYRL (SEQ ID NO: 32) | Pal | 2213.666 | 1107.3 |
| 36 | i1 | GGYQKKLRp(Hyp)TDKYRL (SEQ ID NO: 33) | Pal | 2173.642 | 1087.7 |
| 37 | i1 | GGYQKK(photoLeu)RSATDKYRL (SEQ ID NO: 34) | Pal | 2133.539 | 1061.7 |
| 38 | i1 | GGYQKKHRSATDKYRL (SEQ ID NO: 35) | Pal | 2145.549 | 1073.3 |
| 39 | i1 | GGYQKK1RSATDKYRL (SEQ ID NO: 36) | Pal | 2121.568 | 1061.7 |
| 40 | i1 | GGYQKKLRSATDKYRLH (SEQ ID NO: 37) | Pal | 2258.707 | 1130.2 |
| 41 | i1 | GGYQKKLRTATDKYRL (SEQ ID NO: 38) | Pal | 2135.594 | 1068.7 |
| 42 | i1 | GGYQKKLRSATDKYRL (SEQ ID NO: 23) | LCA-trifluoroacetate | 2337.724 | 1169.3 |
| 45 | i1 | GGYQKKLRSATDKYRL (SEQ ID NO: 23) | Pal | 2171.648 | 1086 |
| 46 | i1 | GGYQKKLRpHTDKYRL (SEQ ID NO: 24) | Pal | 2247.747 | 1124 |
| 47 | i1 | MGYQKKLRSMTDKYRL (SEQ ID NO: 52) | Cholesterol | 2430.07 | 810.5 |

TABLE 7
CXCR4 i1 loop compound structures
| Comp. No. | Structure |
|---|---|
| 1 | 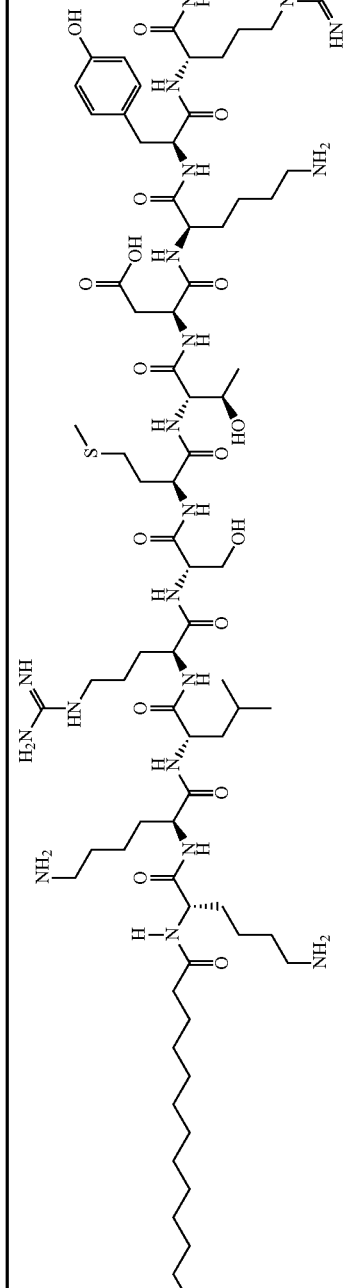 |
| 2 | 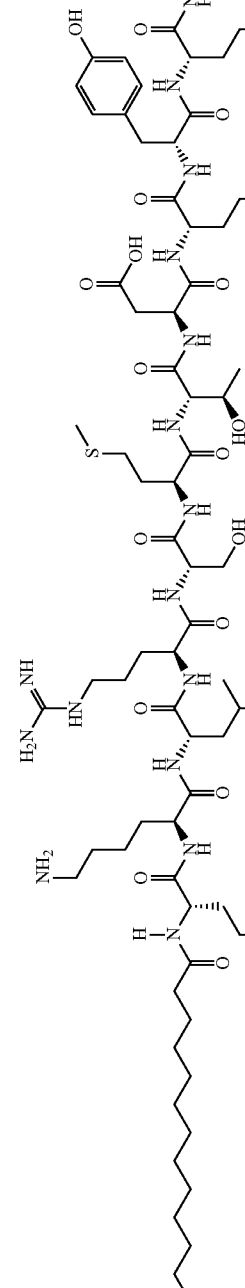 |

TABLE 7-continued
CXCR4 i1 loop compound structures
| Comp. No. | Structure |
|---|---|
| 3 | 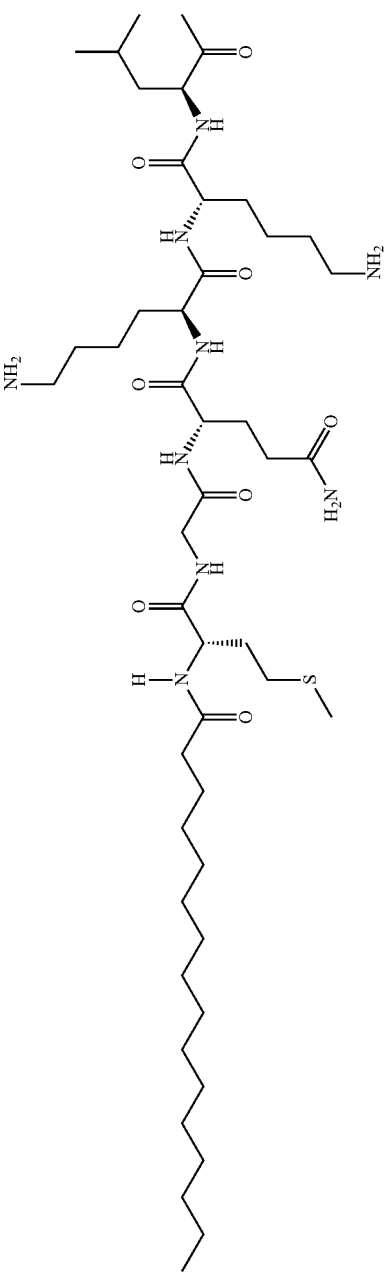 |

TABLE 7-continued
CXCR4 i1 loop compound structures
| Comp. No. | Structure |
|---|---|
| 6 | 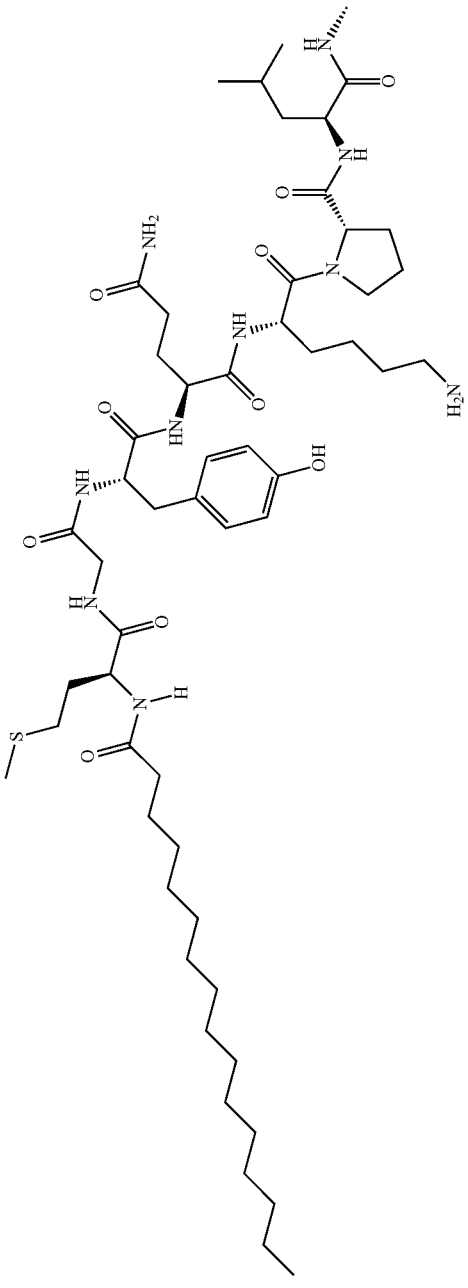 |

TABLE 7-continued
CXCR4 i1 loop compound structures
| Comp. No. | Structure |
|---|---|
| 7 | 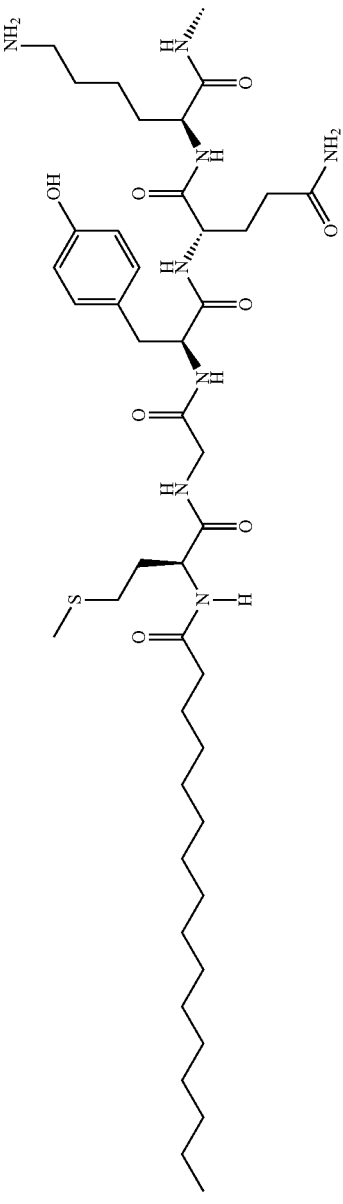 |

TABLE 7-continued

CXCR4 i1 loop compound structures

| Comp. No. | Structure |
|---|---|
| 8 | (chemical structures) |

TABLE 7-continued

CXCR4 i1 loop compound structures

| Comp. No. | Structure |
|---|---|
| 9 | 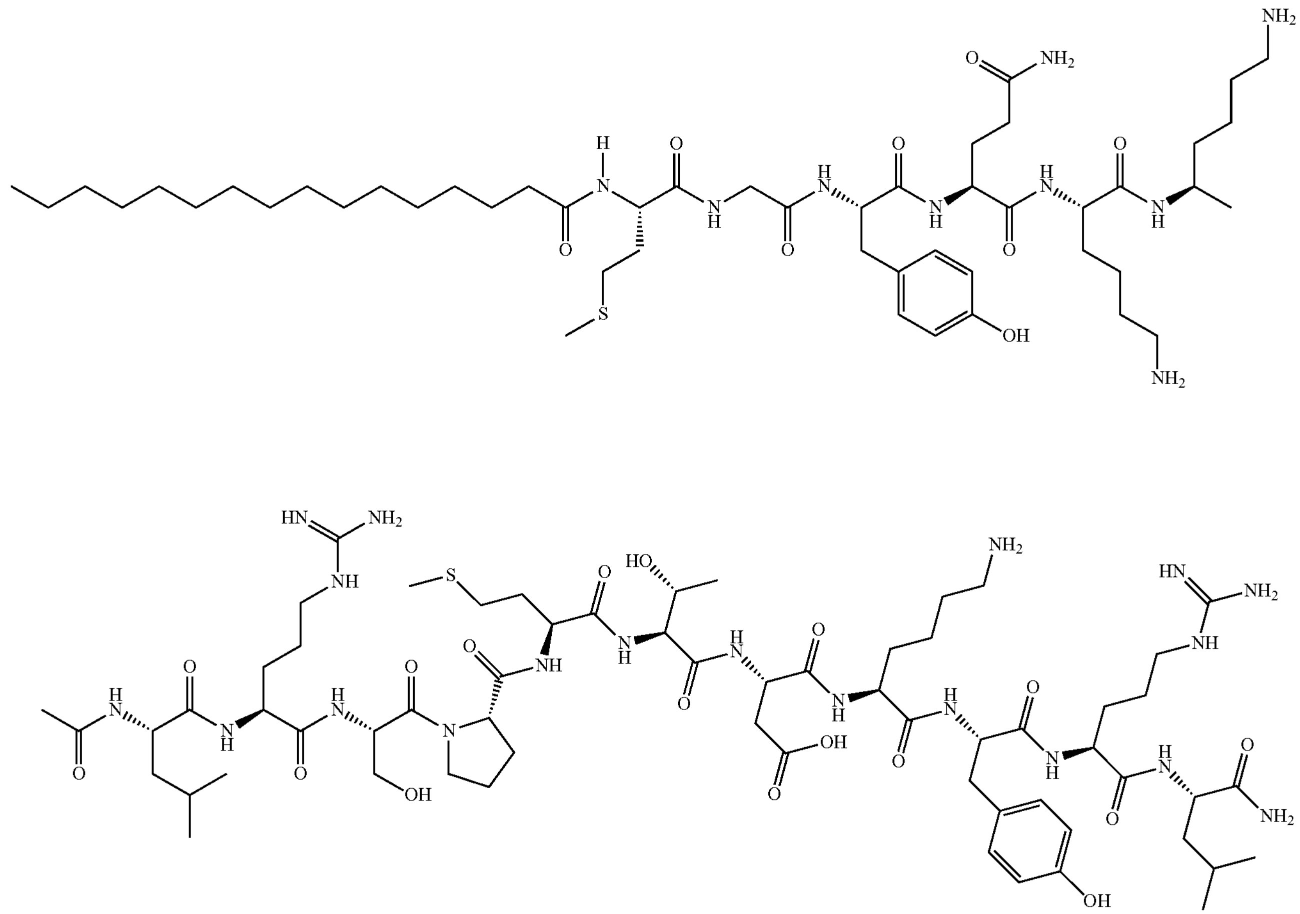 |

TABLE 7-continued
CXCR4 i1 loop compound structures
| Comp. No. | Structure |
|---|---|
| 10 | 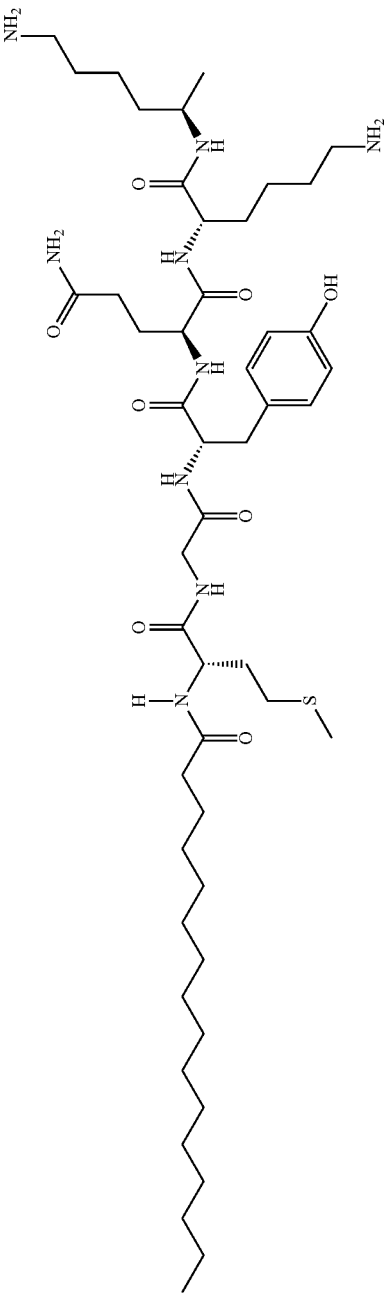 |

TABLE 7-continued
CXCR4 i1 loop compound structures
| Comp. No. | Structure |
|---|---|
| 11 | 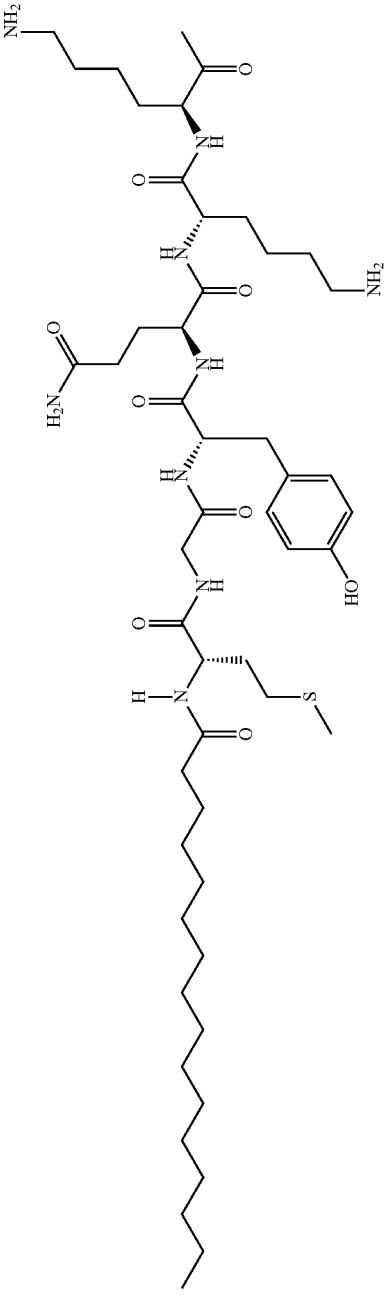 |

TABLE 7-continued
CXCR4 i1 loop compound structures
| Comp. No. | Structure |
|---|---|
| 12 | 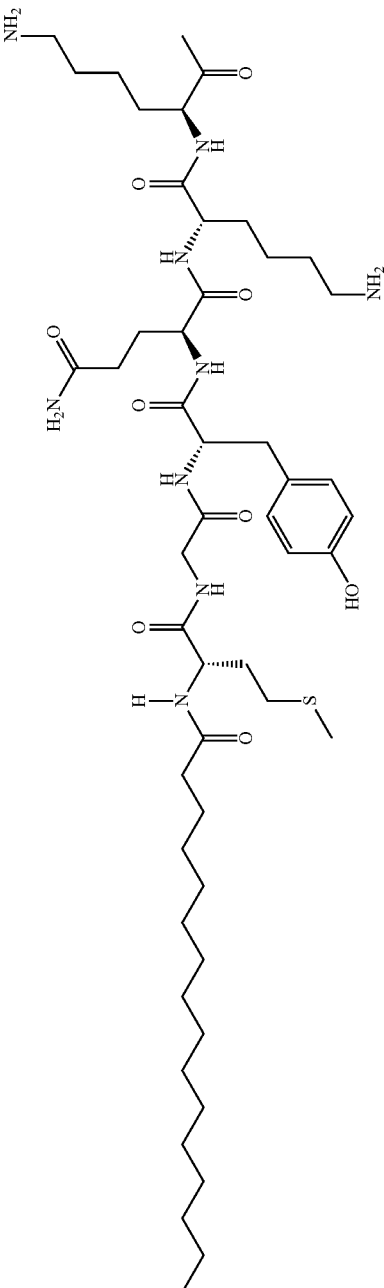 |

TABLE 7-continued
CXCR4 i1 loop compound structures
| Comp. No. | Structure |
|---|---|
| 13 | 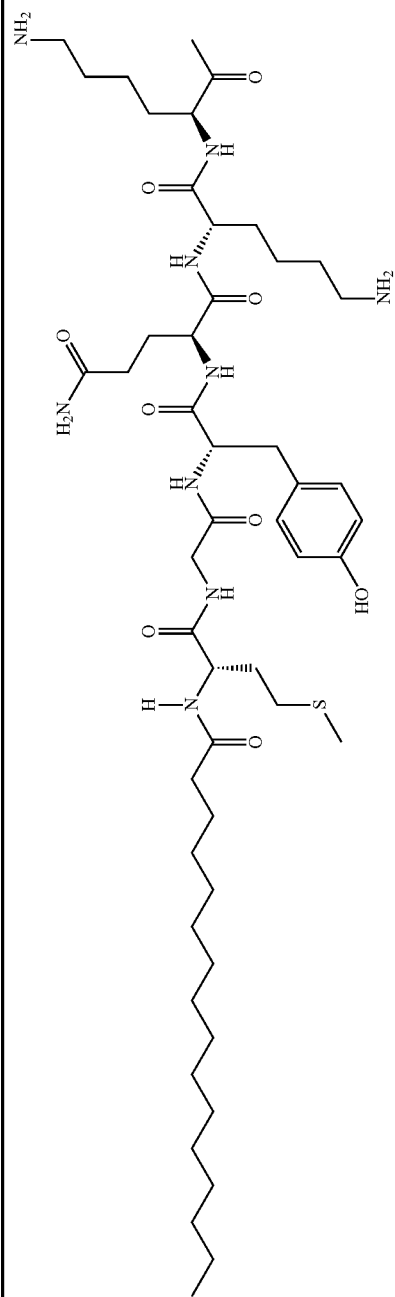 |

TABLE 7-continued
CXCR4 i1 loop compound structures
| Comp. No. | Structure |
|---|---|
| 14 | 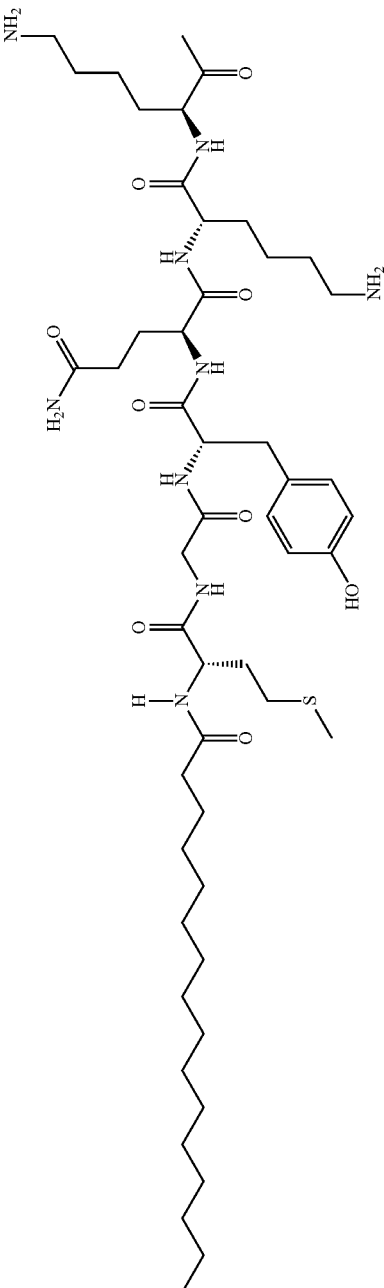 |

TABLE 7-continued
CXCR4 i1 loop compound structures
| Comp. No. | Structure |
|---|---|
| 15 | 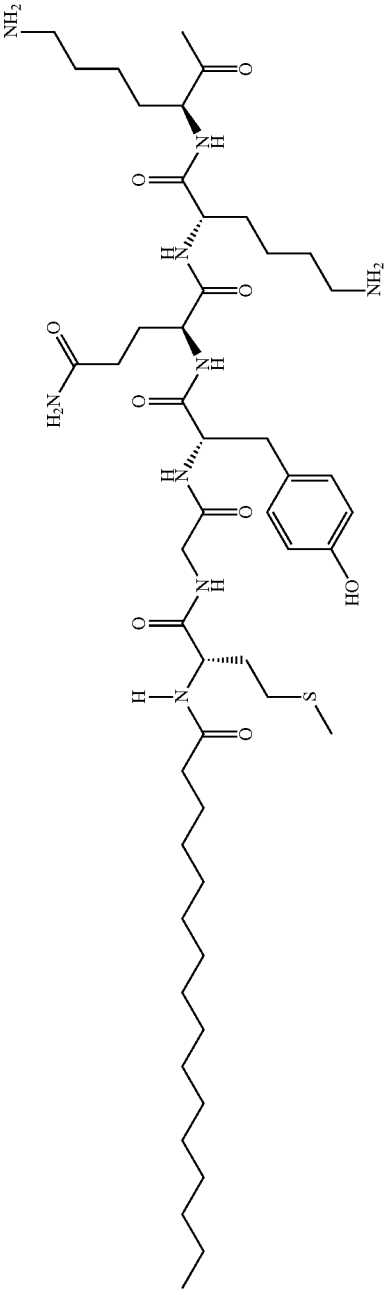 |

TABLE 7-continued
CXCR4 i1 loop compound structures
| Comp. No. | Structure |
|---|---|
| 16 | 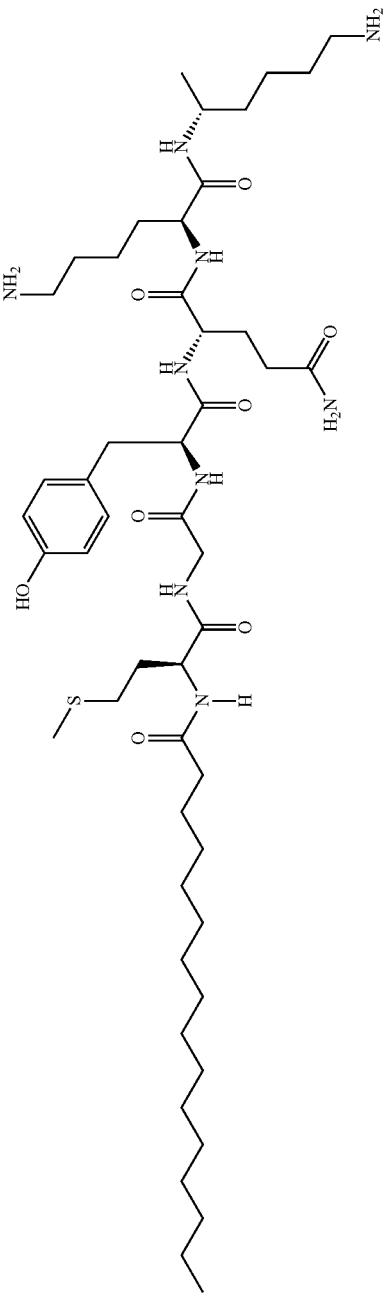 |

TABLE 7-continued
CXCR4 i1 loop compound structures
| Comp. No. | Structure |
|---|---|
| 17 | 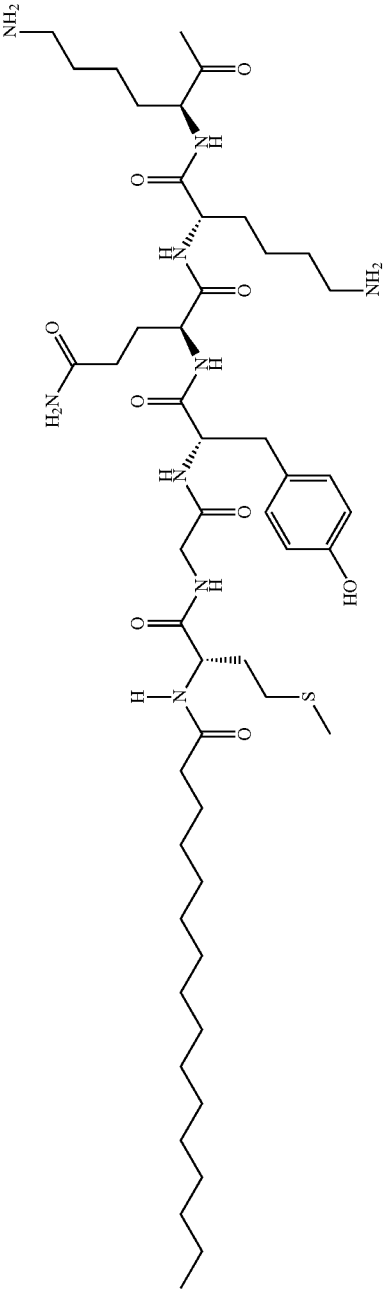 |

TABLE 7-continued

CXCR4 i1 loop compound structures

| Comp. No. | Structure |
|---|---|
| 18 | |

TABLE 7-continued
CXCR4 i1 loop compound structures
| Comp. No. | Structure |
|---|---|
| 19 | 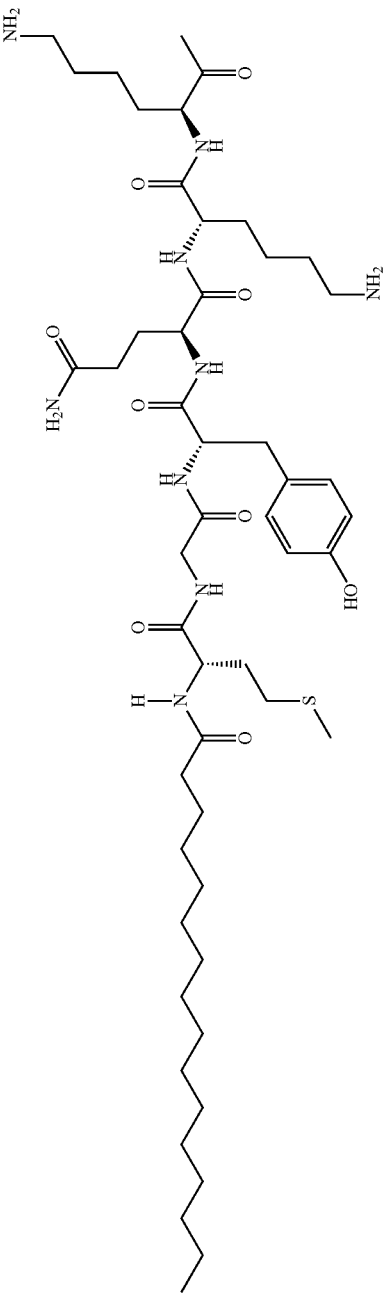 |

TABLE 7-continued
CXCR4 i1 loop compound structures
| Comp. No. | Structure |
|---|---|
| 20 | 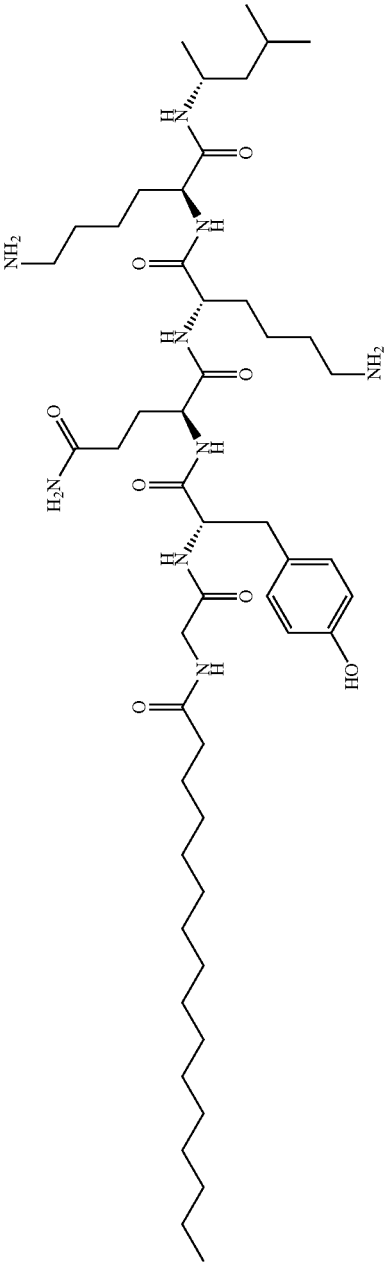 |

TABLE 7-continued
CXCR4 i1 loop compound structures
| Comp. No. | Structure |
|---|---|
| 21 | 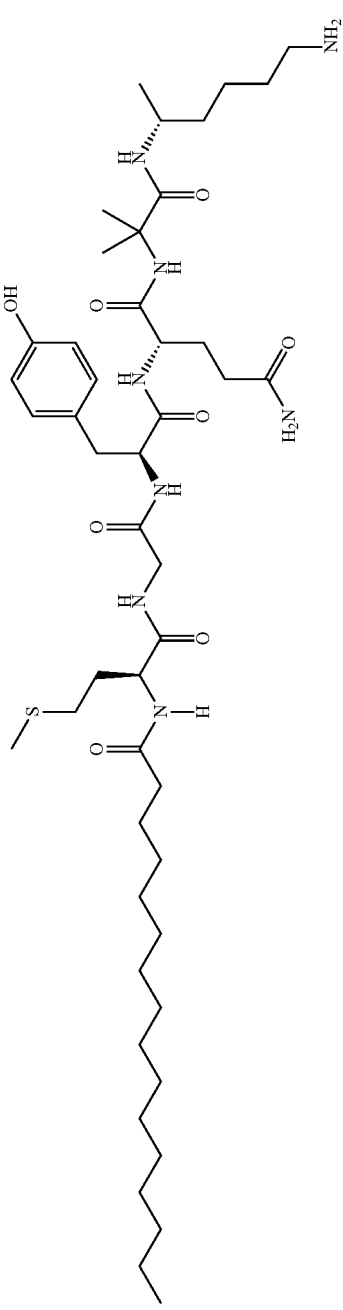 |

TABLE 7-continued
CXCR4 i1 loop compound structures
| Comp. No. | Structure |
|---|---|
| 22 | 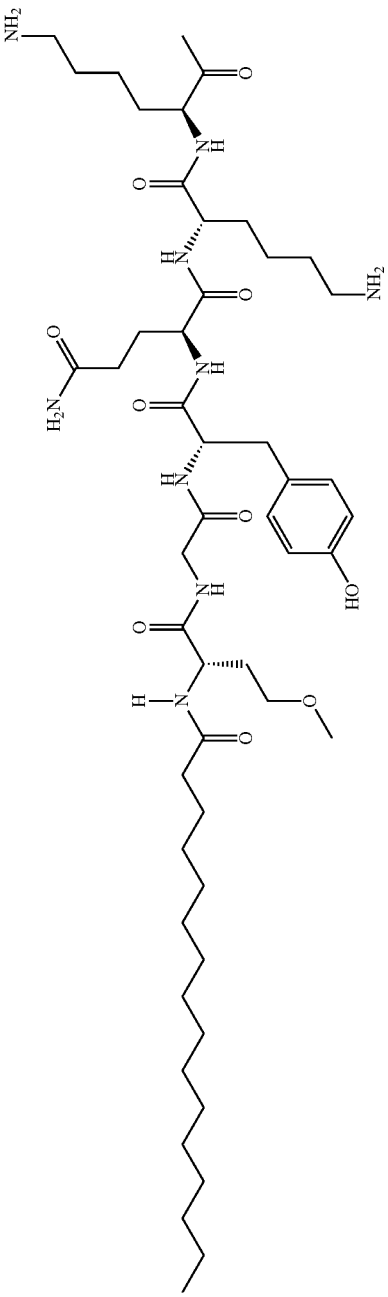 |

TABLE 7-continued
CXCR4 i1 loop compound structures
| Comp. No. | Structure |
|---|---|
| 23 | 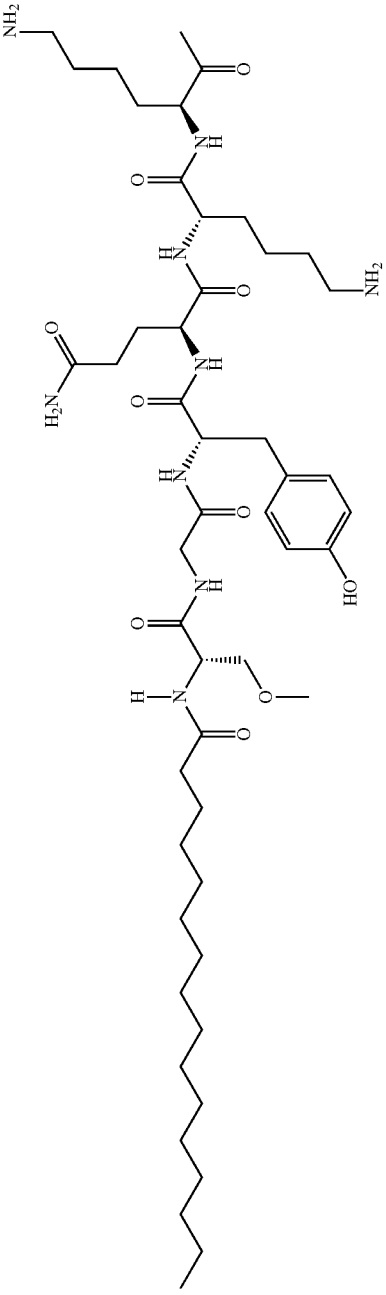 |

TABLE 7-continued
CXCR4 i1 loop compound structures
| Comp. No. | Structure |
|---|---|
| 24 | 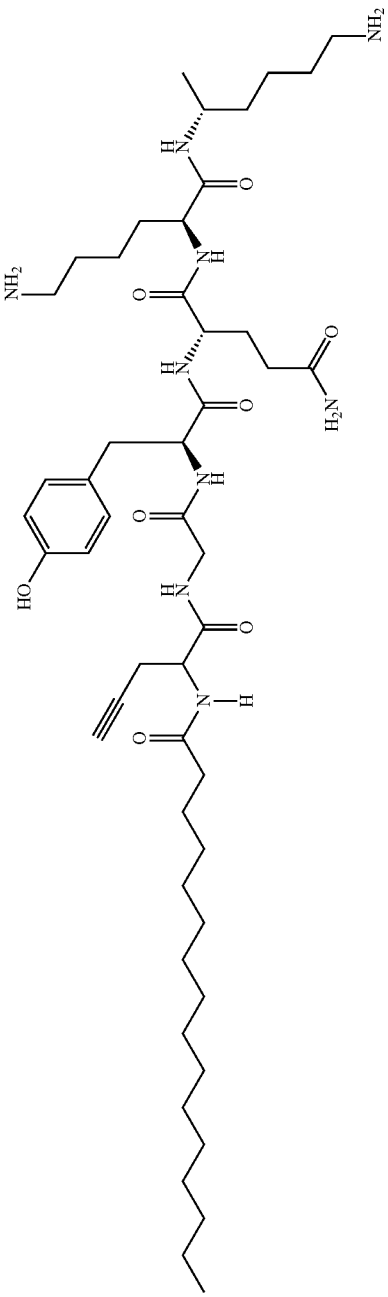 |

TABLE 7-continued
CXCR4 i1 loop compound structures
| Comp. No. | Structure |
|---|---|
| 25 | 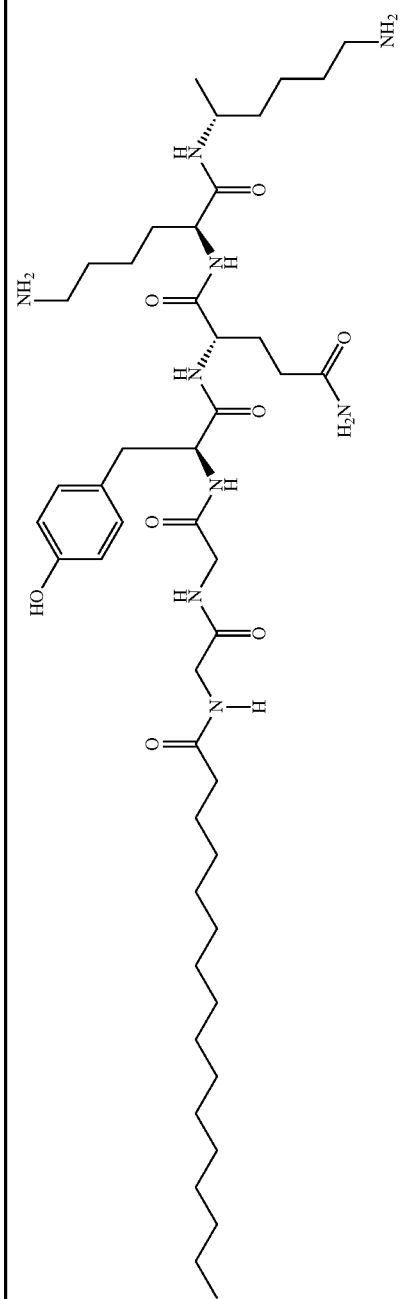 |

TABLE 7-continued
CXCR4 i1 loop compound structures
| Comp. No. | Structure |
|---|---|
| 26 | 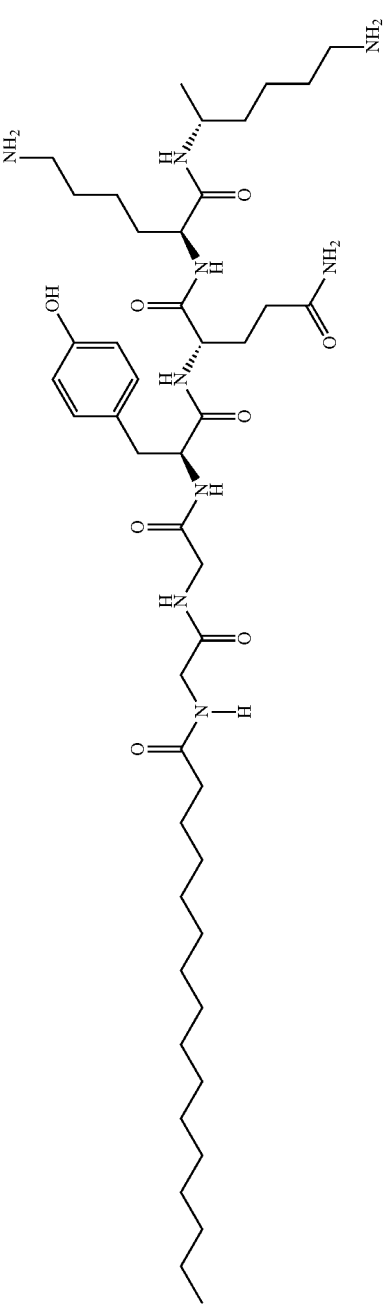 |

TABLE 7-continued
CXCR4 i1 loop compound structures
| Comp. No. | Structure |
|---|---|
| 27 | 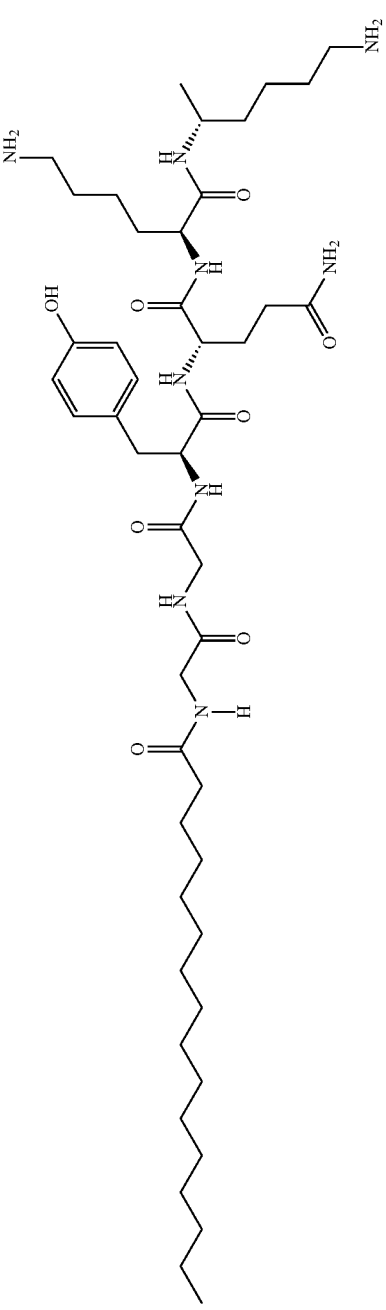 |

TABLE 7-continued

CXCR4 i1 loop compound structures

| Comp. No. | Structure |
|---|---|
| 28 | 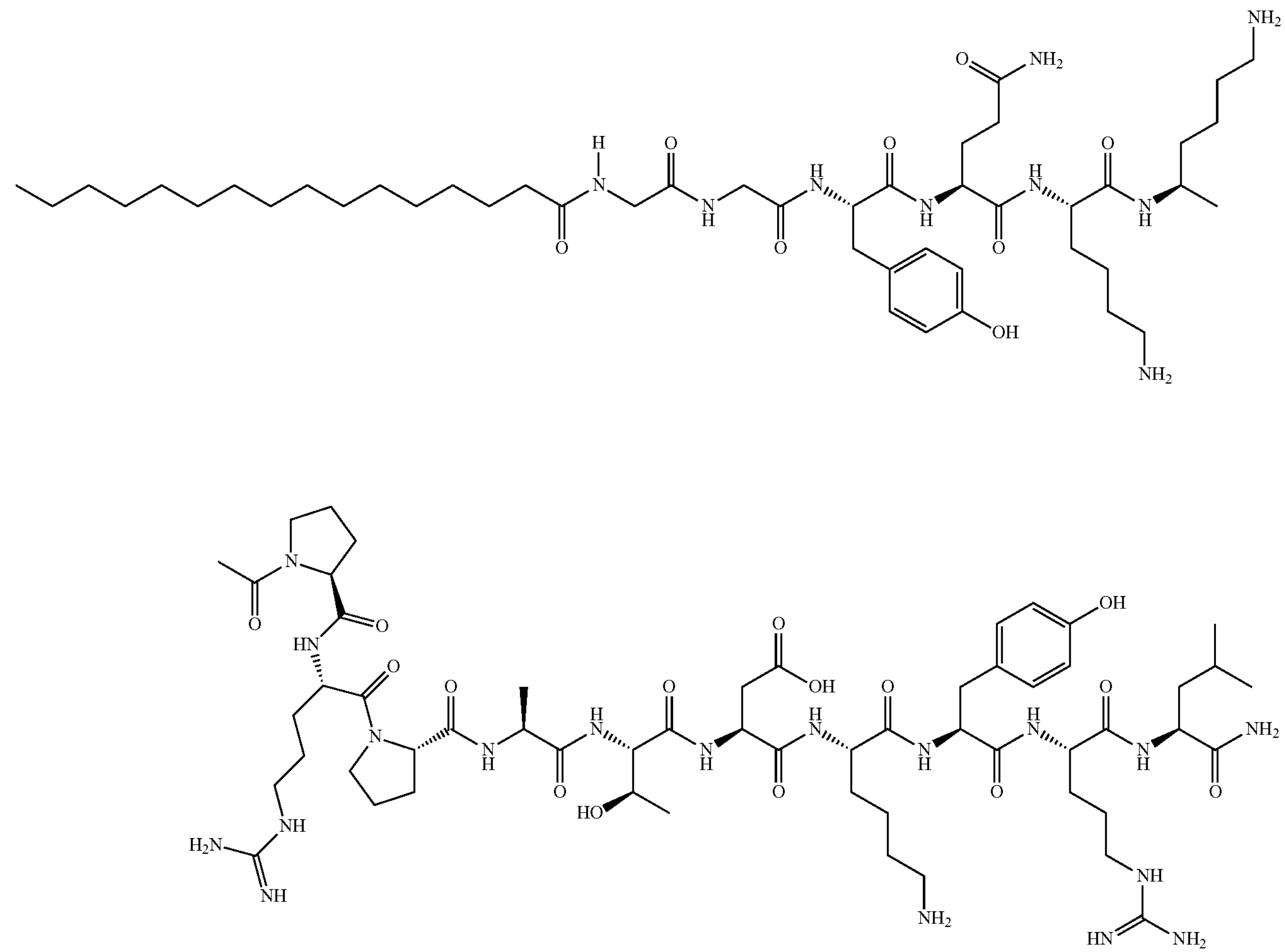 |

TABLE 7-continued
CXCR4 i1 loop compound structures
| Comp. No. | Structure |
|---|---|
| 29 | 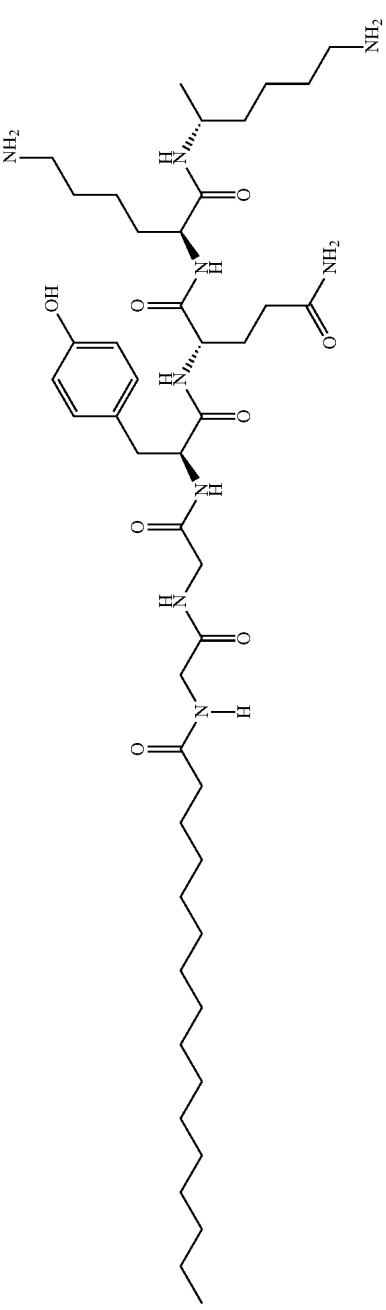 |

TABLE 7-continued
CXCR4 i1 loop compound structures
| Comp. No. | Structure |
|---|---|
| 30 | 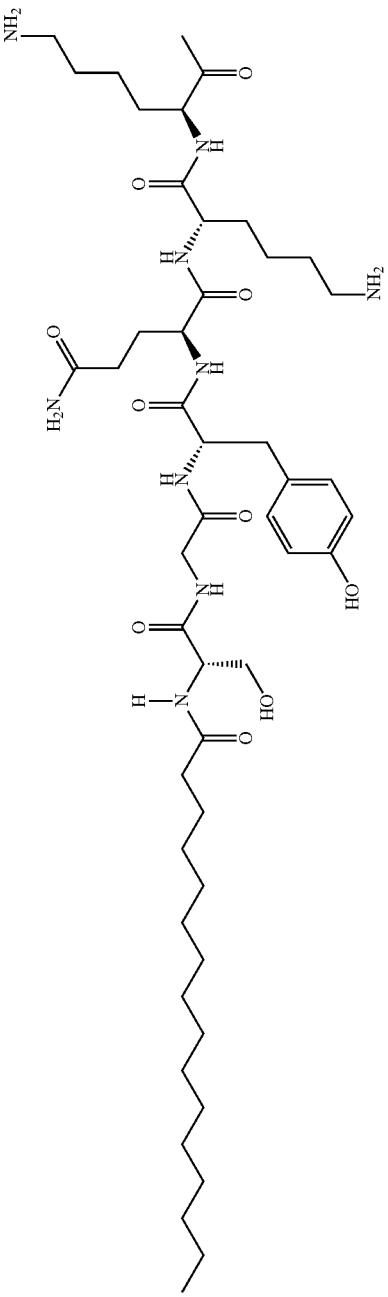 |

TABLE 7-continued
CXCR4 i1 loop compound structures
| Comp. No. | Structure |
|---|---|
| 31 | 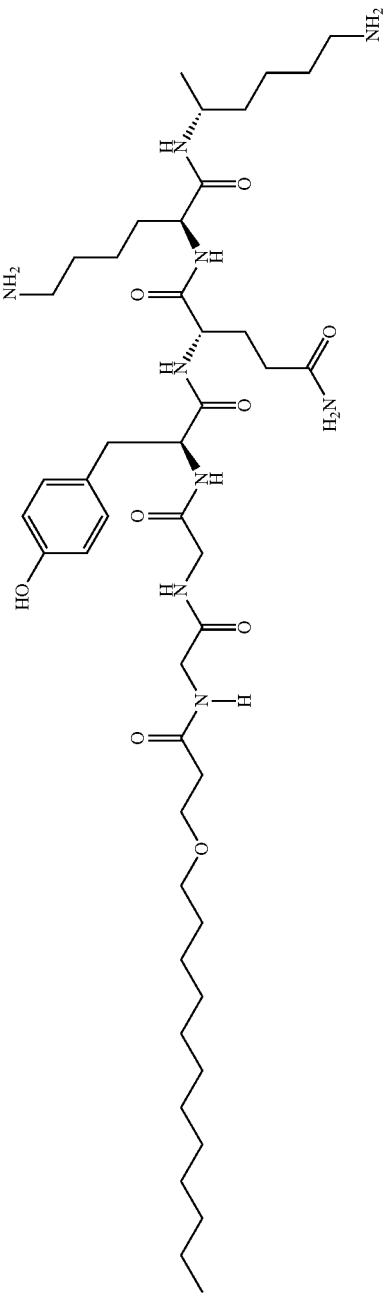 |

TABLE 7-continued
CXCR4 i1 loop compound structures
| Comp. No. | Structure |
|---|---|
| 32 | 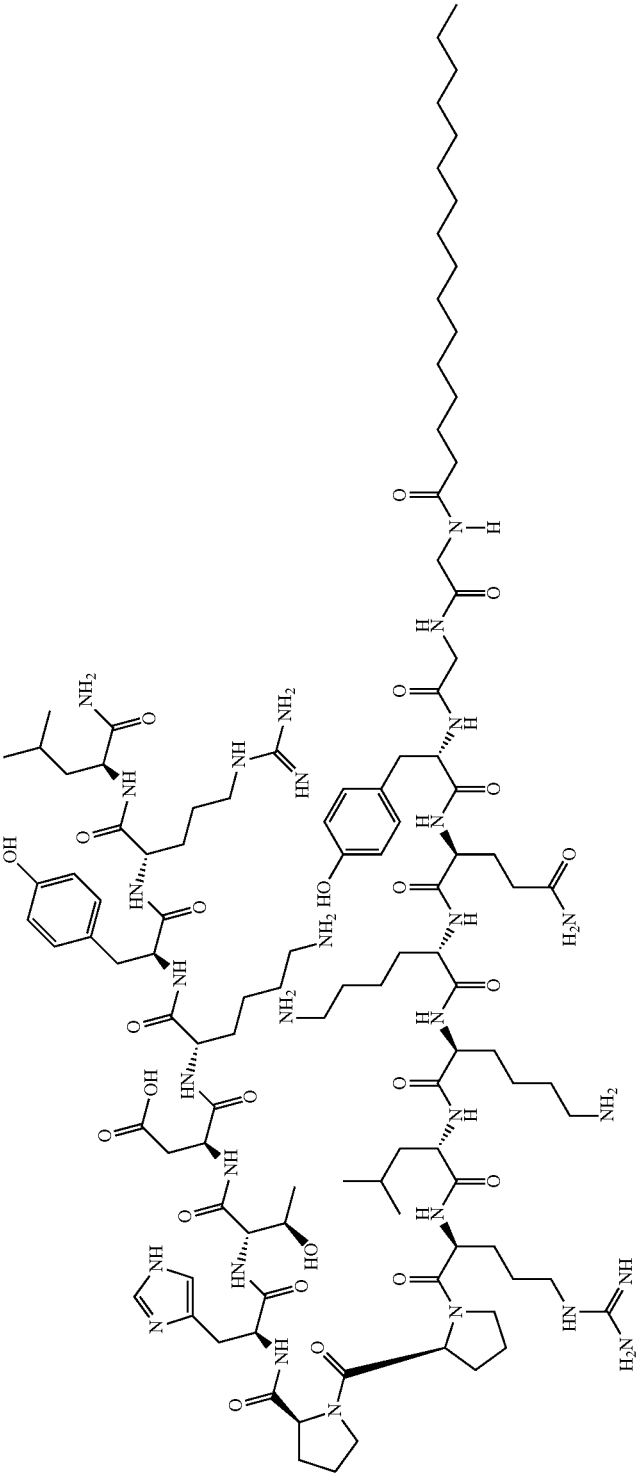 |

TABLE 7-continued
CXCR4 i1 loop compound structures
| Comp. No. | Structure |
|---|---|
| 33 | 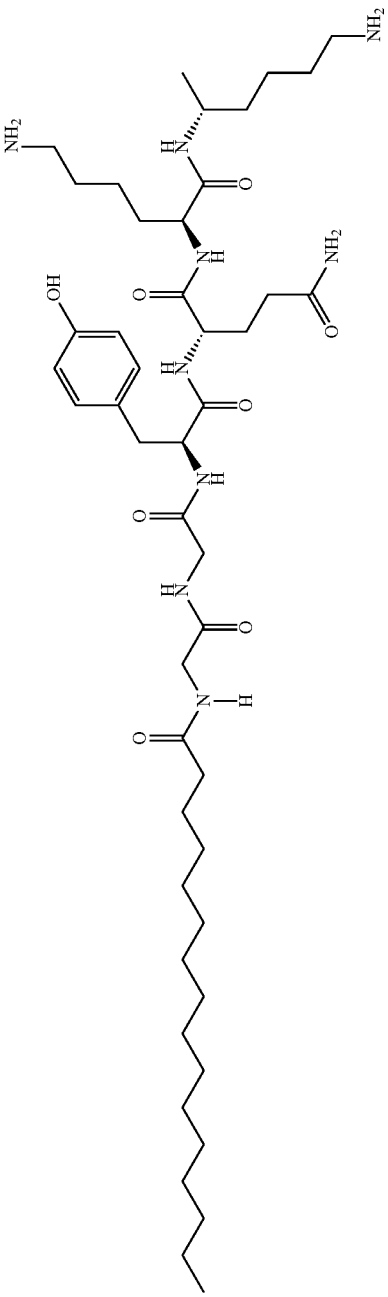 |

TABLE 7-continued
CXCR4 i1 loop compound structures
| Comp. No. | Structure |
|---|---|
| 34 | 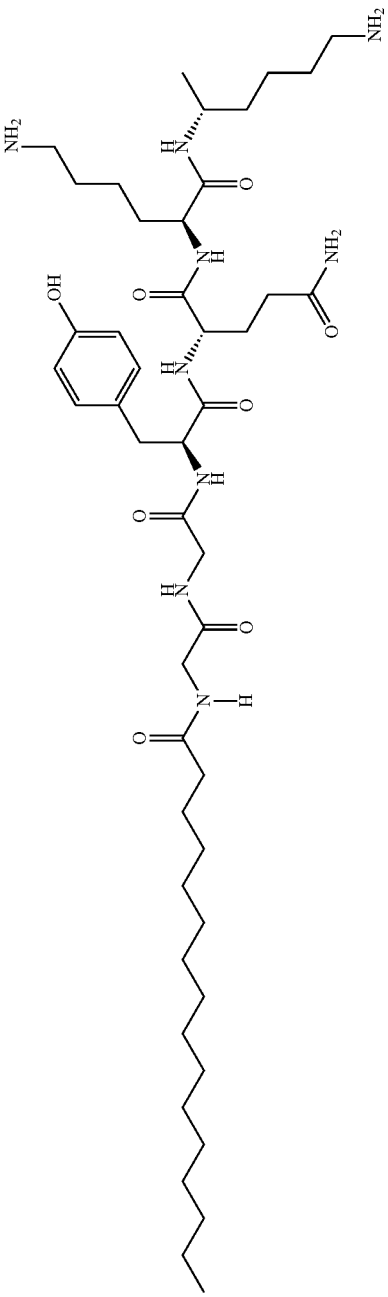 |

TABLE 7-continued
CXCR4 i1 loop compound structures
| Comp. No. | Structure |
|---|---|
| 35 | 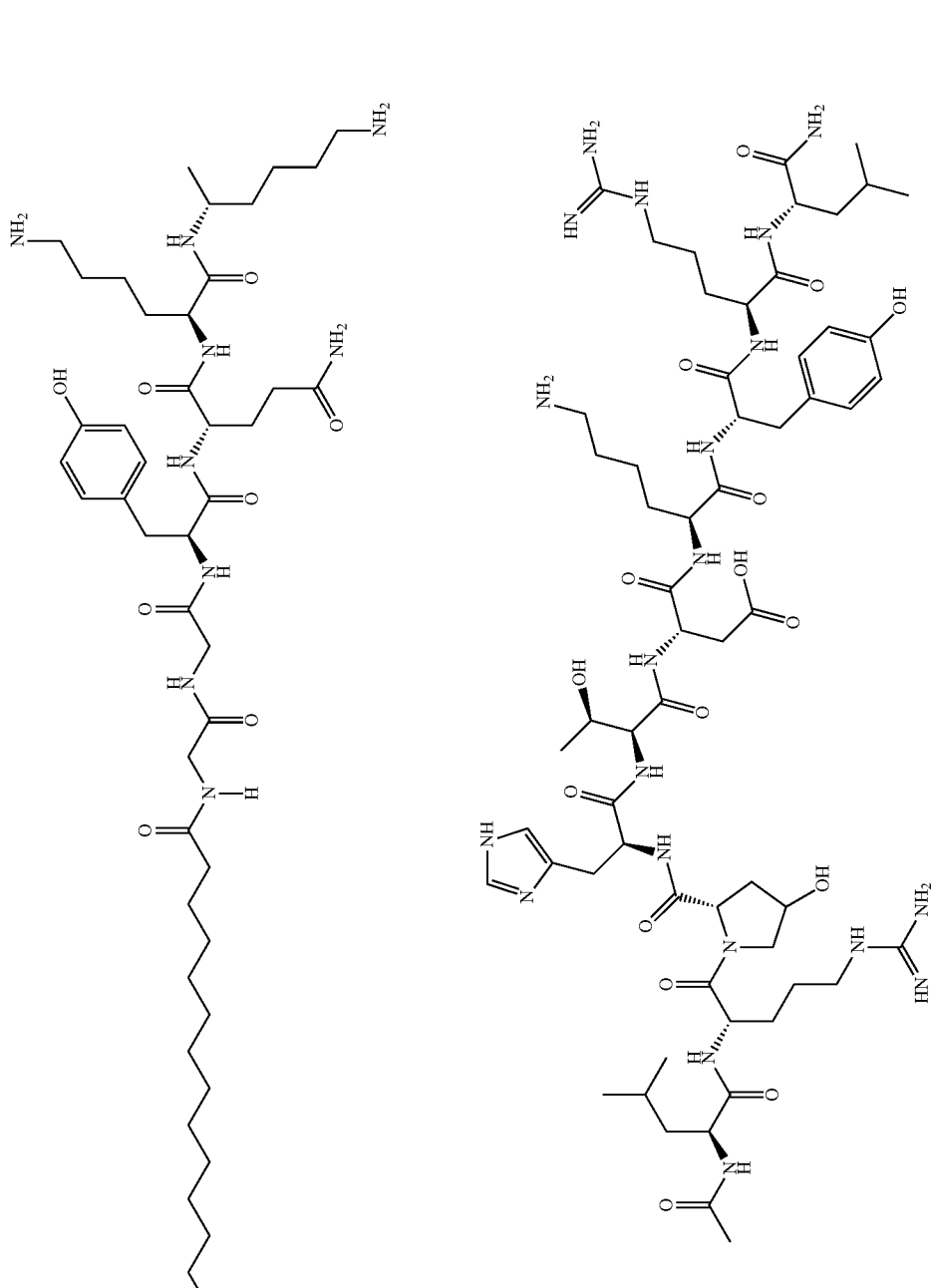 |

TABLE 7-continued
CXCR4 i1 loop compound structures
| Comp. No. | Structure |
|---|---|
| 36 | 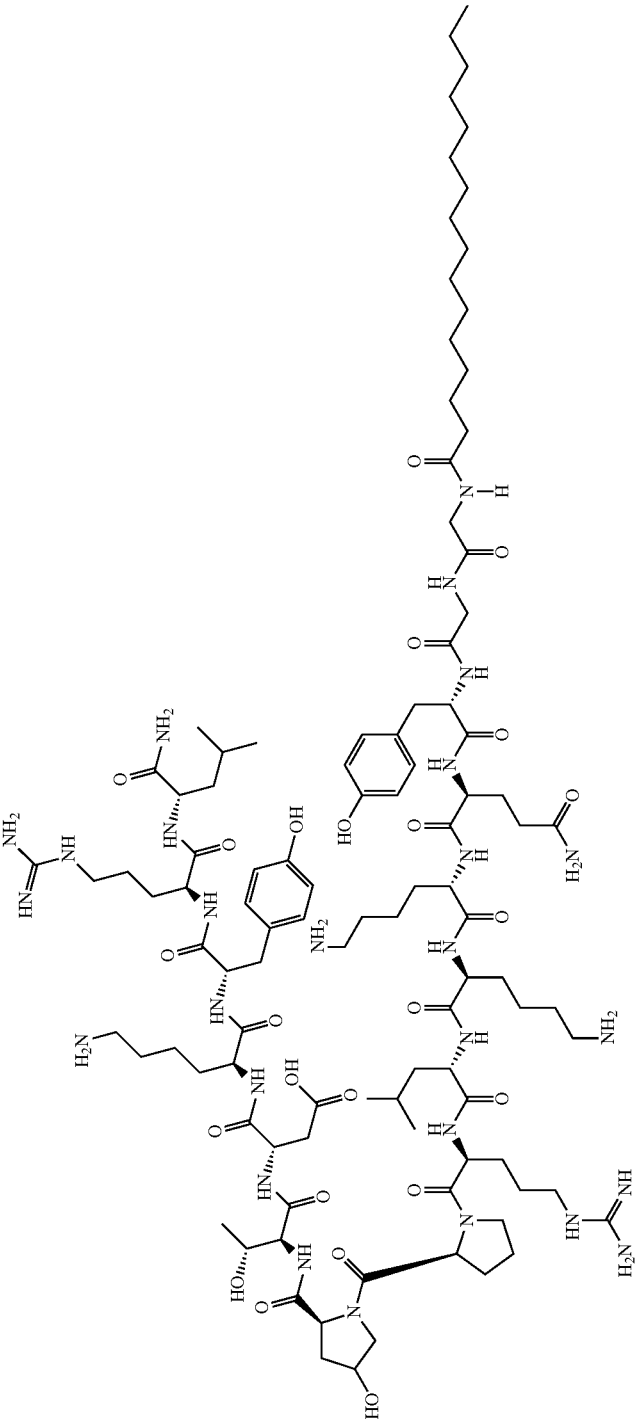 |

TABLE 7-continued
CXCR4 i1 loop compound structures
| Comp. No. | Structure |
|---|---|
| 37 | 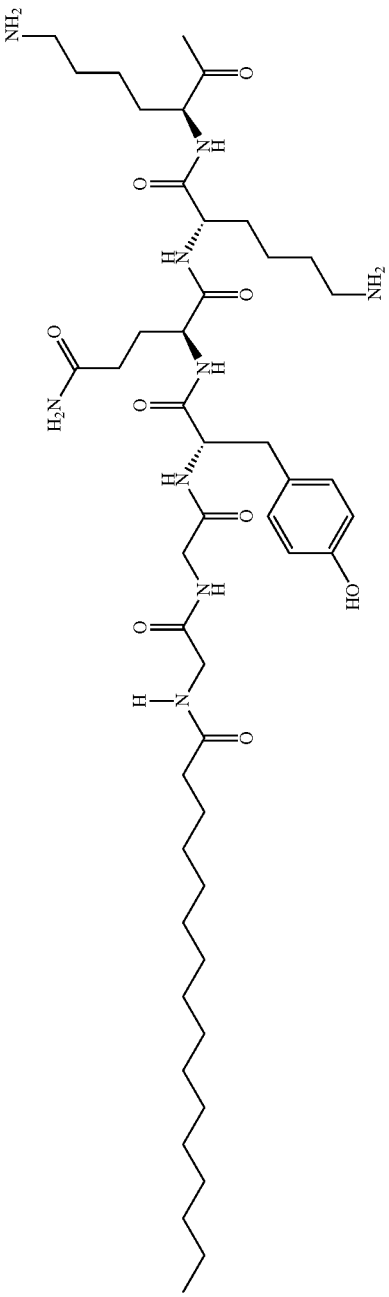 |

TABLE 7-continued
CXCR4 i1 loop compound structures
| Comp. No. | Structure |
|---|---|
| 38 | 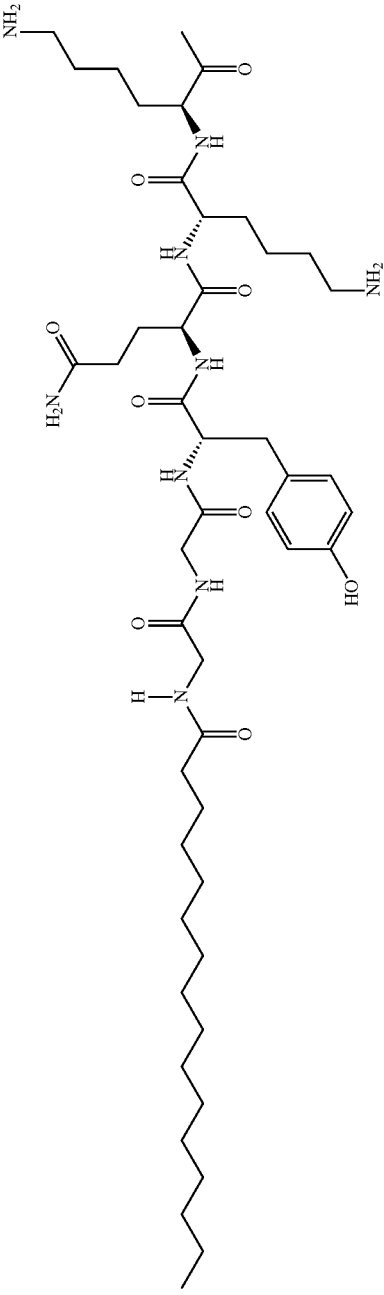 |

TABLE 7-continued
CXCR4 i1 loop compound structures
| Comp. No. | Structure |
|---|---|
| 39 | 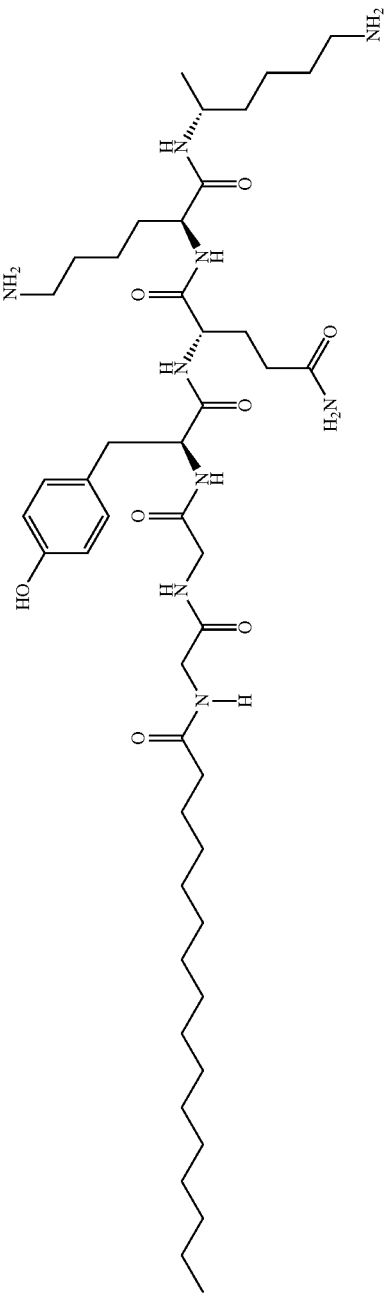 |

TABLE 7-continued
CXCR4 i1 loop compound structures
| Comp. No. | Structure |
|---|---|
| 40 | 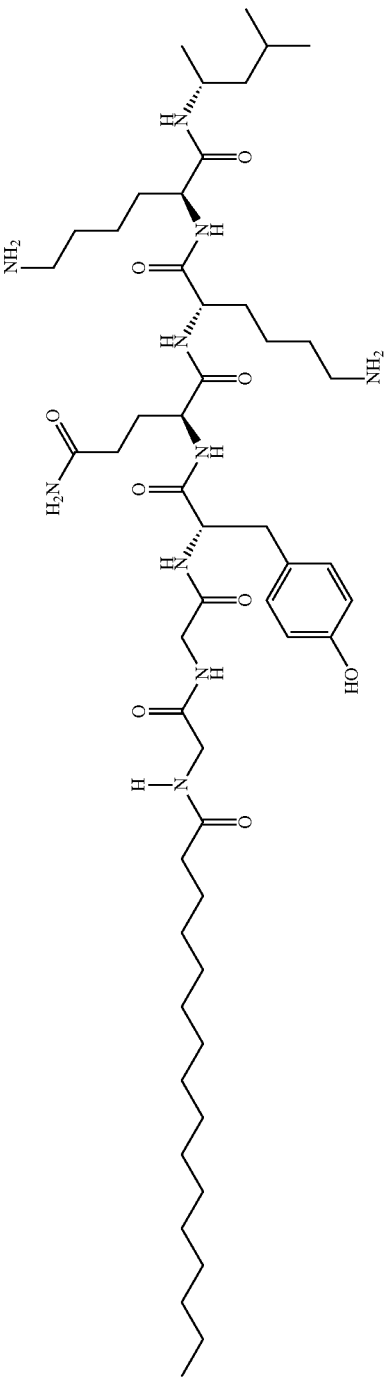 |

TABLE 7-continued
CXCR4 i1 loop compound structures
| Comp. No. | Structure |
|---|---|
| 41 | 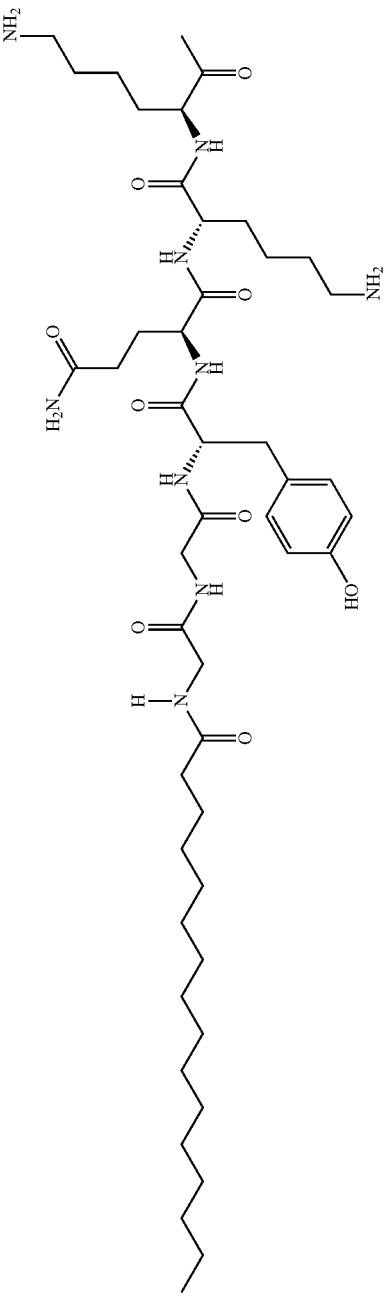 |

TABLE 7-continued

CXCR4 i1 loop compound structures

| Comp. No. | Structure |
|---|---|
| 42 | 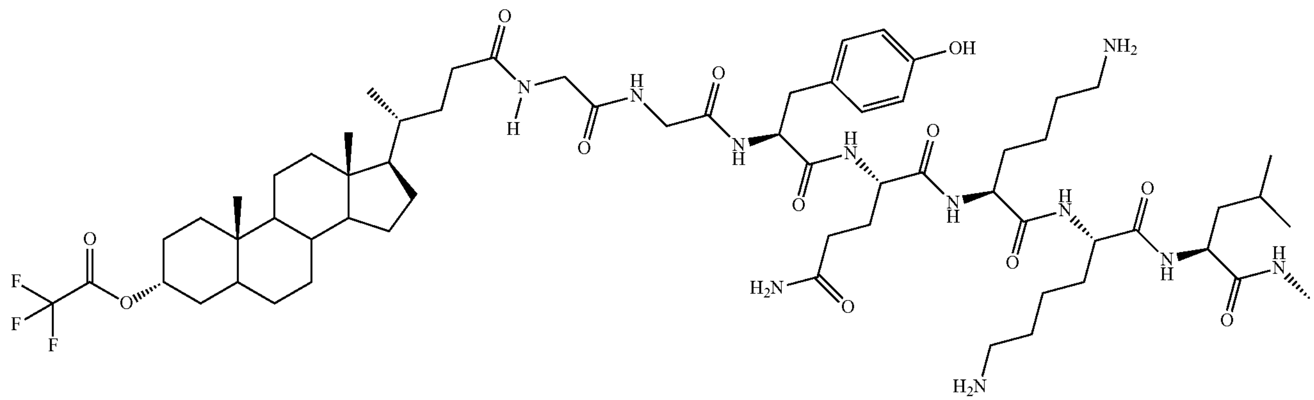 |

TABLE 7-continued
CXCR4 i1 loop compound structures
| Comp. No. | Structure |
|---|---|
| 45 | 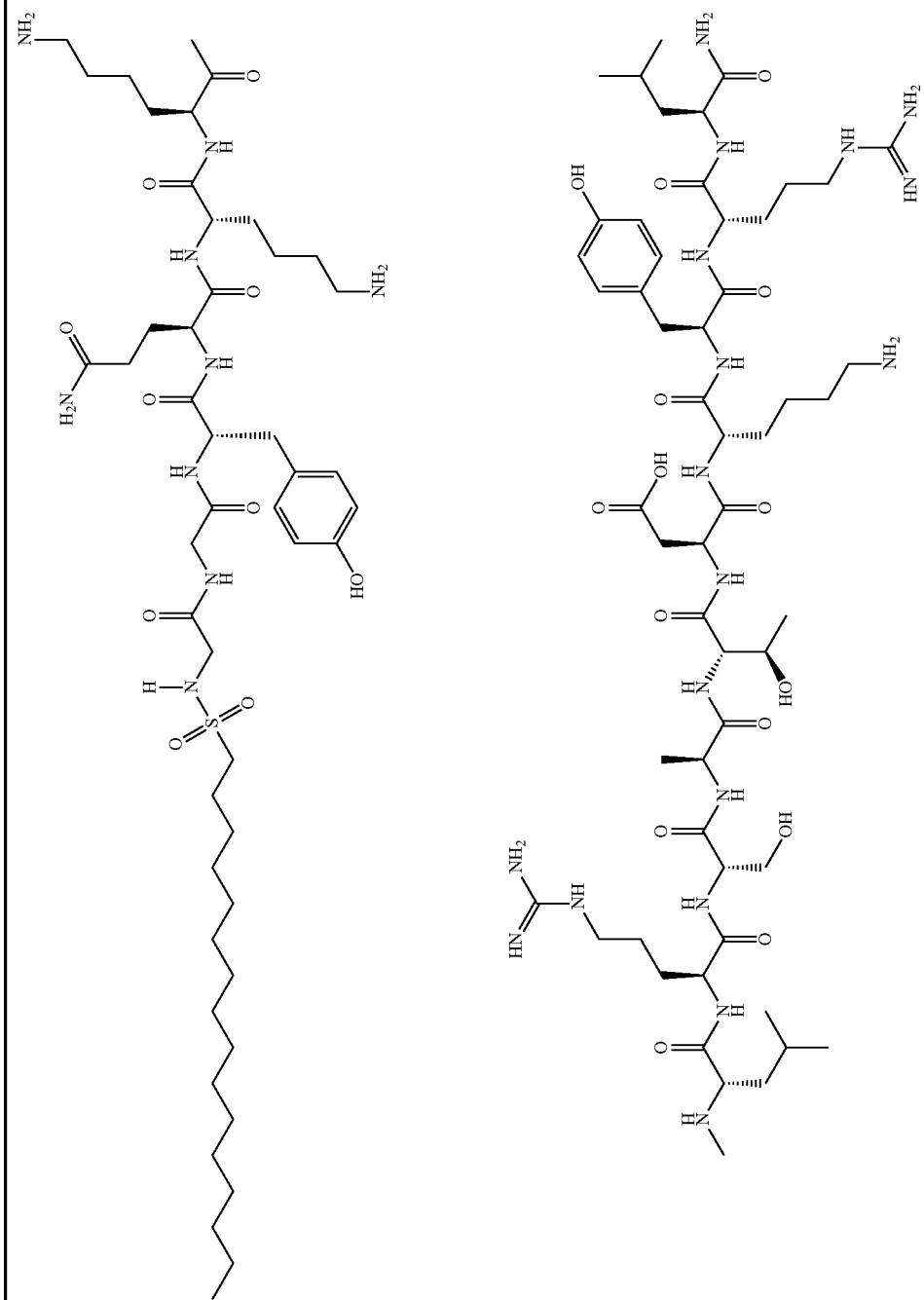 |

TABLE 7-continued
CXCR4 i1 loop compound structures
| Comp. No. | Structure |
|---|---|
| 46 | 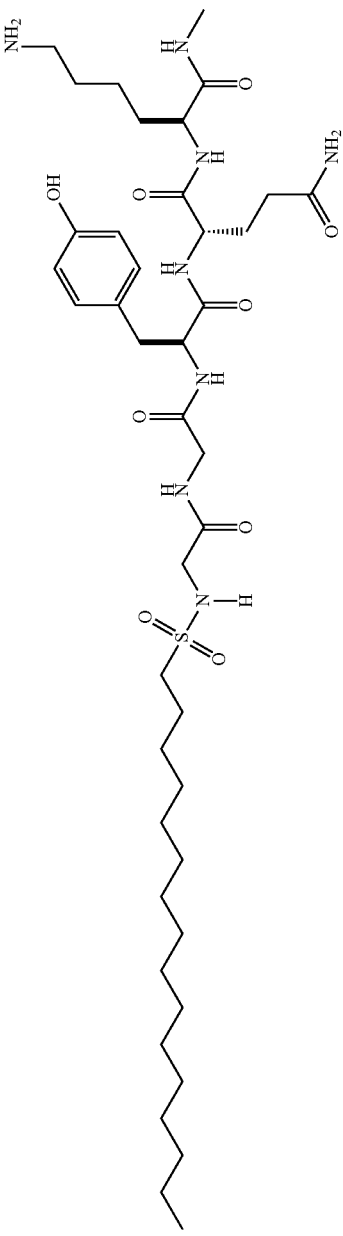 |

TABLE 7-continued
CXCR4 i1 loop compound structures
| Comp. No. | Structure |
|---|---|
| 47 | 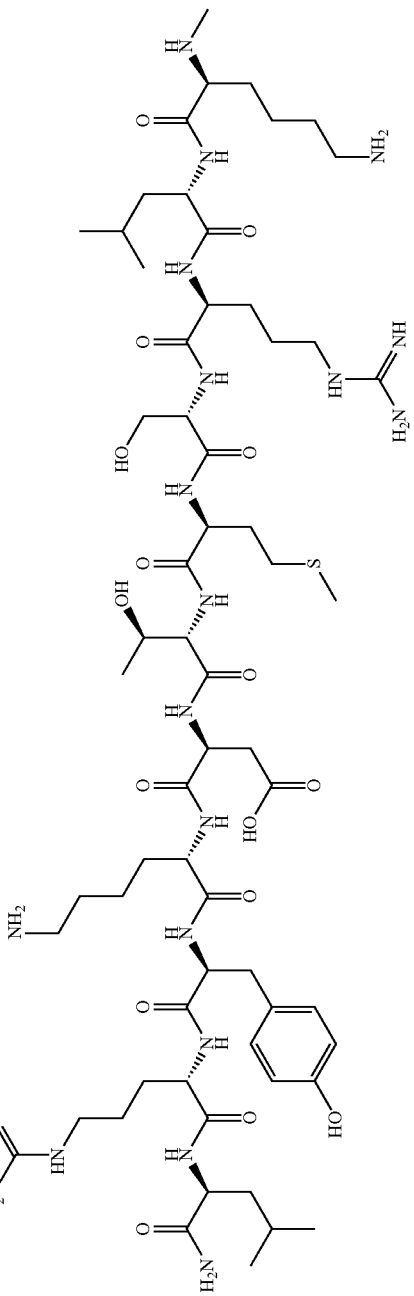 |

TABLE 8
i3 loop compound
| Comp. No | Loop | Sequence | Lipid | Comments | MW |
|---|---|---|---|---|---|
| 43 | i3 | SKLSHSKGHQKRKALKTTVIL (SEQ ID NO: 39) | Pal | | 2598.225 |
TABLE 9
i3 loop compound structure
| Comp. No. | Chemical Structure |
|---|---|
| 43 | 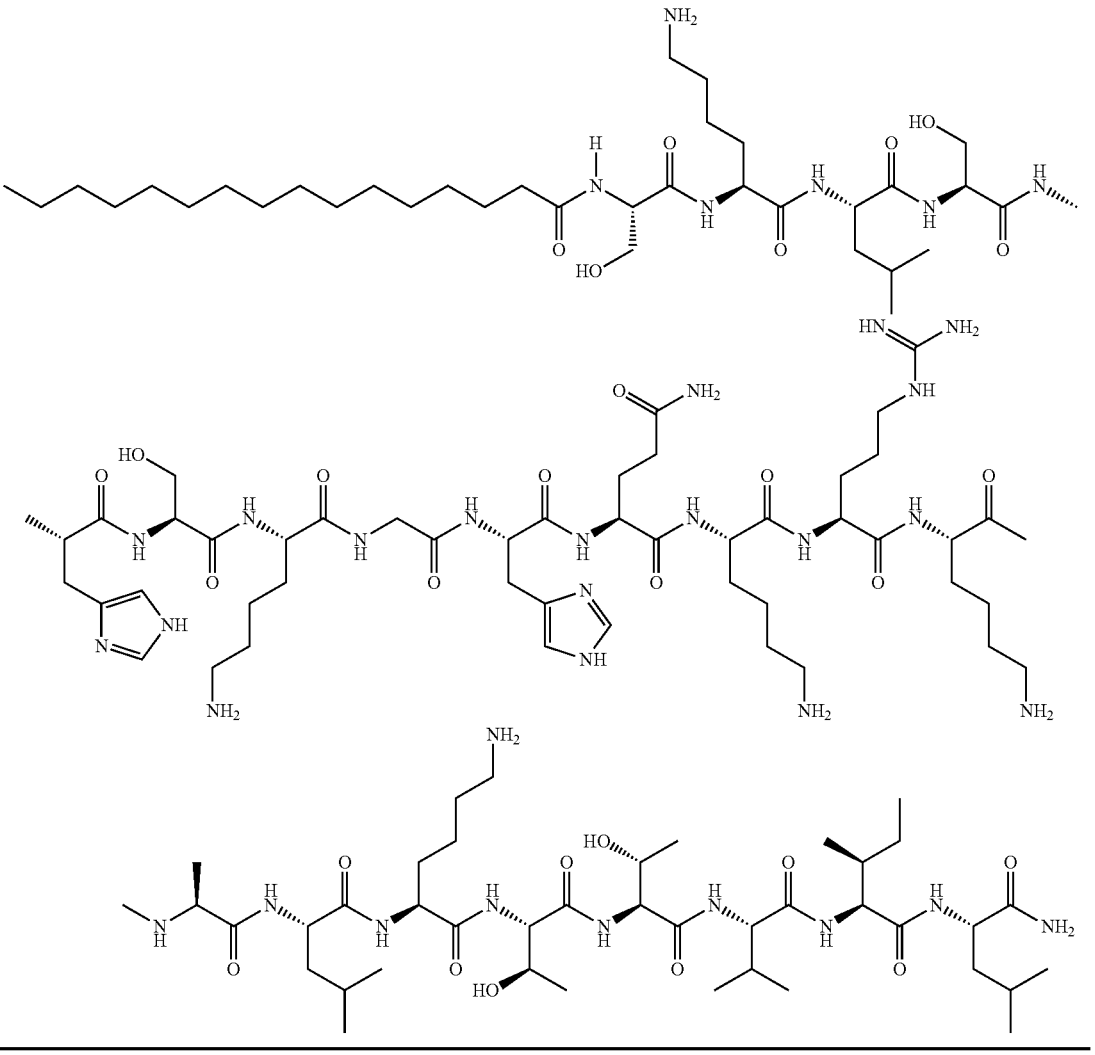 |
TABLE 10
i4 loop compound
| Comp. No. | Loop | Sequence | Lipid | Comments | MW |
|---|---|---|---|---|---|
| 44 | i4 | GAKFKTSAQHALTSVR (SEQ ID NO: 40) | Pal | | 1939.348 |

TABLE 11 i4 loop compound structure

| Comp. No. | Chemical Structure |
|---|---|
| 44 | 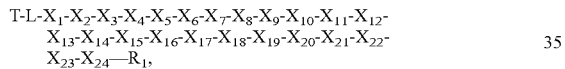 |

In a more specific embodiment, a compound of the invention is represented by Formula A:

$$T\text{-}L\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}\text{—}R_1,$$

or a pharmaceutically acceptable salt thereof, wherein:

L is a linking moiety bonded to P at an N-terminal nitrogen of an N-terminal amino-acid residue selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to the N terminal nitrogen of X$_1$ or the next present amino acid residue if X$_1$ is absent; T is a lipophilic tether moiety bonded to L; and R$_1$ is OR$_2$ or N(R$_2$)$_2$, each R$_2$ is independently H or alkyl, wherein at least three contiguous X$_1$-X$_{24}$ amino acid residues are present, and wherein:

X$_1$ is a valine residue or absent
X$_2$ is a isoleucine residue or absent,
X$_3$ is a leucine residue or absent,
X$_4$ is a valine residue, a glycine residue or absent,
X$_5$ is a methionine residue, a glycine residue, a methyl serine residue, a homoserine residue, a propargyl glycine residue, a cysteine residue or absent,
X$_6$ is a glycine residue or absent,
X$_7$ is a tyrosine residue, a glutamine residue or absent
X$_8$ is a glutamine residue, a lysine residue or absent,
X$_9$ is a lysine residue, or a 2-aminoisobutyric acid (Aib) residue,
X$_{10}$ is a lysine residue, a leucine residue, or a proline residue,
X$_{11}$ is a leucine residue, an arginine residue, a d-leucine residue, a proline residue, a photoleucine residue, or a histidine residue,
X$_{12}$ is an arginine residue, a cyclohexyl alanine residue, a serine residue or a proline residue,
X$_{13}$ is a serine residue, a methionine residue, a d-proline residue, a hydroxy proline residue, a arginine residue, a proline residue, or a threonine residue,
X$_{14}$ is a methionine residue, a threonine residue, an alanine residue, a histidine residue, a methyl serine residue, a proline residue, a Dpr residue, a hydroxy proline residue, a serine residue, a norleucine residue, a homoserine residue, a tryptophan residue or a glycine residue,
X$_{15}$ is a threonine residue, an aspartic acid residue, a d-proline residue, a histidine residue, or a methionine residue,
X$_{16}$ is an aspartic acid residue, a lysine residue or a threonine residue,
X$_{17}$ is a lysine residue, a tyrosine residue, a d-lysine residue or an aspartic acid residue,
X$_{18}$ is a tyrosine residue, a phenylalanine residue, a lysine residue, a naphthyl alanine residue, a d-arginine residue or a d-tyrosine residue,
X$_{19}$ is an arginine residue, a lysine residue, a leucine residue, a citrulline residue, a d-arginine residue or a tyrosine residue,
X$_{20}$ is a leucine residue, a valine residue, a norleucine residue, a d-leucine residue, an arginine residue, or absent,
X$_{21}$ is a histidine residue, a leucine residue or absent,
X$_{22}$ is a leucine residue or absent,
X$_{23}$ is an arginine residue or absent, and
X$_{24}$ is a valine residue or absent;

wherein when $X_1$-$X_4$ and $X_{21}$-$X_{24}$ are absent $X_5$-$X_{20}$ is not MGYQKKLRSMTDKYRL (SEQ ID NO:52) and wherein when $X_1$-$X_8$ is absent and $X_{17}$ is aspartic acid then $X_{18}$ is d-tyrosine or when $X_1$-$X_8$ is absent and $X_{18}$ is tyrosine then $X_{17}$ is d-lysine.

In a further specific embodiment, L is selected from the group: C(O), S*(O)$_2$, NHC*(O), NHC*(S) and OC*(O). In an even further specific embodiment, L is selected from C(O), S*(O)$_2$ and OC*(O). In a most specific embodiment, L is C(O).

In another aspect, a compound of the invention is represented by Formula A-1:

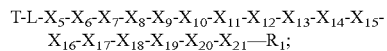

T-L-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$—$R_1$;

or a pharmaceutically acceptable salt thereof, wherein L is a linking moiety bonded to P at an N-terminal nitrogen of an N-terminal amino-acid residue selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to the N terminal nitrogen of $X_5$; T is a lipophilic tether moiety bonded to L; and $R_1$ is OR$_2$ or N(R$_2$)$_2$, each R$_2$ is independently H or alkyl, wherein at least three contiguous $X_5$-$X_{21}$ amino acid residues are present, and wherein:

$X_5$ is a glycine residue, a methyl serine residue, a homoserine residue, a propargyl glycine residue or a cysteine residue, $X_6$ is a glycine residue, $X_7$ is a tyrosine residue, $X_8$ is a glutamine residue, $X_9$ is a lysine residue, $X_{10}$ is a lysine residue, $X_{11}$ is a leucine residue, a proline residue, a photoleucine, a histidine, or a d-leucine, $X_{12}$ is an arginine residue, $X_{13}$ is a serine residue, a d-proline residue, a proline residue, or a hydroxyproline residue, $X_{14}$ is an alanine residue, a homoserine residue, a histidine residue a methyl serine residue, a proline residue, a Dpr residue, a methionine residue, a tryptophan residue, a hydroxyproline residue, or a d-proline residue, $X_{15}$ is a threonine residue or a histidine residue, $X_{16}$ is aspartic acid residue, or a threonine residue $X_{17}$ is a lysine residue, or an aspartic acid residue, $X_{18}$ is a tyrosine residue, a lysine residue or a phenylalanine residue, $X_{19}$ is an arginine residue or a tryptophan residue, $X_{20}$ is a leucine residue or an arginine residue, $X_{21}$ is a histidine residue or a leucine residue or absent or in another aspect, $X_5$ is a glycine or a methyl serine residue, $X_{11}$ is a leucine residue, or a proline residue, $X_{13}$ is a serine residue, a d-proline residue or a hydroxyproline residue, $X_{14}$ is an alanine residue, a histidine residue a methyl serine residue, a d-proline residue or a Dpr residue, $X_{21}$ is a leucine residue or absent.

In a further specific embodiment, L is selected from the group: C(O), S*(O)$_2$, NHC*(O), NHC*(S) and OC*(O). In an even further specific embodiment, L is selected from C(O), S*(O)$_2$ and OC*(O). In a most specific embodiment, L is C(O).

In another embodiment, the invention pertains to a compound of Formula A or Formula A-1 wherein $X_1$-$X_4$ and $X_{21}$-$X_{24}$ are absent and wherein:

$X_5$ is a methionine residue, $X_6$ is a glycine residue, $X_7$ is a tyrosine residue, $X_8$ is a glutamine residue, $X_9$ is a lysine residue or a 2-aminoisobutyric acid (Aib) residue, $X_{10}$ is a lysine residue or a proline residue, $X_{11}$ is a leucine residue or an arginine residue, $X_{12}$ is an arginine residue, a serine residue or a cyclohexyl alanine residue, $X_{13}$ is a serine residue, a methionine residue, an arginine residue, or a proline residue, $X_{14}$ is a methionine residue, an isoleucine residue, a histidine residue, a glycine residue, a threonine residue, a serine residue or a d-proline residue, $X_{15}$ is a threonine residue, an aspartic acid residue, a methionine residue or a d-proline residue, $X_{16}$ is aspartic acid residue, a threonine residue, or a lysine residue, $X_{17}$ is a lysine residue, or an aspartic acid residue, $X_{18}$ is a tyrosine residue, a phenylalanine residue, a lysine residue, a d-arginine, a d-tyrosine residue, or a naphthyl alanine residue, $X_{19}$ is an arginine residue, a lysine residue, a citrulline residue, a leucine residue, or a tyrosine residue, $X_{20}$ is a leucine residue, a norleucine residue, a valine residue, an arginine residue or absent.

In a further specific embodiment, L is selected from the group: C(O), S*(O)$_2$, NHC*(O), NHC*(S) and OC*(O). In an even further specific embodiment, L is selected from C(O), S*(O)$_2$ and OC*(O). In a most specific embodiment, L is C(O).

In a particular embodiment, the compound is a compound represented by Formula II:

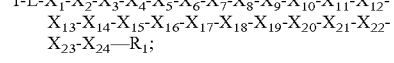

T-L-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$—$R_1$;

or a pharmaceutically acceptable salt thereof, wherein:

L is a linking moiety selected from: C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to the N terminal nitrogen of $X_1$ or the next present amino acid residue if $X_1$ is absent; T is a lipophilic tether moiety bonded to L; and $R_1$ is OR$_2$ or $N(R_2)_2$, each $R_2$ is independently H or alkyl, wherein at least three contiguous $X_1$-$X_{24}$ amino acid residues are present, and wherein:

$X_1$ is a valine residue or absent,
$X_2$ is an isoleucine residue or absent,
$X_3$ is a leucine residue or absent,
$X_4$ is a valine residue, a glycine residue or absent,
$X_5$ is a methionine residue, a glycine residue, a methyl serine residue, a homoserine residue, a propargyl glycine residue, a cysteine residue or absent,
$X_6$ is a glycine residue or absent,
$X_7$ is a tyrosine residue, a glutamine residue or absent
$X_8$ is a glutamine residue, a lysine residue or absent,
$X_9$ is a lysine residue, or a 2-aminoisobutyric acid (Aib) residue,
$X_{10}$ is a lysine residue, a leucine residue, or a proline residue,
$X_{11}$ is a leucine residue, an arginine residue, a d-leucine residue, a proline residue, a photoleucine residue, or a histidine residue,
$X_{12}$ is an arginine residue, a cyclohexyl alanine residue, a serine residue or a proline residue,
$X_{13}$ is a serine residue, a methionine residue, a d-proline residue, a hydroxy proline residue, a arginine residue or a proline residue, or a threonine residue,
$X_{14}$ is a methionine residue, a threonine residue, an alanine residue, a histidine residue, a methyl serine residue, a proline residue, a Dpr residue, a hydroxy proline residue, a serine residue, a norleucine residue, a homoserine residue a tryptophan residue or a glycine residue,
$X_{15}$ is a threonine residue, an aspartic acid residue, a d-proline residue, a histidine residue, or a methionine residue,
$X_{16}$ is an aspartic acid residue, a lysine residue or a threonine residue,
$X_{17}$ is a lysine residue, a tyrosine residue, a d-lysine residue or an aspartic acid residue,
$X_{18}$ is a tyrosine residue, a phenylalanine residue, a lysine residue, a naphthyl alanine residue, a d-arginine residue or a d-tyrosine residue,
$X_{19}$ is an arginine residue, a lysine residue, a leucine residue, a citrulline residue, a d-arginine residue or a tyrosine residue,
$X_{20}$ is a leucine residue, a valine residue, a norleucine residue, a d-leucine residue, an arginine residue, or absent,
$X_{21}$ is a histidine residue, a leucine residue or absent,
$X_{22}$ is a leucine residue or absent,
$X_{23}$ is an arginine residue or absent, and
$X_{24}$ is a valine residue or absent.

In a first aspect of this particular embodiment of Formula II, L is selected from $S^*(O)_2$ and $OC^*(O)$. In a second aspect of this particular embodiment of Formula II, the compound is selected from:

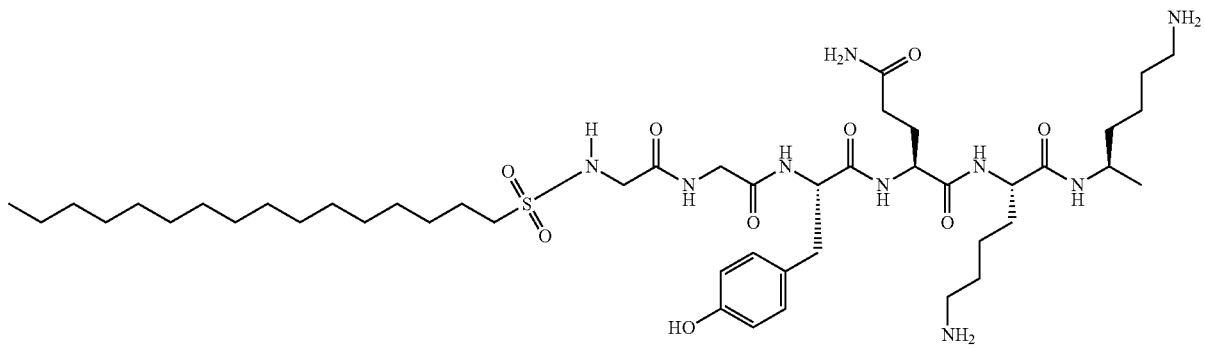

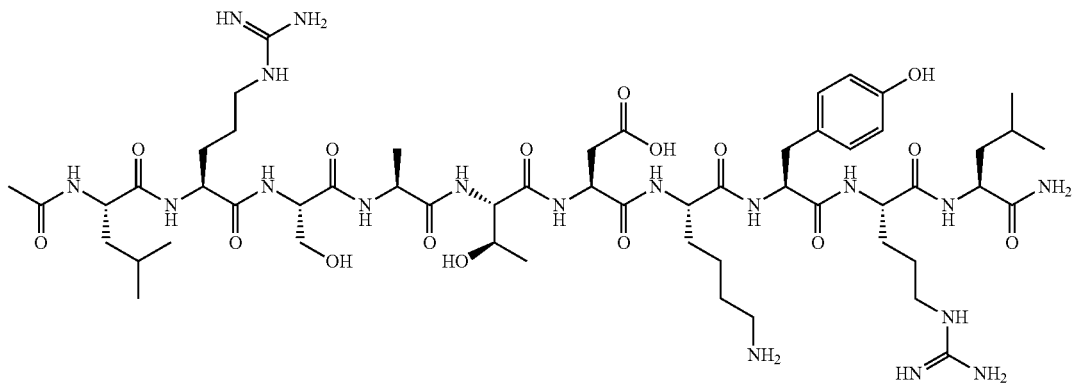

-continued
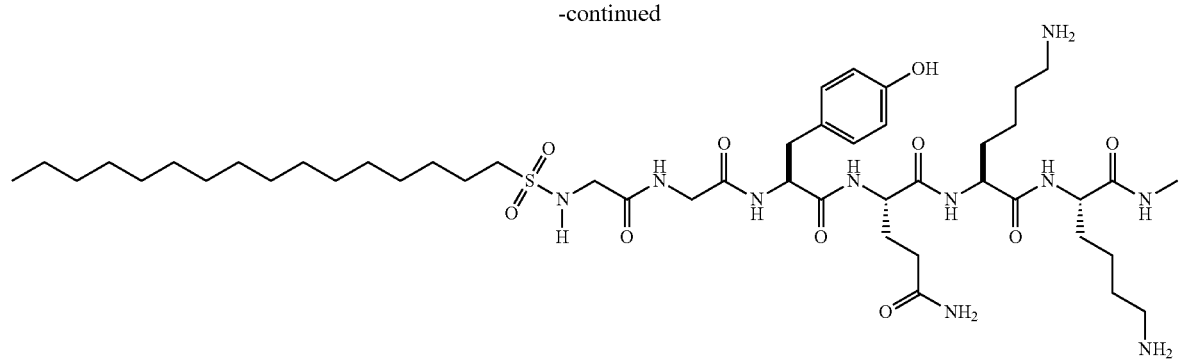
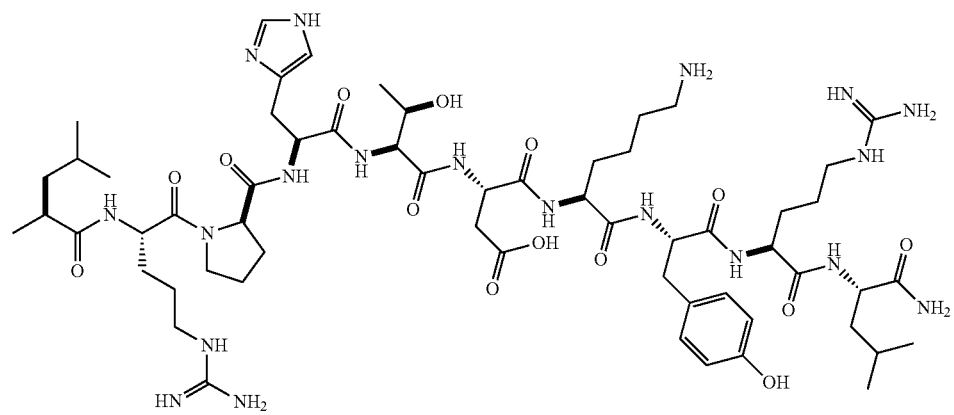
and
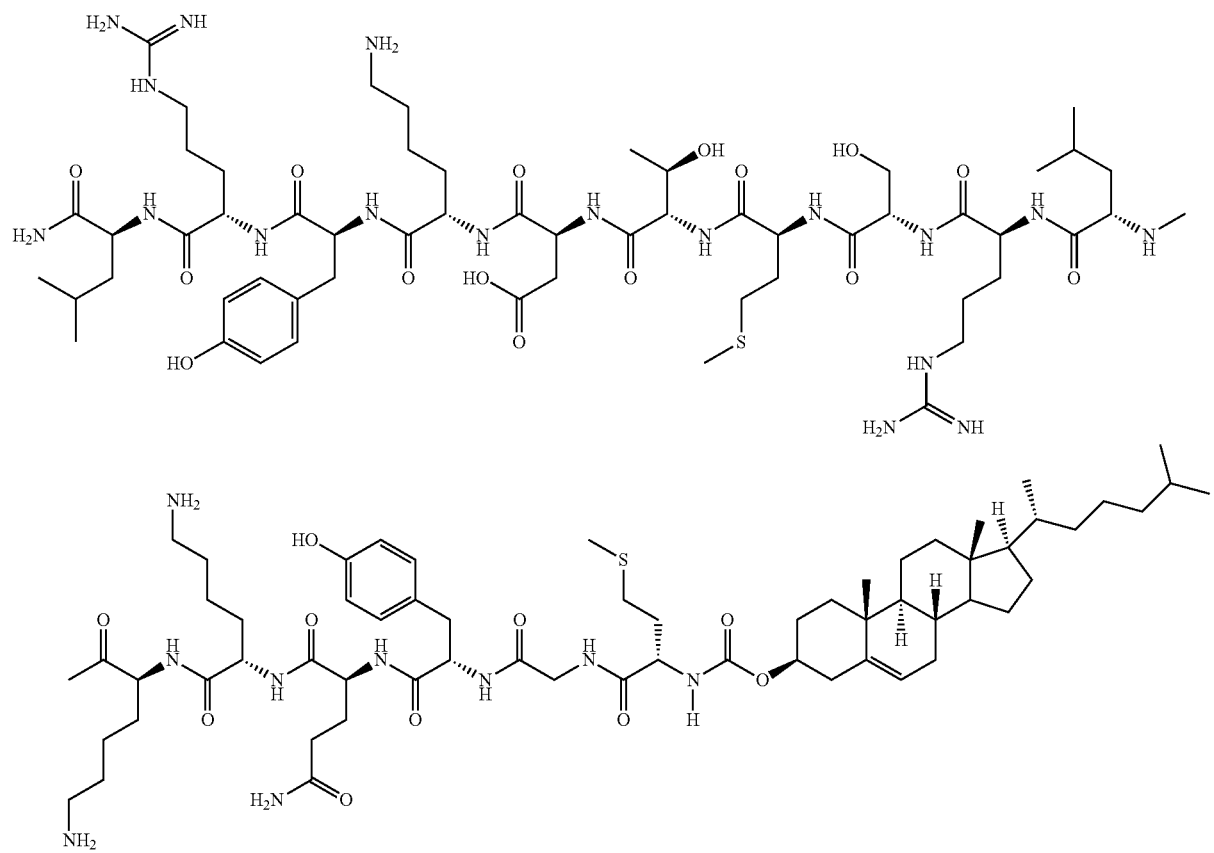

or a pharmaceutically acceptable salt of any of the foregoing.

"Cycloalkyl" used alone or as part of a larger moiety such as "cycloalkylalkyl" refers to a monocyclic or polycyclic, non-aromatic ring system of 3 to 20 carbon atoms, 3 to 12 carbon atoms, or 3 to 9 carbon atoms, which may be saturated or unsaturated. Examples of cycloalkyl groups include cyclopropyl, cyclobutyl, cyclopentyl, cyclohexyl, cyclohexenyl, cyclohexa-1,3-dienyl, cyclooctyl, cycloheptanyl, norbornyl, adamantyl, and the like.

"Heterocycloalkyl" refers to a saturated or unsaturated, non-aromatic, monocyclic or polycyclic ring system of 3 to 20 atoms, 3 to 12 atoms, or 3 to 8 atoms, containing one to four ring heteroatoms chosen from O, N and S. Examples of heterocyclyl groups include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine-1,1-dioxide, tetrahydro-2H-1,2-thiazine-1,1-dioxide, isothiazolidine-1,1-dioxide, pyrrolidin-2-one, piperidin-2-one, piperazin-2-one, and morpholin-2-one, and the like.

"Halogen" and "halo" refer to fluoro, chloro, bromo or iodo.

"Haloalkyl" refers to an alkyl group substituted with one or more halogen atoms. By analogy, "haloalkenyl", "haloalkynyl", etc., refers to the group (for example, alkenyl or alkynyl) substituted by one or more halogen atoms.

"Cyano" refers to the group —CN.

"Oxo" refers to a divalent =O group.

"Thioxo" refers to a divalent =S group.

"Ph" refers to a phenyl group.

"Carbonyl" refers to a divalent —C(O)— group.

"Alkyl" used alone or as part of a larger moiety such as "hydroxyalkyl", "alkoxyalkyl", "alkylamine" refers to a straight or branched, saturated aliphatic group having the specified number of carbons, typically having 1 to 12 carbon atoms. More particularly, the aliphatic group may have 1 to 10, 1 to 8, 1 to 6, or 1 to 4 carbon atoms. This term is exemplified by groups such as methyl, ethyl, n-propyl, isopropyl, n-butyl, isobutyl, tert-butyl, n-hexyl, and the like.

"Alkenyl" refers to a straight or branched aliphatic group with at least one double bond. Typically, alkenyl groups have from 2 to 12 carbon atoms, from 2 to 8, from 2 to 6, or from 2 to 4 carbon atoms. Examples of alkenyl groups include ethenyl (—CH=CH$_2$), n-2-propenyl (allyl, —CH$_2$CH=CH$_2$), pentenyl, hexenyl, and the like.

"Alkynyl" refers to a straight or branched aliphatic group having at least 1 site of alkynyl unsaturation. Typically, alkynyl groups contain 2 to 12, 2 to 8, 2 to 6 or 2 to 4 carbon atoms. Examples of alkynyl groups include ethynyl (—C≡CH), propargyl (—CH$_2$C≡CH), pentynyl, hexynyl, and the like.

"Alkylene" refers to a bivalent saturated straight-chained hydrocarbon, e.g., $C_1$-$C_6$ alkylene includes —(CH$_2$)$_6$—, —CH$_2$—CH—(CH$_2$)$_3$CH$_3$, and the like. "Bivalent means that the alkylene group is attached to the remainder of the molecule through two different carbon atoms.

"Alkenylene" refers to an alkylene group with in which one carbon-carbon single bond is replaced with a double bond.

"Alkynylene" refers to an alkylene group with in which one carbon-carbon single bond is replaced with a triple bond.

"Aryl" used alone or as part of a larger moiety as in "aralkyl" refers to an aromatic carbocyclic group of from 6 to 14 carbon atoms having a single ring or multiple condensed rings. The term "aryl" also includes aromatic carbocycle(s) fused to cycloalkyl or heterocycloalkyl groups. Examples of aryl groups include phenyl, benzo[d][1,3]dioxole, naphthyl, phenantrenyl, and the like.

"Aryloxy" refers to an —OAr group, wherein 0 is an oxygen atom and Ar is an aryl group as defined above.

"Aralkyl" refers to an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

"Alkyl cycloalkyl" refers to an alkyl having at least one alkyl hydrogen atom replaced with a cycloalkyl moiety, such as —CH$_2$-cyclohexyl, —CH$_2$-cyclohexenyl, and the like.

"Heteroaryl" used alone or a part of a larger moiety as in "heteroaralkyl" refers to a 5 to 14 membered monocyclic, bicyclic or tricyclic heteroaromatic ring system, containing one to four ring heteroatoms independently selected from nitrogen, oxygen and sulfur. The term "heteroaryl" also includes heteroaromatic ring(s) fused to cycloalkyl or heterocycloalkyl groups. Particular examples of heteroaryl groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl, benzoquinolyl, and the like.

"Heteroaryloxy" refers to an —OHet group, wherein O is an oxygen atom and Het is a heteroaryl group as defined above.

"Heteroaralkyl" refers to an alkyl having at least one alkyl hydrogen atom replaced with a heteroaryl moiety, such as —CH$_2$-pyridinyl, —CH$_2$-pyrimidinyl, and the like.

"Alkoxy" refers to the group —O—R where R is "alkyl", "cycloalkyl", "alkenyl", or "alkynyl". Examples of alkoxy groups include for example, methoxy, ethoxy, ethenoxy, and the like.

"Alkyl heterocycloalkyl" refers to an alkyl having at least one alkyl hydrogen atom replaced with a heterocycloalkyl moiety, such as —CH$_2$-morpholino, —CH$_2$-piperidyl and the like.

"Alkoxycarbonyl" refers to the group —C(O)OR where R is "alkyl", "alkenyl", "alkynyl", "cycloalkyl", "heterocyloalkyl", "aryl", or "heteroaryl".

"Hydroxyalkyl" and "alkoxyalkyl" are alky groups substituted with hydroxyl and alkoxy, respectively.

"Amino" means —NH$_2$; "alkylamine" and "dialkylamine" mean —NHR and —NR$_2$, respectively, wherein R is an alkyl group. "Cycloalkylamine" and "dicycloalkylamine" mean —NHR and —NR$_2$, respectively, wherein R is a cycloalkyl group. "Cycloalkylalkylamine" means —NHR wherein R is a cycloalkylalkyl group. "[Cycloalkylalkyl][alkyl]amine" means —N(R)$_2$ wherein one R is cycloalkylalkyl and the other R is alkyl.

Haloalkyl and halocycloalkyl include mono, poly, and perhaloalkyl groups where the halogens are independently selected from fluorine, chlorine, bromine and iodine.

Suitable substituents for "alkyl", "alkenyl", "alkynyl", "cycloalkyl", "heterocycloalkyl", "aryl", or "heteroaryl", etc., are those which will form a stable compound of the invention. Examples of suitable substituents are those selected from the group consisting of halogen, —CN, —OH, —NH$_2$, (C$_1$-C$_4$)alkyl, (C$_1$-C$_4$)haloalkyl, aryl, heteroaryl, (C$_3$-C$_7$)cycloalkyl, (5-7 membered) heterocycloalkyl, —NH(C$_1$-C$_6$)alkyl, —N((C$_1$-C$_6$)alkyl)$_2$, (C$_1$-C$_6$)alkoxy, (C$_1$-C$_6$)alkoxycarbonyl, —CONH$_2$, —OCONH$_2$, —NHCONH$_2$, —N(C$_1$-C$_6$)alkylCONH$_2$, —N(C$_1$-C$_6$)alkylCONH(C$_1$-C$_6$)alkyl, —NHCONH(C$_1$-C$_6$)alkyl, —NHCON((C$_1$-C$_6$)alkyl)$_2$, —N(C$_1$-C$_6$)alkylCON((C$_1$-C$_6$)alkyl)$_2$, —NHC(S)NH$_2$, —N(C$_1$-C$_6$)alkylC(S)NH$_2$, —N(C$_1$-C$_6$)alkylC(S)NH(C$_1$-C$_6$)alkyl, —NHC(S)NH(C$_1$-C$_6$)alkyl, —NHC(S)N((C$_1$-C$_6$)alkyl)$_2$, —N(C$_1$-C$_6$)alkylC(S)N((C$_1$-C$_6$)alkyl)$_2$, —CONH(C$_1$-C$_6$)alkyl, —OCONH(C$_1$-C$_6$)alkyl —CON((C$_1$-C$_6$)alkyl)$_2$, —C(S)(C$_1$-C$_6$)alkyl, —S(O)$_p$(C$_1$-C$_6$)alkyl, —S(O)$_p$NH$_2$, —S(O)$_p$NH(C$_1$-C$_6$)alkyl, —S(O)$_p$N((C$_1$-C$_6$)alkyl)$_2$, —CO(C$_1$-C$_6$)alkyl, —OCO(C$_1$-C$_6$)alkyl, —C(O)O(C$_1$-C$_6$)alkyl, —OC(O)O(C$_1$-C$_6$)alkyl, —C(O)H or —CO$_2$H. More particularly, the substituents are selected from halogen, —CN, —OH, —NH$_2$, (C$_1$-C$_4$)alkyl, (C$_1$-C$_4$)haloalkyl, (C$_1$-C$_4$)alkoxy, phenyl, and (C$_3$-C$_7$)cycloalkyl. Within the framework of this invention, said "substitution" is also meant to encompass situations where a hydrogen atom is replaced with a deuterium atom. p is an integer with a value of 1 or 2.

Pharmaceutically acceptable salts of the compounds disclosed herein are included in the present invention. For example, an acid salt of a compound containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

Salts of the compounds containing an acidic functional group can be prepared by reacting with a suitable base. Such a pharmaceutically acceptable salt can be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

PHARMACEUTICAL COMPOSITIONS

The invention also provides pharmaceutical compositions comprising an effective amount of a compound Formula A, Formula A-1, Formula I or Formula II. (e.g., including any of the formulae herein), or a pharmaceutically acceptable salt of said compound; and a pharmaceutically acceptable carrier. The carrier(s) are "pharmaceutically acceptable" in that they are not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and U.S. Patent Publication Nos. US 2006/0094744 and US 2006/0079502.

The pharmaceutical compositions of the invention include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added.

For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved, in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Alternatively, the pharmaceutical compositions of this invention may be topically applied semipermeable matrices of solid hydrophobic polymers containing a compound of this disclosure, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers; and poly-D-(–)-3-hydroxybutyric acid. In another aspect, the pharmaceutical composition is a provided in a substrate. Examples of types of substrates and/or backings that are commercially available, include films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer). These substrates, in conjunction with the compounds of the disclosure are particularly useful as pharmaceutical compositions for wound dressings as they can be customized for the size and location of the wound. Alternatively, these substrates, in conjunction with the compounds of the disclosure are particularly useful as pharmaceutical compositions as or for use with bone grafts or implants as they can be customized for the size and location of the bone injury.

In one example, the substrate can be a bioresorbable implant that includes a polymeric matrix and a compound of this disclosure dispersed in the matrix. The polymeric matrix may be in the form of a membrane, sponge, gel, or any other desirable configuration. The polymeric matrix can be formed from biodegradable polymer. The polymeric matrix can comprise any one or combination of known materials including, for example, chitosan, poly(ethylene oxide), poly (lactic acid), poly(acrylic acid), poly(vinyl alcohol), poly(urethane), poly(N-isopropyl acrylamide), poly(vinyl pyrrolidone) (PVP), poly (methacrylic acid), poly(p-styrene carboxylic acid), polyp-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(caprolactone), polylactide, poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), collagen, gelatin, glycosaminoglycans (GAG), poly (hyaluronic acid), poly(sodium alginate), alginate, hyaluronan, agarose, polyhydroxybutyrate (PHB), and the like.

Application of the patient therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access. In one aspect the compositions of the disclosure are administered via an intracoronary medical device. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, and balloon-expanded stents.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026 and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this disclosure may be administered into the heart or the vasculature of the heart. In one aspect, the compositions are administered into the coronary artery. In another aspect, the compositions are injected directly into myocardium or cardiac valves.

In another embodiment, a composition of this invention further comprises a second therapeutic agent. In one embodiment, the second therapeutic agent is one or more additional compounds of the invention.

In another embodiment, the second therapeutic agent may be selected from any compound or therapeutic agent known to have or that demonstrates advantageous properties when administered with a compound having the same mechanism of action as the CXCR4 receptor compound of Formula A, Formula A-1, Formula I or Formula II.

In a particular embodiment, the second therapeutic is an agent useful in the treatment or prevention of a disease or condition selected from, bone marrow transplantation, chemosensitization, cancer, metastatic disease (e.g., cancer), auto-immune disease (e.g., rheumatoid arthritis), fibrosis disease (e.g., pulmonary), AIDS infection, cardiovascular disease, uveitis, inflammatory diseases, celiac disease HIV infection and stem cell-based regenerative medicine. For example, the second therapeutic agent is an agent useful in improving the quantity and quality of stem cell harvesting prior to bone marrow ablative cancer therapy.

For example, the second therapeutic agent can be selected from: G-CSF (granulocyte colony-stimulating factor), cyclophosphamide, rituximab and fludaraine. In a particular embodiment, the second therapeutic agent is G-CSF. For stem cell-based regenerative medicine applications, such as bone-healing, wound healing, ischemic disease and non-ischemic cardiomyopathy, the second therapeutic agent may be biocompatible cells. The biocompatible cells can also include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the tissue being treated. The cells can include cells that are provided in skin grafts, bone grafts, engineered tissue, and other tissue replacement therapies that are used to treat wounds.

In another embodiment the second therapeutic agent may be an agent used to treat blood-clotting disorders, sickle cell disease, liver disease, tumors, Gaucher's disease, radiation therapy, cardiomyopathies, ischemia, osteoporosis, osteopenia and diabetes.

In one embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) *Cancer Chemother. Rep*, 50: 219. Body surface area may be approximately determined from height and weight of the patient. See, e.g., Scientific Tables, Geigy Pharmaceuticals, Ardsley, N.Y., 1970, 537.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily treatment dose or one of multiple daily treatment doses (e.g., about 1 to 4 or more times per day). When multiple daily treatment doses are used, the unit dosage form can be the same or different for each dose.

METHODS OF TREATMENT

As used herein the term "subject" and "patient" typically means a human, but can also be an animal in need of treatment, e.g., companion animals (dogs, cats, and the like), farm animals (cows, pigs, horses, sheep, goats, and the like) and laboratory animals (rats, mice, guinea pigs, and the like).

The terms "treat" and "treating" are used interchangeably and include both therapeutic treatment and prophylactic treatment (reducing the likelihood of development). Therapeutic treatment means to decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

When a disease or disorder being treated is said to be associated with another disease or disorder, it means that the disease or disorder being treated results in whole or part from the disease or disorder with which it is associated.

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The invention also includes methods of treating diseases, disorders or pathological conditions which benefit from modulation of the CXCR4 receptor comprising administering an effective amount of a CXCR4 receptor compound of the invention to a subject in need thereof. Diseases and conditions which can benefit from modulation (inhibition or activation) of the CXCR4 receptor include, but are not limited to, bone marrow transplantation, chemosensitization, cancer, metastatic disease (e.g., cancer), auto immune disease (e.g., rheumatoid arthritis), fibrosis disease (e.g., pulmonary), AIDS infection, cardiovascular disease, uveitis, inflammatory diseases, celiac disease, HIV infection and stem cell-based regenerative medicine. For example, improving the quantity and quality of stem cell harvesting prior to bone marrow ablative cancer therapy.

Other treatment methods associated with stem cell-based regeneration for which the CXCR4 compounds of this disclosure may be used include treatment of bone injury, treatment of cardiac tissue damage, treatment of ischemia, treatment to promote wound healing, treatment to reduce scarring at a wound and treatment to increase homing or trafficking or stem cells to an area of injury.

Bone marrow transplantation can be for treatment of hematological and non-hematological malignancies, phagocyte disorders, anemias and myeloproliferative disorders, amyloidoses, radiation poisoning, congenital lysosomal storage disorders and congenital immunodefficiencies.

CXCR4 antagonists are useful for autologous and allogeneic hematopoietic stem cell transplantation (HSCT) to treat acquired as well as congenital diseases. The CXCR4 antagonist will be injected into the patients (autologous HSCT) or healthy HLA-matched donor (allogeneic HSCT) before the HSCT procedure. Injecting the CXCR4 antagonist induces mobilization of hematopoietic stem cells from bone marrow niche into the peripheral blood. Treatment with the novel CXCR4 antagonist will increase the yield of peripheral hematopoietic stem cells in the amount sufficient for their successful reengraftment or long term storage. HSCs collected during the apheresis procedure will be further reinfused into the patient undergoing HSCT.

The CXCR4 receptor compounds of the invention having antagonist activity are also useful for chemosensitization treatment of patients with hematological malignancies. These patients will be treated with CXCR4 antagonist to induce egress of malignant white blood cells from hematopoietic organs into peripheral circulation. As a result, these abnormal cells will be more readily targeted by chemotherapeutic agents administered intravenously.

Accumulated preclinical data suggests that CXCR4 is essential for the development and progression of inflammatory diseases including but not limited to rheumatoid arthritis and inflammatory bowel disease. Therefore antagonism of CXCR4 can be beneficial for the patients suffering from these disorders. CXCR4 is also a coreceptor for the entry of several HIV-1 strains. Pharmacological targeting of CXCR4-dependent can potentially modulate HIV-1 tropism and its infectivity.

In one embodiment, CXCR4 agonist compounds of the disclosure can be used to modulate (e.g., increase) stem and/or progenitor cell recruitment, trafficking and homing to a site of injury. Once at the site, the stem and/or progenitor cells can treat damaged tissue. Therapeutic interventions which prolong or re-establish the stem cell homing process and activate tissue protective mechanisms may be beneficial for patients that have suffered tissue damage, such as after a heart attack or stroke, as well as patients with wounds, bony injury, diabetes, peripheral artery disease, critical limb ischemia, ischemic kidney disease, and spinal cord injury.

Cardiac-Related Disorders/Injuries

In another embodiment, CXCR4 agonist compounds of the disclosure can be used to treat cardiac tissue damage in a subject in need thereof. The cardiac tissue damage may be the result of, but not limited to, ischemia, myocardial infarction, valvular disease, cardiomyopathy, and congestive heart failure. In one embodiment, compounds of the disclosure may be administered post-myocardial infarction. In another embodiment of the disclosure, CXCR4 agonist compounds of the disclosure are administered locally or in substantial proximity to the damaged cardiac tissue to recruit, retain and activate stem cells leading to tissue repair and revascularization.

In one aspect, the period of time that a CXCR4 agonist compound of the instant disclosure is administered to the cells of the damaged cardiac tissue can comprise from about onset of the wound and/or tissue injury to about days, weeks, or months after tissue injury.

In certain embodiments of the methods of the disclosure, CXCR4 agonist compounds of the disclosure are used in cell therapy protocols, particularly in cell therapy protocols in order to contribute to the repair and/or regeneration of myocardial tissue in pathophysiological situations in which there has been a loss of functional cardiac tissue. In one embodiment, methods and compositions can be used for cardiac tissue regeneration, or in the preparation of a pharmaceutical composition for the treatment of an ischemic heart disease, or in the preparation of a pharmaceutical composition for the post-myocardial infarction treatment, or for the treatment of congestive heart failure, or in the preparation of a pharmaceutical composition to stimulate angiogenesis.

Treatment of Wounds

Methods provided herein are used to promote or accelerate wound closure and wound healing, mitigate scar fibrosis of the tissue of and/or around the wound, inhibit apoptosis of cells surrounding or proximate the wound, and/or facilitate revascularization of the wounded tissue in a subject. In one embodiment, the invention provides methods for promoting wound healing by administering an effective amount of a CXCR4 receptor agonist compound of the disclosure to a subject in need thereof. The CXCR4 receptor agonist compounds of the disclosure can be administeredproximally to the site of a wound. In certain embodiments, the wounds to be treated may be, for example, ischemic, nonischemic and/or aberrant wounds. In other embodiments, the wounds to be treated may be, for example, chronic or acute wounds.

The CXCR4 agonist compounds described herein can be used to treat a wound (e.g., to promote wound healing) in a subject in need thereof. Treatment comprises administering to a subject in need thereof and effective amount of a CXCR4 agonist compound described herein. In one embodiment, the wound is a surface wound. In another embodiment, the wound is a surgical wound. In a further embodiment, the wound is a burn. In yet another embodiment, the wound is the result of radiation exposure.

In a further embodiment, the wound is an internal wound. In a specific aspect, the internal wound is a chronic wound. In another specific aspect, the wound is a vascular wound. In yet another specific aspect, the internal wound is an ulcer. In more specific aspect, the ulcer is a diabetic ulcer. In yet another more specific aspect, the ulcer is a decubitus ulcer.

In another aspect of the invention, a CXCR4 agonist compound of the disclosure is administered to the wound or cells proximate to the wound in an amount effective to promote or accelerate wound closure. In yet another aspect of the invention, a CXCR4 agonist compound of the disclosure is administered to the wound or cells proximate the wound in an amount effective to mitigate scar fibrosis of the tissue of and/or around the wound. In a further aspect of the invention, a CXCR4 agonist compound of the disclosure is administered to the wound or cells proximate the wound in an amount effective to inhibit apoptosis of cells surrounding or proximate the wound. In an additional aspect of the invention, a CXCR4 agonist compound of the disclosure is administered to the wound or cells proximate the wound in an amount effective to facilitate revascularization of the wounded tissue.

Examples of wounds to which the present method is useful in promoting or accelerating wound closure or wound healing, mitigating scar fibrosis of the tissue around the wound, inhibiting apoptosis of cells surrounding or proximate the wound, and/or facilitating revascularization of the wounded tissue include, but are not limited to, abrasions, avulsions, blowing wounds, burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the method include acute conditions or wounds; such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies, trauma-induced injuries including cuts, incisions, excoriations; injuries sustained from accidents; post-surgical injuries, as well as chronic conditions; such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage; aneurysm and post-operation infections.

In another embodiment, the methods are used for diabetic wound healing or accelerating healing of leg and foot ulcers secondary to diabetes or ischemia in a subject.

The method need not achieve complete healing or closure of the wound; it is sufficient for the method to promote any degree of wound closure. In this respect, the method can be employed alone or as an adjunct to other methods for healing wounded tissue.

The present disclosure also relates to methods and composition of reducing scar formation during wound healing in a subject. In the method, the compounds of the disclosure administered directly to the wound or cells proximate the wound at an amount effective to reduce scar formation in and/or around the wound. The wound can include any injury to any portion of the body of a subject. According to embodiments, methods are provided to ameliorate, reduce, or decrease the formation of scars in a patient that has suffered a burn injury. According to preferred embodiments, methods are provided to treat, reduce the occurrence of, or reduce the probability of developing hypertrophic scars in a patient that has suffered an acute or chronic wound or injury.

The CXCR4 receptor agonist of the disclosure may be administered at or near the wound site by, for example, injection of a solution, injection of an extended release formulation, or introduction of a biodegradable implant comprising the CXCR4 receptor, agonist of the disclosure. The CXCR4 receptor agonist of the disclosure may also be administered (optionally in combination with other methods) to the wound site by coating the wound or applying a bandage, packing material, stitches, etc. that are coated or treated with a CXCR4 receptor agonist of the disclosure.

In one example, the period of time that an CXCR4 agonist compound of the instant disclosure is administered to the cells of the wound and/or proximate the wound can comprise from about onset of the wound and/or tissue injury to about days, weeks, or months after tissue injury.

In one embodiment, provided herein is a method of accelerating healing of leg and foot ulcers secondary to diabetes or ischemia in a subject. The compounds of the disclosure are also useful for treating other wounds and injuries, as well as diseases, disorders, and conditions such as burns, skin aging, in addition to the uses for diabetic wound healing described herein.

The compositions and methods of the invention disclosed herein are useful for treating a patient having acute or chronic wounds. Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions, and/or long-standing wounds. Although particular embodiments are exemplified herein, it is understood that a similar approach can also be used to treat other types of wounds using suitable autologous and/or allogeneic cells in addition to the compositions of the disclosure.

The compounds of the instant disclosure can be delivered to the wound or cells proximate the wound by administering compound of the instant disclosure to the wound or cells. The target cells can include cells within or about the periphery of the wound or ex vivo cells that are biocompatible with tissue being treated. The biocompatible cells can also include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the tissue being treated. The cells can include cells that are provided in skin grafts, bone grafts, engineered tissue, and other tissue replacement therapies that are used to treat wounds.

In another aspect of the present invention, CXCR4 receptor agonists can be formulated for topical administration to treat surface wounds. Topical formulations include those for delivery via the mouth (buccal) and to the skin such that a layer of skin (i.e., the epidermis, dermis, and/or subcutaneous layer) is contacted with CXCR4 agonist. Topical delivery systems may be used to administer topical formulations of the present invention.

Bone Defects/Injuries

The methods of the disclosure include the use of CXCR4 agonist compounds described herein, to treat many types of systemic or local bone defects, such as bony defects from injuries, fractures, or diseases like osteoporosis, osteomyelitis or cancer. In another embodiment, the compounds are used to treat osteonecrosis or avascular necrosis of bone. In one embodiment, osteonecrosis is not a specific disease but a condition in which there is death of a localized area of bone. Examples of osteonecrosis to which the compounds described herein may be useful to treat include traumatic and nontraumatic osteonecrosis. In certain embodiments, the osteonecrosis is associated with the hip, shoulder, jaw, arm, and knee. In another embodiment, the osteonecrosis is caused by a displaced (separated) fracture, high doses of corticosteroids (especially when given for long periods of time), chronic alcohol use, certain blood-clotting disorders, sickle cell disease, liver disease, tumors, Gaucher's disease, radiation therapy, and decompression sickness, or idiopathic osteonecrosis.

In another embodiment the bony injury is associated with osteoporosis, osteomyelitis or osteopenia. In yet another embodiment the bony injury results from cancer. In additional embodiments, the bony injury results from removal of a cyst or cancer from a bone.

In another embodiment, the CXCR4 agonist compounds of the invention are administered to a patient either simultaneous with or after the patient has received a bone graft.

CXCR4 agonists may be used in accordance with the invention to treat hematopoietic cells, in patients in need of such treatment, for example in bone development, bone repair, and skeletal regeneration therapy. CXCR4 can be used to treat many types of systemic or local bone defects, such as bony defects from injuries, fractures, or diseases like osteoporosis, osteomyelitis or cancer. The invention includes methods of promoting healing of a bone fracture in an osteopenic human. The present invention provides compositions and methods useful for enhancing bone and wound healing.

In another embodiment, the compositions of the disclosure can be used in maintaining ductal or islet cell survival, proliferation, and mobilization during pancreatic regeneration.

In certain embodiments of the methods of the disclosure, CXCR4 agonist compounds of the disclosure can be used in treating an ischemic disorder in a subject, the method comprising administering to ischemic tissue of the subject a CXCR4 agonist compound. In another embodiment the ischemic disorder comprises at least one of the following disorders: a peripheral vascular disorder, a pulmonary embolus, a venous thrombosis, a myocardial infarction, a transient ischemic attack, unstable angina, cerebral vascular ischemia, a reversible ischemic neurological deficit, ischemic kidney disease, ischemic liver disease or a stroke disorder.

In one embodiment, the ischemia is peripheral artery disease. In another embodiment, the ischemia is critical limb ischemia.

In another embodiment, an ischemic disorder can that can be treated with the compounds of the disclosure includes an iatrogenically induced ischemic disorder. Examples of the iatrogenic ischemic disorders amenable to use of the compounds of the instant disclosure include those resulting from a subject undergoing, for example, angioplasty, heart surgery, lung surgery, spinal surgery, brain surgery, vascular surgery, abdominal surgery, kidney surgery, or organ transplantation surgery. In certain embodiments, the organ transplantation can comprise heart, lung, pancreas, kidney, or liver transplantation surgery. In a specific embodiment, the ischemia is associated with organ or cell transplantation procedure.

In one embodiment, the method of treatment of ischemic disorder with the compounds of the disclosure may be further enhanced by increasing the number of stem cells and/or progenitor cells in the proximity of the area to be treated. One example of a particular type of stem cell that can be injected or infused in accordance with the present invention is an autologous mesenchymal stem cell (MSC). An example of a progenitor cell that can be potentially injected or infused is an autologous, syngeneic, or allogeneic bone marrow derived multipotent adult progenitor cell (MAPC).

The invention also relates to a method of treating cardiac tissue damage, bone injury, or ischemia or promoting wound healing, or reducing the formation of scarring or increasing homing or trafficking of stem cells in a subject in need thereof using a CXCR4 agonist compound.

In a first embodiment, the method is a method of treating cardiac tissue damage, bone injury, or ischemia or promoting wound healing, or reducing the formation of scarring or increasing homing or trafficking of stem cells in a subject in need thereof, comprising administering to the subject an effective amount of a compound of Formula A,

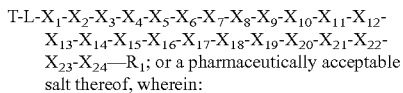

or a pharmaceutically acceptable salt thereof, wherein:

L is a linking moiety selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to the N terminal nitrogen of X$_1$ or the next present amino acid residue if X$_1$ is absent; T is a lipophilic tether moiety bonded to L; and R$_1$ is OR$_2$ or N(R$_2$)$_2$, each R$_2$ is independently H or alkyl, wherein at least three contiguous X$_1$-X$_{24}$ amino acid residues are present, and wherein:

X$_1$ is a valine residue or absent,

X$_2$ is an isoleucine residue or absent,

X$_3$ is a leucine residue or absent,

X$_4$ is a valine residue, a glycine residue or absent,

X$_5$ is a methionine residue, a glycine residue, a methyl serine residue, a homoserine residue, a propargyl glycine residue, a cysteine residue or absent, X$_6$ is a glycine residue or absent, X$_7$ is a tyrosine residue, a glutamine residue or absent X$_8$ is a glutamine residue, a lysine residue or absent, X$_9$ is a lysine residue, or a 2-aminoisobutyric acid (Aib) residue, X$_{10}$ is a lysine residue, a leucine residue, or a proline residue, X$_{11}$ is a leucine residue, an arginine residue, a d-leucine residue, a proline residue, a photoleucine residue, or a histidine residue, X$_{12}$ is an arginine residue, a cyclohexyl alanine residue, a serine residue or a proline residue, X$_{13}$ is a serine residue, a methionine residue, a d-proline residue, a hydroxy proline residue, an arginine residue or a proline residue, or a threonine residue, X$_{14}$ is a methionine residue, a threonine residue, an alanine residue, a histidine residue, a methyl serine residue, a proline residue, a Dpr residue, a hydroxy proline residue, a serine residue, a norleucine residue, a homoserine residue a tryptophan residue, or a glycine residue, X$_{15}$ is a threonine residue, an aspartic acid residue, a d-proline residue, a histidine residue, or a methionine residue, X$_{16}$ is an aspartic acid residue, a lysine residue or a threonine residue, X$_{17}$ is a lysine residue, a tyrosine residue, a d-lysine residue or an aspartic acid residue, X$_{18}$ is a tyrosine residue, a phenylalanine residue, a lysine residue, a naphthyl alanine residue, a d-arginine residue or a d-tyrosine residue, X$_{19}$ is an arginine residue, a lysine residue, a leucine residue, a citrulline residue, a d-arginine residue or a tyrosine residue, X$_{20}$ is a leucine residue, a valine residue, a norleucine residue, a d-leucine residue, an arginine residue, or absent, X$_{21}$ is a histidine residue, a leucine residue or absent, X$_{22}$ is a leucine residue or absent, X$_{23}$ is an arginine residue or absent, and X$_{24}$ is a valine residue or absent;

wherein when X$_1$-X$_4$ and X$_{21}$-X$_{24}$ are absent X$_5$-X$_{20}$ is not MGYQKKLRSMTDKYRL (SEQ ID NO:52) and wherein when X$_1$-X$_8$ is absent and X$_{17}$ is aspartic acid then X$_{18}$ is d-tyrosine or when X$_1$-X$_8$ is absent and X$_{18}$ is tyrosine then X$_{17}$ is d-lysine. In a first aspect of the first embodiment, L is selected from C(O), S*(O)$_2$ and OC*(O). In a first embodiment of the first aspect, L is C(O). In a second aspect of the first embodiment or its first aspect or the first embodiment of the first aspect, X$_1$-X$_4$ and X$_{21}$-X$_{24}$ are absent and X$_5$ is a methionine residue, X$_6$ is a glycine residue, X$_7$ is a tyrosine residue, X$_8$ is a glutamine residue, X$_9$ is a lysine residue or a 2-aminoisobutyric acid (Aib) residue, X$_{10}$ is a lysine residue or a proline residue, X$_{11}$ is a leucine residue or an arginine residue, X$_{12}$ is an arginine residue, a serine residue or a cyclohexyl alanine residue, X$_{13}$ is a serine residue, a methionine residue, an arginine residue, or a proline residue, X$_{14}$ is a methionine residue, an isoleucine residue, a histidine residue, a glycine residue, a threonine residue, a serine residue or a d-proline residue, X$_{15}$ is a threonine residue, an aspartic acid residue, a methionine residue or a d-proline residue, X$_{16}$ is an aspartic acid residue, a threonine residue, or a lysine residue, X$_{17}$ is a lysine residue, or an aspartic acid residue X$_{18}$ is a tyrosine residue, a phenylalanine residue, a lysine residue, a d-arginine, a d-tyrosine residue, or a naphthyl alanine residue, X$_{19}$ is an arginine residue, a lysine residue, a citrulline residue, a leucine residue or a tyrosine residue, X$_{20}$ is a leucine residue, a norleucine residue, a valine residue, an arginine residue or absent.

In a third aspect of the first embodiment or its first aspect or the first embodiment of the first aspect, the compound is selected from:

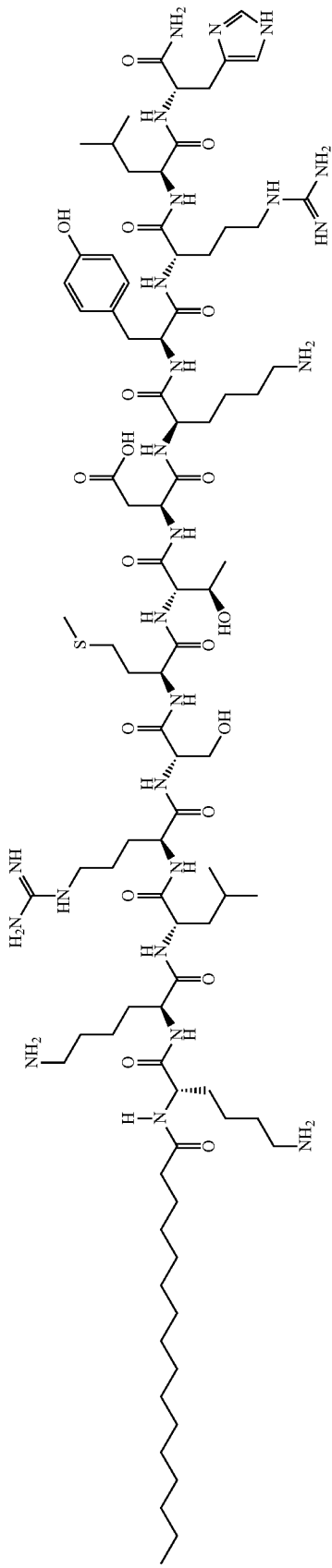
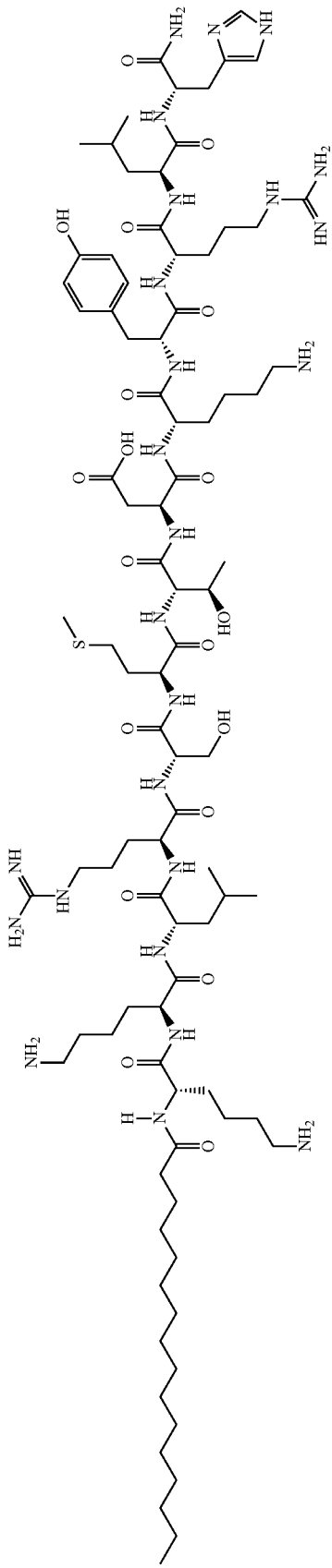

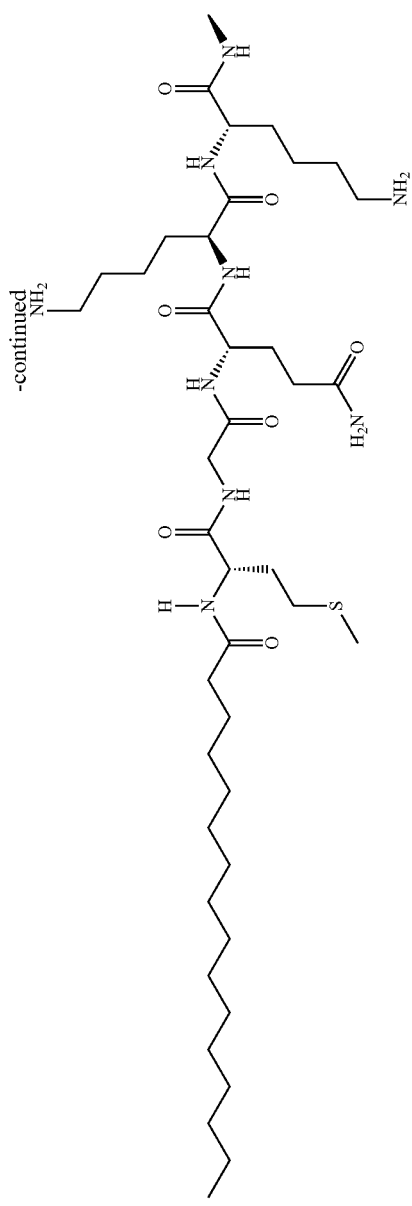
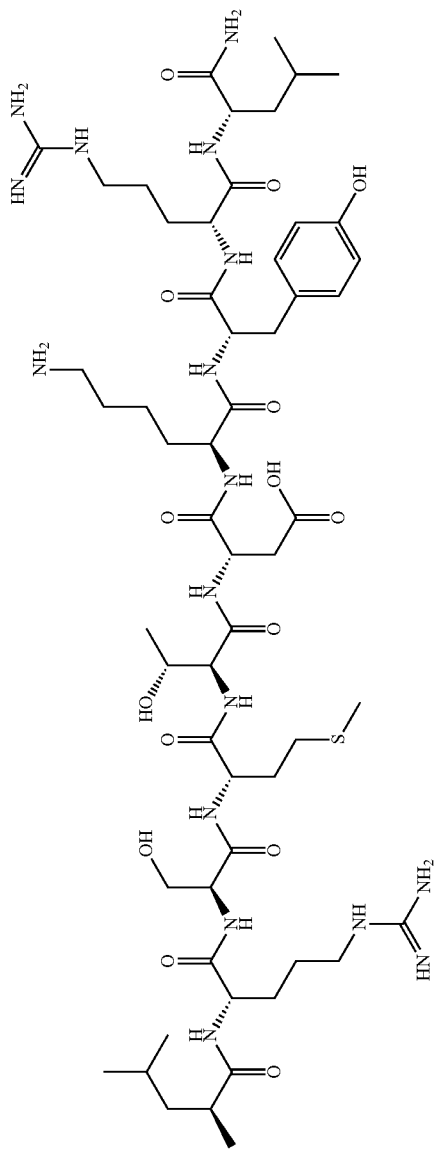

-continued
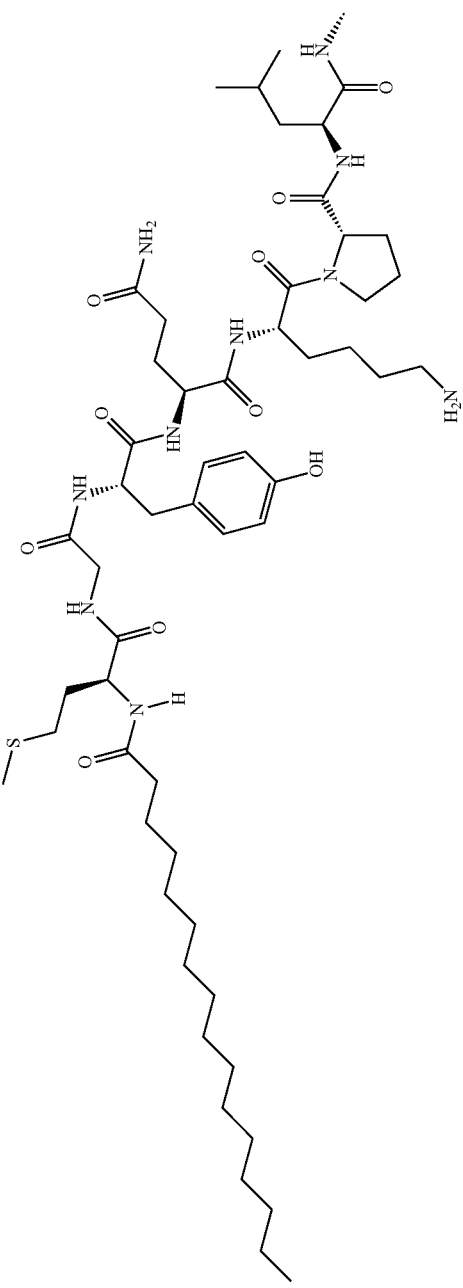
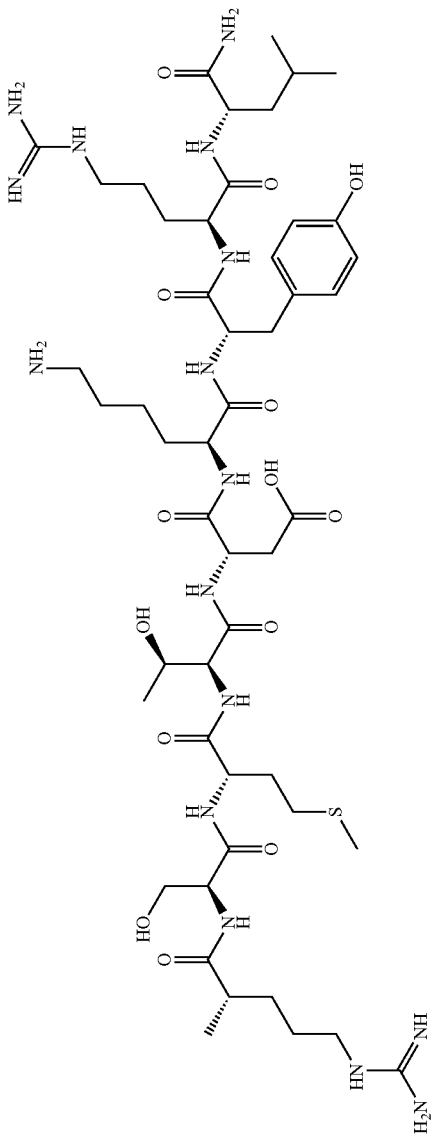

-continued
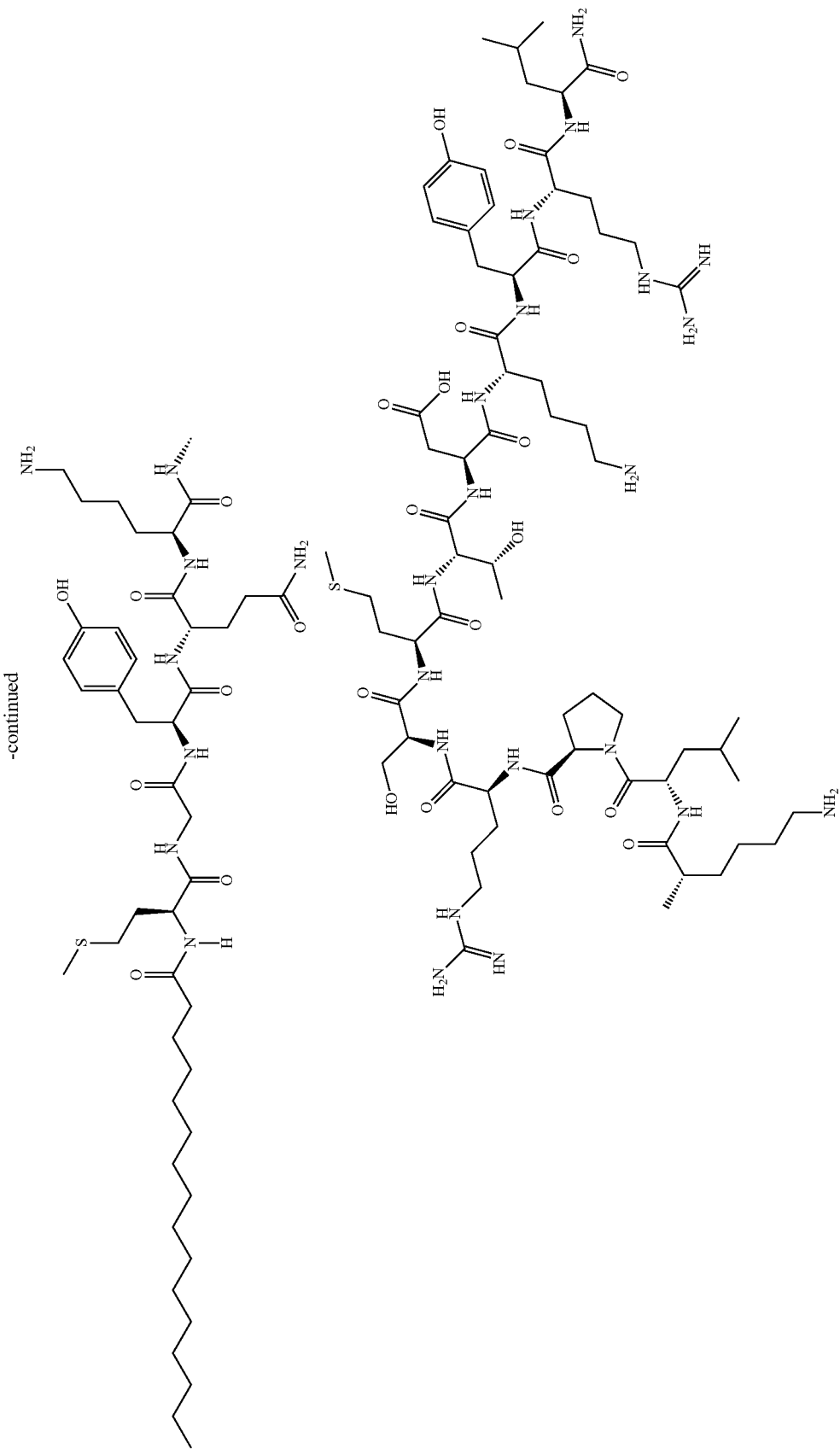

-continued
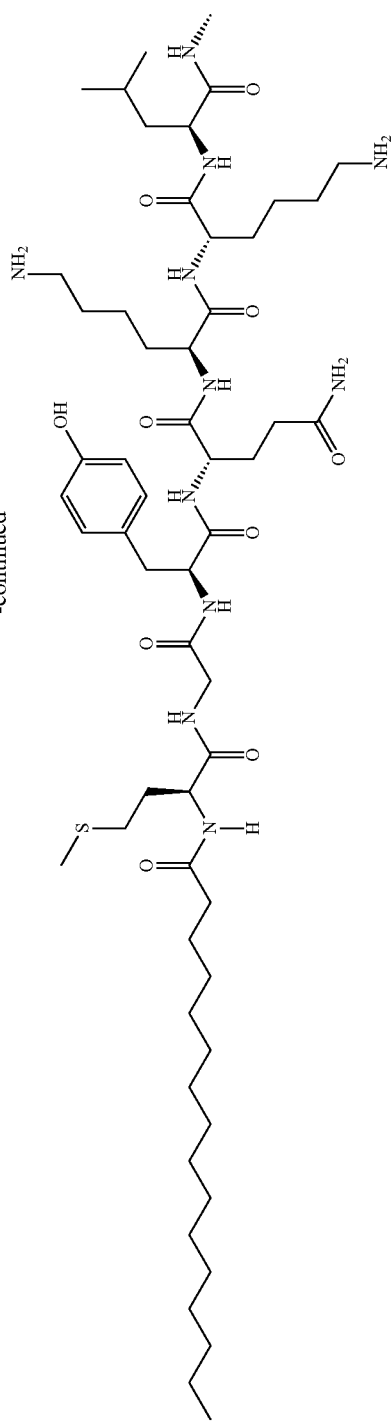
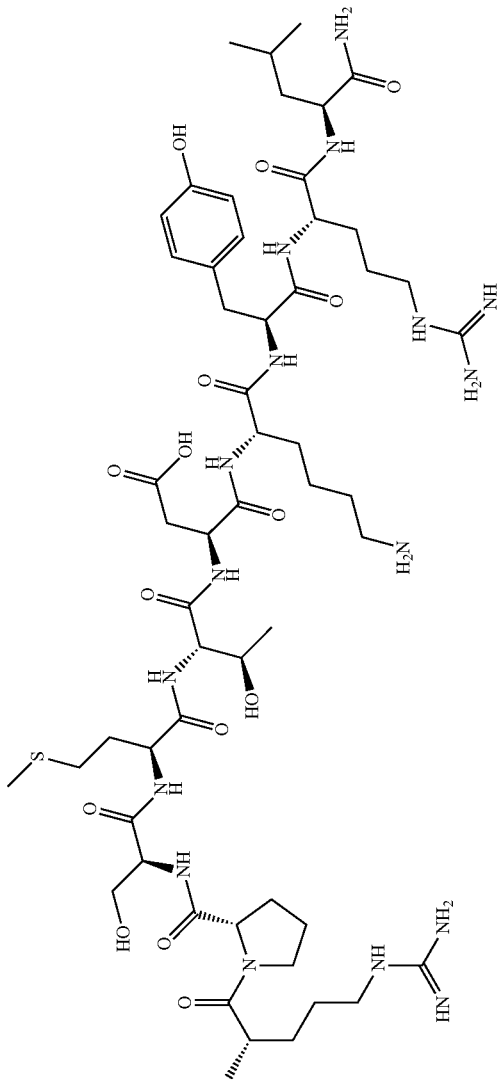

-continued
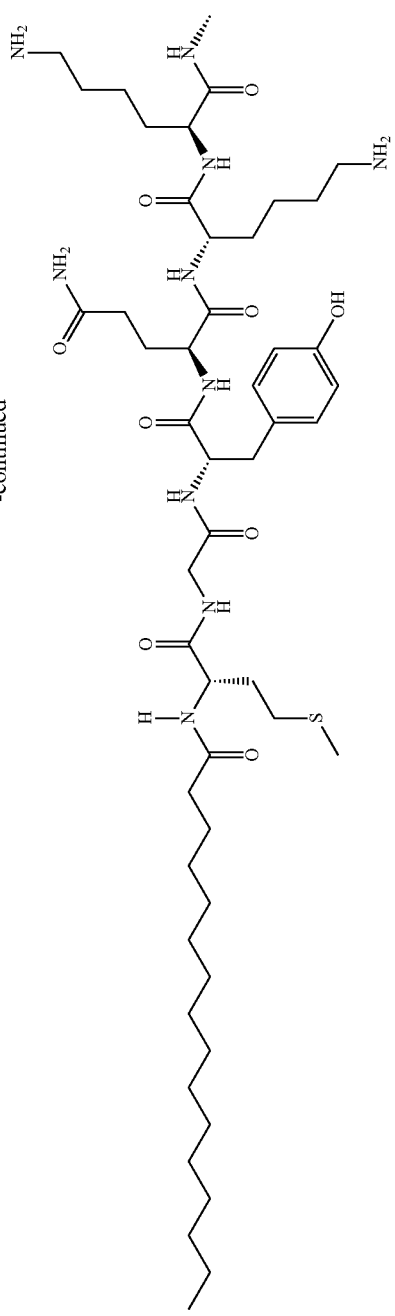
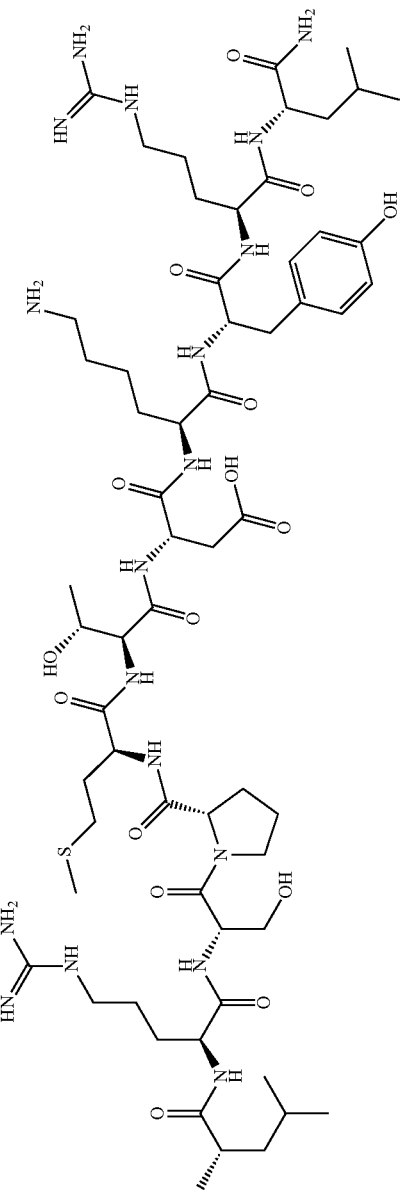

-continued
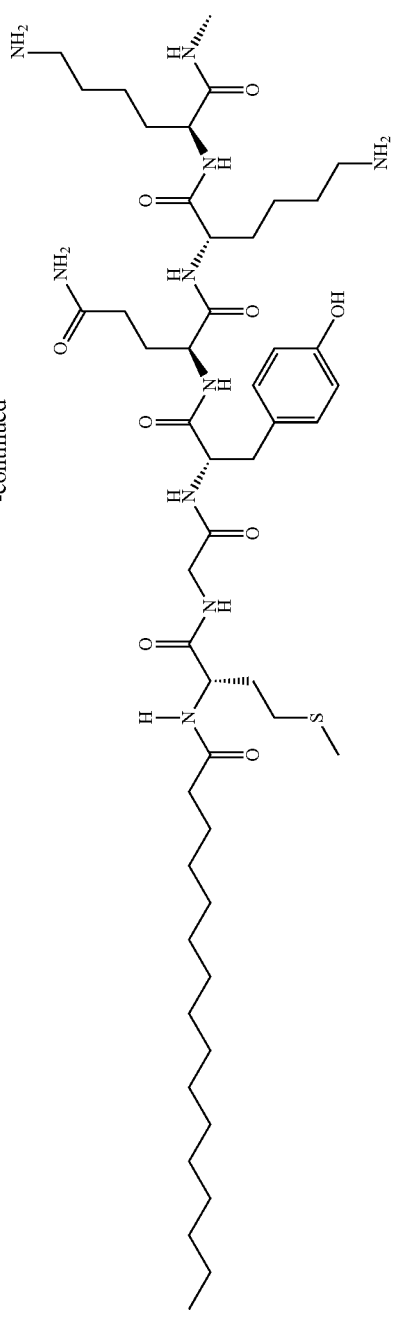
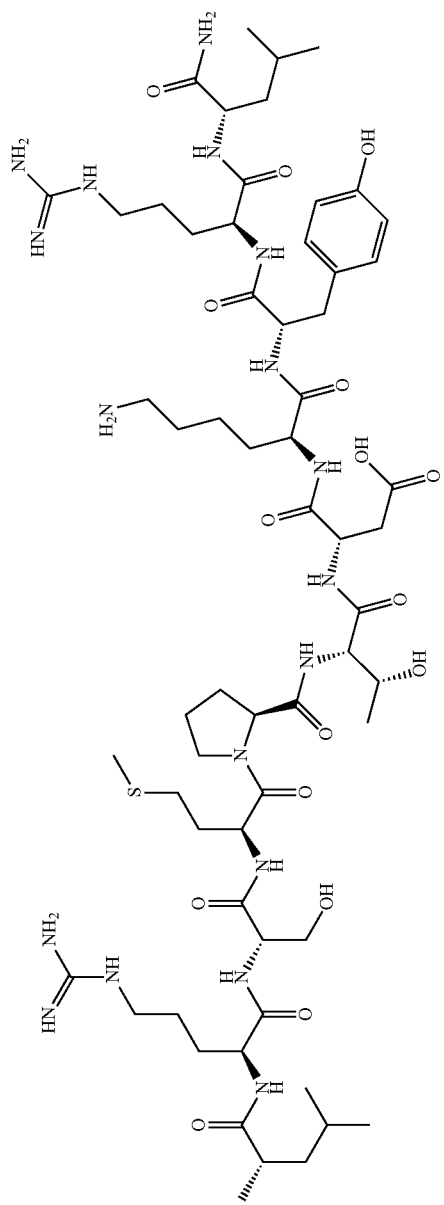

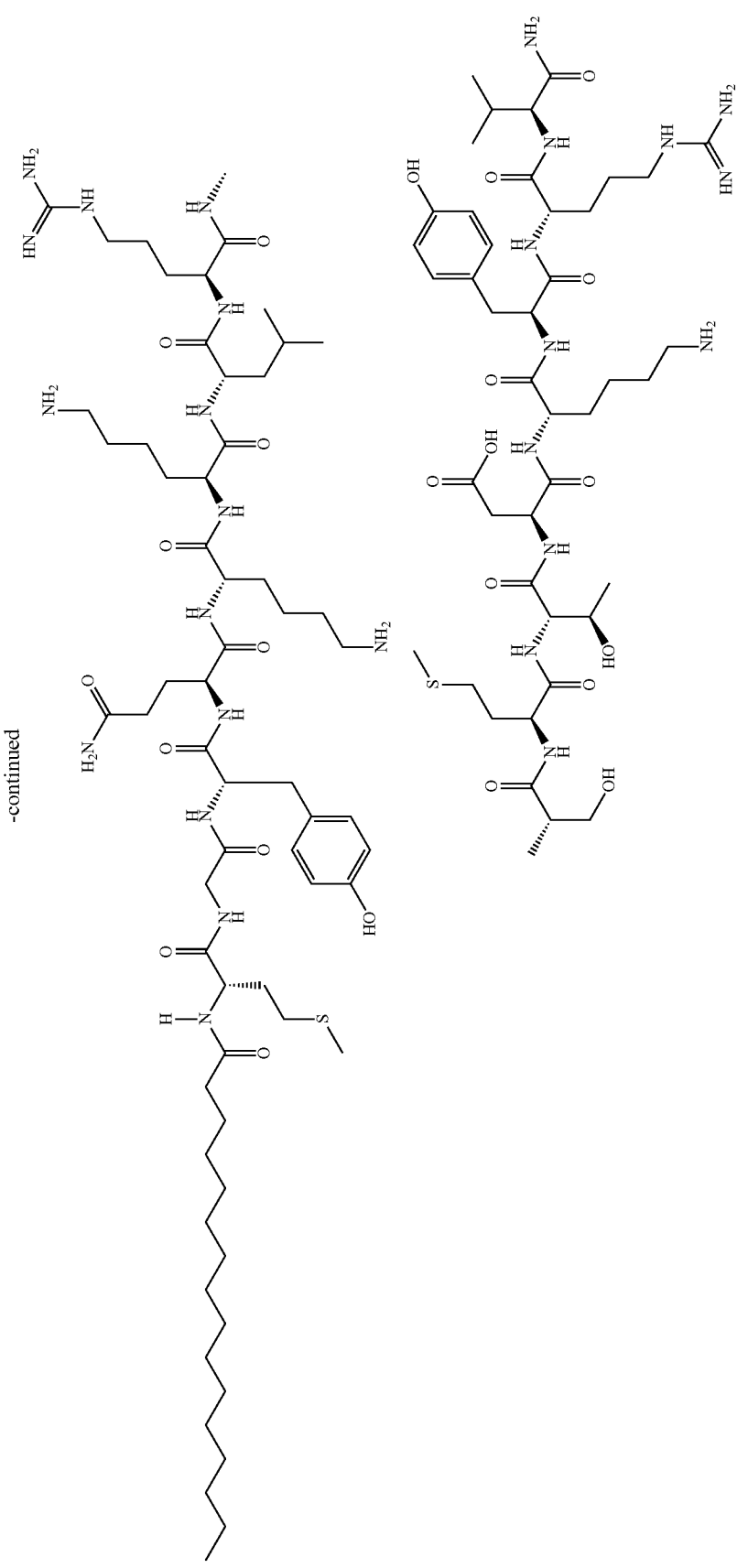

-continued
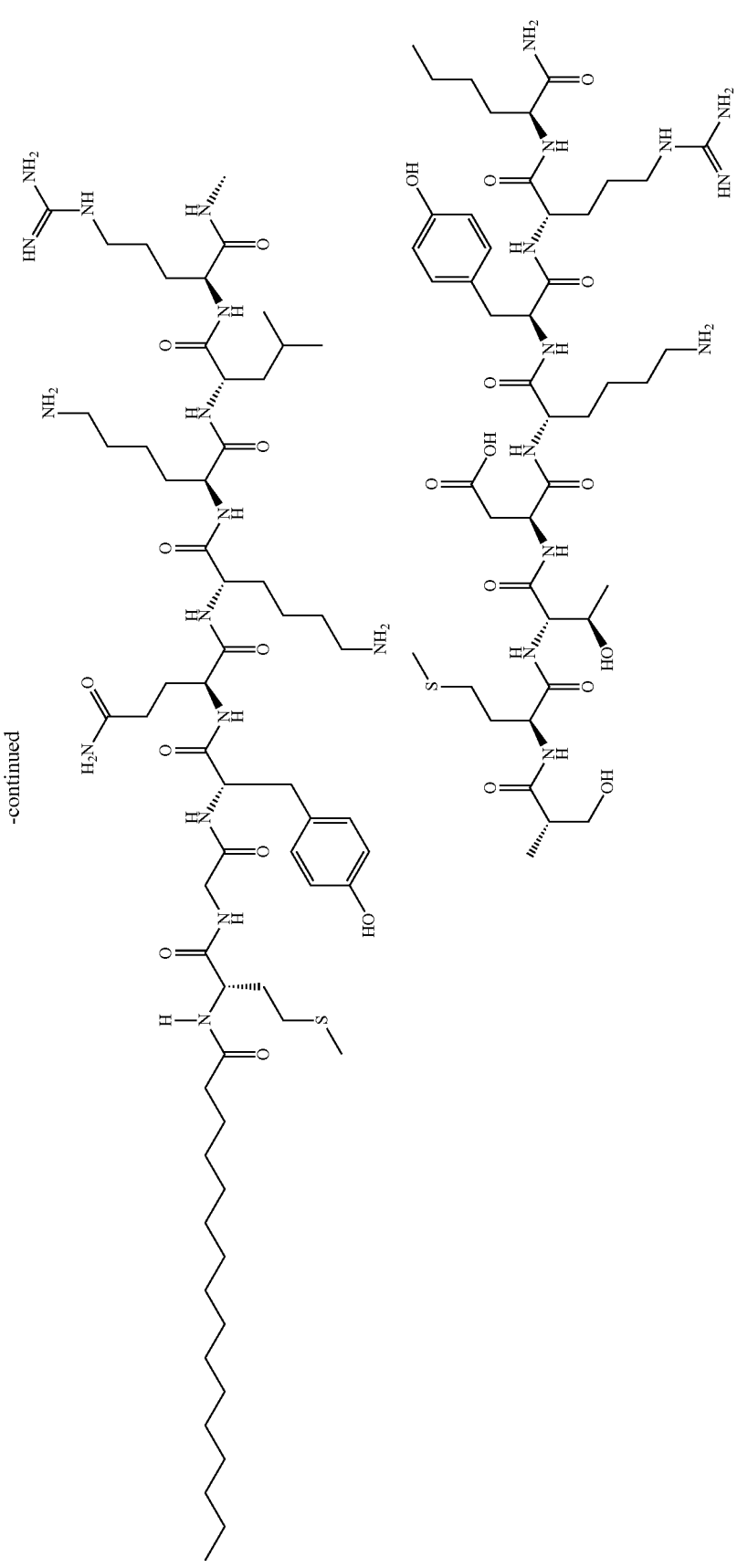

-continued
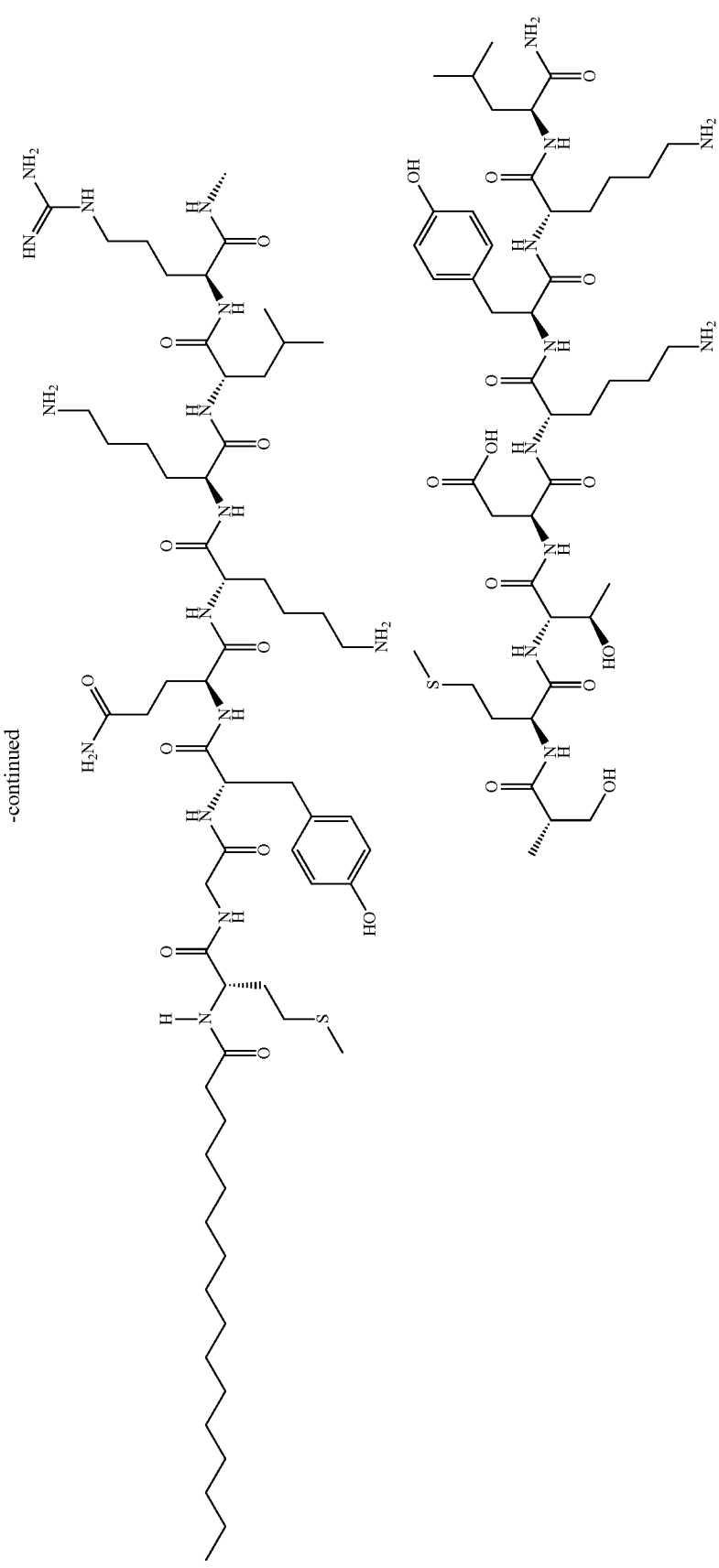

-continued
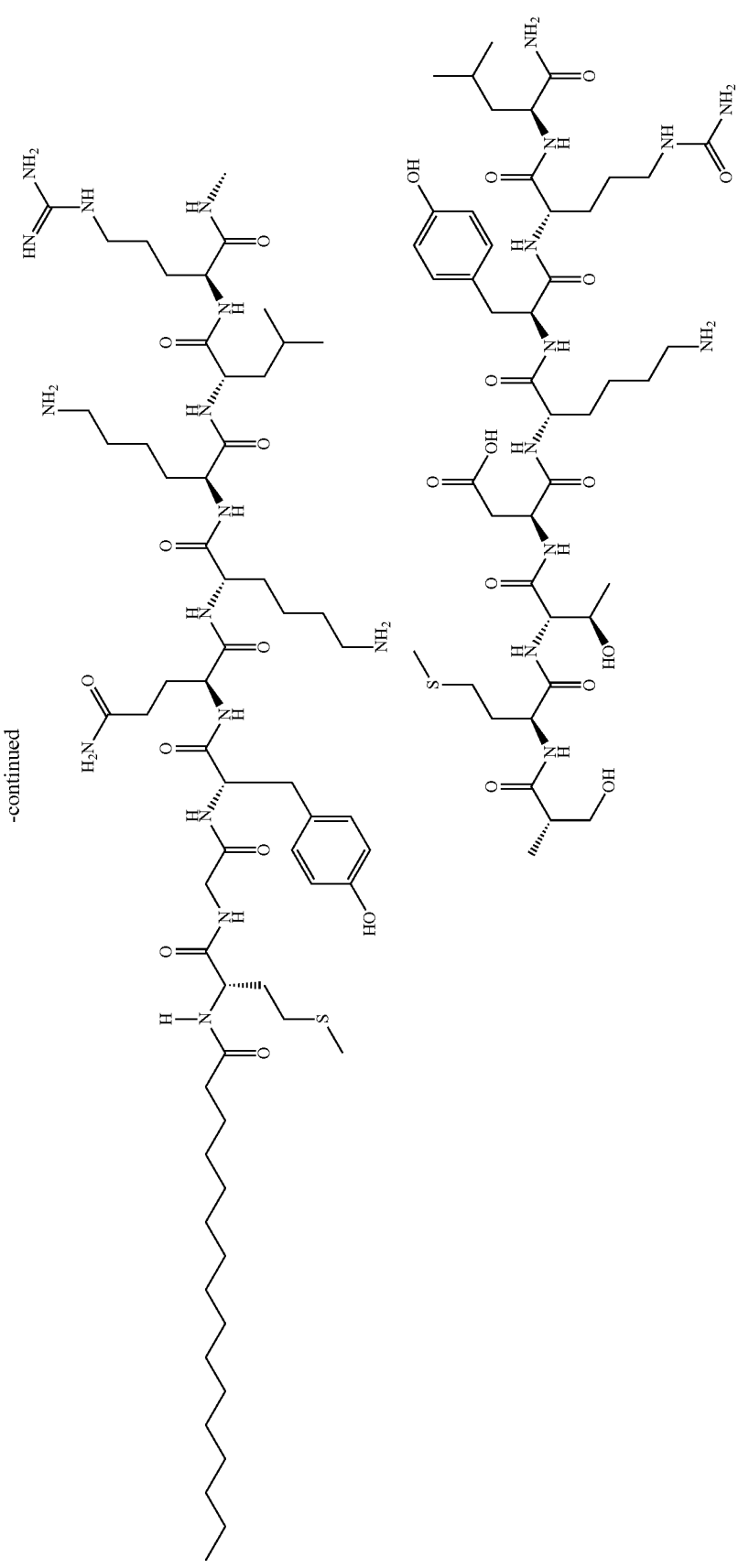

-continued
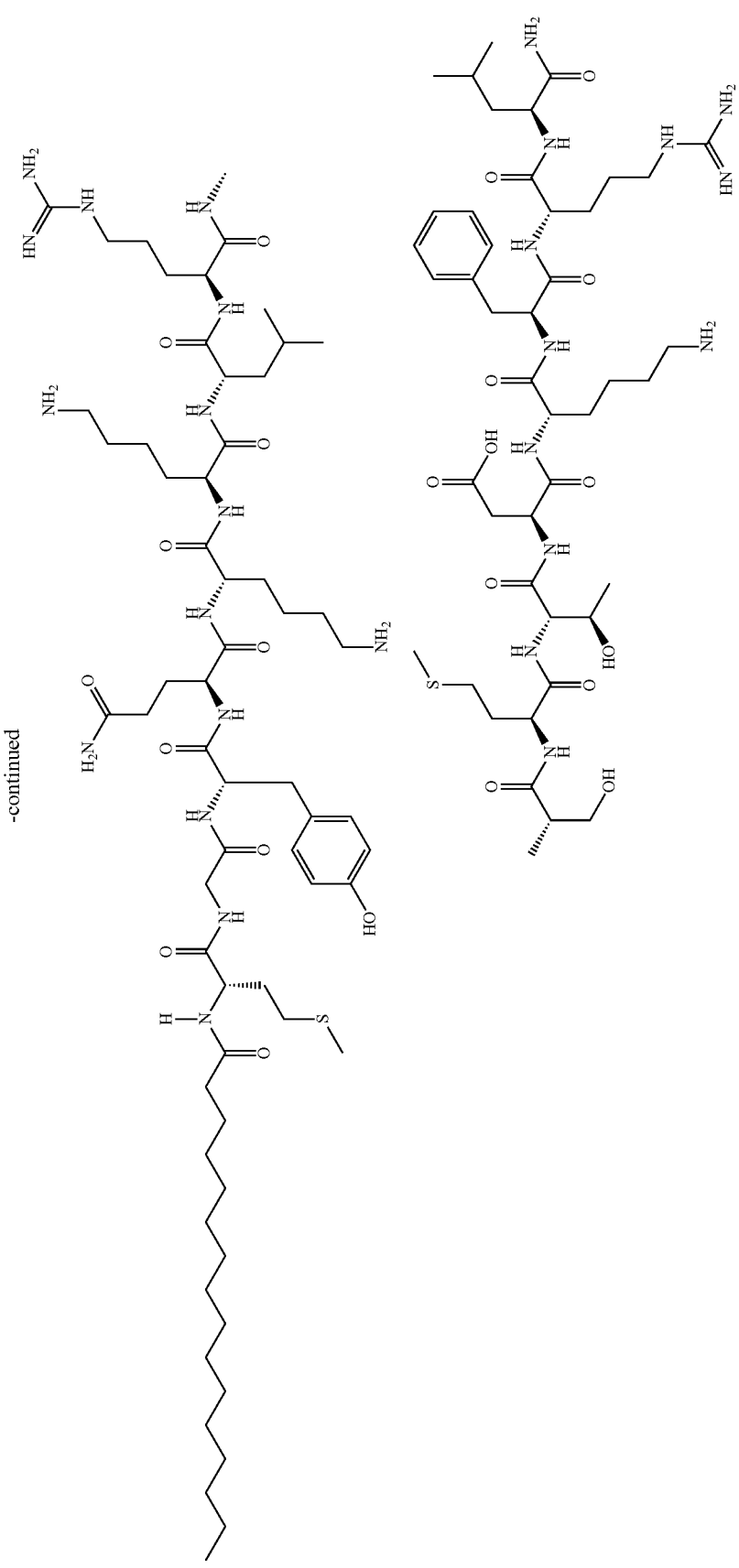

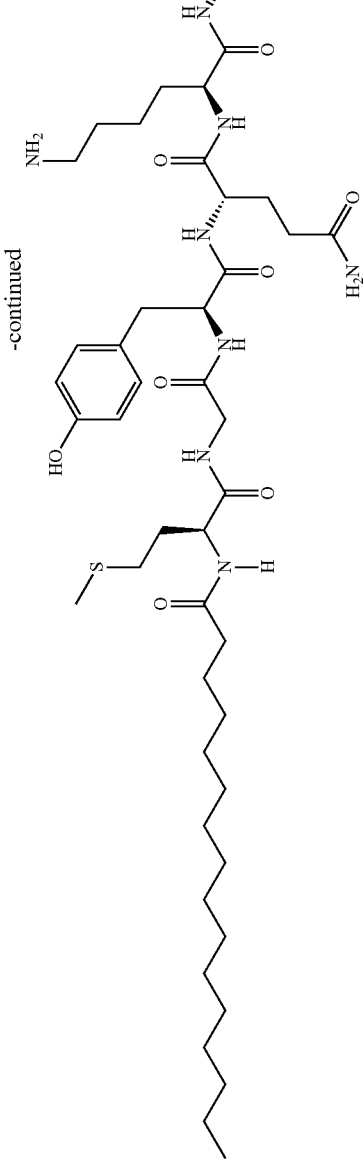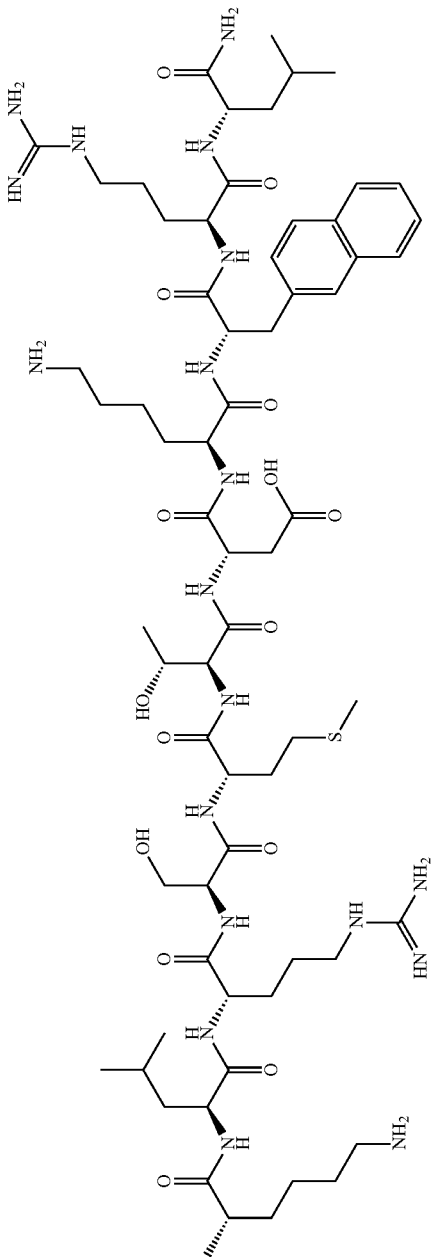

-continued
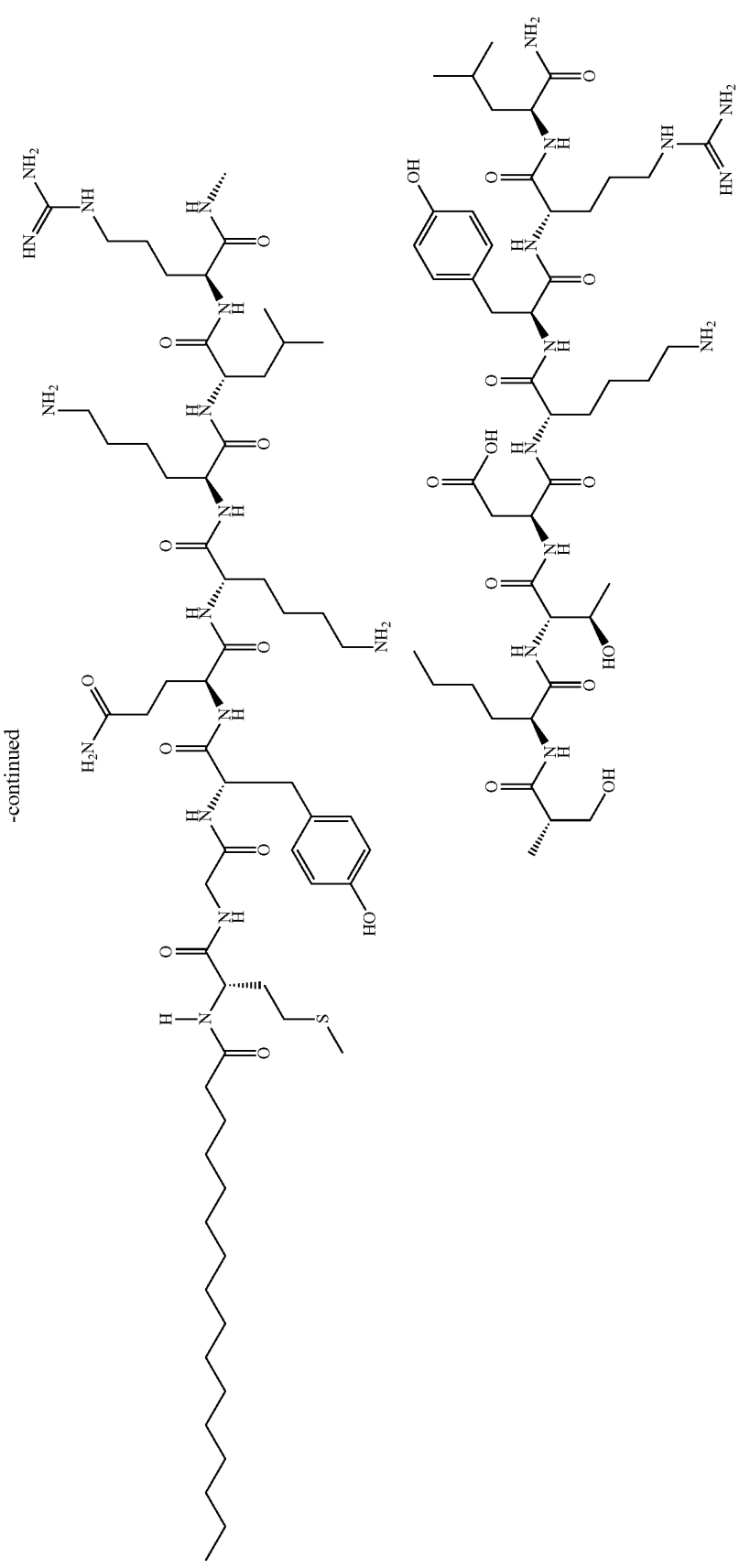

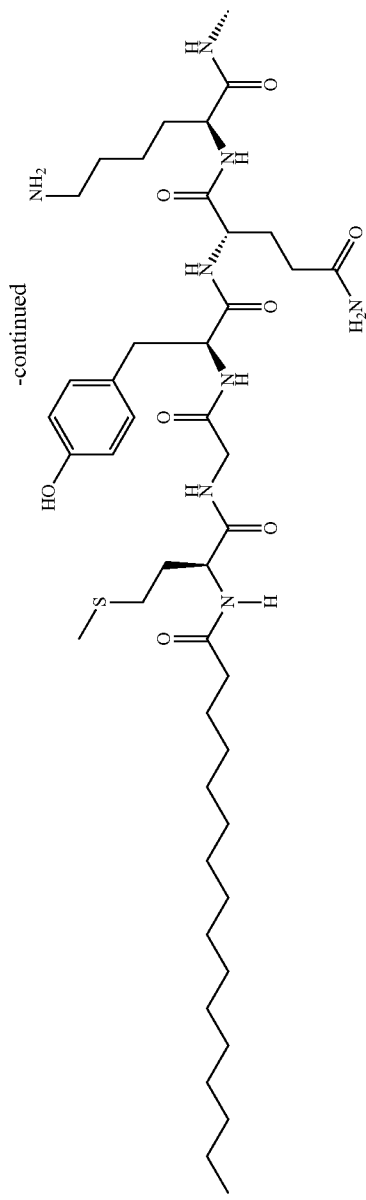
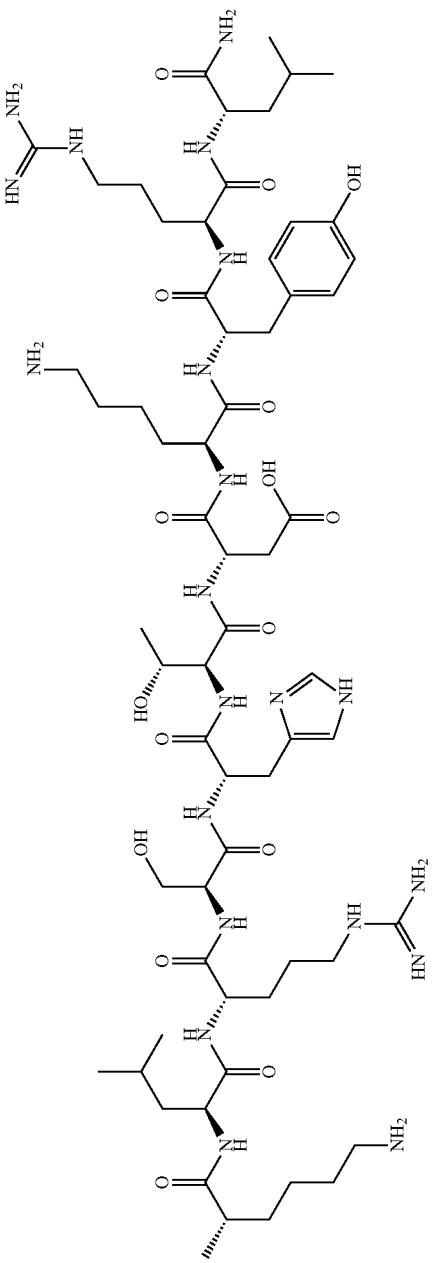

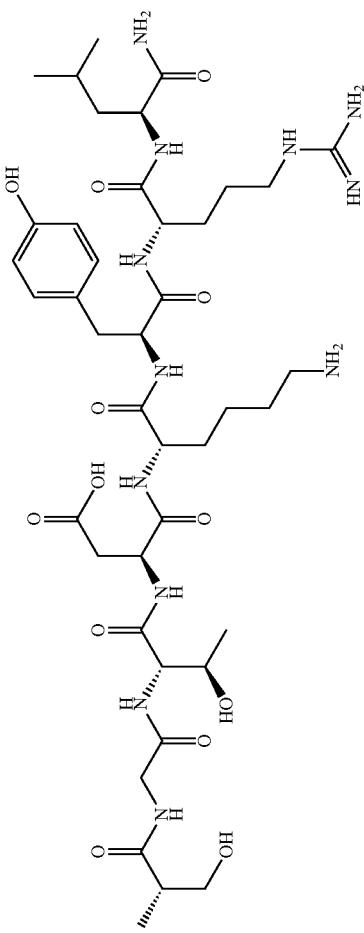
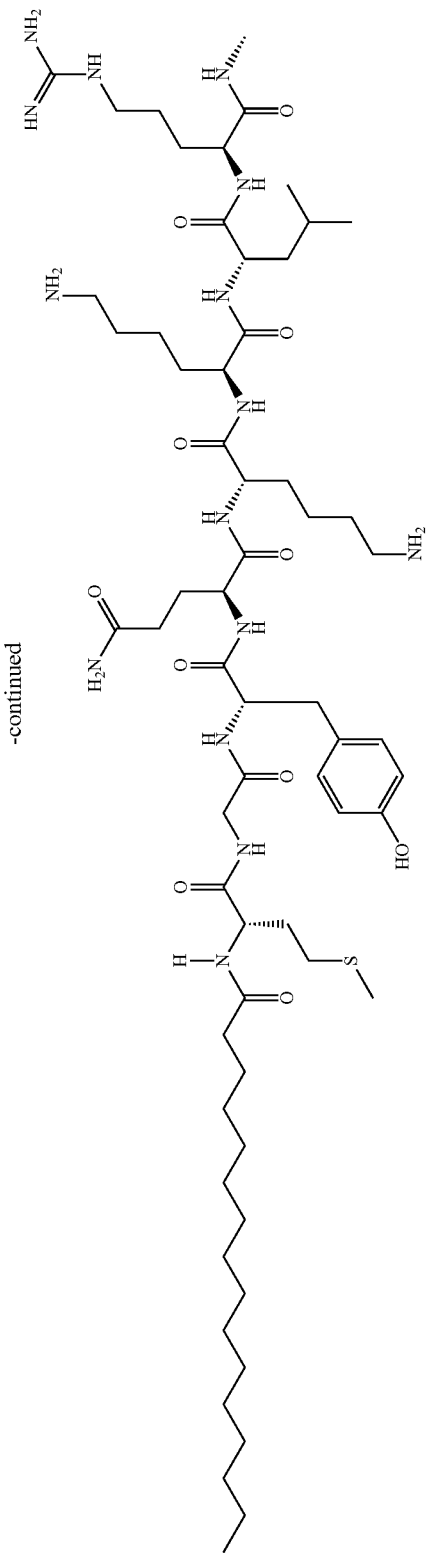

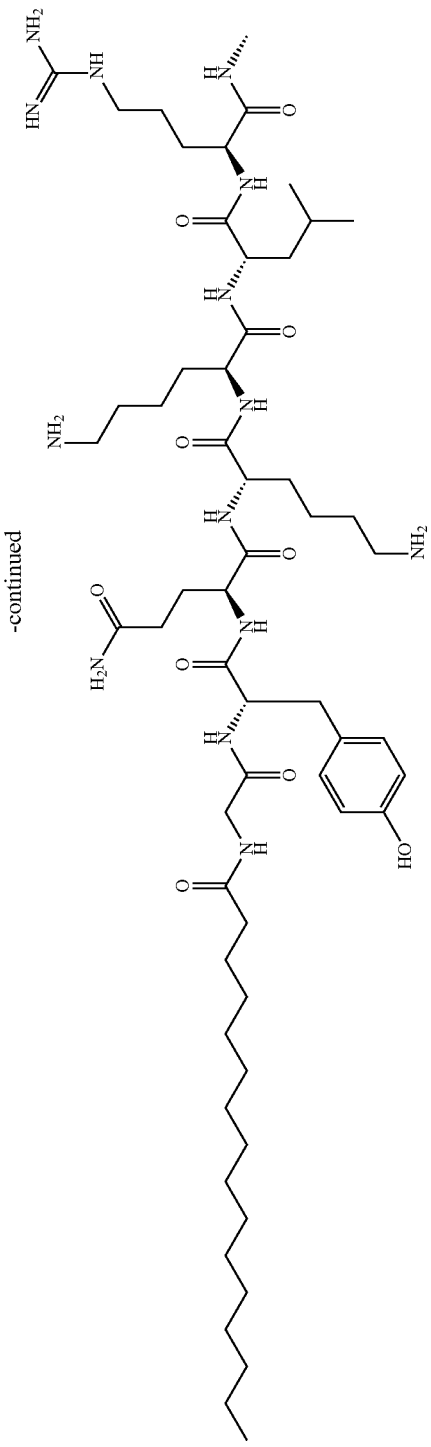
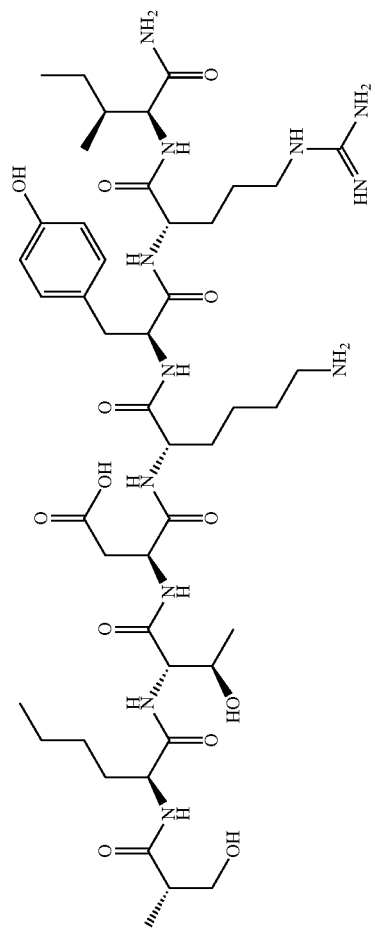

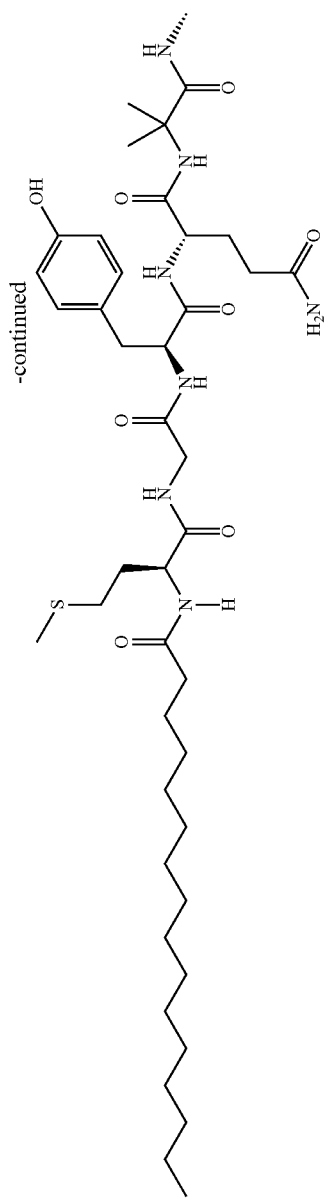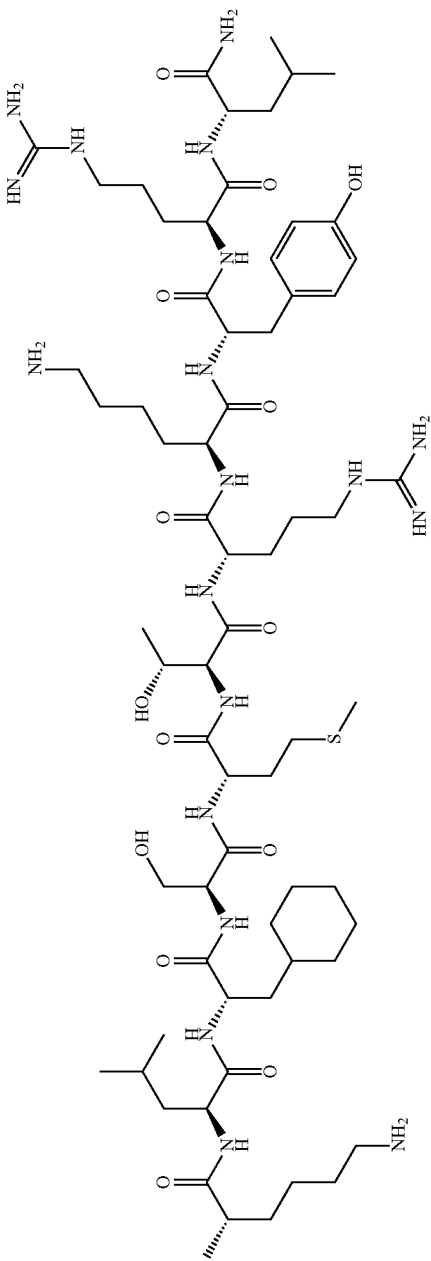

-continued
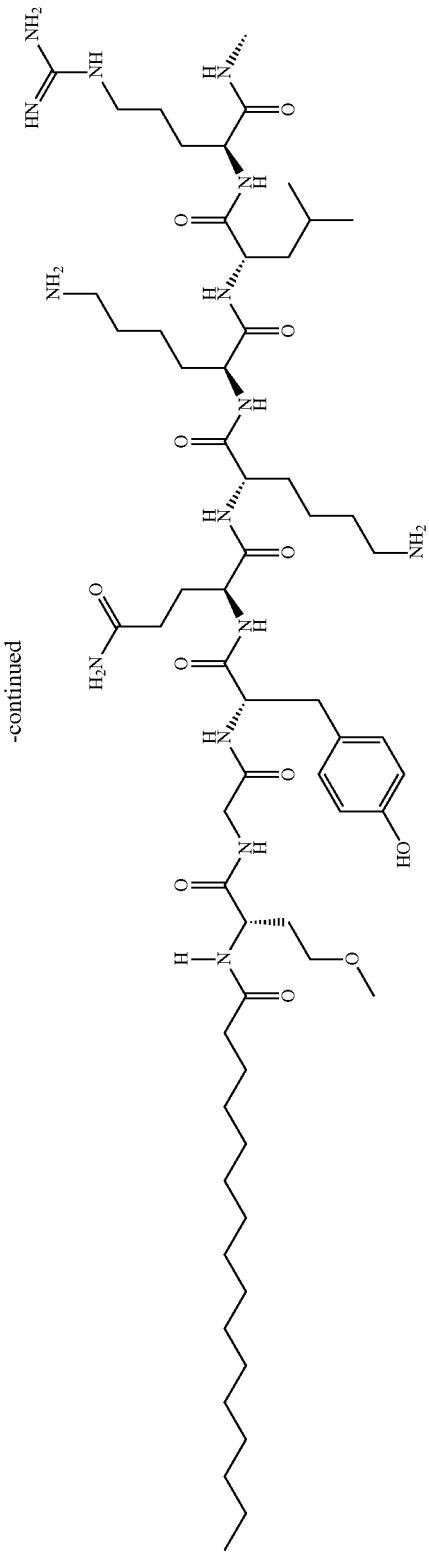
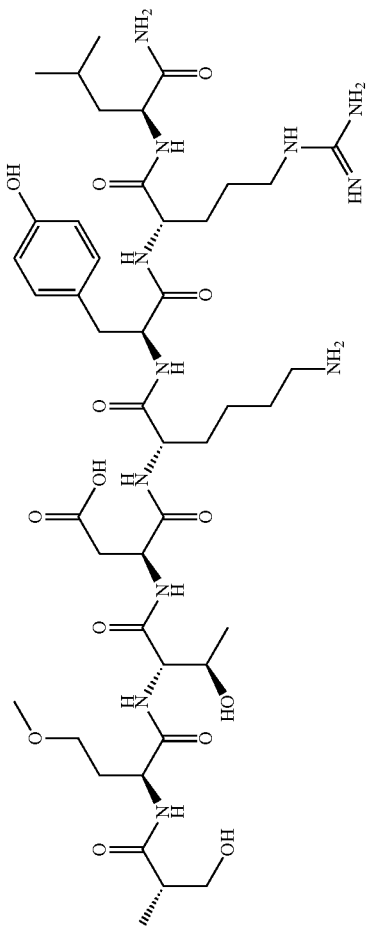

-continued
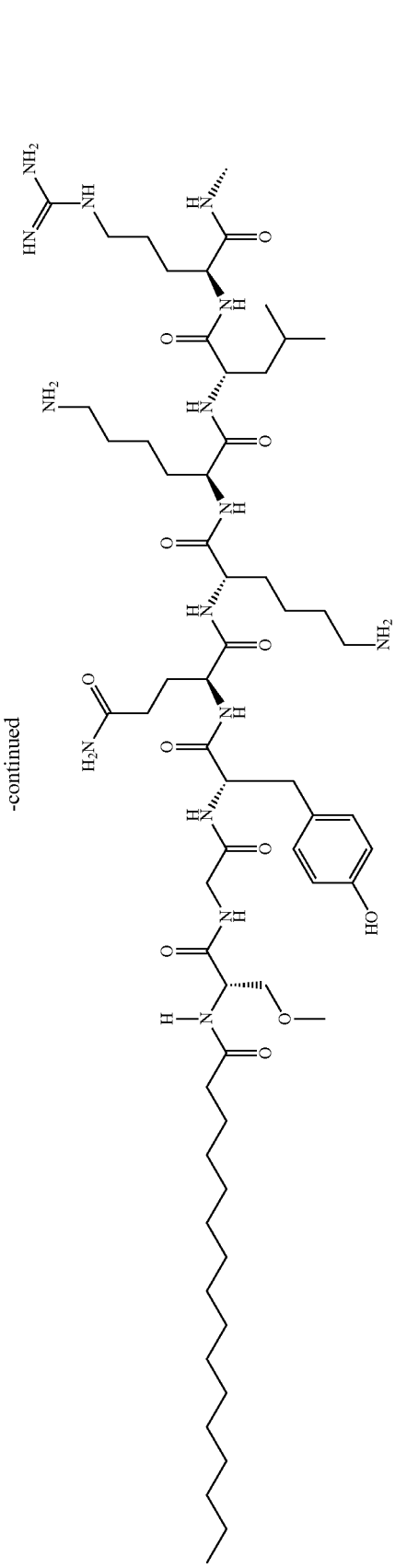
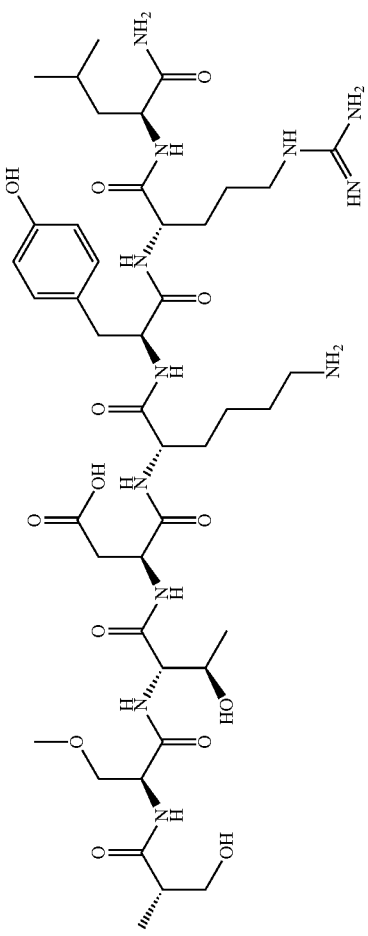

-continued
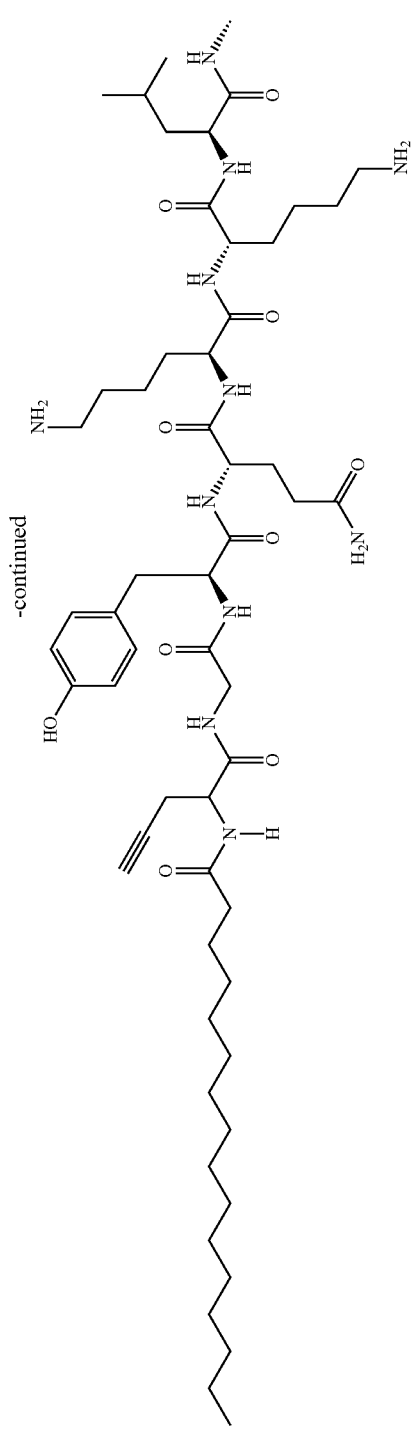

-continued
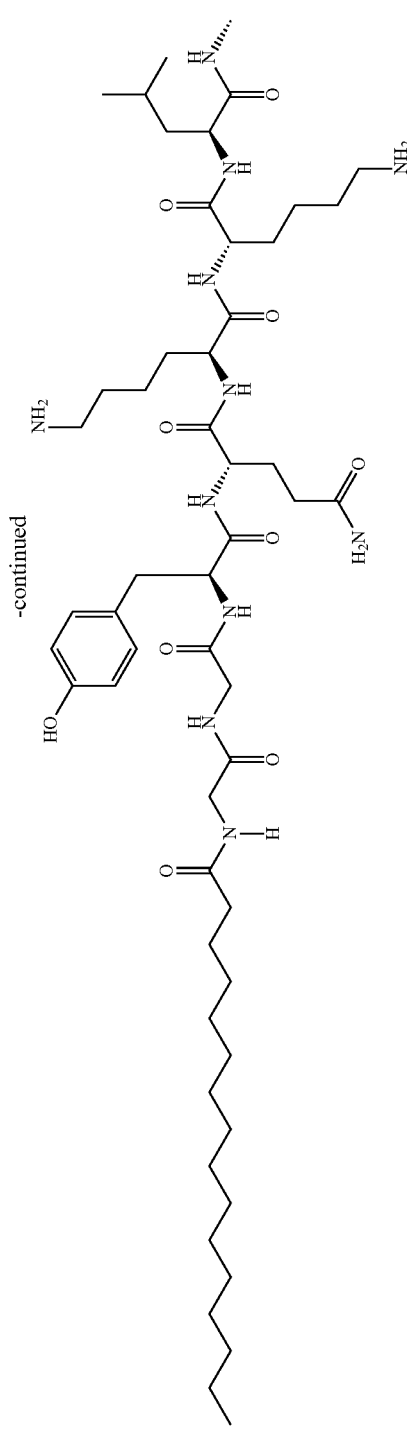
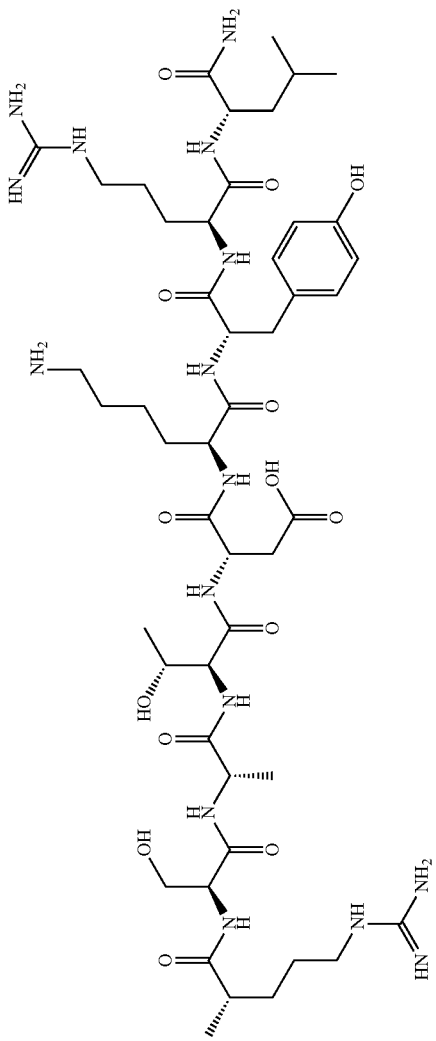

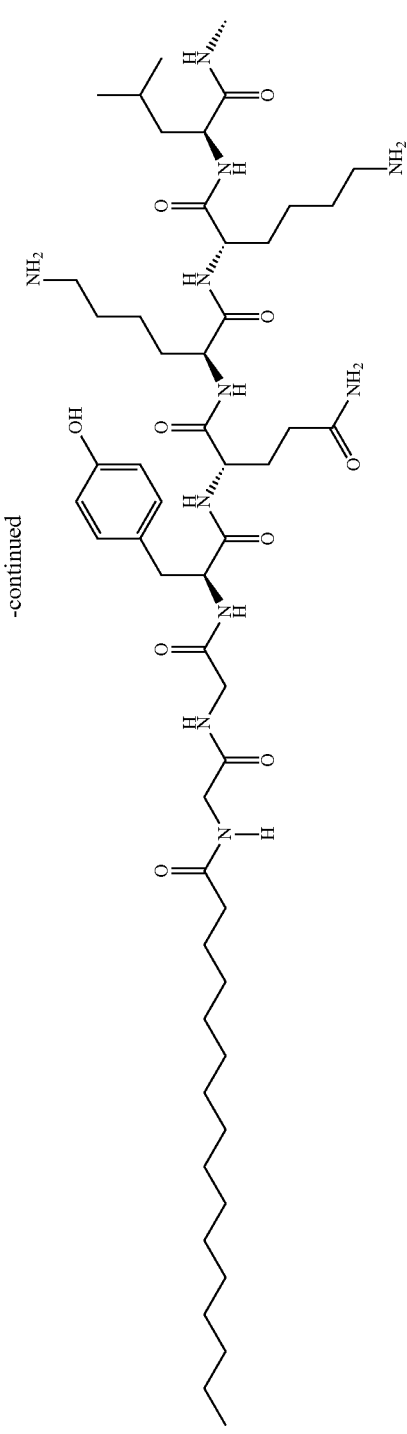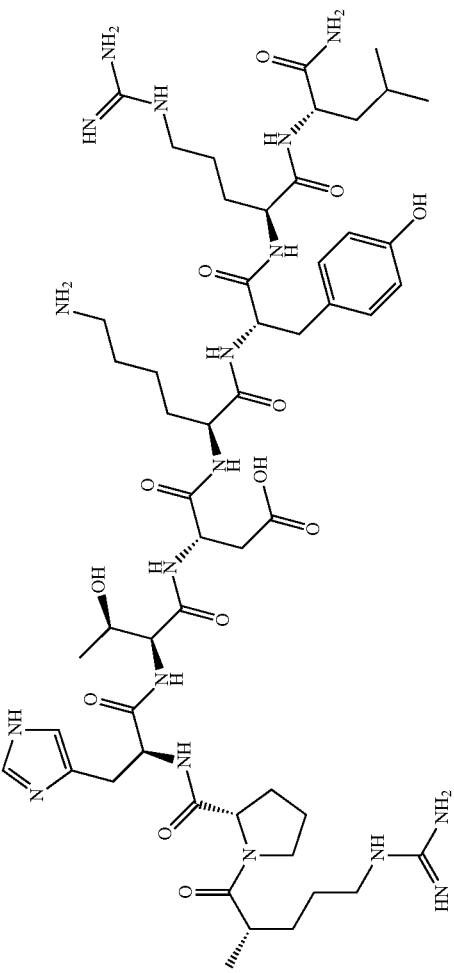

-continued
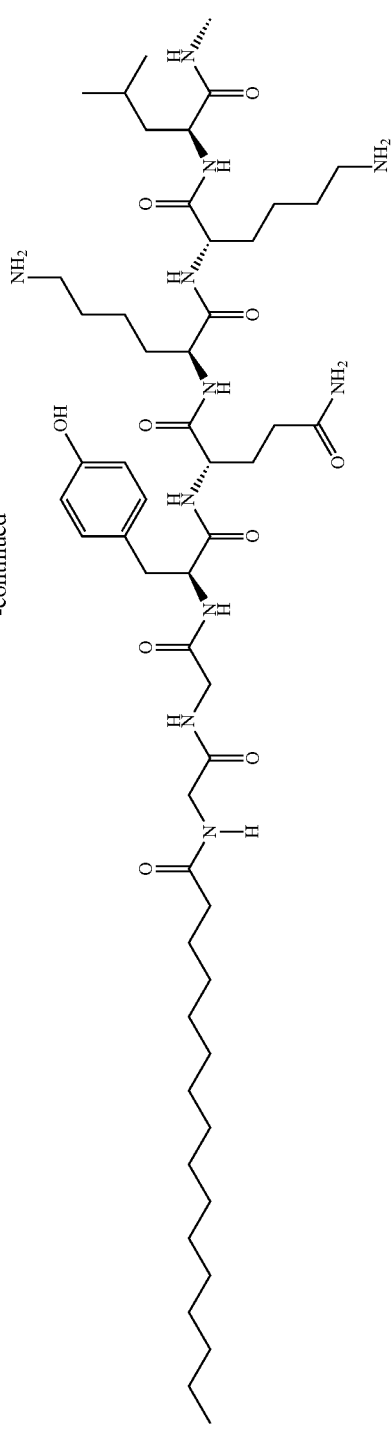
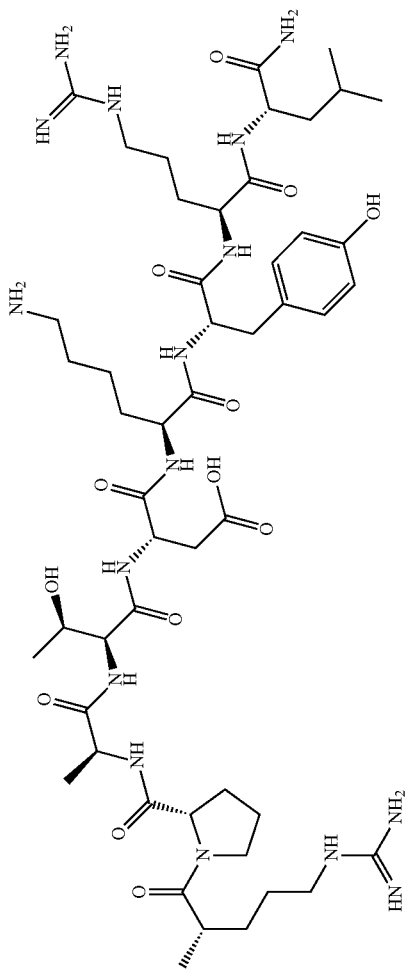

-continued
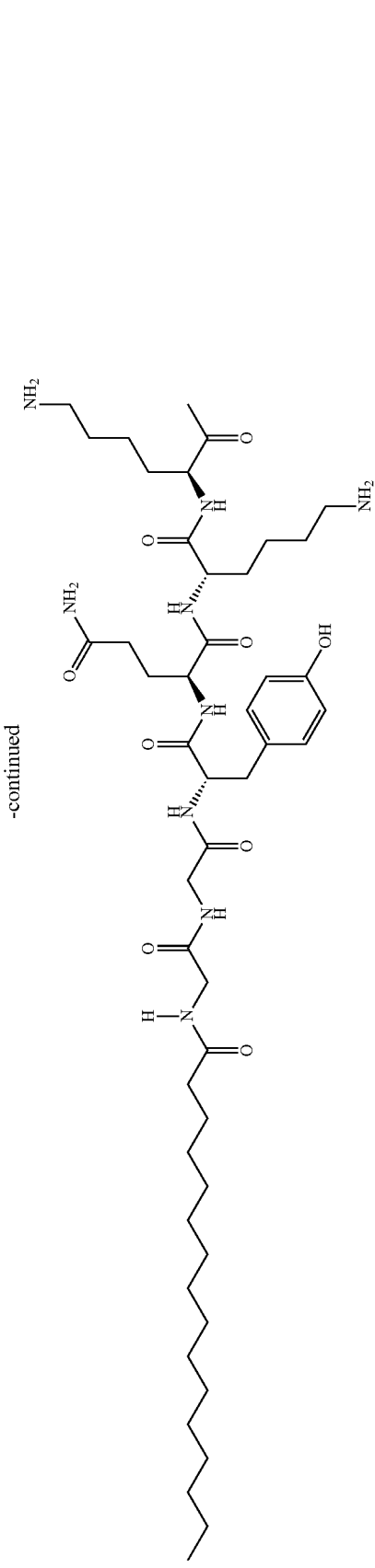
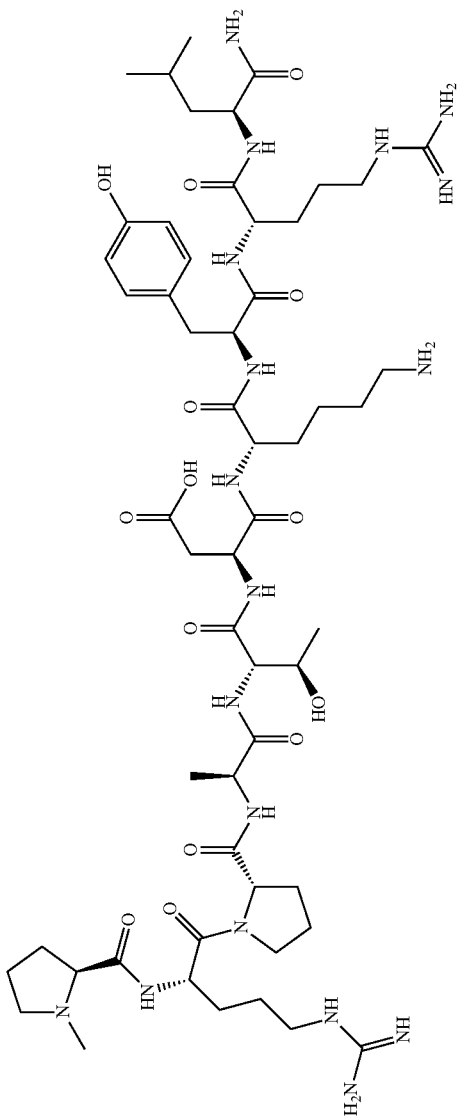

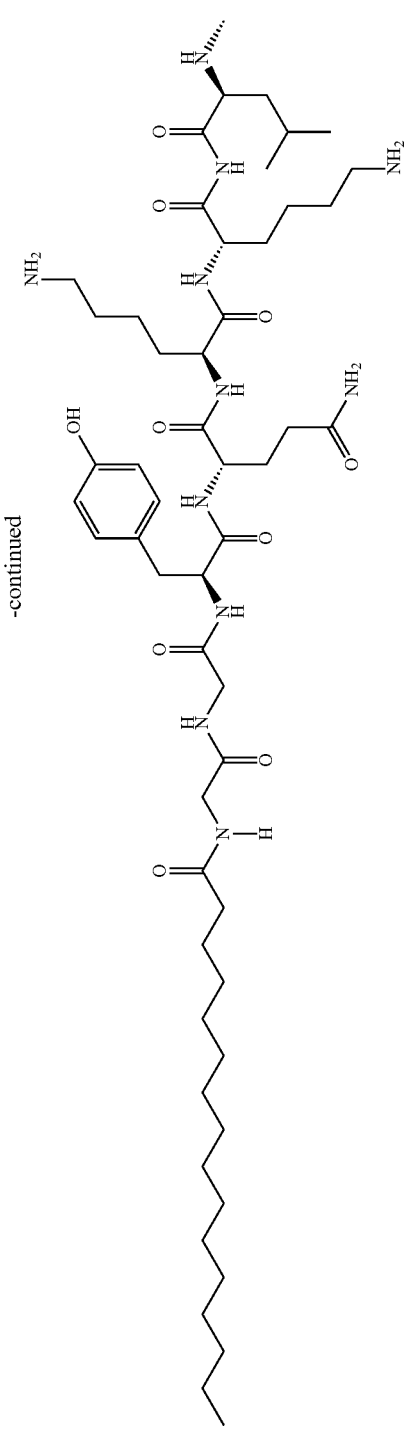
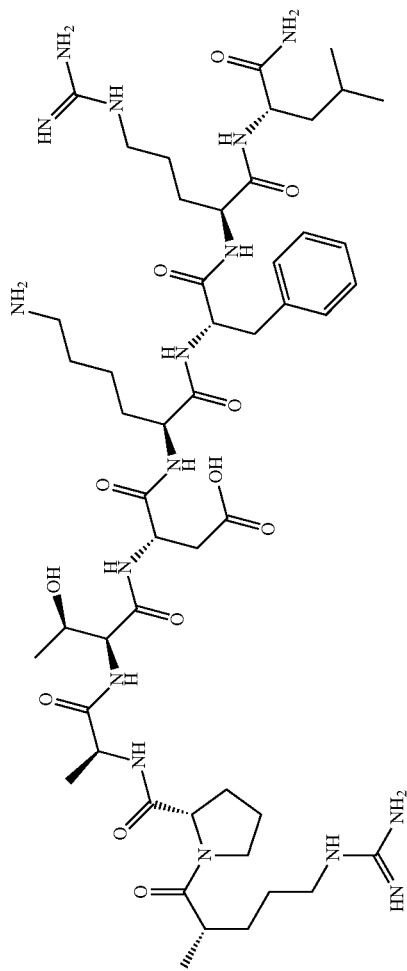

-continued
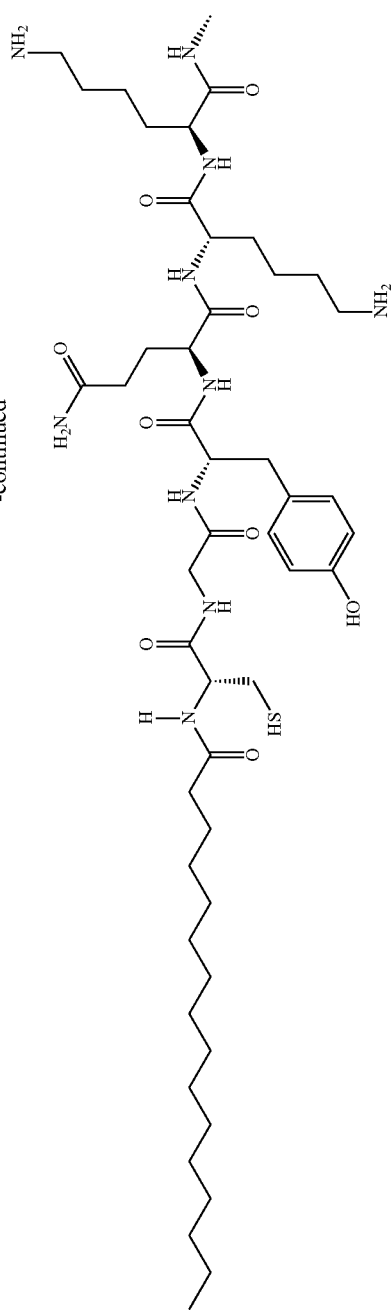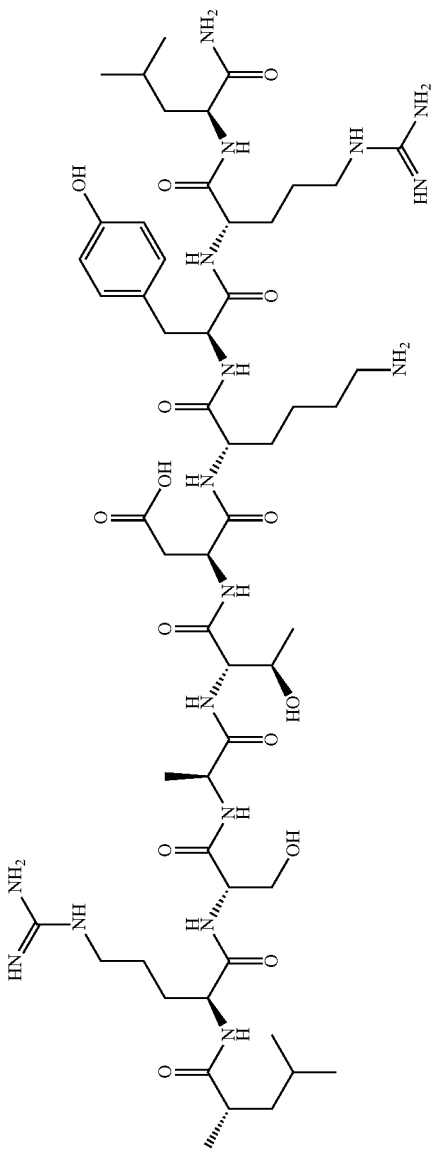

-continued
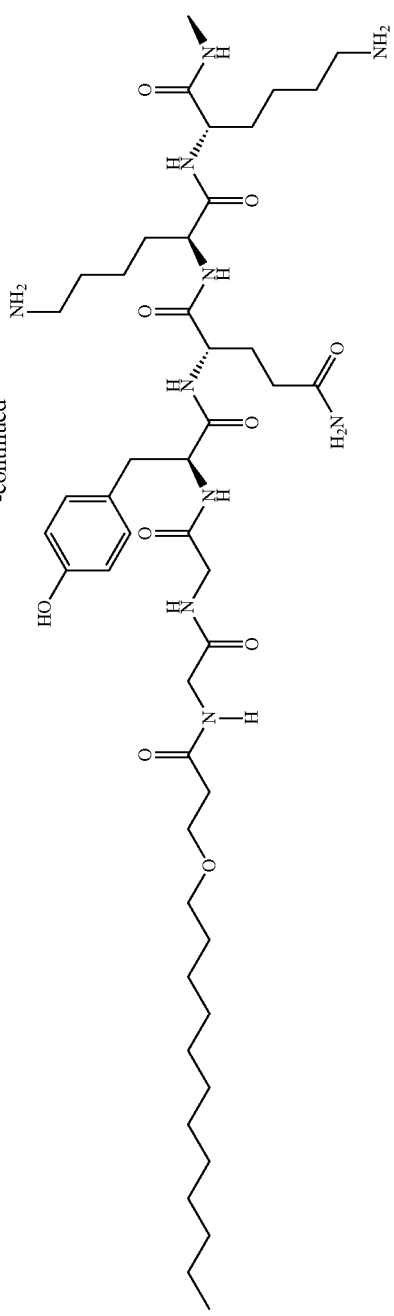
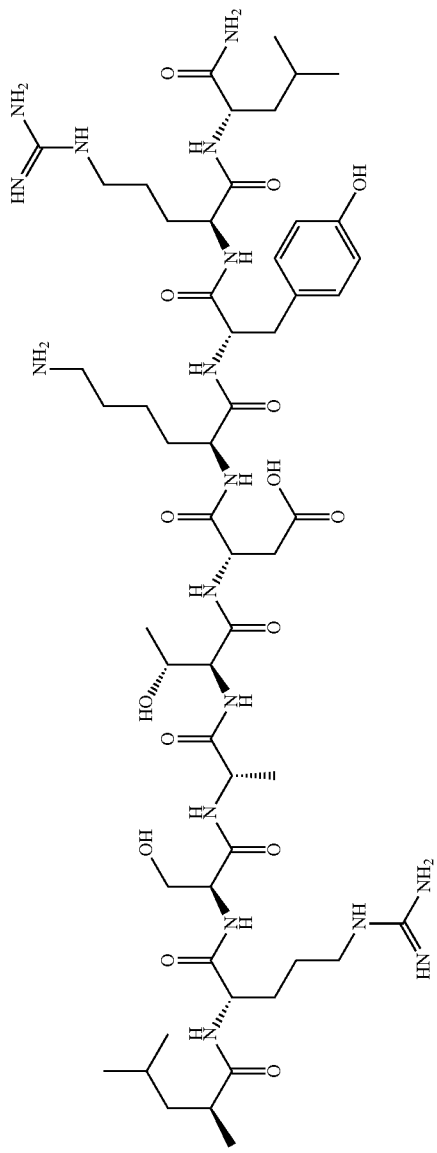

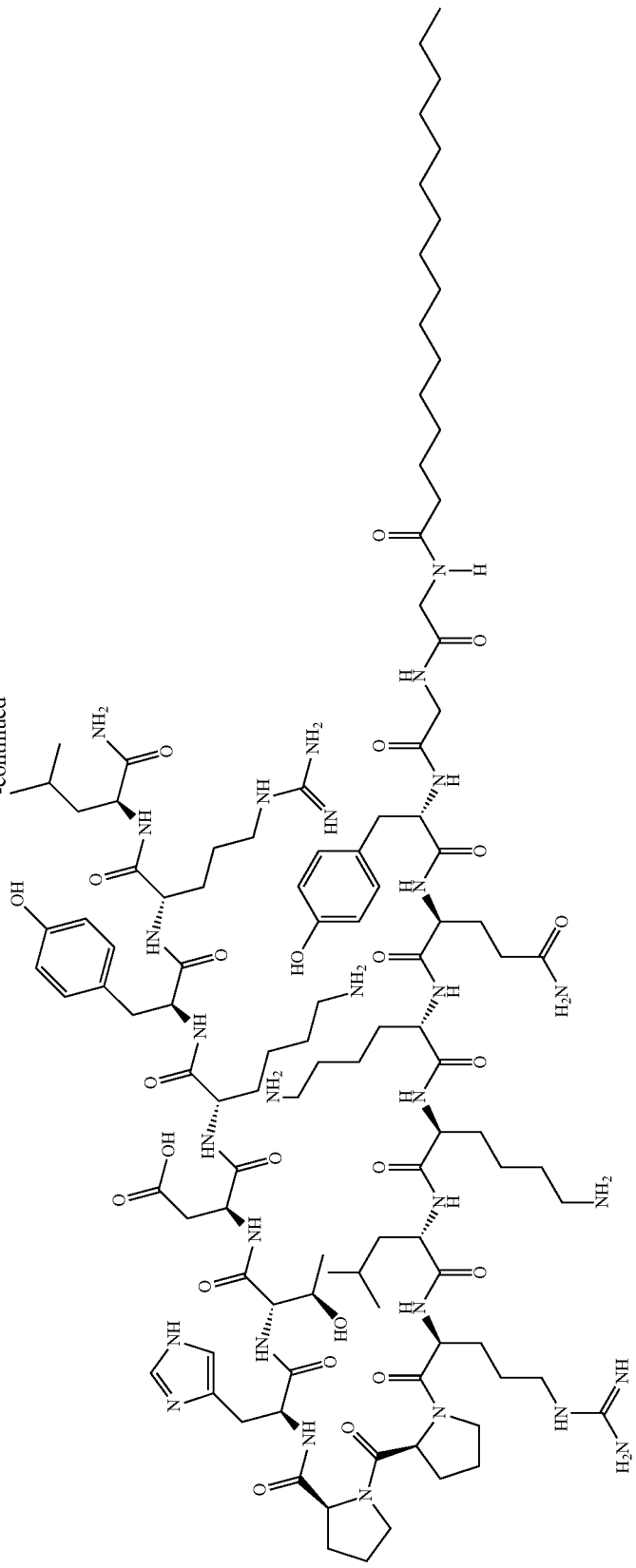

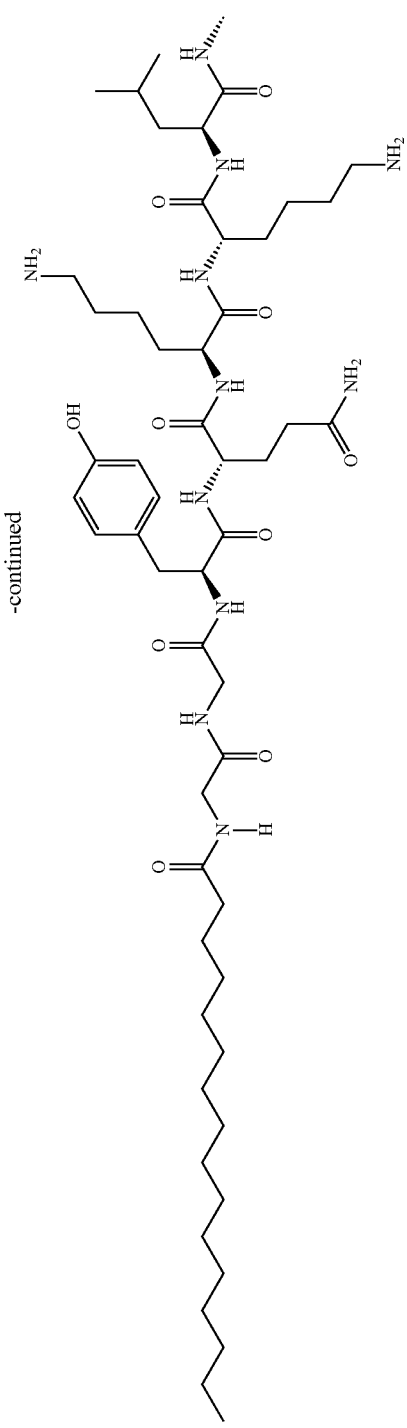
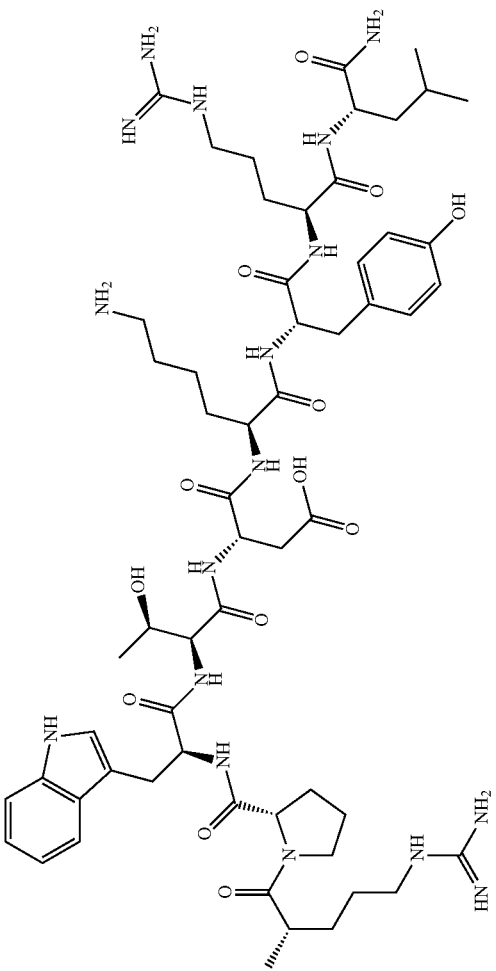

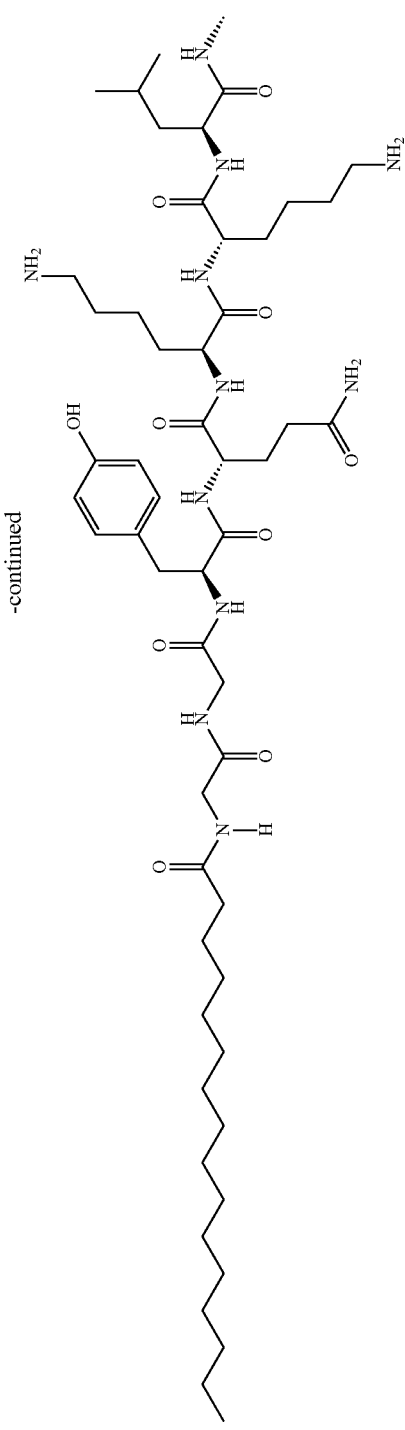
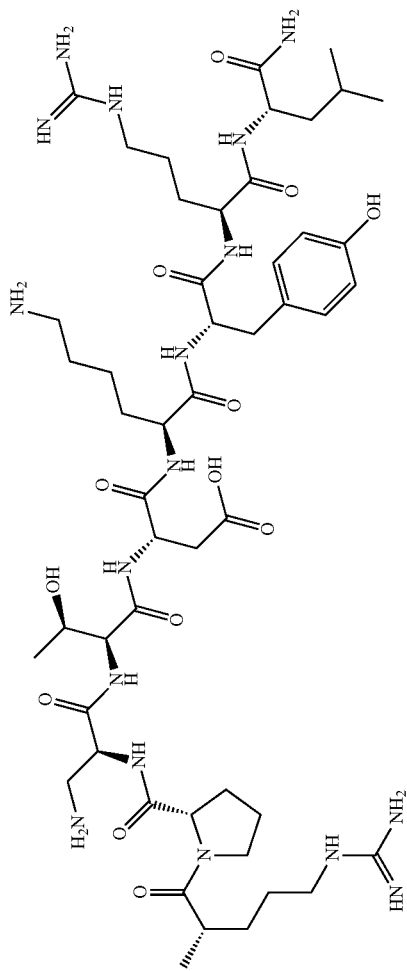

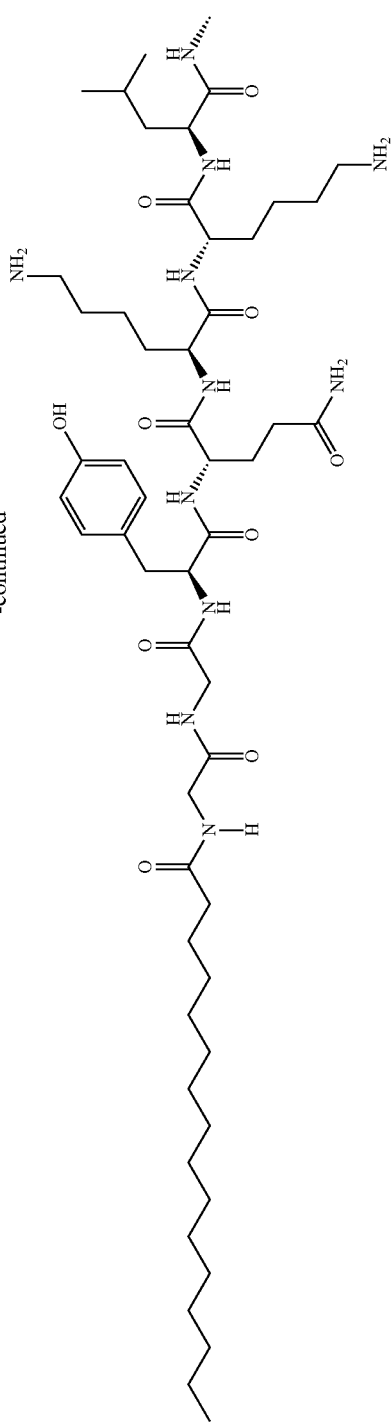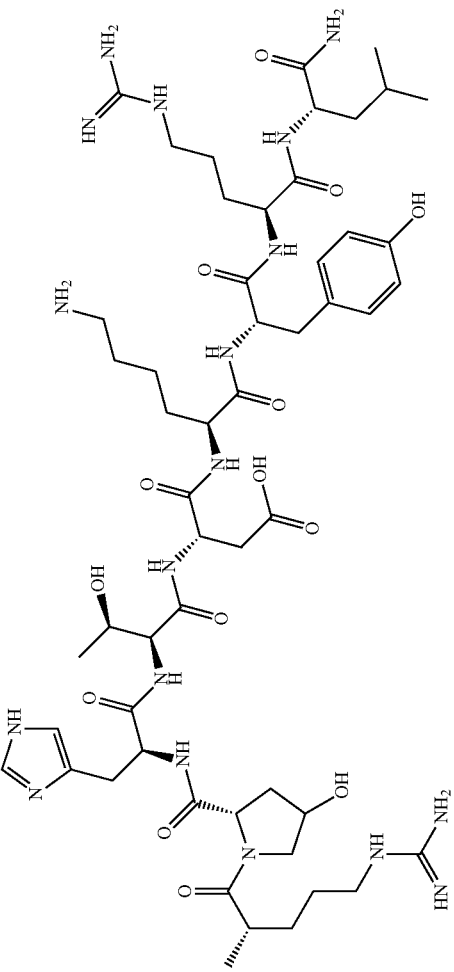

-continued
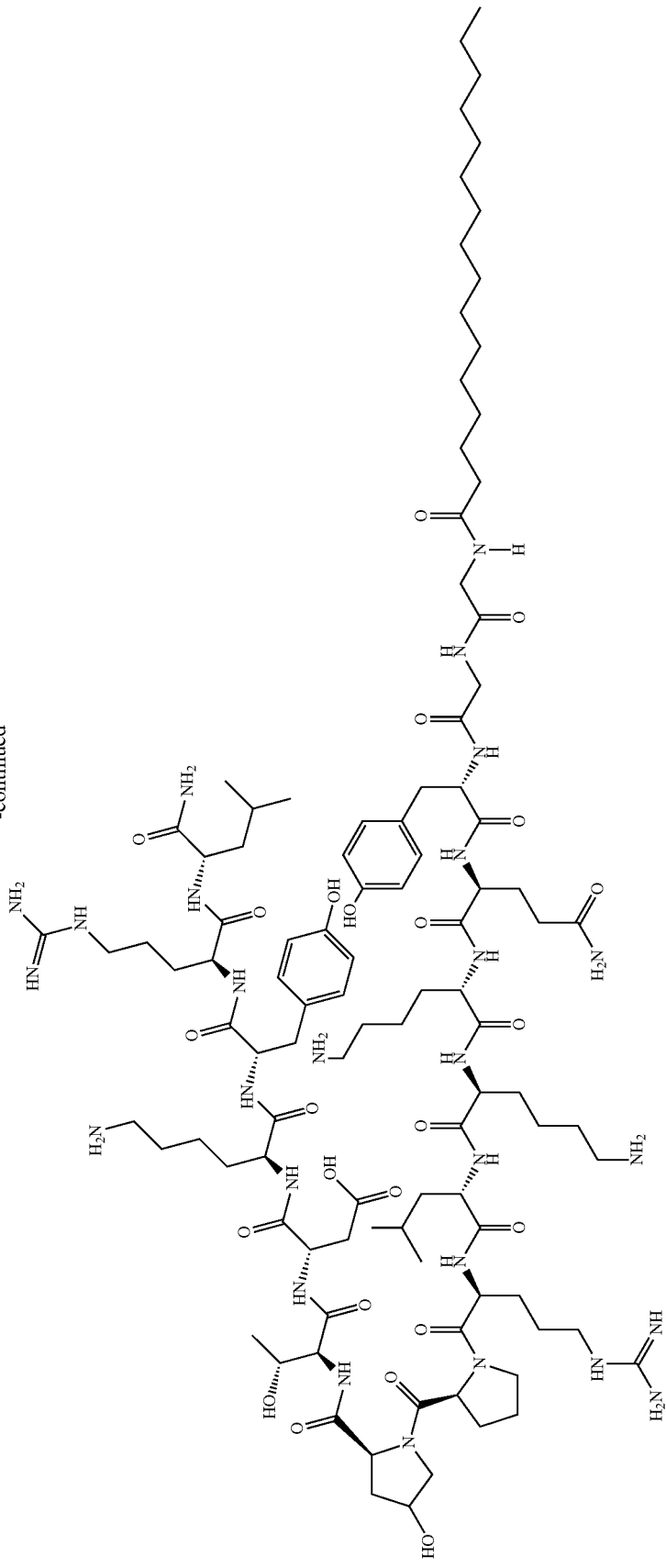

-continued
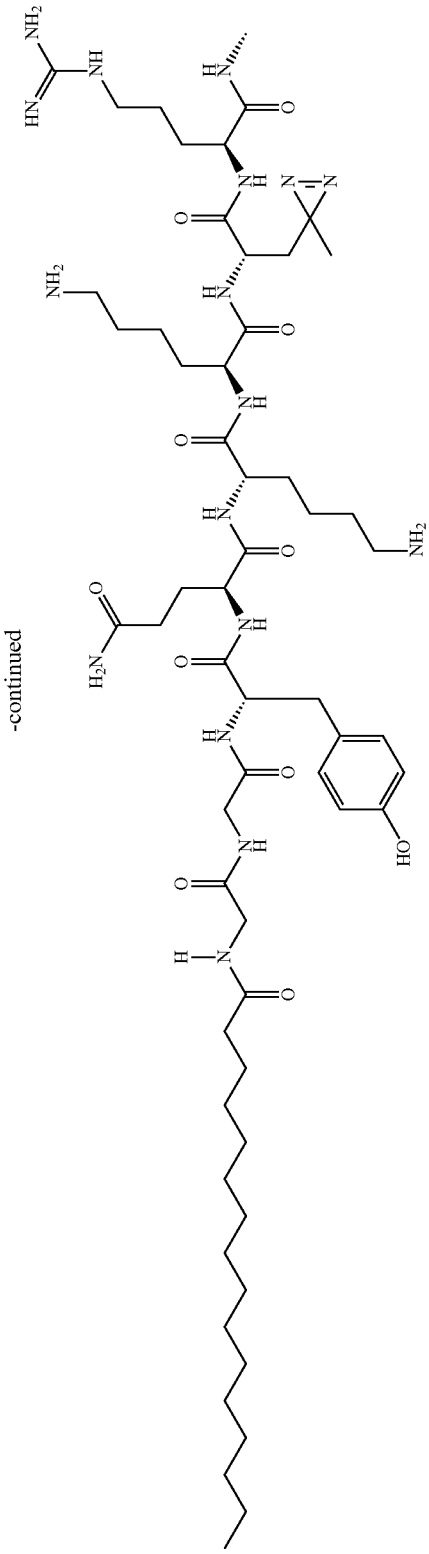
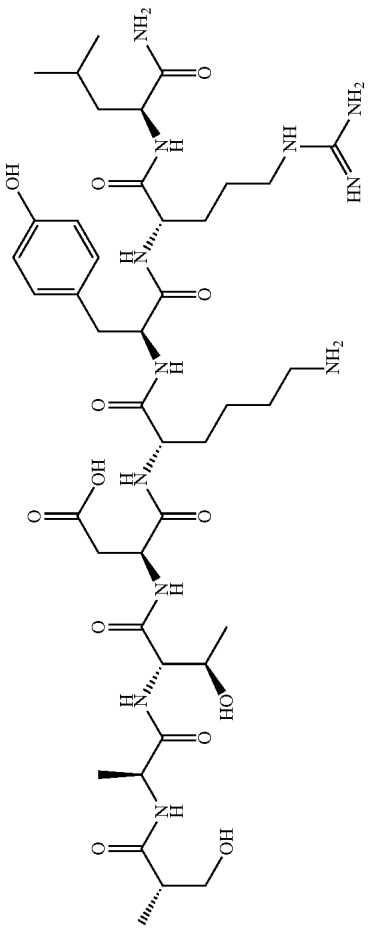

-continued
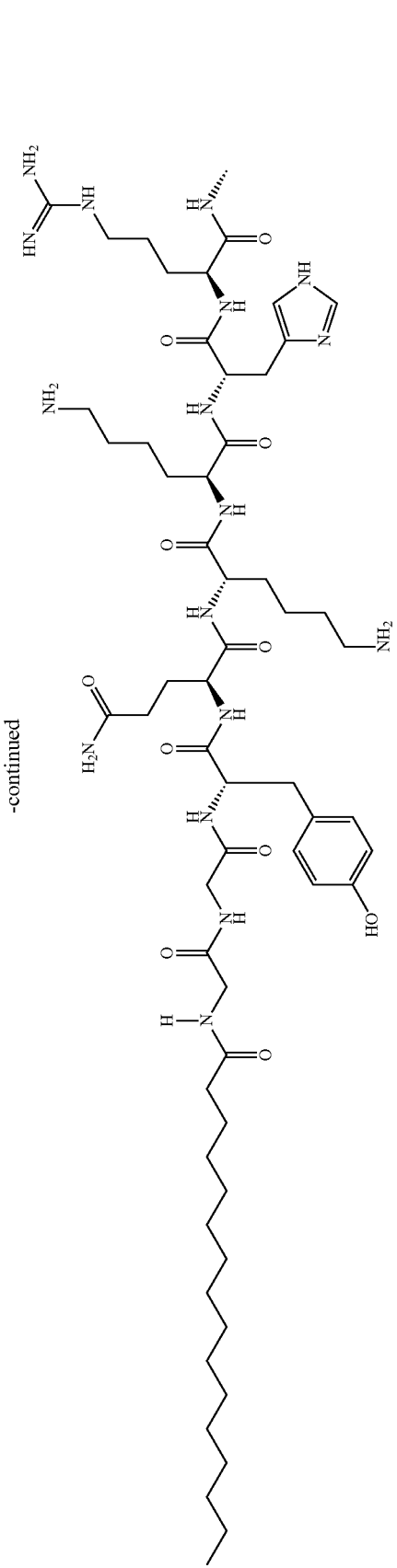
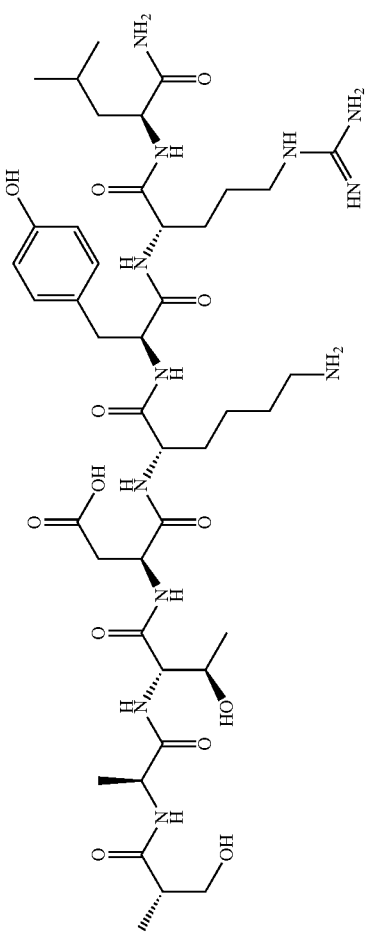

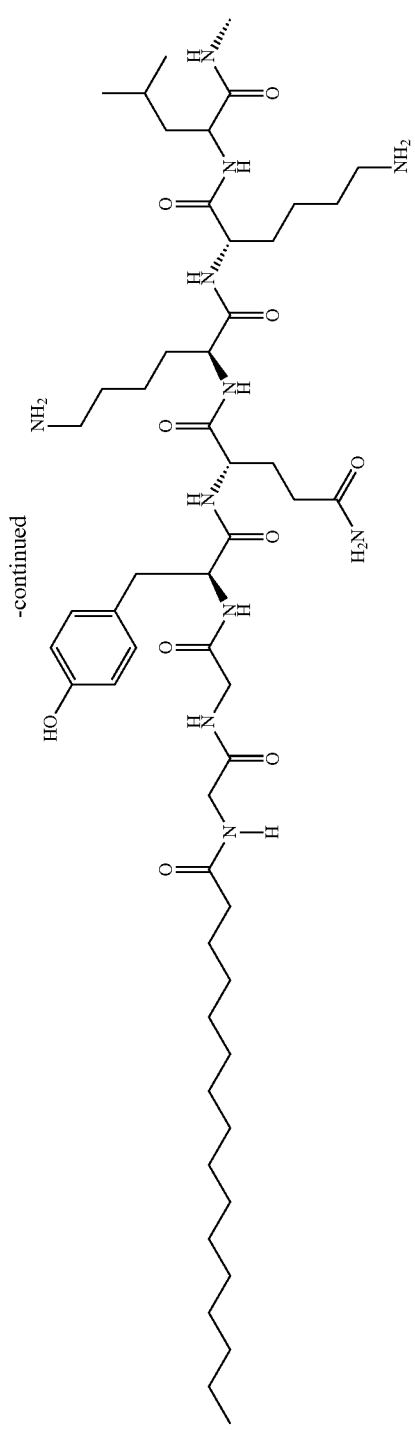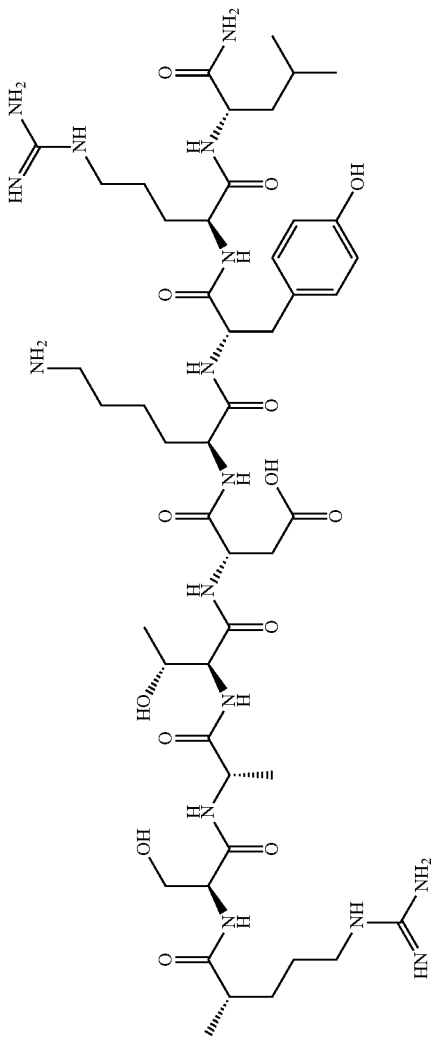

-continued
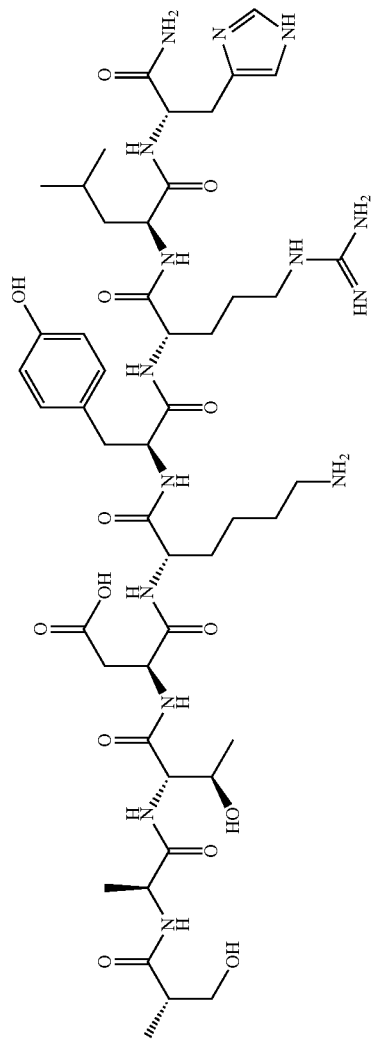
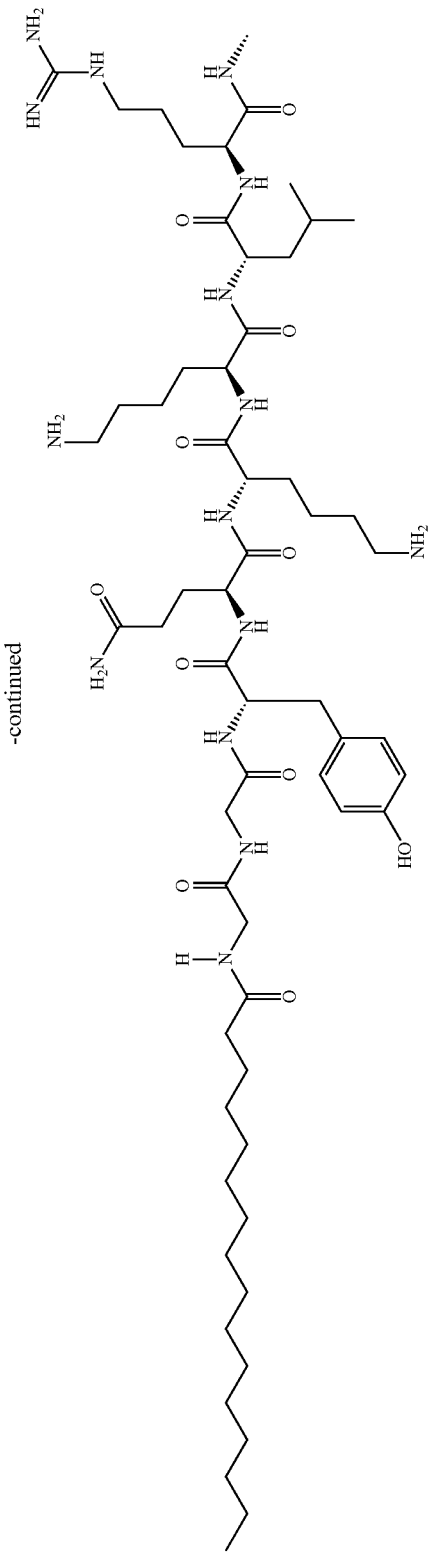

-continued
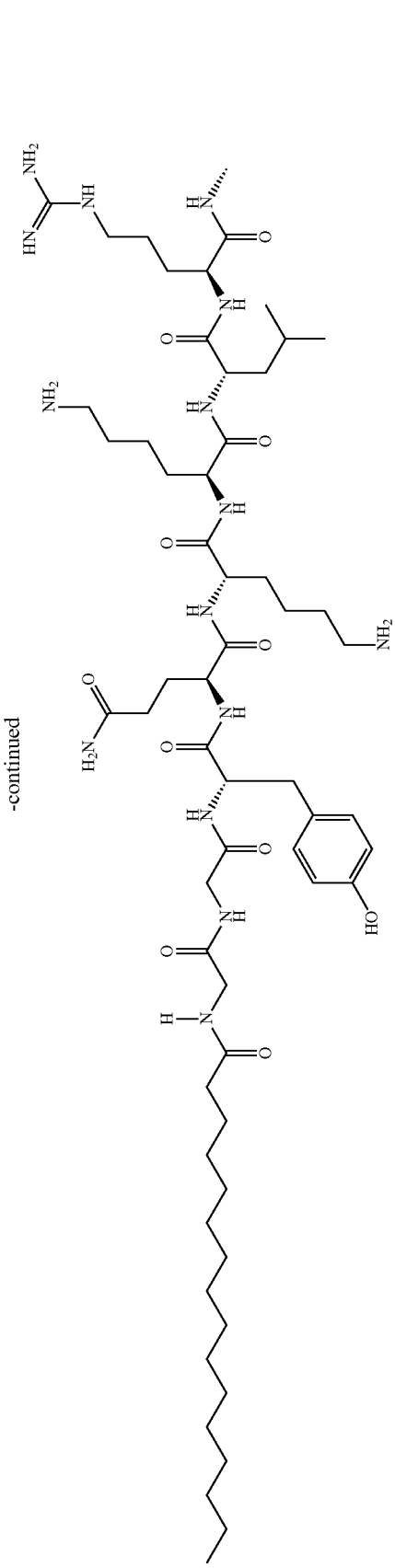
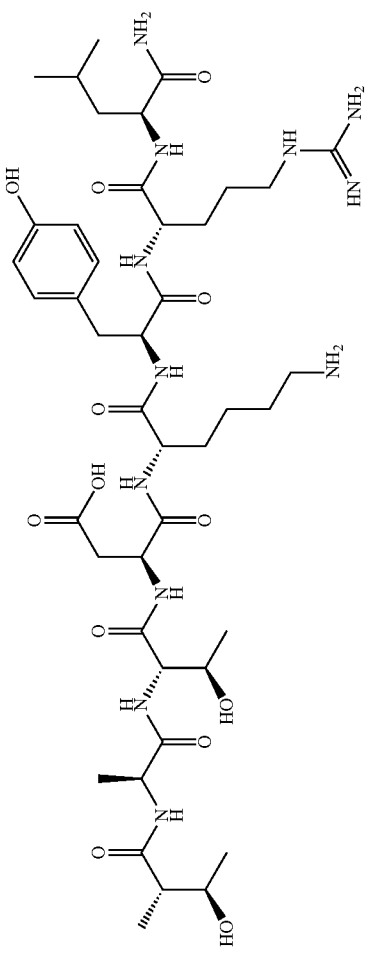

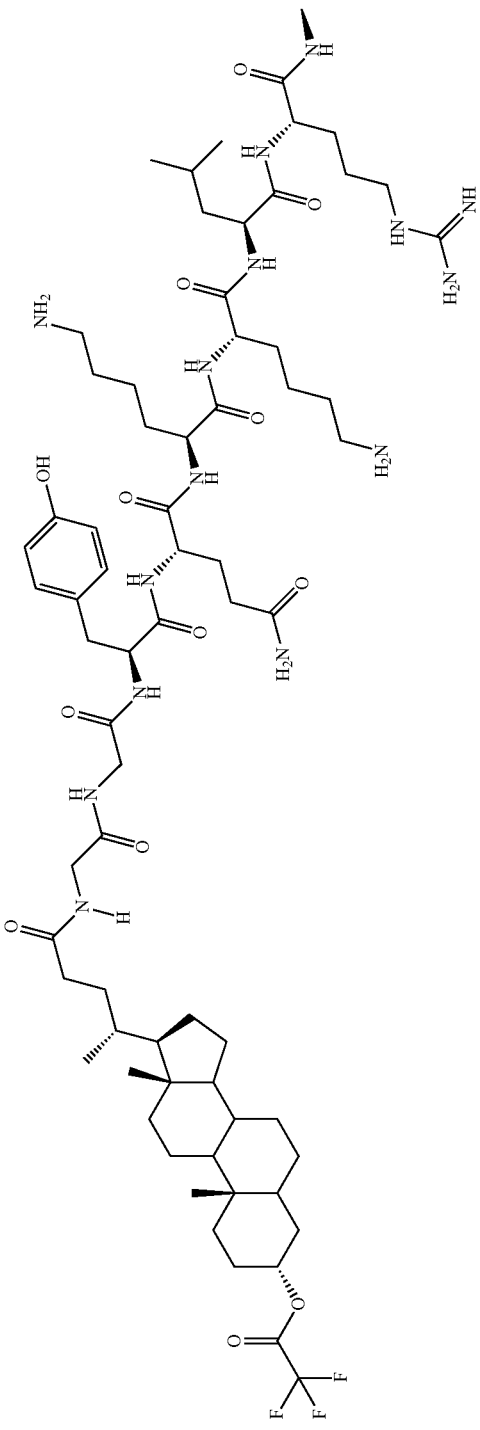
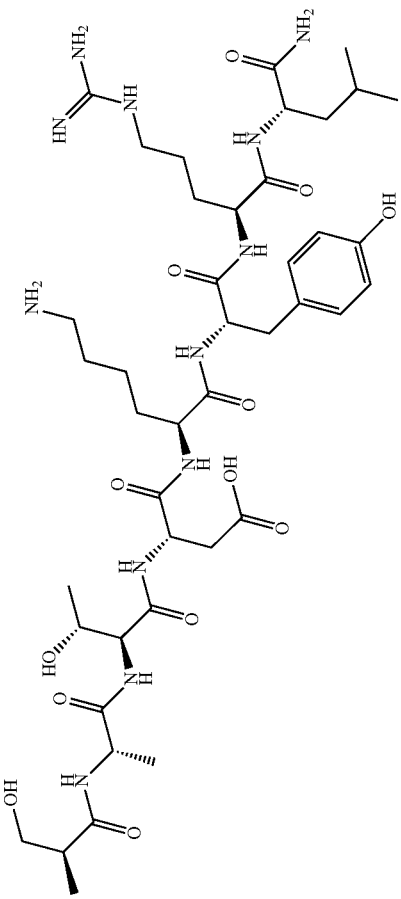

-continued
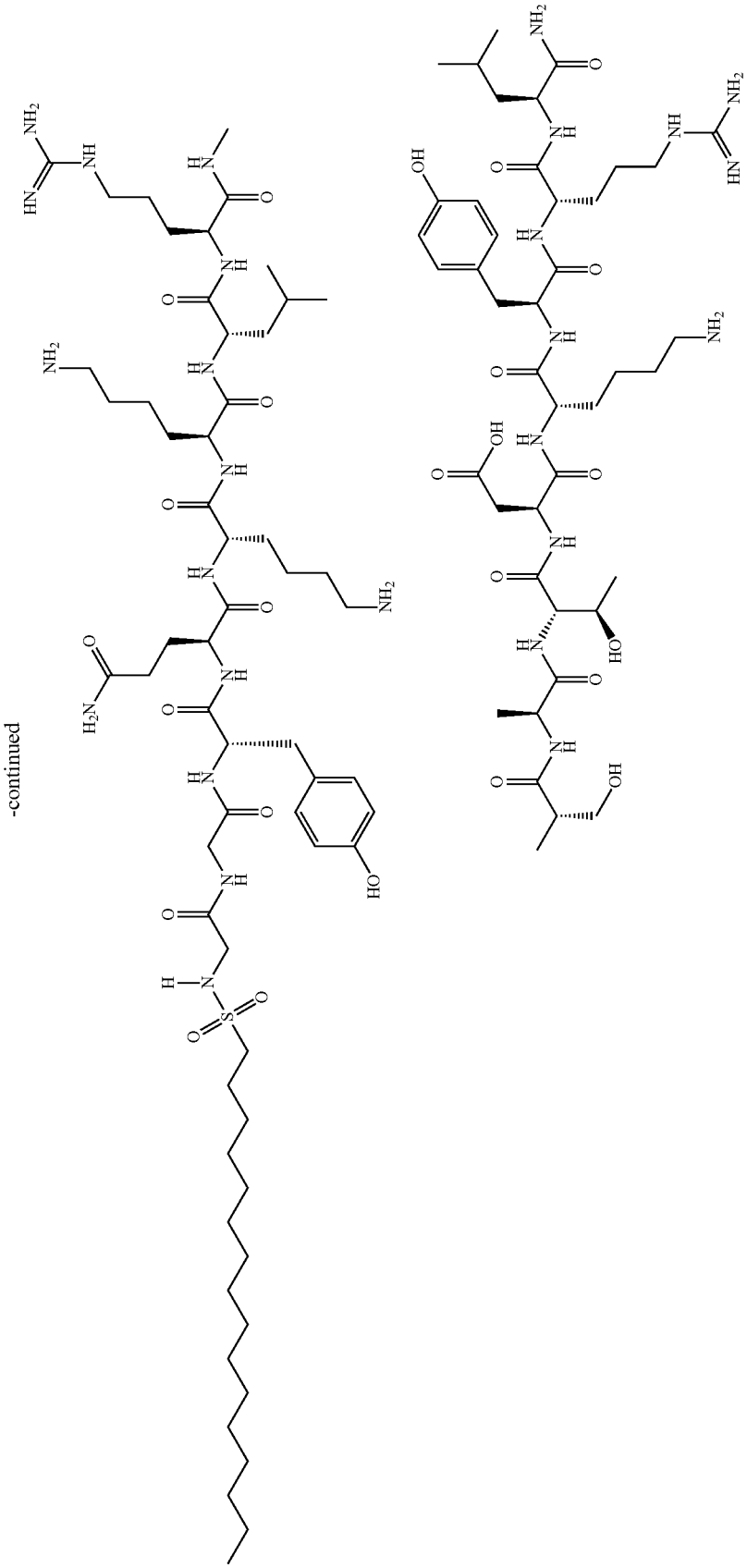

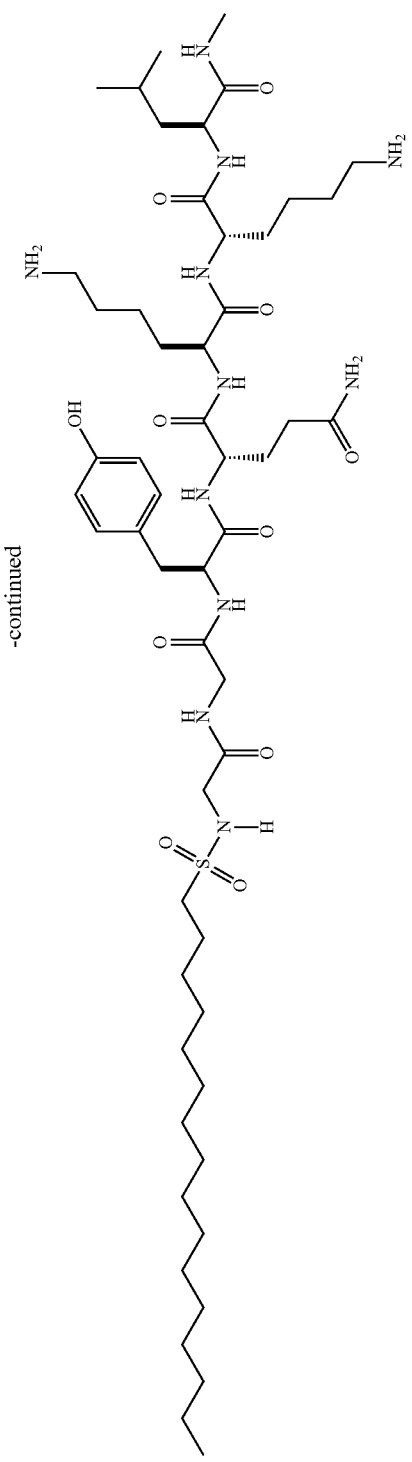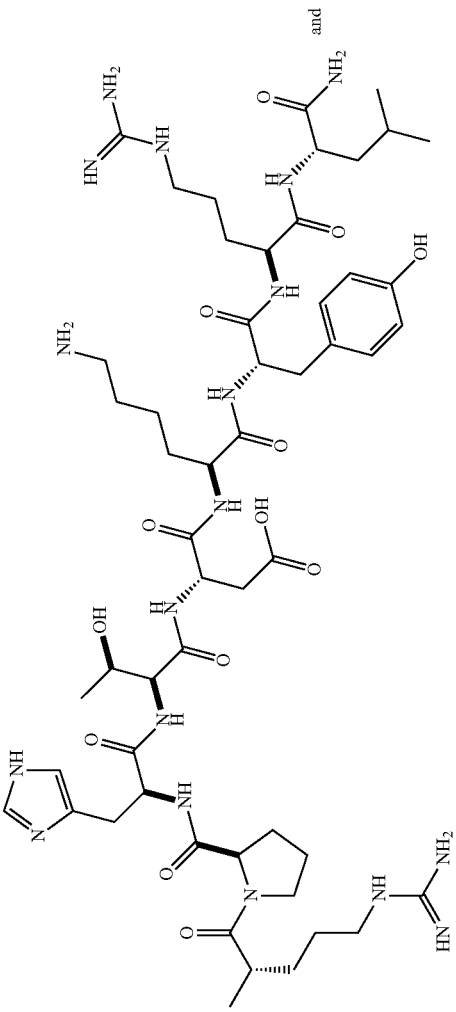

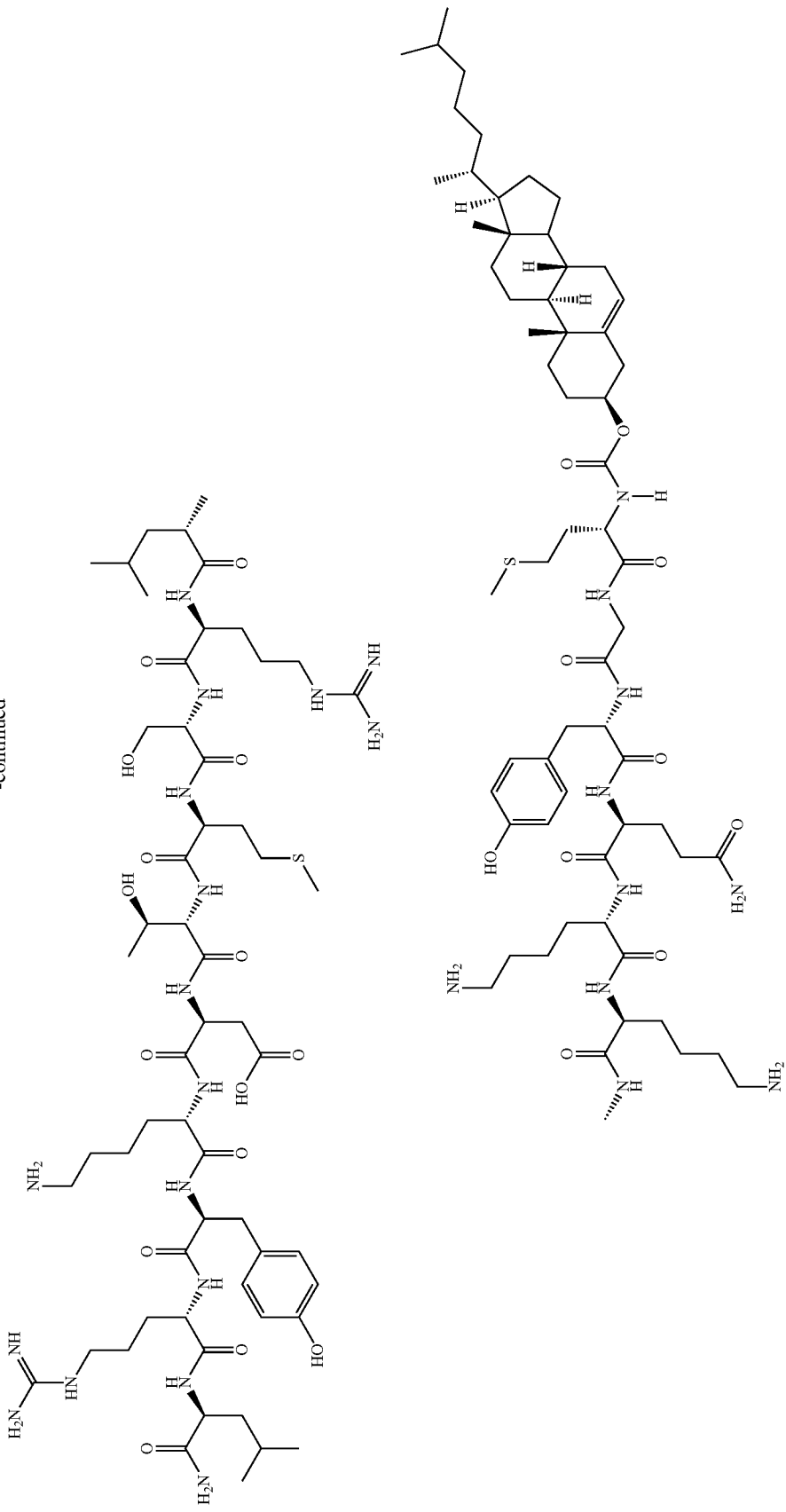

or a pharmaceutically acceptable salt of any of the foregoing.

In a fourth aspect of the first embodiment or its first, second, their aspect or the first embodiment of the first aspect, the compound is administered for treating cardiac tissue damage. In a first embodiment of the fourth aspect, cardiac tissue damage is associated with ischemic cardiac disease. In a second embodiment of the fourth aspect, the cardiac tissue damage is associated with myocardial infarction. In a third embodiment of the fourth aspect, the cardiac tissue damage is associated with congestive heart failure. In a fourth embodiment of the fourth aspect, the cardiac tissue damage is associated with valvular disease.

In a fifth aspect of the first embodiment or its first, second or third aspect or the first the compound is administered for treating bone injury. In a first embodiment of the fifth aspect, the bone injury is associated with osteonecrosis. In a second embodiment of the fifth aspect, the osteonecrosis is in one or more bones selected from the group consisting of jaw, knee, hip, leg, shoulder, ankle and arm. In a third embodiment of the fifth aspect, the bone injury is a fracture. In a fourth embodiment of the fifth aspect, the bone injury is osteoporosis. In a fifth embodiment of the fifth aspect, the bone injury is osteopenia. In a six embodiment of the fifth aspect, the compound is administered in conjunction with a bone graft.

In a sixth aspect of the first embodiment of its first, second or third aspect or the first embodiment of the first aspect, the compound is administered for promoting wound healing. In a first embodiment of the sixth aspect, the wound is a surface wound. In a second embodiment of the sixth aspect, the wound is a surgical wound. In a third embodiment of the sixth aspect, the wound is an internal wound. In a forth embodiment of the sixth aspect the wound is a chronic wound. In a fifth embodiment of the sixth aspect, the wound is an ulcer. In a sixth embodiment of the sixth aspect, the wound is a diabetic ulcer. In a seventh embodiment of the sixth aspect, the ulcer is a decubitus ulcer. In an eighth embodiment of the sixth aspect, the wound is a vascular wound. In a ninth embodiment of the sixth aspect, the wound is a burn. In a tenth embodiment of the sixth aspect, the wound is the result of radiation exposure.

In a seventh aspect of the first embodiment or its first, second, or third aspect or the first embodiment of the first aspect, the compound is administered for reducing the formation of scaring at a wound site to a subject that has suffered a skin injury.

In a eighth aspect of the first embodiment or its first, second, or third aspect or the first embodiment of the first aspect, the compound is administered for increasing homing or trafficking of stem cells to an area of injury. In a first embodiment of the eighth aspect, the compound is administered in substantial proximity to the area of injury. In a second embodiment of the eighth aspect, the compound is administered systemically.

In a ninth aspect of the first embodiment or its first, second, or third aspect or the first embodiment of the first aspect, the compound is administered for treating ischemia. In a first embodiment of the ninth aspect, the ischemia is associated with peripheral artery disease. In a second embodiment of the ninth aspect, the ischemia is critical limb ischemia. In a third embodiment of the ninth aspect, the ischemia is associated with organ or cell transplantation.

In a second embodiment, the method is a method of treating cardiac tissue damage, bone injury, or ischemia or promoting wound healing, or reducing the formation of scarring or increasing homing or trafficking of stem cells in a subject in need thereof, comprising administering to the subject an effective amount of a compound of Formula A-1:

$$T\text{-}L\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{—}R_1;$$

or a pharmaceutically acceptable salt thereof, wherein:
L is a linking moiety selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to the N terminal nitrogen of X$_5$; T is a lipophilic tether moiety bonded to L; and R$_1$ is OR$_2$ or N(R$_2$)$_2$, each R$_2$ is independently H or alkyl, wherein at least three contiguous X$_5$-X$_{21}$ amino acid residues are present, and wherein:
X$_5$ is a glycine residue, a methyl serine residue, a homoserine residue, a propargyl glycine residue or a cysteine residue,
X$_6$ is a glycine residue,
X$_7$ is a tyrosine residue,
X$_8$ is a glutamine residue,
X$_9$ is a lysine residue,
X$_{10}$ is a lysine residue,
X$_{11}$ is a leucine residue, a proline residue, a photoleucine, a histidine, or a d-leucine,
X$_{12}$ is an arginine residue,
X$_{13}$ is a serine residue, a d-proline residue, a proline residue, or a hydroxyproline residue,
X$_{14}$ is a alanine residue, a homoserine residue, a histidine residue a methyl serine residue, a proline residue, a Dpr residue, a methionine residue, a tryptophan residue, a hydroxyproline residue, or a d-proline residue,
X$_{15}$ is a threonine residue or a histidine residue,
X$_{16}$ is aspartic acid residue, or a threonine residue
X$_{17}$ is a lysine residue, or an aspartic acid residue,
X$_{18}$ is a tyrosine residue, a lysine residue or a phenylalanine residue,
X$_{19}$ is an arginine residue or a tryptophan residue,
X$_{20}$ is a leucine residue or an arginine residue,
X$_{21}$ is a histidine residue or a leucine residue or absent.
In a first aspect of the second embodiment, L is selected from C(O), S*(O)$_2$ and OC*(O). In a first embodiment of the first aspect, L is C(O). In a second aspect of the second embodiment or its first aspect or the first embodiment of the first aspect, X$_5$ is a glycine or a methyl serine residue,
X$_{11}$ is a leucine residue, or a proline residue,
X$_{13}$ is a serine residue, a d-proline residue or a hydroxyproline residue,
X$_{14}$ is an alanine residue, a histidine residue a methyl serine residue, a d-proline residue or a Dpr residue, and X$_{21}$ is a leucine residue or absent. In a third aspect of the second embodiment or its first, second or third aspect or the first embodiment of the first aspect, the compound is administered for treating cardiac tissue damage.

In a first embodiment of the third aspect, the cardiac tissue damage is associated with ischemic cardiac disease. In a second embodiment of the third aspect, the cardiac tissue damage is associated with myocardial infarction. In a third embodiment of the third aspect, the cardiac tissue damage is associated with congestive heart failure. In a fourth embodiment of the third aspect, the cardiac tissue damage is associated with valvular disease.

In a fourth aspect of the second embodiment or its first, second or third aspect or the first embodiment of the first aspect, the compound is administered for treating bone injury. In a first embodiment of the fourth aspect, the bone injury is associated with osteonecrosis. In a second embodiment of the fourth aspect, the osteonecrosis is in one or more bones selected from the group consisting of jaw, knee, hip, leg, shoulder, ankle and arm. In a third embodiment of the fourth aspect, the bone injury is a fracture. In a fourth embodiment of the fourth aspect, the bone injury is osteoporosis. In a fifth embodiment of the fourth aspect, the bone injury is osteopenia. In a sixth embodiment of the fourth aspect, the compound is administered in conjunction with a bone graft.

In a first aspect of the second embodiment or its first, second or third aspect or the first embodiment of the first aspect, the compound is administered for promoting wound healing. In a first embodiment of the fifth aspect, wherein the wound is a surface wound. In a second embodiment of the fifth aspect, the wound is a surgical wound. In a third embodiment of the fifth aspect, the wound is an internal wound. In a fourth embodiment of the fifth aspect, the wound is a chronic wound. In a fifth embodiment of the fifth aspect, the wound is an ulcer. In a sixth embodiment of the fifth aspect, the wound is a diabetic ulcer. In a seventh embodiment of the fifth aspect, the ulcer is a decubitus ulcer. In an eighth embodiment of the fifth aspect, the wound is a vascular wound. In a ninth embodiment of the fifth aspect, the wound is a burn. In a tenth embodiment of the fifth aspect, the wound is the result of radiation exposure.

In a sixth aspect of the second embodiment or its first, second or third aspect or the first embodiment of the first aspect, the compound is administered for reducing the formation of scaring at a wound site to a subject that has suffered a skin injury.

In a seventh aspect of the second embodiment or its first, second or third aspect or the first embodiment of the first aspect, the compound is administered for increasing homing or trafficking of stem cells to an area of injury. In a first embodiment of the seventh aspect, the compound is administered in substantial proximity to the area of injury. In a second embodiment of the seventh aspect, the compound is administered systemically.

In an eighth aspect of the second embodiment or its first, second or third aspect or the first embodiment of the first aspect, the compound is administered for treating ischemia. In a first embodiment of the eighth aspect, the ischemia is associated with peripheral artery disease. In a second embodiment of the eighth aspect, the ischemia is critical limb ischemia. In a third embodiment of the eighth aspect, the ischemia is associated with organ or cell transplantation.

In a third embodiment, the method is a method of treating cardiac tissue damage, bone injury, or ischemia or promoting wound healing, or reducing the formation of scarring or increasing homing or trafficking of stem cells in a subject in need thereof, comprising administering to the subject an effective amount of a compound represented by Formula II:

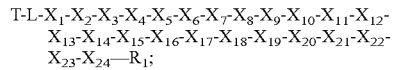

or a pharmaceutically acceptable salt thereof, wherein:

L is a linking moiety selected from: $C(S)$, $S(O)_2$, $N(R^3)S^*(O)$, $N(R^3)S^*(O)_2$, $N(R^3)C^*(O)$, $N(R^3)C^*(S)$, $OC^*(O)$, $OC^*(S)$, $SC^*(O)$, $SC^*(S)$, $C(=NH)$, and $N(R^3)C^*(=NH)$; wherein L is bonded to P at the atom marked with an asterisk (*) and $R^3$ is selected from: H, D, $(C_1-C_6)$alkyl, $(C_2-C_6)$alkenyl, $(C_2-C_6)$alkynyl, $(C_1-C_6)$alkoxy, $(C_3-C_9)$cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to the N terminal nitrogen of $X_1$ or the next present amino acid residue if $X_1$ is absent; T is a lipophilic tether moiety bonded to L; and $R_1$ is $OR_2$ or $N(R_2)_2$, each $R_2$ is independently H or alkyl, wherein at least three contiguous $X_1$-$X_{24}$ amino acid residues are present, and wherein:

$X_1$ is a valine residue or absent, $X_2$ is an isoleucine residue or absent, $X_3$ is a leucine residue or absent, $X_4$ is a valine residue, a glycine residue or absent, $X_5$ is a methionine residue, a glycine residue, a methyl serine residue, a homoserine residue, a propargyl glycine residue, a cysteine residue or absent, $X_6$ is a glycine residue or absent, $X_7$ is a tyrosine residue, a glutamine residue or absent $X_8$ is a glutamine residue, a lysine residue or absent, $X_9$ is a lysine residue, or a 2-aminoisobutyric acid (Aib) residue, $X_{10}$ is a lysine residue, a leucine residue, or a proline residue, $X_{11}$ is a leucine residue, an arginine residue, a d-leucine residue, a proline residue, a photoleucine residue, or a histidine residue, $X_{12}$ is an arginine residue, a cyclohexyl alanine residue, a serine residue or a proline residue, $X_{13}$ is a serine residue, a methionine residue, a d-proline residue, a hydroxy proline residue, a arginine residue or a proline residue, or a threonine residue, $X_{14}$ is a methionine residue, a threonine residue, an alanine residue, a histidine residue, a methyl serine residue, a proline residue, a Dpr residue, a hydroxy proline residue, a serine residue, a norleucine residue, a homoserine residue a tryptophan residue or a glycine residue, $X_{15}$ is a threonine residue, an aspartic acid residue, a d-proline residue, a histidine residue, or a methionine residue, $X_{16}$ is an aspartic acid residue, a lysine residue or a threonine residue, $X_{17}$ is a lysine residue, a tyrosine residue, a d-lysine residue or an aspartic acid residue, $X_{18}$ is a tyrosine residue, a phenylalanine residue, a lysine residue, a naphthyl alanine residue, a d-arginine residue or a d-tyrosine residue, $X_{19}$ is an arginine residue, a lysine residue, a leucine residue, a citrulline residue, a d-arginine residue or a tyrosine residue, $X_{20}$ is a leucine residue, a valine residue, a norleucine residue, a d-leucine residue, an arginine residue, or absent, $X_{21}$ is a histidine residue, a leucine residue or absent, $X_{22}$ is a leucine residue or absent, $X_{23}$ is an arginine residue or absent, and $X_{24}$ is a valine residue or absent.

In a first aspect of the third embodiment, L is selected from $S^*(O)_2$ and $OC^*(O)$. In a second aspect of the third embodiment, the compound is selected from:

229
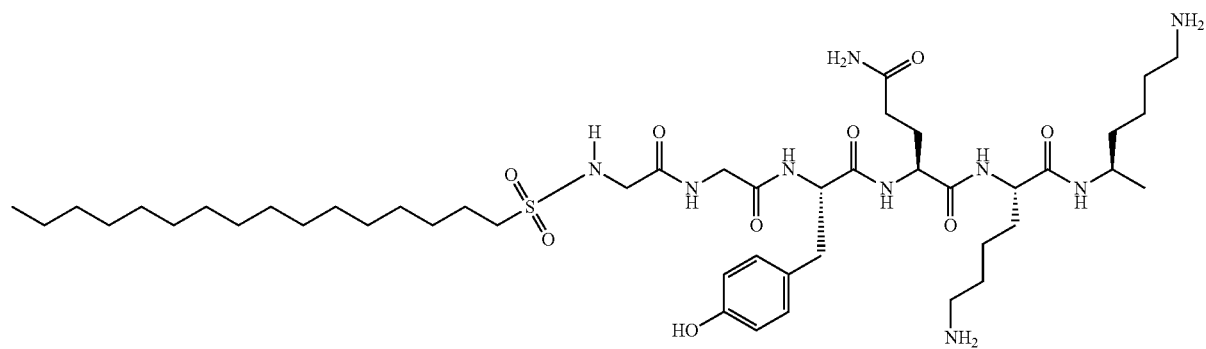
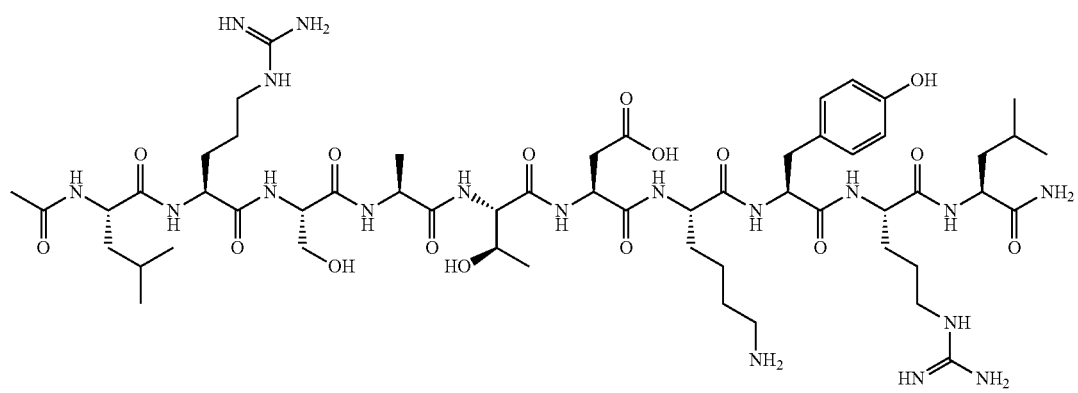
230
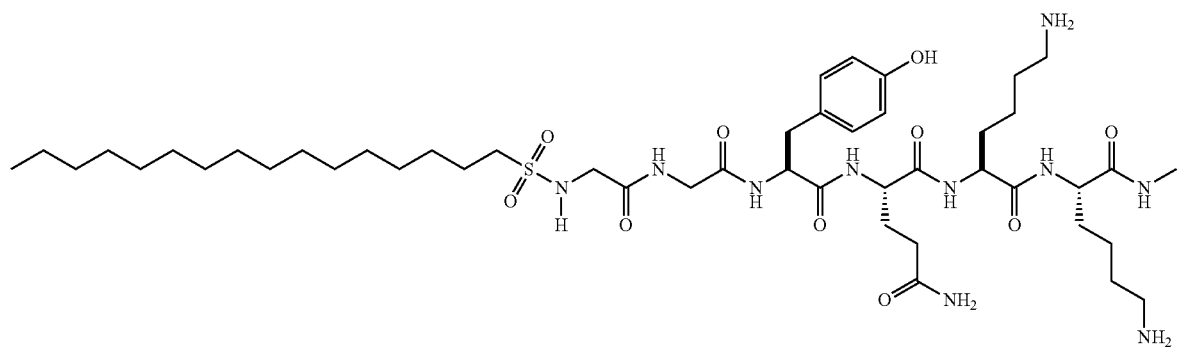
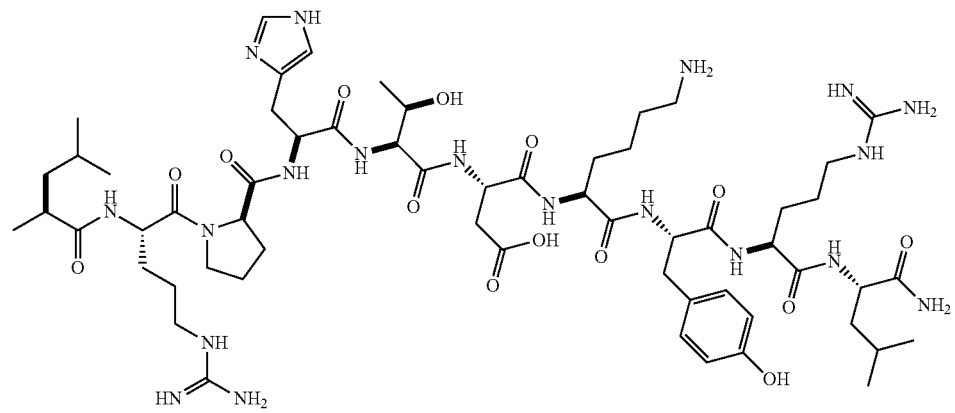
and

-continued

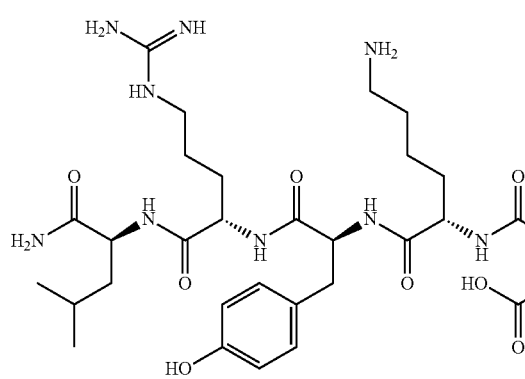

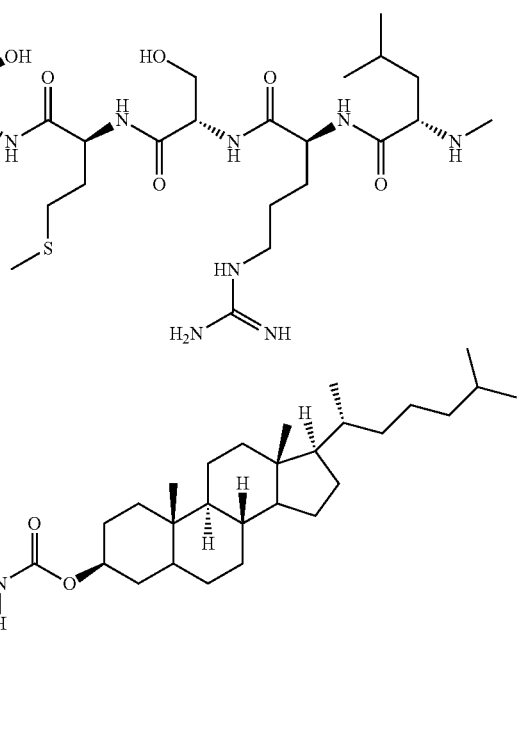

or a pharmaceutically acceptable salt of any of the foregoing.

In a third aspect of the third embodiment or its first or second aspect, the compound is administered for treating cardiac tissue damage. In a first embodiment of the third aspect, the cardiac tissue damage is associated with ischemic cardiac disease. In a second embodiment of the third aspect, the cardiac tissue damage is associated with myocardial infarction. In a third embodiment of the third aspect, the cardiac tissue damage is associated with congestive heart failure. In a forth embodiment of the third aspect, the cardiac tissue damage is associated with valvular disease.

In a fourth aspect of the third embodiment or its first or second aspect, the compound is administered for treating bone injury. In a first embodiment of the fourth aspect, the bone injury is associated osteonecrosis. In a second embodiment of the fourth aspect, the osteonecrosis is in one or more bones selected from the group consisting of jaw, knee, hip, leg, shoulder, ankle and arm. In a third embodiment of the fourth aspect, the bone injury is a fracture. In a fourth embodiment of the fourth aspect, the bone injury is osteoporosis. In a fifth embodiment of the fourth aspect, the bone injury is osteopenia. In a sixth embodiment of the fourth aspect, the compound is administered in conjunction with a bone graft.

In a fifth aspect of the third embodiment or its first or second aspect, the compound is administered for promoting wound healing. In a first embodiment of the fifth aspect, the wound is a surface wound. In a second embodiment of the fifth aspect, the wound is a surgical wound. In a third embodiment of the fifth aspect, the wound is an internal wound. In a fourth embodiment of the fifth aspect, the wound is a chronic wound. In a fifth embodiment of the fifth aspect, the wound is an ulcer. In a sixth embodiment of the fifth aspect, the wound is a diabetic ulcer. In a seventh embodiment of the fifth aspect, the ulcer is a decubitus ulcer. In a eighth embodiment of the fifth aspect, the wound is a vascular wound. In a ninth embodiment of the fifth aspect, the wound is a burn. In a tenth embodiment of the fifth aspect, the wound is the result of radiation exposure.

In a sixth aspect of the third embodiment or its first or second aspect, the compound is administered for reducing the formation of scaring at a wound site to a subject that has suffered a skin injury.

In a seventh aspect of the third embodiment or its first or second aspect, the compound is administered for increasing homing or trafficking of stem cells to an area of injury. In a first embodiment of the seventh aspect, the compound is administered in substantial proximity to the area of injury. In a second embodiment of the seventh aspect, the compound is administered systemically.

In a eighth aspect of the third embodiment or its first or second aspect, the compound is administered for treating ischemia. In a first embodiment of the eighth aspect, the ischemia is associated with peripheral artery disease. In a second embodiment of the eighth aspect, the ischemia is critical limb ischemia. In a third embodiment of the eighth aspect, the ischemia is associated with organ or cell transplantation.

In a fourth embodiment, the method is a method of treating cardiac tissue damage, bone injury, or ischemia or promoting wound healing, or reducing the formation of scarring or increasing homing or trafficking of stem cells in a subject in need thereof, comprising administering to the subject an effective amount of a compound of Formula I:

T-L-P, or a pharmaceutically acceptable salt thereof, wherein:
P is a peptide sequence selected from: SEQ ID NOS:1-40;
L is a linking moiety bonded to P at an N-terminal nitrogen of an N-terminal amino-acid residue selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to P at the atom marked with an asterisk (*) and R$^3$ is selected from: H, D, (C$_1$-C$_6$) alkyl, (C$_2$-C$_6$)alkenyl, (C$_2$-C$_6$)alkynyl, (C$_1$-C$_6$) alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted and bonded to P at an N terminal nitrogen of an N-terminal amino-acid residue;
and T is a lipophilic tether moiety bonded to L.

In a first aspect of the fourth embodiment, L is selected from C(O), S*(O)$_2$ and OC*(O). In a first embodiment, of the first aspect, L is C(O). In a second aspect of the fourth embodiment or its first aspect or the first embodiment of the first aspect, the C-terminus of SEQ ID NOS:1-40 is functionalized with NR$_1$R$_2$, wherein R$_1$ and R$_2$ are each independently H or alkyl. In a first embodiment of the second aspect, the C-terminus of SEQ ID NOS:1-40 is functionalized with NH$_2$. In a particular embodiment of the first embodiment of the second aspect, a lipophilic tether moiety is bonded on the C-terminus of P. In a third aspect of the fourth embodiment, P is selected from SEQ ID NOS:1-38. In a first embodiment of the third aspect, P is selected from SEQ ID NOS: 21-27, 29, 31, 32, 35, and 36. In a second embodiment of the third aspect, P is SEQ ID NO: 39. In a third embodiment of the third aspect, P is SEQ ID NO: 40.

In a fourth aspect of the fourth embodiment, the compound is administered for treating cardiac tissue damage. In a first embodiment of the fourth aspect, the cardiac tissue damage is associated with ischemic cardiac disease. In a second embodiment of the fourth aspect, the cardiac tissue damage is associated with myocardial infarction. In a third embodiment of the fourth aspect, the cardiac tissue damage is associated with congestive heart failure. In a forth embodiment of the fourth aspect, the cardiac tissue damage is associated with valvular disease.

In a fifth aspect of the fourth embodiment, the compound is administered for treatment of bone injury. In a first embodiment of the fifth aspect, the bone injury is associated with osteonecrosis. In a second embodiment of the fifth aspect, the osteonecrosis is in one or more bones selected from the group consisting of jaw, knee, hip, leg, shoulder, ankle and arm. In a third embodiment of the fifth aspect, the bone injury is a fracture. In a fourth embodiment of the fifth aspect, the bone injury is osteoporosis. In a fifth embodiment of the fifth aspect, the bone injury is osteopenia. In a sixth embodiment of the fifth aspect, the compound is administered in conjunction with a bone graft.

In a sixth aspect of the fourth embodiment, the compound is administered for promoting wound healing. In a first embodiment of the sixth aspect, the wound is a surface wound. In a second embodiment of the sixth aspect, the wound is a surgical wound. In a third embodiment of the sixth aspect, the wound is an internal wound. In a fourth embodiment of the sixth aspect, the wound is a chronic wound. In a fifth embodiment of the sixth aspect, the wound is an ulcer. In a sixth embodiment of the sixth aspect, the wound is a diabetic ulcer. In seventh embodiment of the sixth aspect, the ulcer is a decubitus ulcer. In an eighth embodiment of the sixth aspect, the wound is a vascular wound. In a ninth embodiment of the sixth aspect, the wound is a burn. In a tenth embodiment of the sixth aspect, the wound is the result of radiation exposure.

In a seventh aspect of the fourth embodiment, the compound is administered for reducing the formation of scarring at a wound site to a subject that has suffered a skin injury.

In an eight aspect of the fourth embodiment, the compound is administered for increasing homing or trafficking of stem cells to an area of injury. In a first embodiment of the eighth aspect, the compound is administered in substantial proximity to the area of injury. In a second embodiment of the eighth aspect, the compounds are administered systemically.

In a ninth aspect of the fourth embodiment, the compound is administered for treating ischemia. In a first embodiment of the ninth aspect, the ischemia is peripheral artery disease. In a second embodiment of the ninth aspect, the ischemia is critical limb ischemia. In a third embodiment of the ninth aspect, the ischemia results from organ or cell transplantation.

The method of any one of the first, second, third or fourth embodiments described above or any of the above aspects of the first, second, third or fourth embodiments or any of the specific embodiments of the aspects, wherein T is an optionally substituted (C$_6$-C$_{30}$)alkyl, (C$_6$-C$_{30}$)alkenyl, (C$_6$-C$_{30}$) alkynyl, wherein 0-3 carbon atoms are replaced with oxygen, sulfur, nitrogen or a combination thereof.

The method of any one of the first, second, third or fourth embodiments described above or any of the above aspects of the first, second, third or fourth embodiments or any of the specific embodiments of the aspects, wherein T is selected from the group consisting of: CH$_3$(CH$_2$)$_{16}$, CH$_3$(CH$_2$)$_{15}$, CH$_3$(CH$_2$)$_{14}$, CH$_3$(CH$_2$)$_{13}$, CH$_3$(CH$_2$)$_{12}$, CH$_3$(CH$_2$)$_{11}$, CH$_3$(CH$_2$)$_{10}$, CH$_3$(CH$_2$)$_9$, CH$_3$(CH$_2$)$_8$, CH$_3$(CH$_2$)$_9$OPh-, CH$_3$(CH$_2$)$_6$C=C(CH$_2$)$_6$, CH$_3$(CH$_2$)$_{11}$O(CH$_2$)$_3$, and CH$_3$(CH$_2$)$_9$—O—(CH$_2$)$_2$.

The method of any one of the first, second, third or fourth embodiments described above or any of the above aspects of the first, second, third or fourth embodiments or any of the specific embodiments of the aspects, wherein T is a fatty acid derivative.

The method of any one of the first, second, third or fourth embodiments described above or any of the above aspects of the first, second, third or fourth embodiments or any of the specific embodiments of the aspects, wherein the fatty acid is selected from the group consisting of: butyric acid, caproic acid, caprylic acid, capric acid, lauric acid, myristic acid, palmitic acid, stearic acid, arachidic acid, behenic acid, lignoceric acid, myristoleic acid, palmitoleic acid, oleic acid, linoleic acid, α-linolenic acid, arachidonic acid, eicosapentaenoic acid, erucic acid, docosahexaenoic acid.

The method of any one of the first, second, third or fourth embodiments described above or any of the above aspects of the first, second, third or fourth embodiments or any of the specific embodiments of the aspects, wherein T is a bile acid derivative.

The method of any one of the first, second, third or fourth embodiments described above or any of the above aspects of the first, second, third or fourth embodiments or any of the specific embodiments of the aspects, wherein the bile acid is selected from the group consisting of: lithocholic acid, chenodeoxycholic acid, deoxycholic acid, cholanic acid, cholic acid, ursocholic acid, ursodeoxycholic acid, isoursodeoxycholic acid, lagodeoxycholic acid, dehydrocholic acid, hyocholic acid, and hyodeoxycholic acid.

The method of any one of the first, second, third or fourth embodiments described above or any of the above aspects of the first, second, third or fourth embodiments or any of the specific embodiments of the aspects, wherein T is selected from sterols; progestagens; glucocorticoids; mineralcorticoids; androgens; and estrogens.

The method of any one of the first, second, third or fourth embodiments described above or any of the above aspects of the first, second, third or fourth embodiments or any of the specific embodiments of the aspects, wherein TL is selected from:

$CH_3(CH_2)_{15}$—C(O);

$CH_3(CH_2)_{13}$—C(O);

$CH_3(CH_2)_9O(CH_2)_2C(O)$;

$CH_3(CH_2)_{10}O(CH_2)_2C(O)$;

$CH_3(CH_2)_6C=C(CH_2)_6$—C(O);

LCA-C(O); and $CH_3(CH_2)_9OPh-C(O)$ wherein

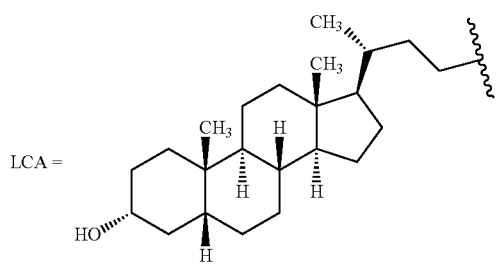

The method of any one of the first, second, third or fourth embodiments described above or any of the above aspects of the first, second, third or fourth embodiments or any of the specific embodiments of the aspects, wherein T is selected from:

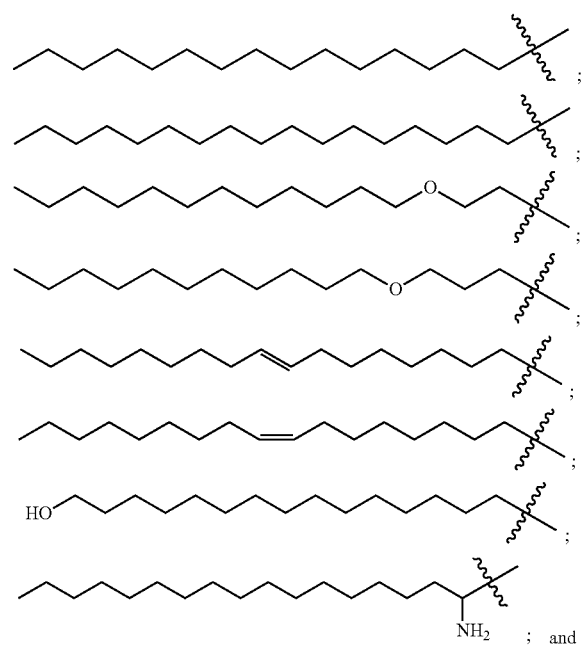

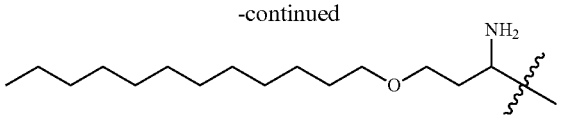

In one embodiment, an effective amount of a compound of this invention can range from about 0.005 mg to about 5000 mg per treatment. In more specific embodiments, the range is from about 0.05 mg to about 1000 mg, or from about 0.5 mg to about 500 mg, or from about 5 mg to about 50 mg. Treatment can be administered one or more times per day (for example, once per day, twice per day, three times per day, four times per day, five times per day, etc.). When multiple treatments are used, the amount can be the same or different.

It is understood that a treatment can be administered every day, every other day, every 2 days, every 3 days, every 4 days, every 5 days, etc. For example, with every other day administration, a treatment dose can be initiated on Monday with a first subsequent treatment administered on Wednesday, a second subsequent treatment administered on Friday, etc. Treatment is typically administered from one to two times daily. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

Alternatively, the effective amount of a compound of the invention is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

In another embodiment, any of the above methods of treatment comprises the further step of co-administering to said patient one or more second therapeutic agents. The choice of second therapeutic agent may be made from any second therapeutic agent known to be useful for co-administration with a compound that modulates the CXCR4 receptor. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In a particular embodiment, combination therapy can be used in the treatment of HIV-1 viral infection. In a specific embodiment, the patient being treated for the HIV-1 viral infection is an experienced patient.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized Other potential advantages (including without limitation improved dosing regimens and/or reduced drug cost) will be apparent to those of skill in the art.

Kits

The present invention also provides kits for use to treat the target disease, disorder or condition. These kits comprise (a) a pharmaceutical composition comprising a compound of Formula A, Formula A-1, Formula I or Formula II, or a salt thereof, wherein said pharmaceutical composition is in a container; and (b) instructions describing a method of using the pharmaceutical composition to treat the target disease, disorder or condition.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

GENERAL METHODS FOR PREPARING CXCR4 RECEPTOR COMPOUNDS

Synthesis of Peptides

The peptide component (P) of the compounds of the invention can be synthesized by incorporating orthogonally protected amino acids in a step-wise fashion. Any suitable synthetic methods can be used. Traditional Fmoc or Boc chemistry can be easily adapted to provide the desired peptide component (P) of the compounds of the invention. Fmoc is generally preferred, because the cleavage of the Fmoc protecting group is milder than the acid deprotection required for Boc cleavage, which requires repetitive acidic deprotections that lead to alteration of sensitive residues, and increase acid catalyzed side reactions. (Fields, G. B. et al. in *Int. J. Pept. Protein*, 1990, 35, 161).

The peptides can be assembled linearly via Solid Phase Peptide Synthesis (SPPS), can be assembled in solution using modular condensations of protected or unprotected peptide components or a combination of both.

Solid Phase Peptide Synthesis

For SPPS, an appropriate resin is chosen that will afford the desired moiety on the C-terminus upon cleavage. For example upon cleavage of the linear peptide, a Rink amide resin will provide a primary amide on the C-terminus, whereas a Rink acid resin will provide an acid. Rink acid resins are more labile than Rink amide resins and the protected peptide could also be cleaved and subsequently the free acid activated to react with amines or other nucleophiles. Alternatively, other resins could provide attachment of other moieties prior to acylation, leading to cleavage of an alkylated secondary amide, ester or other desired C-terminal modification. A review of commonly used resins and the functional moiety that results after cleavage can be found in manufacturer literature such as NovaBiochem or Advanced Chemtech catalogues.

Typically a resin is chosen such that after cleavage the C-terminus is an amide bond. Rink amide resin is a resin that results in a C-terminal amide during cleavage. The orthogonally protected Fmoc amino acids are added stepwise using methods well known in literature (Bodansky M., Principles of Peptide Synthesis (1993) 318 p; Peptide Chemistry, a Practical Textbook (1993); Spinger-Verlag). These procedures could be done manually or by using automated peptide synthesizers.

The process involves activating the acid moiety of a protected amino acid, using activating agents such as HBTU, HATU, PyBop or simple carbodiimides. Often an additive is used to decrease racemization during coupling such as HOBt or HOAt (Schnölzer, M. et al., *Int. J. Pept. Protein Res.,* 1992, 40, 180). Manually, the coupling efficiency can be determined photometrically using a ninhydrin assay. If the coupling efficiency is below 98%, a second coupling may be desired. After the second coupling a capping step may be employed to prevent long deletion sequences to form, simplifying the purification of the desired final compound. With automation, second couplings are not commonly required, unless a residue is known to be problematic such as Arginine.

Deprotection of the Fmoc is most commonly accomplished using piperidine (20%) in dimethylformamide (DMF). Alternatively other secondary amines may also be used such as morpholine, diethylamine or piperazine. This reaction is facile and normally is accomplished within 20 minutes using piperidine. After deprotection the resin is washed several times with DMF and DCM prior to coupling with the next residue. This process is repeated, assembling the peptide linearly until the sequence is complete. The final Fmoc is removed, which allows for coupling with the tether moiety.

In a preferred synthesis, the peptide is formed by SPPS accomplished manually or in an automated fashion using a commercially available synthesizer such as the CEM Microwave peptide synthesizer, Rainin Symphony synthesizer, or ABI 433 flow-through synthesizer. Commercially available Rink Amide resin is used for synthesizing the C-terminal amide peptides (Rink, H., *Tetrahedron Lett,* 28, 4645, 1967). Peptide synthesis reagents (coupling, deprotection agents) are commercially available and include HOBT, HBTU (Novabiochem) as well as DMF, DCM, Piperidine, NMP, and DIEA (Sigma-Aldrich). Suitably protected amino acids for use in solid phase peptide synthesis are commercially available from many sources, including Sigma-Aldrich and CEM Corporation.

For example, a convenient preparation of peptides on a 0.1 mmol or 0.25 mmol scale uses Rink amide solid-phase resin with a substitution of about 0.6 mmol/g. Linear attachment of the amino acids is accomplished on a ABI continuous flow automated synthesizer using 5 eq. of orthogonally protected amino acid (AA), and using HBTU/HOBt coupling protocol, (5 eq. of each reagent). In another preferred synthesis, peptides can be synthesized using a microwave instrument using 10 eq of reagents. Deprotection of Fmoc can be accomplished with 20% piperidine in DMF followed by washing with DMF and DCM.

In both cases (i.e., Rink acid and Rink amide resins), final Fmoc deprotection of the N-terminus would leave a free amine after cleavage from the resin unless it is modified prior to cleavage. In the compounds of the invention, tether moieties are attached to the terminal amine via amide, thioamide, sulfonamide, urea, thiourea, carbamate, thiocarbamate, carbamodithioate, imine, imidamide, or guanidine bonds.

Solution Phase Synthesis of Peptides

For solution phase synthesis the desired peptide is generally broken down into peptide fragments in units of 2-4 amino acids. The selected unit is dependent on the sequence, the stability of the fragment to racemization, and the ease of assembly. As each amino acid is added, only 1-1.5 eq of the residue is required, versus the 5-10 equivalents of reagent required for SSPS. Preactivated amino acids such as OSu active ester and acid fluorides also can be used, requiring only a base for completion of the reaction.

Coupling times require 1.5-2 hours for each step. Two fragments are condensed in solution, giving a larger fragment that then can be further condensed with additional fragments until the desired sequence is complete. The solution phase protocol uses only 1 eq of each fragment and will use coupling reagents such as carbodiimides (DIC). For racemized prone fragments, PyBop or HBTU/HOBt can be used. Amino acids with Bsmoc/tBu or Fmoc/tBu and Boc/Benzyl protection are equally suitable for use.

When Fmoc is used, the use of 4-(aminomethyl)piperidine or tris(2-aminoethyl)amine as the deblocking agent can avoid undesired side reactions. The resulting Fmoc adduct can be extracted with a phosphate aqueous buffer of pH 5.5 (Organic Process Research & Development 2003, 7, 2837). If Bsmoc is used, no buffer is required, only aqueous extractions are needed. Deprotections using these reagents occur in 30-60 minutes. Deblocking of the Fmoc group on the N-terminal residue provides a free terminal amine that is used for attachment of the tether moiety. In the compounds of the invention, tether moieties are attached through amide, thioamide, sulfonamide, urea, thiourea, carbamate, thiocarbamate, carbamodithioate, imine, imidamide, or guanidine bonds to the N-terminal amine. One advantage of solution phase synthesis is the ability to monitor the compound after every coupling step by mass spectrometry to see that the product is forming. In addition, a simple TLC system could be used to determine completion of reaction.

Attachment of Tethers

Tethers can be attached to the terminal nitrogen of the N-terminal amino acid of the peptide chain using amide bond coupling:

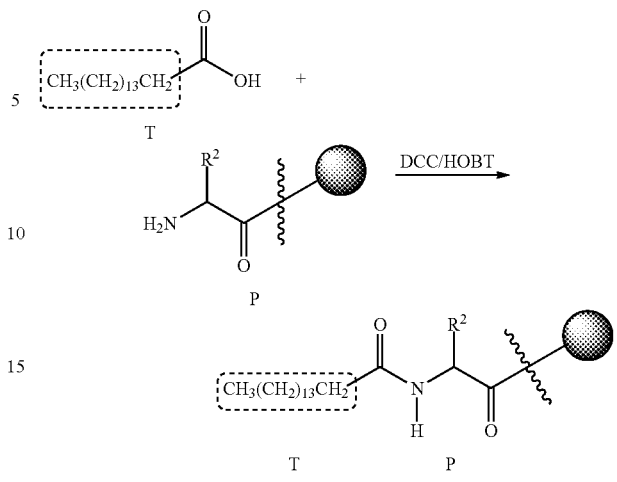

Linkers can be attached to the N-terminal nitrogen of the N-terminal amino acid residue of P using chemistries that are compatible with covalent linkage to nitrogen, including, but not limited to, amide bond, urea, thiourea, carbamate, and sulfonamide formation.

For example, sulfonamide formation can occur as detailed below:

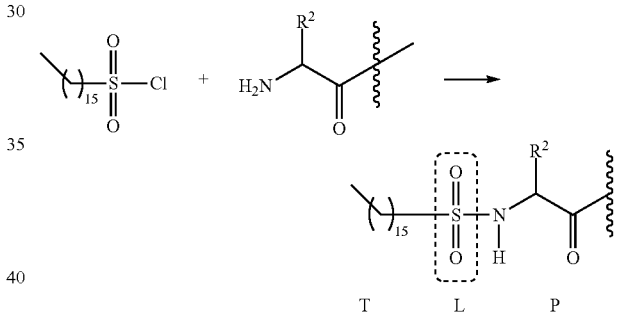

The tether can be attached using solid phase procedures or in solution using an amide bond coupling. After the N-terminus is suitably coupled, the final compound is cleaved from the resin using an acidic cocktail (*Peptide Synthesis and Applications*, John Howl, Humana Press, 262 p, 2005). Typically these cocktails use concentrated trifluoroacetic acid (80-95%) and various scavengers to trap carbocations and prevent side chain reactions. Typical scavengers include isopropylsilanes, thiols, phenols and water. The cocktail mixture is determined by the residues of the peptide. Special care needs to be taken with sensitive residues, such as methionine, aspartic acid, and cysteine. Typical deprotection occurs over 2-5 hours in the cocktail. A preferred deprotection cocktail include the use of triisopropylsilane (TIS), Phenol, thioanisole, dodecanethiol (DDT) and water. Methane sulfonic acid (MSA) may also be used in the cocktail (4.8%). A more preferred cocktail consists of (TFA:MSA:TIS:DDT:Water 82: 4.5:4.5: 4.5:4.5; 10 mL/0.1 mmol resin).

After deprotection, the resin is removed via filtration, and the final compound is isolated via precipitation from an organic solvent such as diethyl ether, m-tert-butyl ether, or ethyl acetate and the resulting solid collected via filtration or lyophilized to a powder. Purification of the peptide using reverse phase HPLC may be required to achieve sufficient purity. Generally, a gradient of aqueous solvent with an organic solvent will provide sufficient separation from impurities and deletion sequences. Typically 0.1% TFA is used as the aqueous and organic modifier, however, other modifiers such as ammonium acetate can also be used. After purification, the compound is collected, analyzed and fractions of sufficient purity are combined and lyophilized, providing the compound as a solid.

Amino Acid Reagents

The following commercially available orthogonally protected amino acids used can be used in the synthesis of compounds of the invention: Fmoc-Tyr(tBu)-OH, Fmoc-Ala-OH*$H_2O$, Fmoc-Arg(Pbf)-OH, Fmoc, Asn(Trt)-OH, Fmoc-Asp(tBu), Fmoc-Cys(tBu)-OH, Fmoc-Glu(tBu)-OH, Fmoc-Glx(Pbf)-OH, Fmoc-Gly-OH, Fmoc-His(Trt)-OH, Fmoc-Leu-OH, Fmoc-Ile-OH, Fmoc, Lys(tBu)-OH, Fmoc-Met-OH, Fmoc-Phe-OH, Fmoc-Ser(tBu)-OH, Fmoc-Thr(tBu)-OH, Fmoc-Typ-OH, and Fmoc-Val-OH. Additional amino acids suitable for incorporation into the compounds of the invention (e.g., D amino acids, substituted amino acids and other protecting group variations) are also commercially available or synthesized by methods known in the art.

Analytical Methods

The compounds of the invention are analyzed for purity by HPLC using the methods listed below. Purification is achieved by preparative HPLC.

Fast LC/MS Method
Column: Phenomenex Luna C-5 20×30 mm
Flow: 1.0 ml/min
Solvent A: 0.1% TFA in Type I water
Solvent B: 0.1% TFA in Acetonitrile
UV 220 nm
Injection: 20 ul
Gradient 5-95% B (7 minutes); 95-5% B (1 minute); 5% B (4 minutes)
Analytical Purity Method
Column: Phenomenex Luna C-5 20×30 mm
Flow: 1.0 ml/min
Solvent A: 0.1% TFA in Type I water
Solvent B: 0.1% TFA in Acetonitrile
UV: 220 nm
Injection: 20 ul
Gradient: 2-95% B (10 minutes); 95-2% B (2 minutes); 2% B (2 minutes)
Preparative LC/MS Method
Column: Phenomenex Luna C-5 250×150 mm
Flow: 5.0 ml/min
Solvent A: 0.1% TFA in Type I water
Solvent B: 0.1% TFA in Acetonitrile
UV: 220 nm
Injection: 900 ul
Gradient: 35% B (5 minutes); 35-85% B (13 minutes); 85-35% B (0.5 minutes); 35% B (1.5 minutes)

Synthesis of Selected Compounds

Compound No. 45 ($CH_3(CH_2)_{15}SO_2$—GGYQKKL-RSATDKYRL-amide) (SEQ. ID No. 23)

Compound 45 was synthesized as described above on Rink amide resin at 0.1 mmol scale. Amino acids were coupled sequentially as described above. Following deprotection of the Fmoc group on the N-terminal residue serine, the N-terminal amine was capped with 1-hexadecane sulfonyl chloride (10 eq.). The compound was cleaved from the resin by TFA containing MS, TIS, DDT, and water (82: 4.5:4.5:4.5:4.5; 10 mL), filtered through a coarse fit Buchner full, triturated with ether and the resulting precipitate collected by centrifugation. Crude peptide was taken up in minimum amount of DMSO and TFA and purified by RP-HPLC. Fractions with correct MW were pooled and lyophilized and analyzed for purity using Method A to yield 2.9 mg of compound 45.

Synthesis of Selected Compounds

Compound No. 46 $CH_3(CH_2)_{15}SO_2$—GGYQKKL-RpHTDKYRL-amide) (SEQ. ID No. 24)

Compound 46 was synthesized as described above on Rink amide resin at 0.1 mmol scale. Amino acids were coupled sequentially as described above. Following deprotection of the Fmoc group on the N-terminal residue serine, the N-terminal amine was capped with 1-hexadecane sulfonyl chloride (10 eq.). The compound was cleaved from the resin by TFA containing MS, TIS, DDT, and water (82: 4.5:4.5:4.5:4.5; 10 mL), filtered through a coarse frit Buchner full, triturated with ether and the resulting precipitate collected by centrifugation. Crude peptide was taken up in minimum amount of DMSO and TFA and purified by RP-HPLC. Fractions with correct MW were pooled and lyophilized and analyzed for purity using Method A to yield 3.5 mg of compound 46.

Synthesis of Selected Compounds

Compound No. 47 ($C_{28}H_{45}O_2$—MGYQKKL-RSMTDKYRL-amide) (SEQ. ID No. 52)

Compound 47 was synthesized as described above on Rink amide resin at 0.1 mmol scale. Amino acids were coupled sequentially as described above. Following deprotection of the Fmoc group on the N-terminal residue serine, the N-terminal amine was capped with cholesteryl chloroformate (10 eq.). The compound was cleaved from the resin by TFA containing MS, TIS, DDT, and water (82: 4.5:4.5:4.5:4.5; 10 mL), filtered through a coarse frit Buchner full, triturated with ether and the resulting precipitate collected by centrifugation. Crude peptide was taken up in minimum amount of DMSO and TFA and purified by RP-HPLC. Fractions with correct MW were pooled and lyophilized and analyzed for purity using Method A to yield 1.8 mg of compound 47.

The compounds listed in Tables 6-11 pharmaceutically acceptable salts thereof were prepared according to the methods described herein.

METHODS OF SCREENING

Functional Assays

Functional assays suitable for use in detecting and characterizing GPCR signaling include Gene Reporter Assays and Calcium Flux assays, cAMP and kinase activation assays. Several suitable assays are described in detail below.

Gene Reporter Assays

Cells expressing the GPCR of interest can be transiently or stably transfected with a reporter gene plasmid construct containing an enhancer element which responds to activation of a second messenger signaling pathway or pathways, thereby controlling transcription of a cDNA encoding a detectable reporter protein. GPCR expression can be the result of endogenous expression on a cell line or cell type or the result of stable or transient transfection of DNA encoding the receptor of interest into a cell line by means commonly used in the art. Immortalized cell lines or primary cell cultures can be used.

If the activated pathway is stimulatory (e.g., Gs or Gq), agonist activity results in activation of transcription factors, in turn causing an increase in reporter gene transcription, detectable by an increase in reporter activity. To test for agonist or inverse agonist activity, cells expressing the GPCR and the reporter gene construct can be challenged by the test compound for a predetermined period of time (e.g., 2-12 hours, typically 4 hours). Cells can then be assessed for levels of reporter gene product. Inverse agonists will suppress levels of reporter to below basal levels in a dose dependent manner. To test for antagonist or inhibitory activity through a stimulatory pathway, cells expressing both the GPCR and the reporter gene construct can be activated by a receptor agonist to increase gene reporter product levels. Treatment with antagonists will counter the effect of agonist stimulation in a dose- and receptor-dependent manner To test for agonist activity on receptor signaling through an inhibitory pathway (e.g., Gi, which couples to CXCR4), cells can be treated with a systematic activator (e.g., forskolin) to increase levels of reporter gene product. Activation of Gi by treatment with receptor agonist will inhibit this expression by inhibiting adenylyl cyclase. To screen for antagonist activity, test compounds can be assessed for the ability to counter agonist inhibition of adenylyl cyclase, resulting in increase reporter transcription.

Alternatively, a plasmid construct expressing the promiscuous G-protein Gal 6 can be used to obtain a positive signal from a GPCR which normally couples to an inhibitory G-protein. Co-expression of the chimeric G-protein Gaq/Gai5 (Coward et al. *Analytical Biochemistry*, 270, 242-248 (1999)) allows coupling to Gi-coupled receptors and conversion of second messenger signaling from the inhibitory Gi pathway to the stimulatory Gq pathway. Agonist and antagonist assessment in these systems is the same as the stimulatory pathways. Well-to-well variation caused by such factors as transfection efficiency, unequal plating of cells, and cell survival rates can be normalized in transient transfection assays by co-transfecting a constitutively expressing reporter gene with a non-interfering signal independent of the regulated reporter.

Chemotaxis Assay

Chemotaxis assays are utilized to determine the effect of compound on the directed migration of cells in response to chemokine. In general, cells that express a receptor of interest are placed in the upper chamber of a Transwell chemotaxis plate (Corning) and allowed to migrate through a polycarbonate membrane to a lower chamber containing the appropriate receptor-specific ligand. To test for antagonist or potentiating activity, cells are mixed with the desired concentration of compound prior to addition to the upper chamber. Conversely, agonist activity is determined by adding compound in the bottom chamber only without endogenous chemokine. The effect of compound is quantified by several parameters, including the extent of maximum response, the shift of agonist dose-response curves, and the area under the curve.

To measure the CXCR4 test compound elicited CXCR4-dependent migration of cells, the appropriate concentration of control agonist CXCL12 or test compound is diluted in phenol red-free RMPI-1640/20 mM HEPES/0.5% BSA buffer and placed in the bottom chamber of a transwell apparatus. CCRF-CEM cells, a human T-cell ALL line that endogenously expresses CXCR4, are washed twice in buffer and resuspended at 133,000 cells/ml. A 75 µl sample of the cell suspension is mixed with the test compound of interest and placed in the upper chamber of a 5-micron transwell apparatus.

To measure the effect of test compound on CXCL12 elicited CXCR4-dependent migration of cells, the appropriate concentration of CXCL12 is diluted in phenol red-free RMPI-1640/20 mM HEPES/0.5% BSA buffer and placed in the bottom chamber of a transwell apparatus. CCRF-CEM cells, a human T-cell ALL line that endogenously expresses CXCR4, are washed twice in buffer and resuspended at 133,000 cells/ml. A 75 µl sample of this suspension is mixed with the test compound of interest and placed in the upper chamber of a 5-micron transwell apparatus.

To initiate cell migration, the assembled transwell plate is placed in a 37° C., 0.5% $CO_2$ incubator for a specified time interval, typically between 30 and 120 minutes. After incubation, the unit is disassembled and the lower chamber placed at −80° C. overnight to facilitate lysis of cells. To quantify migrated cells, plates are thawed at 37° C. in a humidified chamber, and then a sample volume is removed from each well and mixed with an equal volume of CyQuant (Invitrogen) working solution in opaque plates. The fluorescence intensity of each well represents the DNA content and is directly proportional to cell number. Each sample is typically run in duplicate or triplicate and each plate include two separate negative controls. The plate background control, which includes no cells in the upper chamber, is subtracted from all values. The negative control has no agonist added in the lower chamber, and serves to establish the baseline for random migration.

Results

Figure 1B:
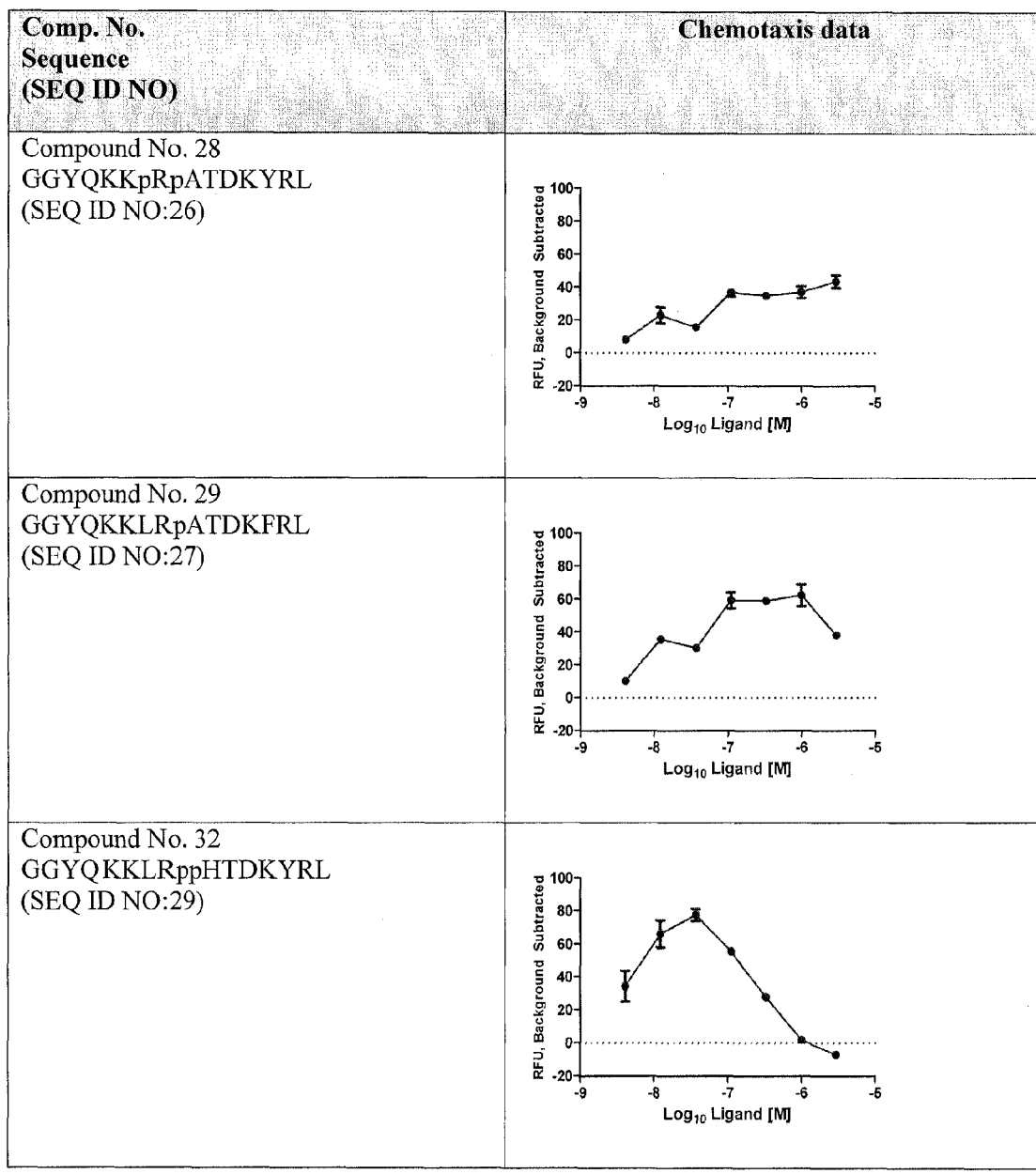
Figure 1C:
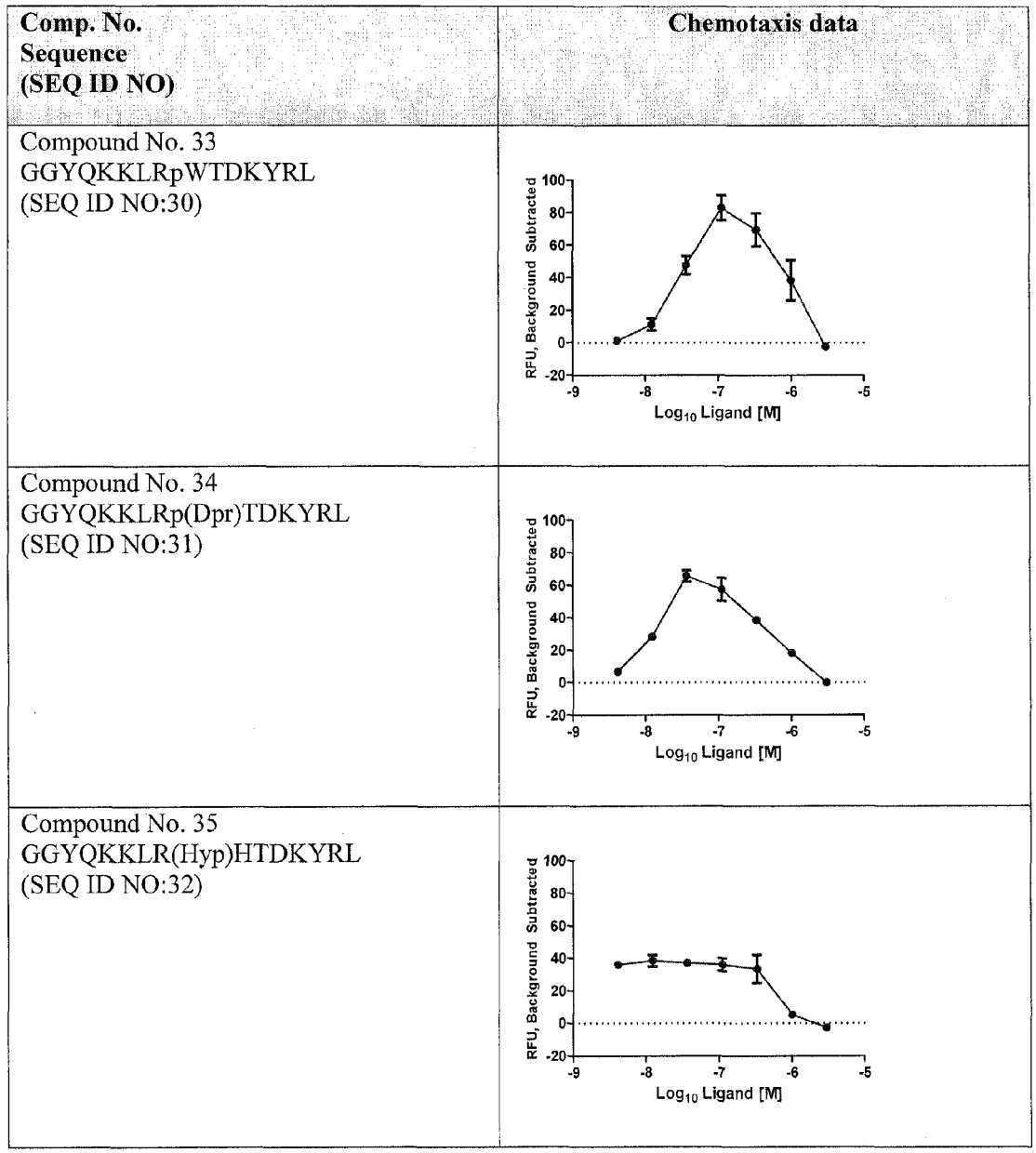

Results are shown in FIGS. 1A-1C for i1 loop compounds and the following table for i3 and i4 loop compounds.

| | | CXCR4 Chemotaxis Data Table (CEM cells, DMSO vehicle) | | |
|---|---|---|---|---|
| Comp. No. | Loop | Sequence | AUC (% of Vehicle) | Max (% of Vehicle) |
| 43 | i3 | SKLSHSKGHQKR KALKTTVIL (SEQ ID NO: 39) | 226.59 | 202.16 |
| 44 | i4 | GAKFKTSAQHAL TSVR (SEQ ID NO: 40) | 56.75 | 56.7 |

Calcium Flux Assay

Calcium Flux Assay is one of the most popular cell-based GPCR functional assays. It most often uses calcium sensing fluorescent dyes such as fura2 AM, fluo-4 and Calcium-4 to measure changes in intracellular calcium concentration. It is used mainly to detect GPCR signaling via Gαq subunit. Activation of these Gq-coupled GPCRs leads to activation of phospholipase C, which subsequently leads to increase in inositol phosphate production. IP3 receptors on endoplasmic reticulum sense the change then release calcium into cytoplasm. Intracellular calcium binding to the fluorescent dyes can be detected by instruments that quantify fluorescent intensities, such as FLIPR Tetra, Flexstation (MDS) and FDSS (Hamamatsu). In addition, to assess Gq-couple receptor signaling, a calcium flux assay can also be used to study Gs and Gi couple receptors by co-expressing CNG (cyclic nucleotide gated calcium channel) or chimeric G-proteins (Gqi5, Gsi5 for example). Activation of some Gi-coupled receptors can also be detected by calcium flux assay via Gβγ mediated phospholipase C activation.

CXCR4 Testing

Flexstation

Antagonist Mode:

The calcium flux assay was used to assess SDF-1α activation of the CXCR4 receptor and antagonist properties of the CXCR4 compounds in CCRF-CEM cells (human T lymphoblasts from acute lymphoblastic leukemia). CCRF-CEM cells were seeded into 96-well black plates with clear bottom at 200K/well in RPMI 1640 media with 20 mM HEPES containing 0.2% BSA. After dye loading by incubating with Calcium-4 dye at 37° C. for 1 hour, cell plates were read at 37° C. using the Flexstation 3 workstation. The addition of test compounds or reference antagonists was accomplished either by manual pipetting or by liquid handling using the Flexstation. The latter allows the assessment of intrinsic agonist activity of the test compounds by measuring initial changes in fluorescent intensity. After incubation of 24 minutes at 37° C., SDF-1α was added and receptor activation was assessed by measuring changes in fluorescent intensity using the Flexstation.

No antagonists were identified following the above method.

Agonist Mode:

The calcium flux assay was used to assess the test compounds' ability to activate the CXCR4 receptor in CCRF-CEM cells (human T lymphoblasts from acute lymphoblastic leukemia). CCRF-CEM cells were seeded into 96-well black plates with clear bottom at 200K/well in RPMI 1640 media with 20 mM HEPES containing 0.2% BSA. After dye loading by incubating with Calcium-4 dye at 37° C. for 1 hour, cell plates were read at 37° C. using the using the Flexstation 3 workstation. Receptor activation was assessed by measuring changes in fluorescent intensity after the addition of the test compounds or the reference agonist SDF-1α on the using the Flexstation 3 workstation. $EC_{50}$ and percent intrinsic actively were derived from the data collected. Intrinsic activity refers to the efficacy of the test compound and is calculated as the percent of maximum response compared with the response of the reference standard (i.e., natural agonist, SDF-1α).

FLIPR

Agonist Mode:

The calcium flux assay was used to assess the test compounds' ability to activate the CXCR4 receptor in CCRF-CEM cells (human T lymphoblasts from acute lymphoblastic leukemia). CCRF-CEM cells were seeded into 96-well black plates with clear bottom at 200K/well in RPMI 1640 media with 20 mM HEPES containing 0.2% BSA. After dye loading by incubating with Calcium-4 dye at 37° C. for 1 hour, cell plates were read at 37° C. using the Fluorescent Imaging Plate Reader (FLIPR). Receptor activation was assessed by measuring changes in fluorescent intensity after the addition of the test compounds or the reference agonist SDF-1α on the FLIPR.

Representative Results

CXCR4 i1 Loop Compound Calcium Flux Data (CEM Cells)

| | | Loop Sequence | EC50 (nM) | % Intrinsic Activity |
|---|---|---|---|---|
| 6 | i1 | MGYQKPLRSMTDKYRL (SEQ ID NO: 4) | 161.4 | 90.2 |
| 7 | i1 | MGYQKKLPRSMTDKYRL (SEQ ID NO: 5) | 152.55 | 100.1 |
| 8 | i1 | MGYQKKLRPSMTDKYRL (SEQ ID NO: 6) | 169.05 | 88 |
| 9 | i1 | MGYQKKLRSpMTDKYRL (SEQ ID NO: 7) | 122.65 | 77.9 |
| 11 | i1 | MGYQKKLRSMTDKYRV (SEQ ID NO: 9) | 1317.65 | 61.71 |
| 12 | i1 | MGYQKKLRSMTDKYRJ (SEQ ID NO: 10) | 249 | 73.2 |
| 13 | i1 | MGYQKKLRSMTDKYKL (SEQ ID NO: 11) | 194.5 | 61.4 |
| 14 | i1 | MGYQKKLRSMTDKY(Cit)L (SEQ ID NO: 12) | 10000 | 3.61 |
| 15 | i1 | MGYQKKLRSMTDKFRL (SEQ ID NO: 13) | 135.25 | 81.54 |
| 16 | i1 | MGYQKKLRSMTDK(Nal)RL (SEQ ID NO: 14) | 3021 | 34.39 |
| 17 | i1 | MGYQKKLRSJTDKYRL (SEQ ID NO: 15) | 208.15 | 62.70 |
| 18 | i1 | MGYQKKLRSHTDKYRL (SEQ ID NO: 16) | 109.56 | 93.37 |
| 19 | i1 | MGYQKKLRSGTDKYRL (SEQ ID NO: 17) | 369.65 | 101.22 |
| 20 | i1 | GYQKKLRSJTDKYRI (SEQ ID NO: 18) | 232.5 | 62.52 |
| 22 | i1 | xGYQKKLRSxTDKYRL (SEQ ID NO: 20) | 125 | 77.7 |
| 23 | i1 | zGYQKKLRSzTDKYRL (SEQ ID NO: 21) | 83 | 87.25 |
| 24 | i1 | (Pra)GYQKKLRSMTDKYRL (SEQ ID NO: 22) | 267.1 | 76.6 |
| 25 | i1 | GGYQKKLRSATDKYRL (SEQ ID NO: 23) | 36.8 | 89.4 |
| 26 | i1 | GGYQKKLRpHTDKYRL (SEQ ID NO: 24) | 55.2 | 91.2 |
| 27 | i1 | GGYQKKLRpATDKYRL (SEQ ID NO: 25) | 85.9 | 110.8 |
| 28 | i1 | GGYQKKpRpATDKYRL (SEQ ID NO: 26) | 24.98 | 107 |
| 29 | i1 | GGYQKKLRpATDKFRL (SEQ ID NO: 27) | 26.29 | 88.86 |
| 30 | i1 | CGYQKKLRSATDKYRL (SEQ ID NO: 28) | 143.6 | 95.32 |
| 31 | i1 | GGYQKKLRSATDKYRL (SEQ ID NO: 23) | 153.95 | 84.23 |
| 32 | i1 | GGYQKKLRppHTDKYRL (SEQ ID NO: 29) | 73.2 | 91.13 |
| 33 | i1 | GGYQKKLRpWTDKYRL (SEQ ID NO: 30) | 108.8 | 92.98 |
| 34 | i1 | GGYQKKLRp(Dpr)TDKYRL (SEQ ID NO: 31) | 89 | 102.9 |
| 35 | i1 | GGYQKKLR(Hyp)HTDKYRL (SEQ ID NO: 32) | 44.98 | 89.42 |
| 36 | i1 | GGYQKKLRp(Hyp)TDKYRL (SEQ ID NO: 33) | 602.65 | 55.24 |
| 37 | i1 | GGYQKK(photoLeu)RSATDKYRL (SEQ ID NO: 34) | 71.15 | 85.67 |

| | | Loop Sequence | EC50 (nM) | % Intrinsic Activity |
|---|---|---|---|---|
| 38 | i1 | GGYQKKHRSATDKYRL (SEQ ID NO: 35) | 26.98 | 86.80 |
| 39 | i1 | GGYQKK1RSATDKYRL (SEQ ID NO: 36) | 42.6 | 104.2 |
| 40 | i1 | GGYQKKLRSATDKYRLH (SEQ ID NO: 37) | 296.75 | 78.7 |
| 41 | i1 | GGYQKKLRTATDKYRL (SEQ ID NO: 38) | 106.38 | 149.34 |
| 46 | i1 | GGYQKKLRpHTDKYRL (SEQ ID NO: 24) | 12.5 # | 106.6 |

Compound 46 analyzed using FLIPR. Ass other compounds were analyzed using the Flexstation.
The average % CV (coefficient of variation) across all the $EC_{50}$ assays is approximately 28% and 16% for the Intrinsic Activity.

CXCR4 i1 loop CHTX Data

Compounds with varying biological activities at the CXCR4 receptor have been identified. These include positive allosteric modulating activity, negative allosteric modulating activity, and allosteric agonists. Compounds exhibiting negative allosteric modulating activity at the CXCR4 receptor are evidenced by their ability to inhibit chemoattraction in response to SDF-1α induced chemoattraction. Compound receptor modulators are capable of modifying CXCR4 dependent activity in several characteristic patterns. In FIGS. 1A-1C. Selected compounds demonstrate agonist activity as evidences by a dose related increase in RFU corresponding to the number of migrating cells.

One such possible phenotype found in this assay is left- or right-shifting of the SDF-1α dependent chemotactic response. Another phenotype is positive allosteric modulation of the SDF-1α dependent chemotactic response (i.e., the larger RFU response indicates that a greater number of cells migrate toward SDF1α in the presence of an active compound).

In another example, a compound that negatively modulates the SDF-1α induced chemotactic response in CEM cells as would be evidenced by the lower raw relative fluorescent units (RFU) which reflects the number of cells migrating toward an SDF-1α gradient. The lower RFU response, the fewer migrating cells.

Compounds with allosteric agonist activity are evidenced by their ability to induce CXCR4 dependent calcium mobilization and/or chemoattraction of leukocytes expressing CXCR4. Like the endogenous agonist SDF-1α activity, these CXCR4 agonists exhibit a bell-shaped activity curve with respect to chemoattraction.

HTRF cAMP Assay and IP-One Assay (Cisbio)

HTRF (homogeneous time resolved fluorescence) is a technology developed by Cisbio Bioassays based on TR-FRET (time-resolved fluorescence resonance energy transfer). Cisbio Bioassays has developed a wide selection of HTRF-based assays compatible with whole cells, thereby enabling functional assays run under more physiological conditions. cAMP kits are based on a competitive immunoassay using cryptate-labeled anti-cAMP antibody and d2-labeled cAMP. This assay allows the measurement of increase in intracellular cAMP upon Gs-coupled receptor activation as well as decrease in forskolin stimulated increase in cAMP upon Gi-coupled receptor activation. The IP-One assays are competitive immunoassays that use cryptate-labeled anti-IP1 monoclonal antibody and d2-labeled IP1. IP1 is a relatively stable downstream metabolite of IP3, and accumulates in cells following Gq receptor activation.

Alphascreen Cellular Kinase Assays.

GPCR activation results in modulation of downstream kinase systems and is often used to probe GPCR function and regulation. TGR Bioscience and PerkinElmer have developed Surefire cellular kinase assay kits that are HTS capable and useful in screening kinase regulation. Such kits enable the monitoring of Gi regulated downstream kinases like ERK1/2. The assay allows the measurement of increases in ERK1/2 kinase phosphorylation upon Gi coupled receptor (e.g., CXCR4) activation and this signal in turn can be used to assay Gi coupled receptor modulator. Similar kits are also available to assay other pathway dependent signaling kinases such as MAP and BAD.

In Vivo Assays

Animal models are currently available for in vivo validation of novel therapeutics targeting the CXCR4/SDF-1 signaling axis include the mouse air pouch WBCs recruitment model, the PMN mobilization model, the HPCs mobilization model and BM transplantation models including NOD/SCID mice repopulation model.

In the mouse air pouch WBCs recruitment model, the air pouch is formed by 2 subcutaneous injections (on day 0 and day 3) of 3 ml of sterile air. On day 6 mice receive an injection of 1 ml of SDF-1 solution into the formed air pouch. Six or 24 hours later WBCs recruited to the air pouch are recovered and WBCs subsets are analyzed using differential cell count and Flow Cytometry. In this model the concentration of SDF-1 in air pouch is controlled by an investigator.

The other animal models that are widely used for the in vivo validation of novel CXCR4 antagonists are PMNs mobilization model and hematopoietic progenitor's cells (HPCs) mobilization models. These two models are very similar and they exploit the fact that bone marrow niche express high level of SDF-1. Bone marrow SDF-1 interacts with the CXCR4 on bone marrow cells and constitutively activates it, This SDF-1/CXCR4 interaction is critical for the retention of HPCs and immature PMNs within the bone marrow. Disruption of this interaction causes release of PMNs and HPCs into peripheral blood where they can be readily detected and counted using differential cell counter (for PMNs), Flow Cytometry and colony forming units assay (for HPCs). In contrast to the air pouch model, in this model the concentration of SDF-1 is physiological. In addition, PMNs/HPCs mobilization models do not require preliminary preparation of animals for actual experiment as is the case in air pouch WBCs recruitment model.

Bone marrow transplantation models allow assessing long term engraftment potential of mobilized into peripheral blood hematopoietic stem cells (HSCs). The donor cells can be of either mouse or human origin like in the NOD/SCID mice repopulation model. In long term repopulation model dilutions of donor blood cells compete with the recipient marrow cells for engraftment in lethally irradiated recipients. This model is relatively long and takes up to 4 months to accomplish.

Recently hematological malignancies such as Acute Myeloid Leukemia (AML) were recognized as potential indications for anti-CXCR4 therapy. Preclinical data suggests that dislodging of malignant cells from bone marrow environment using CXCR4 antagonists significantly improves survival of animals and outcome of chemotherapy. Several animal models of chemo sensitization were developed. They are based on the induction of AML following adoptive transfer of malignant cells such APL cells from mCG-PML-PARα mice, A20 cells, or Ba/F3 cells. To facilitate the detection of malignant cells genes encoding fluorescent proteins or luciferase are introduced into them. The progression of AML and efficacy of anti-AML chemotherapy is assessed using FACS analysis of cells from peripheral blood, spleen and bone marrow. In addition, whole body in vivo bioluminescence imaging allows quantization of the effect of CXCR4 antagonists on anti-AML therapy in individual animal over time.

Animal models that can be used for the in vivo validation of novel CXCR4 agonists on ischemia and cardiac disorders include ischemia-myocardial reperfusion injury, myocardial infarction, and hind limb ischemia models. Temporary interruption of blood flow in the animal model of myocardial reperfusion injury closely resembles the clinical setting of myocardial injury.

Animal models that can be used for validation of CXCR4 agonists on wound healing and attenuation of scar formation are known. The rabbit ear chamber and the Algire chamber are used for visualizing vascularization and measuring angiogenesis. Various superficial wound models that separate the different layers of the skin in order to evaluate epidermal regeneration and matrix production can be used. Partial- or full-thickness wound made by excision or punch biopsy can be used to evaluate the situation where tissue damage occurs in conjunction with tissue loss. This model is used to study wounds that heal by re-epithelialization, dermal reconstitution, and wound contraction where any phase of healing or of the entire healing process can be evaluated. Other examples are discussed in Gottrup F, Agren M S, Karlsmark T. Models for use in wound healing research: a survey focusing on in-vitro and in-vivo adult soft tissue. *Wound Repair Regen.* 2000; 8(2):83-96,

PHARMACOKINETIC ANALYSIS

To determine the pharmacokinetic profile of the CXCR4 modulators, compounds were administered as single subcutaneous injection to 6-8 week old male mice at doses of either 2.5 or µmol/kg (three or four mice/group). The dosing solution was 625 or 1250 µM, respectively and the dosing volume was 4 mL/kg. Dosing of 0.5 µmol/kg or 1 µmol/kg were used for intravenous dosing. The dosing solution was 125 or 250 µM, respectively and the dosing volume was 4 mL/Kg. Mice were sacrificed and blood samples collected at 15 minutes, 30 minutes, 1 hour, 2 hours, 4 hours, 8 hours, and 24 hours after dosing. The concentration of compound in plasma samples was analyzed by LC/MS according to the method below.

Plasma Standard Extraction Procedure:

In a 500 µL tube, 95 µL of blank plasma was added. To this, 5 µL of the analyte compound in AcN:H$_2$O:FA (70:30:1%) of 100 µM concentration was added to get 5 µM concentration. This concentration was serially diluted in blank plasma to generate a calibration curve of 12 concentration levels ranging from 2.44 nM to 5000 nM.

Serial calibration standards in plasma or plasma samples were transferred to clean labeled tubes and mixed with 3 volumes of acetonitrile with internal standard, tolbutamide, in order to precipitate proteins. The mixtures were vortexed and centrifuged at 12000 RPM (15320 g) for 10 minutes. Supernatants were transferred to HPLC injection vials or 96-well plates and 5 µL were injected into the LC-MS/MS system.

| UPLC/MS/MS Conditions for Plasma Analysis: | | | | |
|---|---|---|---|---|
| Mass Spectrometer | Water Quattro Premier XE; Electrospray, positive ion | | | |
| Scan Mode | Multiple Reaction Monitoring (MRM) | | | |
| Analyte (MRM) | Test compound | | | |
| Dwell (s)/Cone (V)/ Collision (V) | 0.1/30/20 | | | |
| Internal Standard (MRM) | tolbutamide/271.09 > 154.65 | | | |
| Dwell (s)/Cone (V)/ Collision (V) | 0.1/32/18 | | | |
| LC Pump | Waters Acquity UPLC | | | |
| Column | Waters BEH, C18, 1.7 µm 2.1 × 50 mm | | | |
| Mobile Phase A | 0.1% formic acid in water | | | |
| Mobile Phase B | 0.1% formic acid in acetonitrile | | | |
| Pump Gradient | Time (min) | % A | % B | Flow Rate |
| | 0.00 | 95 | 5 | 0.4 |
| | 2.0 | 20 | 80 | 0.4 |
| | 2.1 | 2 | 98 | 0.4 |
| | 2.6 | 2 | 98 | 0.4 |
| | 2.7 | 95 | 5 | 0.400 |
| | 3.5 | 95 | 5 | 0.400 |
| After column splitting 1:1 ratio | | | | |
| Column Temperature (° C.) | 60 | | Sample Temperature (° C.) | 4 |
| Injection Volume (µL) | 5 | | Run Time (min) | 3.5 |

Noncompartmental pharmacokinetic analyses were performed using WinNonlin Professional (version 5.2) software (Pharsight, Cary, N.C.). The data were analyzed using the extravascular input model. For each subject, pharmacokinetic parameters were calculated individually as follows and then averaged. The maximum drug concentration in plasma, $C_{max}$, and $T_{max}$, the time to achieve $C_{max}$, were calculated directly from the concentration-time curves. The area under the plasma concentration-time curve from hour 0 to the last measurable concentration in plasma, $AUC_{last}$, was estimated by the linear trapezoidal rule. The area under the plasma concentration-time curve from hour 0 to infinity estimated using the following formula: $AUC_{inf\_obs}=AUC_{last}+C_t/Lambda\_z$, where $C_t$ is the last measurable concentration in plasma, and Lambda_z is the terminal elimination rate constant estimated using log-linear regression during the terminal elimination phase. The number of points used in Lambda_z calculation was determined by visual inspection of the data describing the terminal phase and evaluation of the correlation coefficient associated with the regression line. $T_{1/2}$, the terminal elimination half-life=ln(2)/Lambda_z. Mean residence time MRT, was calculated as following: $MRT=(AUMC_{inf}/AUC_{inf})$. Subcutaneous absorption bioavailability was calculated as the $AUC_{inf}$ following subcutaneous dosing divided by the $AUC_{inf}$ following intravenous dosing. Results were expressed as percentages.

Representative Results

| PK Parameter | Compound 26 (2.5 µmol/kg) | Compound 48 (2.5 µmol/kg) |
|---|---|---|
| Half-life$_{elimination}$ (hr) | 2.4 | 1.5 |
| T$_{max}$ (hr) | 2 | 2 |
| MRT INF$_{obs}$ (hr) | 4.5 | 2.6 |
| Bioavailability (%) | 88 | <30 |

The bioavailablity of compound 26 was greater than that of compound 48 following subcutaneous administration.

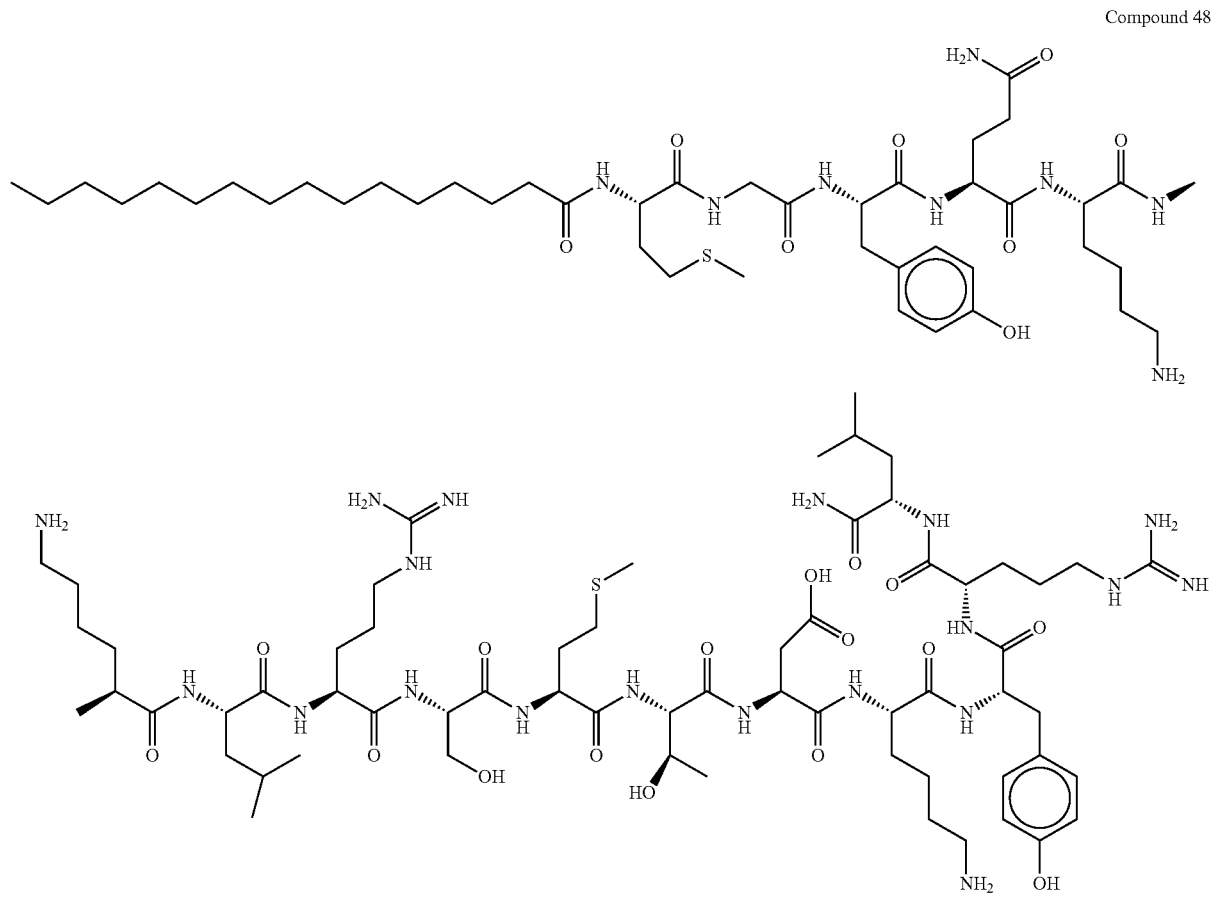

Mobilization of Polymorphonuclear Leukocytes (PMNs)

The effect of Compound 26 on mobilization of PMNs following subcutaneous administration was evaluated in mice. Various doses of Compound 26 were injected subcutaneously at a volume of 0.2 mL to groups of ten 8 week old male BALB/c mice (Charles River Laboratories) per group. A dose of 6.6 µmol/kg AMD3100 (Sigma, St. Louis, Mo.) was administered subcutaneously to 10 mice. Ten mice were injected with vehicle only (10 mM ammonium acetate, pH 7; 5% Cremaphor; 8.5% Sucrose) and five mice received no treatment. Mice were euthanized by $CO_2$ asphyxiation and heparinized blood was collected via the inferior vena cava 3 hours following compound injection. Neutrophil and lymphocyte counts were determined using a Hemavet Model 950FS cell counter (Drew Scientific, Dallas, Tex.).

Representative Results

| Treatment | Dose | PMNs (×10³ µl) Mean ± SD | Lymphocytes (×10³ µl) Mean ± SD |
|---|---|---|---|
| None (n = 5) | NA | 2.20 ± 0.91 | 5.53 ± 1.86 |
| Vehicle | NA | 3.90 ± 2.43 | 6.10 ± 1.64 |
| AMD3100 | 6.66 µmol/kg | 7.83 ± 3.20*** | 8.76 ± 1.67* |
| Compound 26 | 6.66 µmol/kg | 7.11 ± 2.82** | 3.74 ± 2.12 |
| Compound 26 | 2 µmol/kg | 5.92 ± 1.73* | 4.15 ± 1.97 |
| Compound 26 | 0.66 µmol/kg | 5.03 ± 1.97 | 5.14 ± 2.22 |
| Compound 26 | 0.2 µmol/kg | 3.60 ± 1.89 | 4.39 ± 1.33 |

NA: Not applicable
*Significantly different than vehicle control; $p < 0.01$
**Significantly different than vehicle control; $p < 0.05$
***Significantly different than vehicle control; $p < 0.001$ When administered systemically via subcutaneous injection, Compound 26 acted as a functional antagonist to elicit release of bone marrow PMNs in a dose responsive fashion. The CXCR4 agonist Compound 26 is hypothesized to mobilize CXCR4-bearing cells via disruption of the normal CXCL12 gradient in the bone marrow niche, and/or down regulation of the CXCR4 receptor.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Formula A-1:

$$T\text{-}L\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}R_1;$$

or a pharmaceutically acceptable salt thereof, wherein:
L is a linking moiety selected from: C(O), C(S), S(O)$_2$, N(R$^3$)S*(O), N(R$^3$)S*(O)$_2$, N(R$^3$)C*(O), N(R$^3$)C*(S), OC*(O), OC*(S), SC*(O), SC*(S), C(=NH), and N(R$^3$)C*(=NH); wherein L is bonded to the N-terminal nitrogen of $X_5$ at the atom marked with an asterisk (*) and R$^3$ is selected from: H, D, (C$_1$-C$_6$)alkyl, (C$_2$-C$_6$)alkenyl, (C$_2$-C$_6$)alkynyl, (C$_1$-C$_6$)alkoxy, (C$_3$-C$_9$)cycloalkyl, 5-10 membered heterocycloalkyl, aryl, aryloxy, heteroaryloxy, aralkyl, heteroaryl, and heteroaralkyl; wherein said alkyl, alkenyl, alkynyl, alkoxy, cycloalkyl, heterocycloalkyl, aryl, aryloxy, heteroaryloxy, aralkyl, heteroaryl, and heteroaralkyl are optionally and independently substituted; T is a lipophilic tether moiety bonded to L; and R$_1$ is OR$_2$ or N(R$_2$)$_2$, each R$_2$ is independently H or alkyl,
wherein at least sixteen contiguous $X_5$-$X_{21}$ amino acid residues are present, and wherein:
$X_5$ is a glycine residue, a methyl serine residue, a homoserine residue, a propargyl glycine residue or a cysteine residue,
$X_6$ is a glycine residue,
$X_7$ is a tyrosine residue,
$X_8$ is a glutamine residue,
$X_9$ is a lysine residue,
$X_{10}$ is a lysine residue,
$X_{11}$ is a leucine residue, a proline residue, a photoleucine, a histidine, or a d-leucine,
$X_{12}$ is an arginine residue,
$X_{13}$ is a d-proline residue,
$X_{14}$ is an alanine residue, a homoserine residue, a histidine residue a methyl serine residue, a proline residue, a Dpr residue, a methionine residue, a tryptophan residue, a hydroxyproline residue, or a d-proline residue,
$X_{15}$ is a threonine residue or a histidine residue,
$X_{16}$ is an aspartic acid residue or a threonine residue
$X_{17}$ is a lysine residue,
$X_{18}$ is a tyrosine residue,
$X_{19}$ is an arginine residue,
$X_{20}$ is a leucine residue,
$X_{21}$ is a histidine residue or a leucine residue or absent.

2. The compound of claim 1, wherein L is selected from C(O), S*(O)$_2$ and OC*(O).

3. The compound of claim 2, wherein L is C(O).

4. The compound of claim 1, wherein,
$X_5$ is a glycine or a methyl serine residue,
$X_{11}$ is a leucine residue or a proline residue,
$X_{13}$ is a d-proline residue,
$X_{14}$ is an alanine residue, a histidine residue, a methyl serine residue, a d-proline residue or a Dpr residue, and
$X_{21}$ is a leucine residue or absent.

5. A compound of claim 1 selected from:

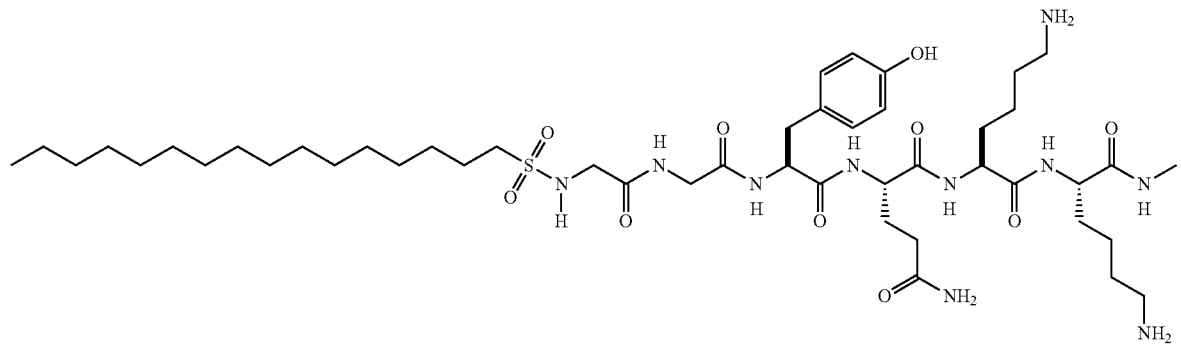

Compound 46

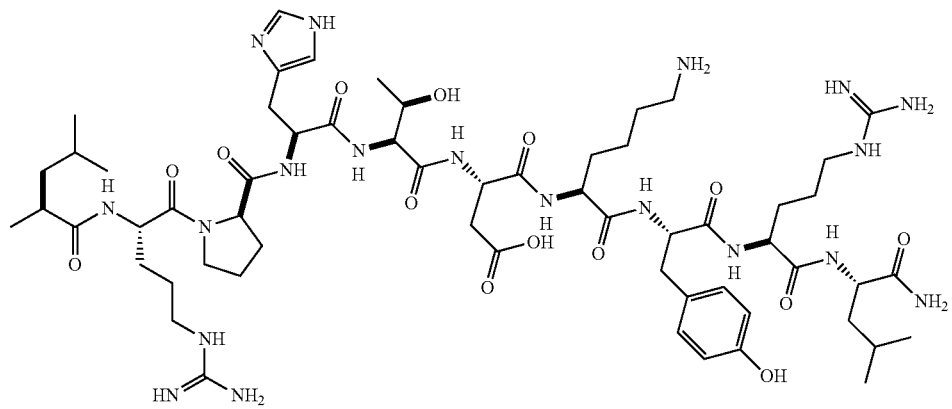

or a pharmaceutically acceptable salt of the foregoing.

6. A compound of claim 1 selected from:

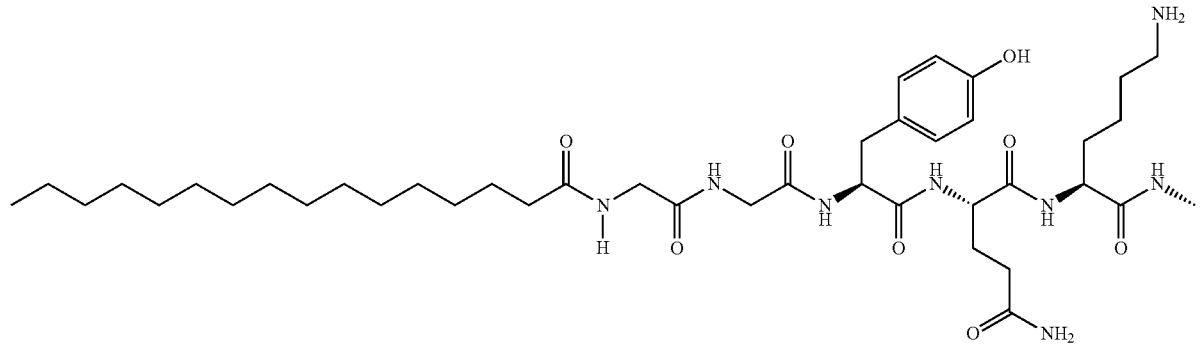

Compound 26

-continued
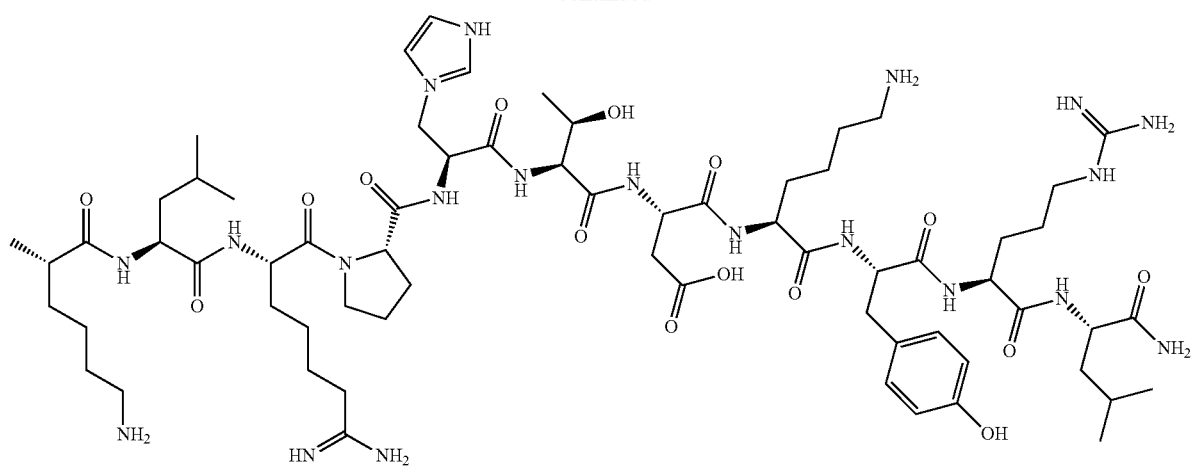
Compound 27
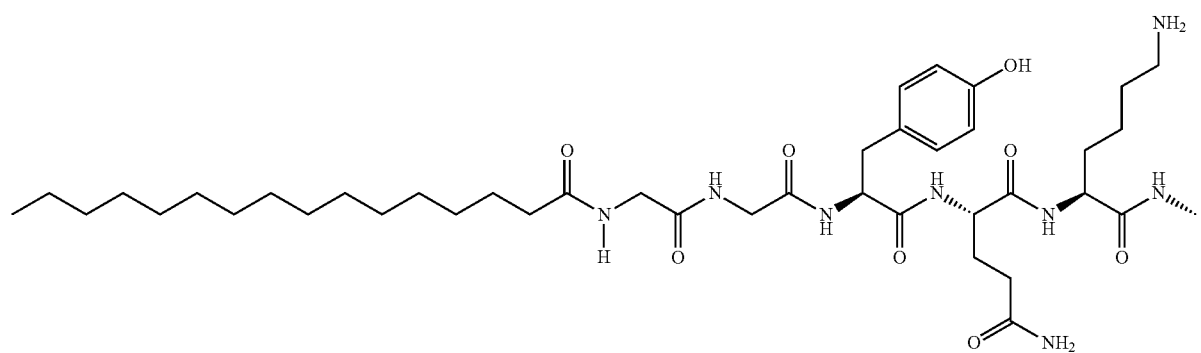
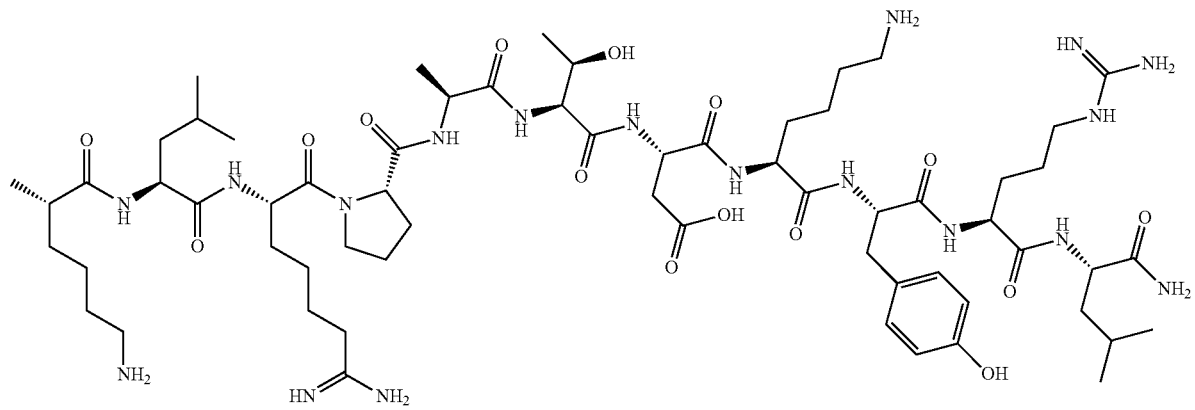

-continued
Compound 32
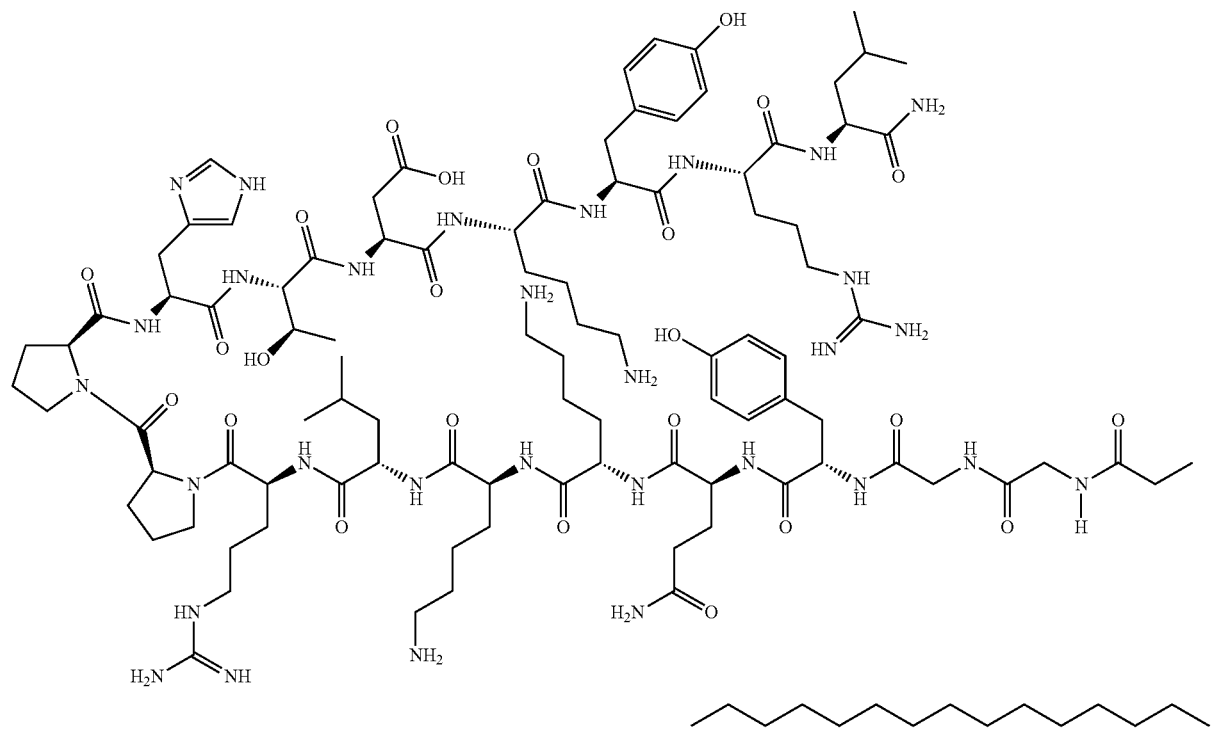
Compound 33
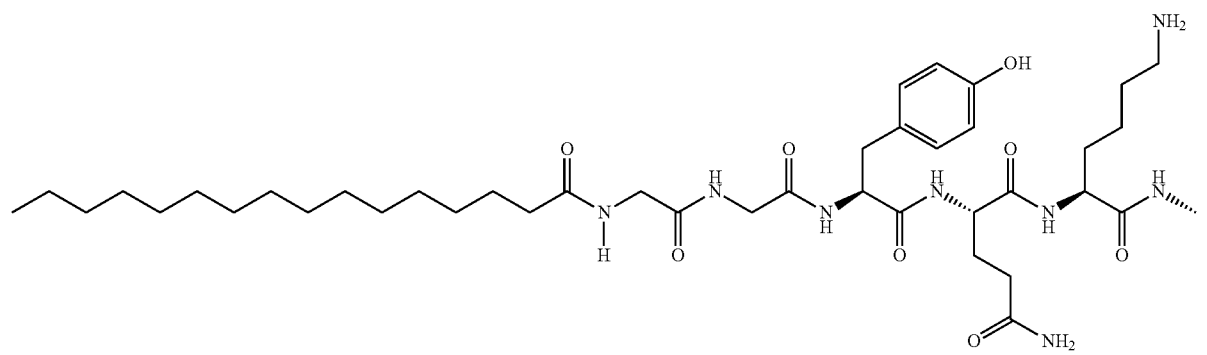
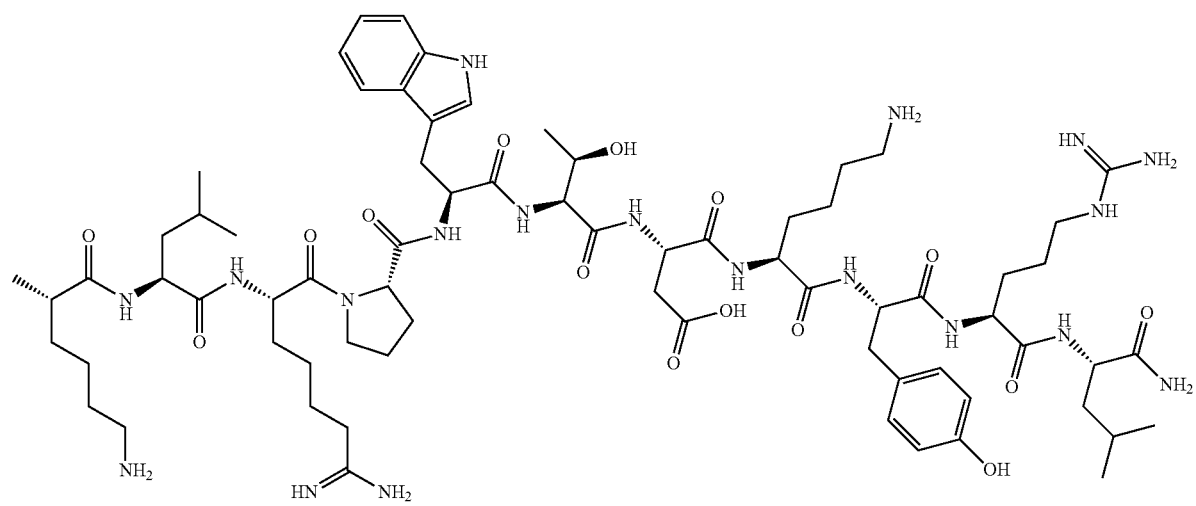

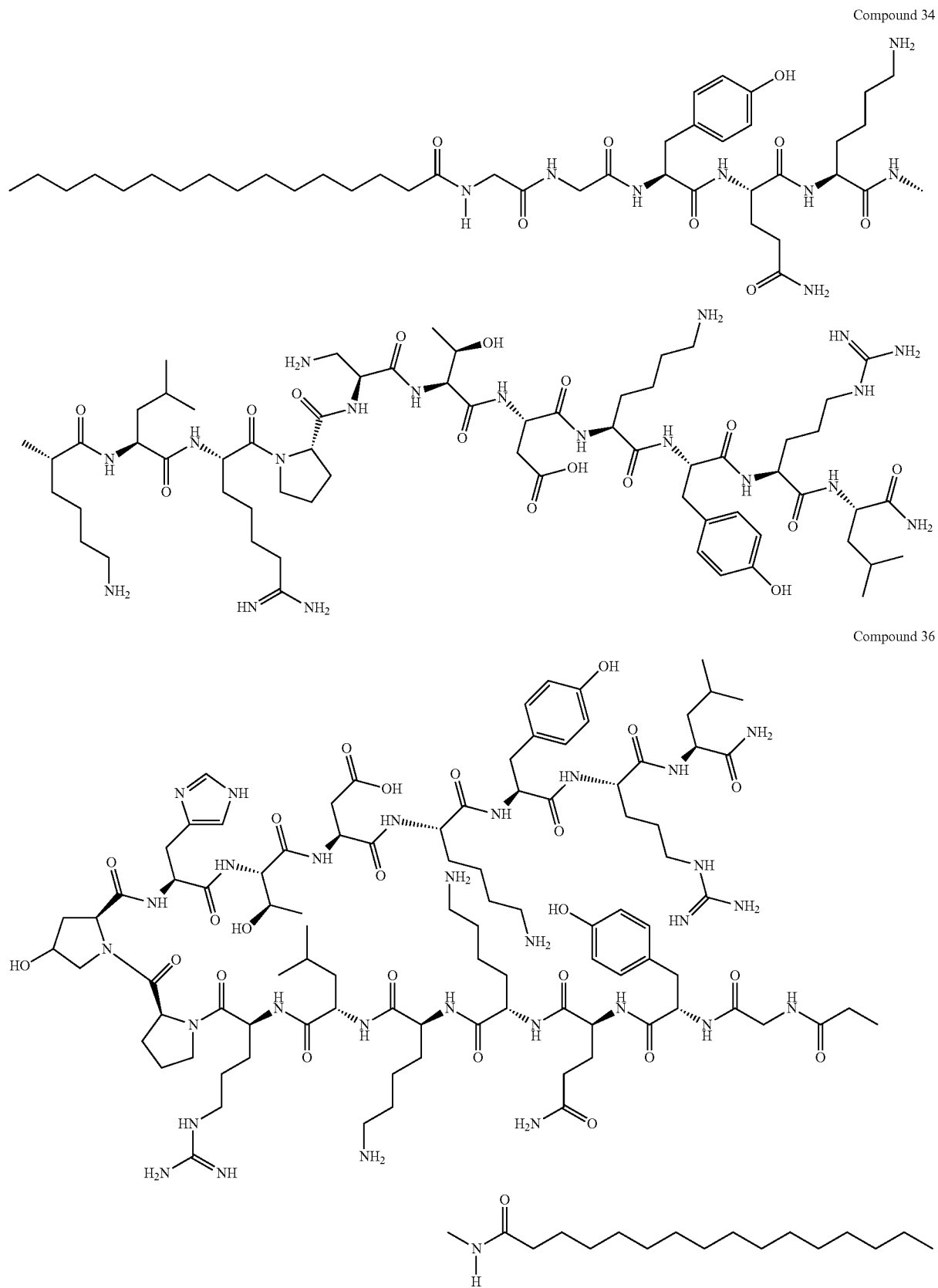
Compound 34
Compound 36
and

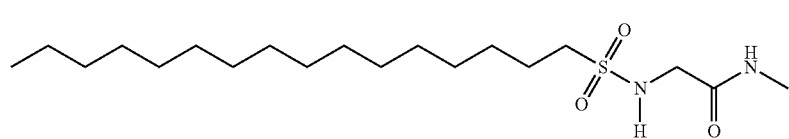
Compound 46
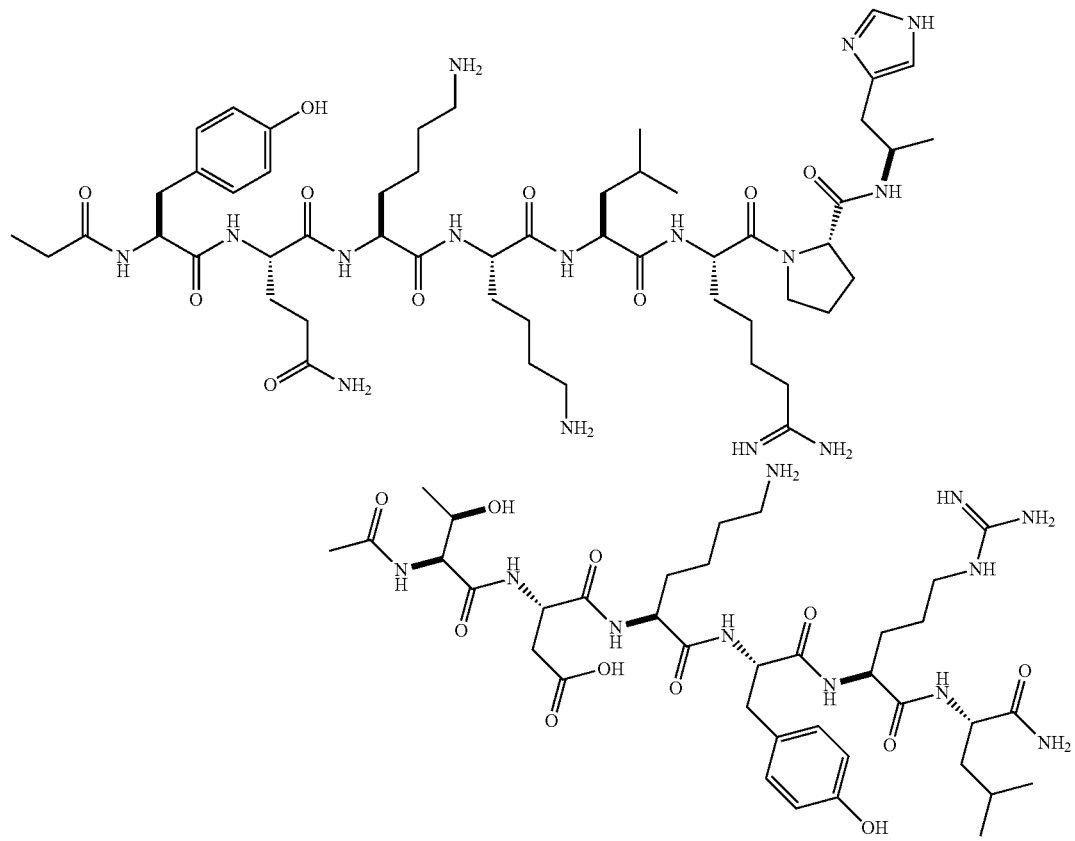
or a pharmaceutically acceptable salt of any of the foregoing.
7. A compound of claim 1 selected from:
Compound 26
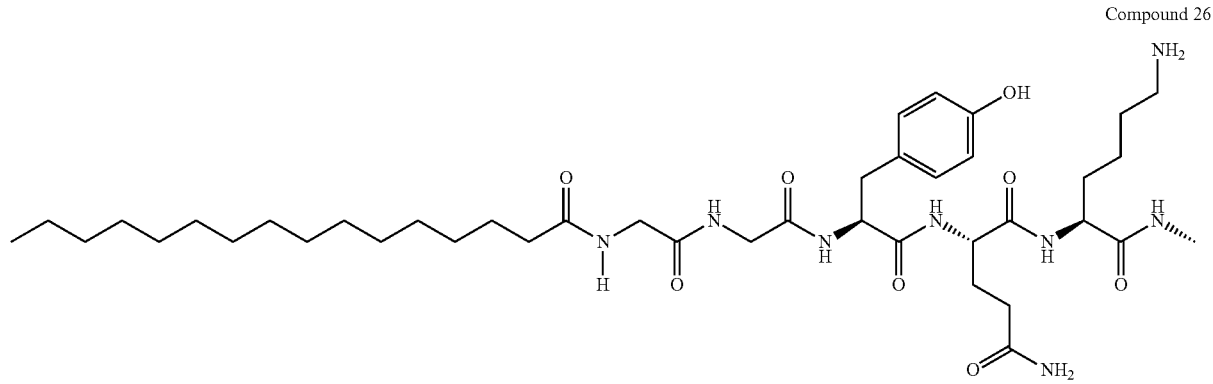

287
-continued
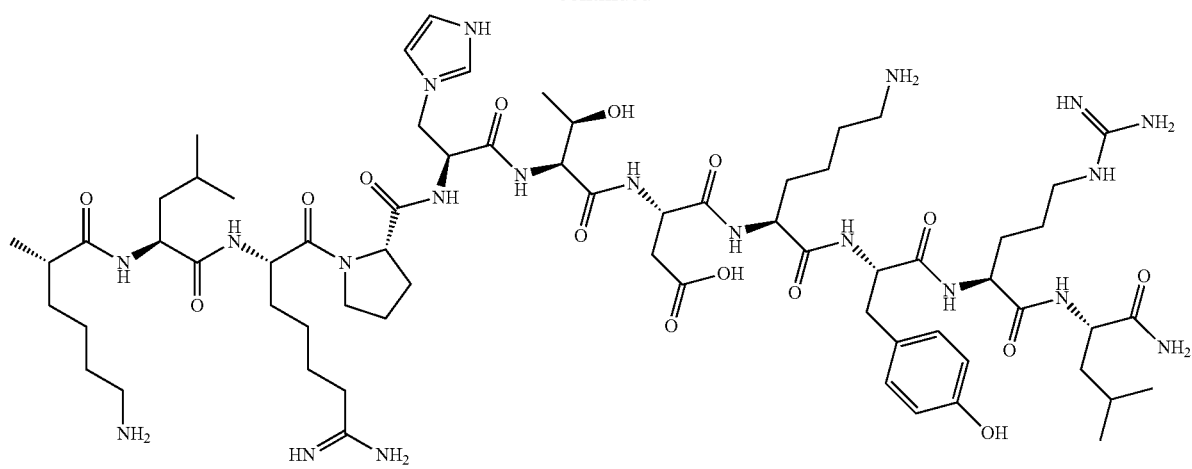
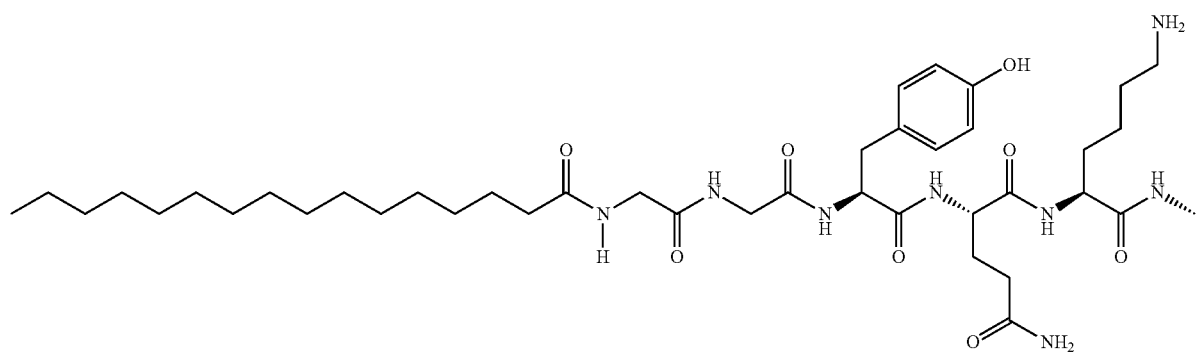
Compound 27
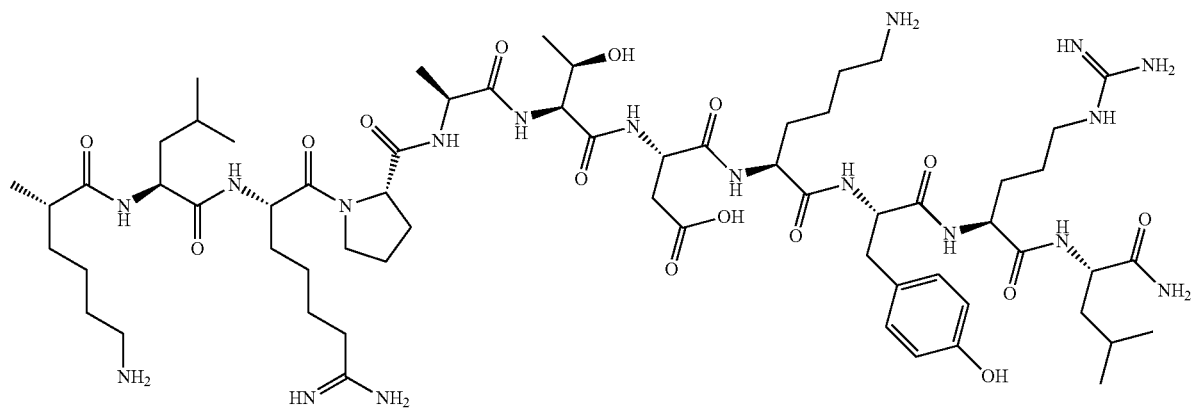

-continued
Compound 32
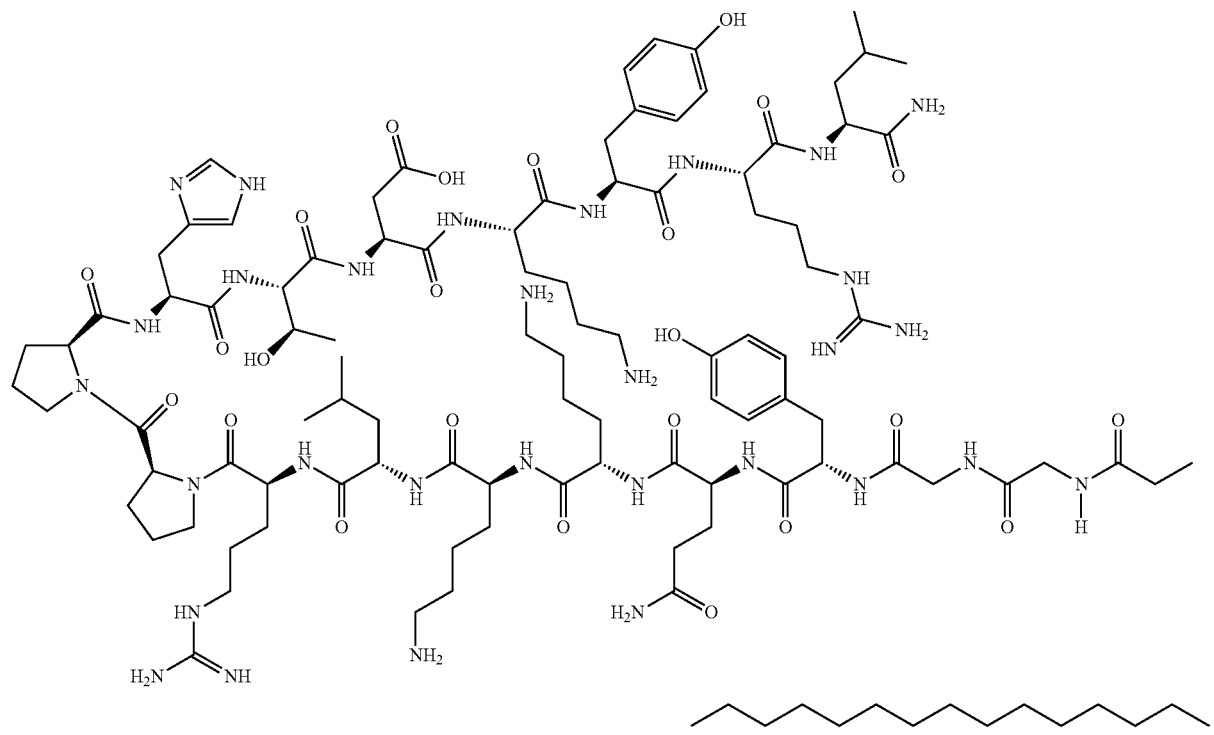
Compound 33
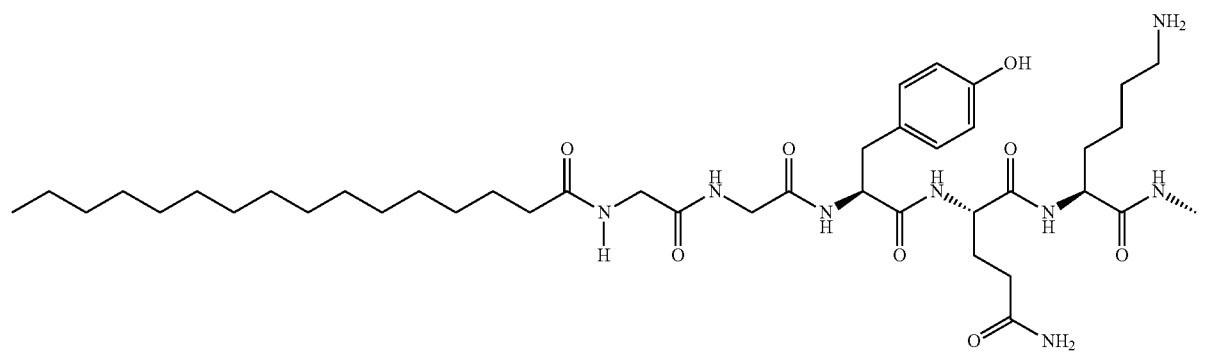
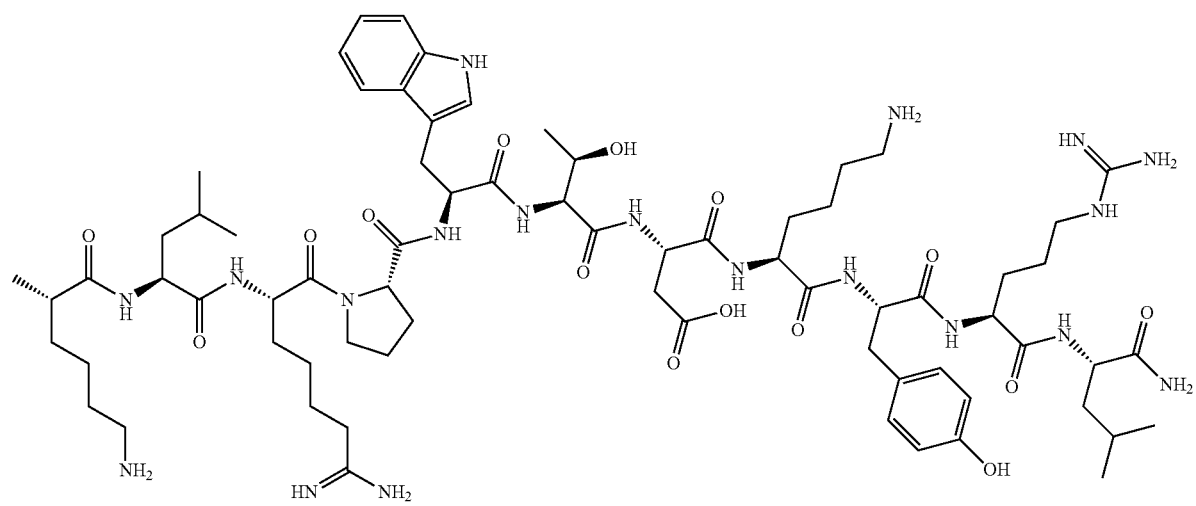

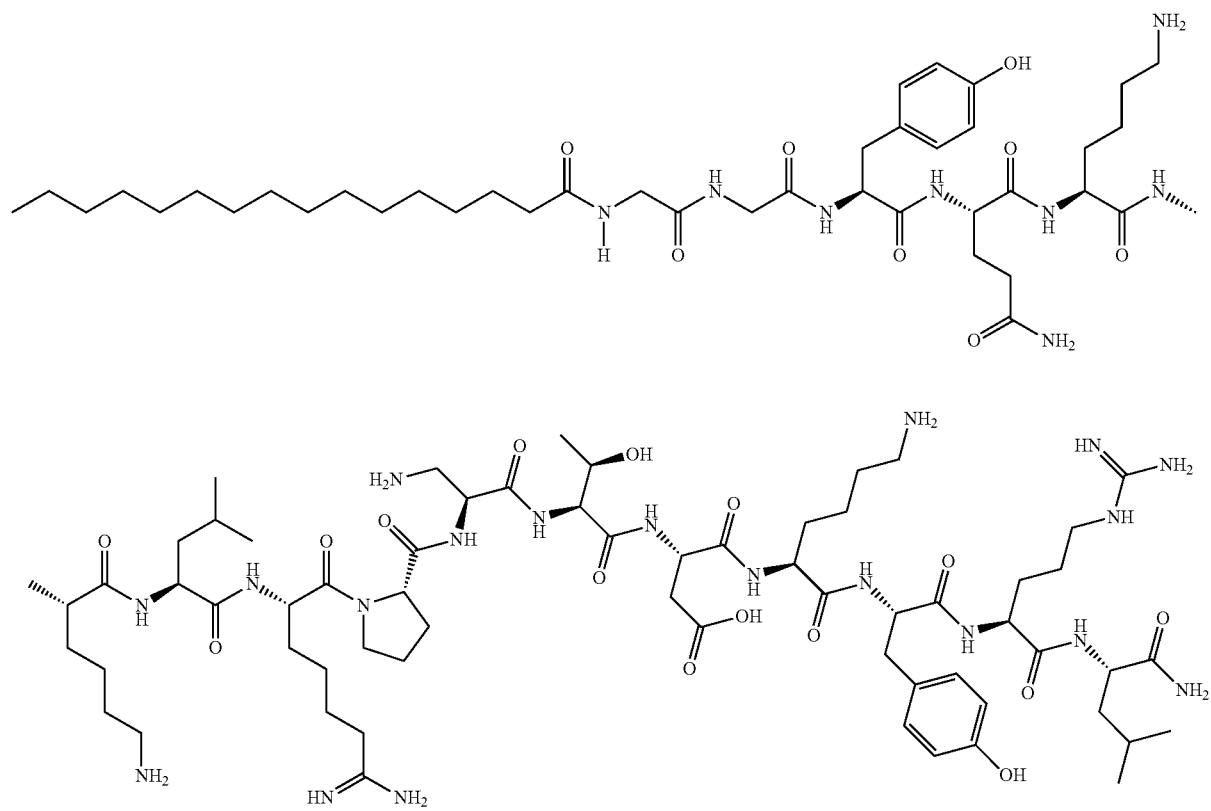
Compound 34
and
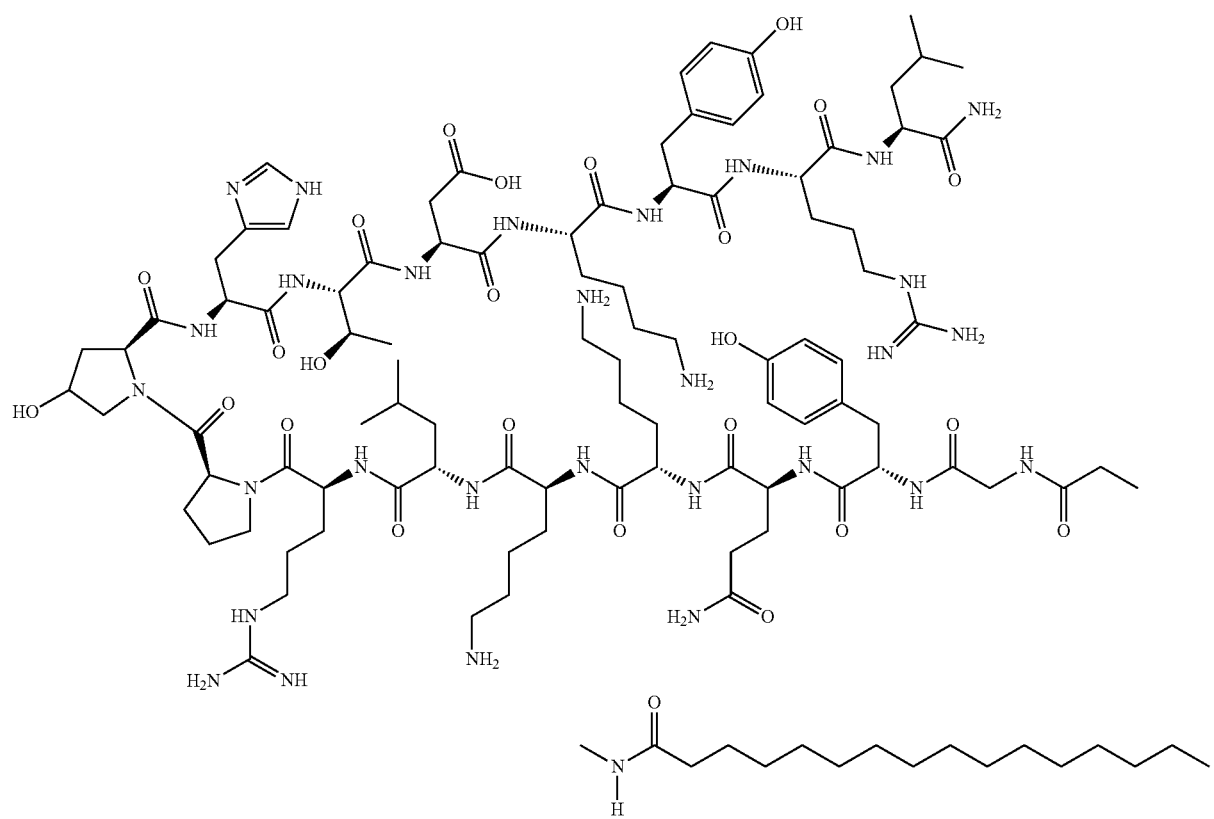
Compound 36 or a pharmaceutically acceptable salt of any of the foregoing.

8. The compound of any one of claims 1-4, wherein T is an optionally substituted ($C_6$-$C_{30}$)alkyl, ($C_6$-$C_{30}$)alkenyl, or ($C_6$-$C_{30}$)alkynyl, wherein 0-3 carbon atoms are replaced with oxygen, sulfur, nitrogen or a combination thereof.

9. The compound of any one of claims 1-4, wherein T is a fatty acid derivative.

10. The compound of claim 9, wherein the fatty acid is selected from the group consisting of: butyric acid, caproic acid, caprylic acid, capric acid, lauric acid, myristic acid, palmitic acid, stearic acid, arachidic acid, behenic acid, lignoceric acid, myristoleic acid, palmitoleic acid, oleic acid, linoleic acid, α-linolenic acid, arachidonic acid, eicosapentaenoic acid, erucic acid, and docosahexaenoic acid.

11. The compound of any one of claims 1-4, wherein T is a bile acid derivative.

12. The compound of claim 1, wherein TL is selected from:
$CH_3(CH_2)_{15}$—C(O);
$CH_3(CH_2)_{13}$—C(O);
$CH_3(CH_2)_9O(CH_2)_2C(O)$;
$CH_3(CH_2)_{10}O(CH_2)_2C(O)$;
$CH_3(CH_2)_6C$=$C(CH_2)_6$—C(O);
LCA-C(O); and
$CH_3(CH_2)_9OPh$-C(O) wherein LCA = 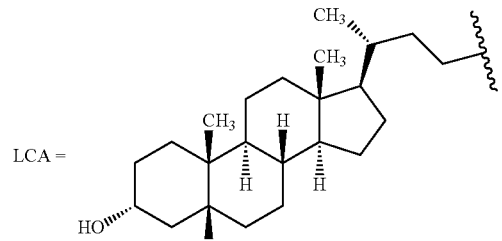

* * * * *

SEQUENCE LISTING

<160> NUMBER OF SEQ ID NOS: 56

<210> SEQ ID NO 1
<211> LENGTH: 13
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = d-lysine

<400> SEQUENCE: 1

Lys Lys Leu Arg Ser Met Thr Asp Xaa Tyr Arg Leu His
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 10
<223> OTHER INFORMATION: Xaa = d-tyrosine

<400> SEQUENCE: 2

Lys Lys Leu Arg Ser Met Thr Asp Lys Xaa Arg Leu His
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 14
<223> OTHER INFORMATION: Xaa = d-arginine

<400> SEQUENCE: 3

Met Gly Gln Lys Lys Leu Arg Ser Met Thr Asp Lys Tyr Xaa Leu
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic Protein

<400> SEQUENCE: 4

Met Gly Tyr Gln Lys Pro Leu Arg Ser Met Thr Asp Lys Tyr Arg Leu
1               5                   10                  15

<210> SEQ ID NO 5
<211> LENGTH: 17
<212> TYPE: PRT
<213> ORGANISM: Artificial Sequence
<220> FEATURE:
<223> OTHER INFORMATION: Synthetic Protein

<400> SEQUENCE: 5

Met Gly Tyr Gln Lys Lys Leu Pro Arg Ser Met Thr Asp Lys Tyr Arg
1               5                   10                  15

Leu

<210> SEQ ID NO 6
<211> LENGTH: 17
<212> TYPE: PRT
<213> ORGANISM: Artificial Sequence
<220> FEATURE:
<223> OTHER INFORMATION: Synthetic Protein

<400> SEQUENCE: 6

Met Gly Tyr Gln Lys Lys Leu Arg Pro Ser Met Thr Asp Lys Tyr Arg
 1               5                  10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 10
<223> OTHER INFORMATION: Xaa = d-proline

<400> SEQUENCE: 7

Met Gly Tyr Gln Lys Lys Leu Arg Ser Xaa Met Thr Asp Lys Tyr Arg
 1               5                  10                  15

Leu

<210> SEQ ID NO 8
<211> LENGTH: 17
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 11
<223> OTHER INFORMATION: Xaa = d-proline

<400> SEQUENCE: 8

Met Gly Tyr Gln Lys Lys Leu Arg Ser Met Xaa Thr Asp Lys Tyr Arg
 1               5                  10                  15

Leu

<210> SEQ ID NO 9
<211> LENGTH: 16
<212> TYPE: PRT
<213> ORGANISM: Artificial Sequence
<220> FEATURE:
<223> OTHER INFORMATION: Synthetic Protein

<400> SEQUENCE: 9

Met Gly Tyr Gln Lys Lys Leu Arg Ser Met Thr Asp Lys Tyr Arg Val
 1               5                  10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 16
<223> OTHER INFORMATION: Xaa = norleucine

<400> SEQUENCE: 10

Met Gly Tyr Gln Lys Lys Leu Arg Ser Met Thr Asp Lys Tyr Arg Xaa
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic Protein

<400> SEQUENCE: 11

Met Gly Tyr Gln Lys Lys Leu Arg Ser Met Thr Asp Lys Tyr Lys Leu
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 15
<223> OTHER INFORMATION: Xaa = citrulline

<400> SEQUENCE: 12

Met Gly Tyr Gln Lys Lys Leu Arg Ser Met Thr Asp Lys Tyr Xaa Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic Protein

<400> SEQUENCE: 13

Met Gly Tyr Gln Lys Lys Leu Arg Ser Met Thr Asp Lys Phe Arg Leu
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 14
<223> OTHER INFORMATION: Xaa = 2-naphthylalanine

<400> SEQUENCE: 14

Met Gly Tyr Gln Lys Lys Leu Arg Ser Met Thr Asp Lys Xaa Arg Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 10
<223> OTHER INFORMATION: Xaa = norleucine

<400> SEQUENCE: 15

```
Met Gly Tyr Gln Lys Lys Leu Arg Ser Xaa Thr Asp Lys Tyr Arg Leu
1               5                   10                  15
```

<210> SEQ ID NO 16
<211> LENGTH: 16
<212> TYPE: PRT
<213> ORGANISM: Artificial Sequence
<220> FEATURE:
<223> OTHER INFORMATION: Synthetic Protein

<400> SEQUENCE: 16

```
Met Gly Tyr Gln Lys Lys Leu Arg Ser His Thr Asp Lys Tyr Arg Leu
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: Synthetic Protein

<400> SEQUENCE: 17

```
Met Gly Tyr Gln Lys Lys Leu Arg Ser Gly Thr Asp Lys Tyr Arg Leu
1               5                   10                  15
```

<210> SEQ ID NO 18
<211> LENGTH: 15
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = norleucine

<400> SEQUENCE: 18

```
Gly Tyr Gln Lys Lys Leu Arg Ser Xaa Thr Asp Lys Tyr Arg Ile
1               5                   10                  15
```

<210> SEQ ID NO 19
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 5
<223> OTHER INFORMATION: Xaa = 2-aminoisobutyric acid
<220> FEATURE:
<221> NAME/KEY: MOD_RES
<222> LOCATION: 8
<223> OTHER INFORMATION: Xaa = cyclohexylalanine

<400> SEQUENCE: 19

```
Met Gly Tyr Gln Xaa Lys Leu Xaa Ser Met Thr Arg Lys Tyr Arg Leu
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 1, 10
<223> OTHER INFORMATION: Xaa = homoserine

```
<400> SEQUENCE: 20

Xaa Gly Tyr Gln Lys Lys Leu Arg Ser Xaa Thr Asp Lys Tyr Arg Leu
 1               5                  10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 1, 10
<223> OTHER INFORMATION: Xaa = methylserine

<400> SEQUENCE: 21

Xaa Gly Tyr Gln Lys Lys Leu Arg Ser Xaa Thr Asp Lys Tyr Arg Leu
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 1
<223> OTHER INFORMATION: Xaa = propargylglycine

<400> SEQUENCE: 22

Xaa Gly Tyr Gln Lys Lys Leu Arg Ser Met Thr Asp Lys Tyr Arg Leu
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Protein

<400> SEQUENCE: 23

Gly Gly Tyr Gln Lys Lys Leu Arg Ser Ala Thr Asp Lys Tyr Arg Leu
 1               5                  10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = d-proline

<400> SEQUENCE: 24

Gly Gly Tyr Gln Lys Lys Leu Arg Xaa His Thr Asp Lys Tyr Arg Leu
 1               5                  10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
```

```
<222> LOCATION: 9
<223> OTHER INFORMATION: Xaa = d-proline

<400> SEQUENCE: 25

Gly Gly Tyr Gln Lys Lys Leu Arg Xaa Ala Thr Asp Lys Tyr Arg Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 7, 9
<223> OTHER INFORMATION: Xaa = d-proline

<400> SEQUENCE: 26

Gly Gly Tyr Gln Lys Lys Xaa Arg Xaa Ala Thr Asp Lys Tyr Arg Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = d-proline

<400> SEQUENCE: 27

Gly Gly Tyr Gln Lys Lys Leu Arg Xaa Ala Thr Asp Lys Phe Arg Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Protein

<400> SEQUENCE: 28

Cys Gly Tyr Gln Lys Lys Leu Arg Ser Ala Thr Asp Lys Tyr Arg Leu
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9, 10
<223> OTHER INFORMATION: Xaa = d-proline

<400> SEQUENCE: 29

Gly Gly Tyr Gln Lys Lys Leu Arg Xaa Xaa His Thr Asp Lys Tyr Arg
1               5                   10                  15

Leu

<210> SEQ ID NO 30
<211> LENGTH: 16
<212> TYPE: PRT
<213> ORGANISM: Artificial Sequence
```

```
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = d-proline

<400> SEQUENCE: 30

Gly Gly Tyr Gln Lys Lys Leu Arg Xaa Trp Thr Asp Lys Tyr Arg Leu
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = d-proline
<220> FEATURE:
<221> NAME/KEY: MOD_RES
<222> LOCATION: 10
<223> OTHER INFORMATION: Xaa = 2,3-diaminopropionic acid

<400> SEQUENCE: 31

Gly Gly Tyr Gln Lys Lys Leu Arg Xaa Xaa Thr Asp Lys Tyr Arg Leu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = hydroxyproline

<400> SEQUENCE: 32

Gly Gly Tyr Gln Lys Lys Leu Arg Xaa His Thr Asp Lys Tyr Arg Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 9
<223> OTHER INFORMATION: Xaa = d-proline
<220> FEATURE:
<221> NAME/KEY: MOD_RES
<222> LOCATION: 10
<223> OTHER INFORMATION: Xaa = hydroxyproline

<400> SEQUENCE: 33

Gly Gly Tyr Gln Lys Lys Leu Arg Xaa Xaa Thr Asp Lys Tyr Arg Leu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic Protein
<220> FEATURE:
```

```
<221> NAME/KEY: MOD_RES
<222> LOCATION: 7
<223> OTHER INFORMATION: Xaa = photo leucine

<400> SEQUENCE: 34

Gly Gly Tyr Gln Lys Lys Xaa Arg Ser Ala Thr Asp Lys Tyr Arg Leu
 1               5                  10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic Protein

<400> SEQUENCE: 35

Gly Gly Tyr Gln Lys Lys His Arg Ser Ala Thr Asp Lys Tyr Arg Leu
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic Protein
<220> FEATURE:
<221> NAME/KEY: MOD_RES
<222> LOCATION: 7
<223> OTHER INFORMATION: Xaa = d-leucine

<400> SEQUENCE: 36

Gly Gly Tyr Gln Lys Lys Xaa Arg Ser Ala Thr Asp Lys Tyr Arg Leu
 1               5                  10                  15

<210> SEQ ID NO 37
<211> LENGTH: 17
<212> TYPE: PRT
<213> ORGANISM: Artificial Sequence
<220> FEATURE:
<223> OTHER INFORMATION: Synthetic Protein

<400> SEQUENCE: 37

Gly Gly Tyr Gln Lys Lys Leu Arg Ser Ala Thr Asp Lys Tyr Arg Leu
 1               5                  10                  15

His

<210> SEQ ID NO 38
<211> LENGTH: 16
<212> TYPE: PRT
<213> ORGANISM: Artificial Sequence
<220> FEATURE:
<223> OTHER INFORMATION: Synthetic Protein

<400> SEQUENCE: 38

Gly Gly Tyr Gln Lys Lys Leu Arg Thr Ala Thr Asp Lys Tyr Arg Leu
 1               5                  10                  15

<210> SEQ ID NO 39
<211> LENGTH: 21
<212> TYPE: PRT
<213> ORGANISM: Artificial Sequence
<220> FEATURE:
<223> OTHER INFORMATION: Synthetic Protein

<400> SEQUENCE: 39

Ser Lys Leu Ser His Ser Lys Gly His Gln Lys Arg Lys Ala Leu Lys
 1               5                  10                  15
```

```
Thr Thr Val Ile Leu
            20

<210> SEQ ID NO 40
<211> LENGTH: 17
<212> TYPE: PRT
<213> ORGANISM: Artificial Sequence
<220> FEATURE:
<223> OTHER INFORMATION: Synthetic Protein

<400> SEQUENCE: 40

Gly Ala Lys Phe Lys Thr Ala Ser Ala Gln His Ala Leu Thr Ser Val
1               5                   10                  15

Arg

<210> SEQ ID NO 41
<211> LENGTH: 17
<212> TYPE: PRT
<213> ORGANISM: Artificial Sequence
<220> FEATURE:
<223> OTHER INFORMATION: Synthetic Protein

<400> SEQUENCE: 41

Met Gly Tyr Gln Lys Lys Leu Arg Ser Met Thr Asp Lys Tyr Arg Leu
1               5                   10                  15

His

<210> SEQ ID NO 42
<211> LENGTH: 22
<212> TYPE: PRT
<213> ORGANISM: Artificial Sequence
<220> FEATURE:
<223> OTHER INFORMATION: Synthetic Protein

<400> SEQUENCE: 42

Asp Arg Tyr Leu Ala Ile Val His Ala Thr Asn Ser Gln Arg Pro Arg
1               5                   10                  15

Lys Leu Leu Ala Glu Lys
            20

<210> SEQ ID NO 43
<211> LENGTH: 23
<212> TYPE: PRT
<213> ORGANISM: Artificial Sequence
<220> FEATURE:
<223> OTHER INFORMATION: Synthetic Protein

<400> SEQUENCE: 43

Ile Ile Ile Ser Lys Leu Ser His Ser Lys Gly His Gln Lys Arg Lys
1               5                   10                  15

Ala Leu Lys Thr Thr Val Ile
            20

<210> SEQ ID NO 44
<211> LENGTH: 47
<212> TYPE: PRT
<213> ORGANISM: Artificial Sequence
<220> FEATURE:
<223> OTHER INFORMATION: Synthetic Protein

<400> SEQUENCE: 44

Gly Ala Lys Phe Lys Thr Ser Ala Gln His Ala Leu Thr Ser Val Ser
1               5                   10                  15
```

Arg Gly Ser Ser Leu Lys Ile Leu Ser Lys Gly Lys Arg Gly Gly His
            20                  25                  30

Ser Ser Val Ser Thr Glu Ser Glu Ser Ser Phe His Ser Ser
        35                  40                  45

<210> SEQ ID NO 45
<211> LENGTH: 18
<212> TYPE: PRT
<213> ORGANISM: Artificial Sequence
<220> FEATURE:
<223> OTHER INFORMATION: Synthetic Protein

<400> SEQUENCE: 45

Met Gly Tyr Gln Lys Lys Leu Arg Ser Met Thr Asp Lys Tyr Arg Leu
1               5                   10                  15

His Leu

<210> SEQ ID NO 46
<211> LENGTH: 19
<212> TYPE: PRT
<213> ORGANISM: Artificial Sequence
<220> FEATURE:
<223> OTHER INFORMATION: Synthetic Protein

<400> SEQUENCE: 46

Met Gly Tyr Gln Lys Lys Leu Arg Ser Met Thr Asp Lys Tyr Arg Leu
1               5                   10                  15

His Leu Ser

<210> SEQ ID NO 47
<211> LENGTH: 20
<212> TYPE: PRT
<213> ORGANISM: Artificial Sequence
<220> FEATURE:
<223> OTHER INFORMATION: Synthetic Protein

<400> SEQUENCE: 47

Met Gly Tyr Gln Lys Lys Leu Arg Ser Met Thr Asp Lys Tyr Arg Leu
1               5                   10                  15

His Leu Ser Val
            20

<210> SEQ ID NO 48
<211> LENGTH: 18
<212> TYPE: PRT
<213> ORGANISM: Artificial Sequence
<220> FEATURE:
<223> OTHER INFORMATION: Synthetic Protein

<400> SEQUENCE: 48

Val Met Gly Tyr Gln Lys Lys Leu Arg Ser Met Thr Asp Lys Tyr Arg
1               5                   10                  15

Leu His

<210> SEQ ID NO 49
<211> LENGTH: 19
<212> TYPE: PRT
<213> ORGANISM: Artificial Sequence
<220> FEATURE:
<223> OTHER INFORMATION: Synthetic Protein

<400> SEQUENCE: 49

Leu Val Met Gly Tyr Gln Lys Lys Leu Arg Ser Met Thr Asp Lys Tyr
1               5                   10                  15

Arg Leu His

<210> SEQ ID NO 50
<211> LENGTH: 20
<212> TYPE: PRT
<213> ORGANISM: Artificial Sequence
<220> FEATURE:
<223> OTHER INFORMATION: Synthetic Protein

<400> SEQUENCE: 50

Ile Leu Val Met Gly Tyr Gln Lys Lys Leu Arg Ser Met Thr Asp Lys
1               5                   10                  15

Tyr Arg Leu His
            20

<210> SEQ ID NO 51
<211> LENGTH: 21
<212> TYPE: PRT
<213> ORGANISM: Artificial Sequence
<220> FEATURE:
<223> OTHER INFORMATION: Synthetic Protein

<400> SEQUENCE: 51

Val Ile Leu Val Met Gly Tyr Gln Lys Lys Leu Arg Ser Met Thr Asp
1               5                   10                  15

Lys Tyr Arg Leu His
            20

<210> SEQ ID NO 52
<211> LENGTH: 16
<212> TYPE: PRT
<213> ORGANISM: Artificial Sequence
<220> FEATURE:
<223> OTHER INFORMATION: Synthetic Protein

<400> SEQUENCE: 52

Met Gly Tyr Gln Lys Lys Leu Arg Ser Met Thr Asp Lys Tyr Arg Leu
1               5                   10                  15

<210> SEQ ID NO 53
<211> LENGTH: 33
<212> TYPE: PRT
<213> ORGANISM: Artificial Sequence
<220> FEATURE:
<223> OTHER INFORMATION: Synthetic Protein

<400> SEQUENCE: 53

Gly Asn Gly Leu Val Ile Leu Val Met Gly Tyr Gln Lys Lys Leu Arg
1               5                   10                  15

Ser Met Thr Asp Lys Tyr Arg Leu His Leu Ser Val Ala Asp Leu Leu
            20                  25                  30

Phe

<210> SEQ ID NO 54
<211> LENGTH: 38
<212> TYPE: PRT
<213> ORGANISM: Artificial Sequence
<220> FEATURE:
<223> OTHER INFORMATION: Synthetic Protein

<400> SEQUENCE: 54

Leu Ile Leu Ala Phe Ile Ser Leu Asp Arg Tyr Leu Ala Ile Val His
1               5                   10                  15

```
Ala Thr Asn Ser Gln Arg Pro Arg Lys Leu Leu Ala Glu Lys Val Val
            20                  25                  30

Tyr Val Gly Val Trp Ile
            35

<210> SEQ ID NO 55
<211> LENGTH: 39
<212> TYPE: PRT
<213> ORGANISM: Artificial Sequence
<220> FEATURE:
<223> OTHER INFORMATION: Synthetic Protein

<400> SEQUENCE: 55

Ile Val Ile Leu Ser Cys Tyr Cys Ile Ile Ile Ser Lys Leu Ser His
 1               5                  10                  15

Ser Lys Gly His Gln Lys Arg Lys Ala Leu Lys Thr Thr Val Ile Leu
            20                  25                  30

Ile Leu Ala Phe Phe Ala Cys
            35

<210> SEQ ID NO 56
<211> LENGTH: 55
<212> TYPE: PRT
<213> ORGANISM: Artificial Sequence
<220> FEATURE:
<223> OTHER INFORMATION: Synthetic Protein

<400> SEQUENCE: 56

Asn Pro Ile Leu Tyr Ala Phe Leu Gly Ala Lys Phe Lys Thr Ser Ala
 1               5                  10                  15

Gln His Ala Leu Thr Ser Val Ser Arg Gly Ser Ser Leu Lys Ile Leu
            20                  25                  30

Ser Lys Gly Lys Arg Gly Gly His Ser Ser Val Ser Thr Glu Ser Glu
            35                  40                  45

Ser Ser Ser Phe His Ser Ser
            50                  55
```